US011390859B2

(12) United States Patent
Braddock

(10) Patent No.: US 11,390,859 B2
(45) Date of Patent: Jul. 19, 2022

(54) COMPOSITIONS AND METHODS FOR STROKE PREVENTION IN PEDIATRIC SICKLE CELL ANEMIA PATIENTS

(71) Applicant: YALE UNIVERSITY, New Haven, CT (US)

(72) Inventor: Demetrios Braddock, Guilford, CT (US)

(73) Assignee: Yale University, New Haven, CT (US)

( * ) Notice: Subject to any disclaimer, the term of this patent is extended or adjusted under 35 U.S.C. 154(b) by 634 days.

(21) Appl. No.: 16/322,037

(22) PCT Filed: Aug. 3, 2017

(86) PCT No.: PCT/US2017/045280
§ 371 (c)(1),
(2) Date: Jan. 30, 2019

(87) PCT Pub. No.: WO2018/027024
PCT Pub. Date: Feb. 8, 2018

(65) Prior Publication Data

US 2020/0181589 A1 Jun. 11, 2020

Related U.S. Application Data

(60) Provisional application No. 62/371,269, filed on Aug. 5, 2016.

(51) Int. Cl.

| | |
|---|---|
| ***C12N 9/14*** | (2006.01) |
| ***A61P 9/00*** | (2006.01) |
| ***C07K 14/765*** | (2006.01) |
| ***A61K 38/00*** | (2006.01) |
| ***A61K 45/06*** | (2006.01) |
| ***A61P 25/28*** | (2006.01) |
| ***A61K 38/46*** | (2006.01) |

(52) U.S. Cl.
CPC .................. *C12N 9/14* (2013.01); *A61P 9/00* (2018.01); *C07K 14/765* (2013.01); *C12Y 306/01009* (2013.01); *A61K 38/00* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,043,056 | A | 3/2000 | Yue et al. |
| 6,358,923 | B1 | 3/2002 | Yue et al. |
| 7,323,542 | B2 | 1/2008 | Balian et al. |
| 7,888,372 | B2 | 2/2011 | Millan et al. |
| 8,846,603 | B2 | 9/2014 | Quinn et al. |
| 9,744,219 | B2 | 8/2017 | Braddock et al. |
| 9,913,881 | B2 | 3/2018 | Braddock et al. |
| 10,064,917 | B2 | 9/2018 | Braddock et al. |
| 10,213,483 | B2 | 2/2019 | Otterlei et al. |
| 10,213,484 | B2 | 2/2019 | Braddock et al. |
| 10,517,927 | B2 | 12/2019 | Braddock et al. |
| 10,583,170 | B2 | 3/2020 | Braddock et al. |
| 10,624,958 | B2 | 4/2020 | Braddock et al. |
| 2007/0004913 | A1 | 1/2007 | Challita-Eid et al. |
| 2007/0015145 | A1 | 1/2007 | Woolf et al. |
| 2008/0273206 | A1 | 11/2008 | Genge et al. |
| 2014/0154774 | A1 | 6/2014 | Quinn et al. |
| 2014/0377859 | A1 | 12/2014 | Quinn et al. |
| 2015/0024460 | A1 | 1/2015 | Quinn et al. |
| 2015/0359858 | A1 | 12/2015 | Braddock et al. |

FOREIGN PATENT DOCUMENTS

| | | | |
|---|---|---|---|
| WO | 02092020 | A2 | 11/2002 |
| WO | 2011113027 | A2 | 9/2011 |
| WO | 2012125182 | A1 | 9/2012 |
| WO | 2014126965 | A2 | 8/2014 |
| WO | 2016100803 | A2 | 6/2016 |
| WO | 2016187408 | A1 | 11/2016 |
| WO | 2017087936 | A1 | 5/2017 |

OTHER PUBLICATIONS

Kassim (Clinical Advances in Hematology & Oncology vol. 14, Issue May 5, 2016 pp. 307-309).*
Li et al. (Serum phosphate concentration and incidence of stroke: a systemic review and meta-analysis, Neurol Sci (2014) 35:1877-1882).*
Extended European Search Report for European Patent Application No. 17837677.8 dated Mar. 24, 2020.
International Search Report and Written Opinion for PCT International Application No. PCT/US2017/045280 dated Dec. 26, 2017.
UniProt Accession No. O14638, ENPP3_HUMAN, Jan. 7, 2015 [online]. [Retrieved on Jan. 19, 2017]. Retrieved from the internet <URL: http://www.uniprot.org/uniprot/O14638.txt?version=133>.
"Chronic Renal Failure: From the Perspective of Internal Medicine", Clinical Imagiology 21(11), 2005, 1142-1149 (Partial Translation).
"Pharmacokinetic Control of Biopharmaceuticals", Journal of Pharmaceutical Science and Technology, Japan, 2014, 27-32 (Partial Translation).
Albright , et al., "ENPP1-Fc prevents mortality and vascular calcifications in rodent model of generalized arterial calcification of infancy", Nat Commun. 6, 2015, 10006.

(Continued)

*Primary Examiner* — Suzanne M Noakes
*Assistant Examiner* — Jae W Lee
(74) *Attorney, Agent, or Firm* — Saul Ewing Arnstein & Lehr LLP; Kathryn Doyle; Domingos J. Silva

(57) ABSTRACT

The present invention includes compositions and methods for treating stroke in sickle cell anemia (SCA) patients. In certain embodiments, the patient is administered certain ENPP1- or ENNP3-containing polypeptides, mutants, or mutant fragments thereof.

24 Claims, 5 Drawing Sheets

Specification includes a Sequence Listing.

(56) References Cited

OTHER PUBLICATIONS

Albright , et al., "Molecular basis of purinergic signal metabolism by ectonucleotide pyrophosphatase/phosphodiesterases 4 and 1 and implications in stroke", J Biol Chem. 289(6), 2014, 3294-3306.
Albright , et al., "NPP4 is a procoagulant enzyme on the surface of vascular endothelium", Blood. 120(22), 2012, 4432 4440.
Anonymous , "UPI000511D809", Retrieved from the Internet Mar. 7, 2019, <https://www.uniprot.org/uniparc/UPI000 511D809>, Oct. 2014.
Belisário , et al., "Association between ENPP1 K173Q and stroke in a newborn cohort of 395 Brazilian children with sickle cell anemia", Blood. 126(10), 2015, 1259-1260.
Cimpean , et al., "Substrate-specifying determinants of the nucleotide pyrophosphatases/phosphodiesterases NPP1 and NPP2", Biochem J. 381(Pt 1), 2004, 71-77.
Eller , et al., "Impact of ENPP1 genotype on arterial calcification in patients with end-stage renal failure", Nephrol Dial Transplant. 23(1), 2008, 321-327.
Flanagan , et al., "Genetic mapping and exome sequencing identify 2 mutations associated with stroke protection in pediatric patients with sickle cell anemia", Blood. 121(16), 2013, 3237-3245.
Gijsbers , et al., "Functional characterization of the non-catalytic ectodomains of the nucleotide pyrophosphatase/phosphodiesterase NPP1", Biochem J. 371(Pt 2), Apr. 15, 2003, 321-330.
Goding , et al., "Physiological and pathophysiological functions of the ecto-nucleotide pyrophosphatase/phosphodiesterase family", Biochim Biophys Acta. 1638(1), 2003, 1-19.
Guo , et al., "Clinical outcomes of various continued antiplatelet therapies in patients who were administered DAPT following the implantation of drug-eluting stents and developed gastrointestinal hemorrhage", Exp Ther Med. 12(2), Aug. 2016, 1125-1129.
Jansen , et al., "ABCC6 prevents ectopic mineralization seen in pseudoxanthoma elasticum by inducing cellular nucleotide release", Proc Natl Acad Sci U S A. 110(50), 2013, 20206-20211.
Jansen , et al., "ABCC6-mediated ATP secretion by the liver is the main source of the mineralization inhibitor inorganic pyrophosphate in the systemic circulation—brief report", Arterioscler Thromb Vasc Biol. 34(9), 2014, 1985-1989.
Jansen , et al., "Proteolytic maturation and activation of autotaxin (NPP2), a secreted metastasis-enhancing lysophospholipase D", J Cell Sci. 118(Pt 14), 2005, 3081-3089.
Jansen , et al., "Structure of NPP1, an ectonucleotide pyrophosphatase/phosphodiesterase involved in tissue calcification", Structure. 20(11), 2012, 1948-1959.
Jin-Hua , et al., "Molecular Coning and Chromosomal Localization of PD-I62 (PDNP3), a New Member of the Human Phosphodiesterase I Genes", Genomics 45, 1997, 412-415.
Johnson , et al., "Differential mechanisms of inorganic pyrophosphate production by plasma cell membrane glycoprotein-1 and B10 in chondrocytes", Arthritis Rheum. 42(9), 1999, 1986-1997.
Johnson , et al., "Linked deficiencies in extracellular PP(i) and osteopontin mediate pathologic calcification associated with defective PC-1 and ANK expression", J Bone Miner Res. 18(6), 2003, 994-1004.
Johnson , et al., "The Nucleoside Triphosphate Pyrophosphohydrolase Isozyme PC-1 Directly Promotes Cartilage Calcification Through Chondrocyte Apoptosis and Increased Calcium Precipitation by Mineralizing Vesicles", The Journal of Rheumatology 28 (12), Dec. 2001, 2681-2691.
Lee , et al., "Cloning, chromosomal localization, and tissue expression of autotaxin from human teratocarcinoma cells", Biochem Biophys Res Commun. 218(3, 1996, 714-719.
Lieben , et al., "Normocalcemia is maintained in mice under conditions of calcium malabsorption by vitamin D-induced inhibition of bone mineralization", J Clin Invest. 122(5), 2012, 1803-1805.
Schetter , et al., "Nucleoporins NPP-1, NPP-3, NPP-4, NPP-11 and NPP-13 are required for proper spindle orientation in C. elegans", Dev Biol. 289(2), Jan. 15, 2006, 360-371.
Shankar , et al., "Progeria—A Brief Review", International Journal of Pharma and Bio Sciences 2, 2010, 1-14.
Sheehan , et al., "Genetic modifiers of sickle cell anemia in the BABY HUG cohort: influence on laboratory and clinical phenotypes", Am J Hematol. 88(7), 2013, 571-576.
Silcox , et al., "Measurement of inorganic pyrophosphate in biological fluids. Elevated levels in some patients with osteoarthritis, pseudogout, acromegaly, and uremia", J Clin Invest. 52(8), Aug. 1973, 1863-1870.
Stefan , et al., "NPP-type ectophosphodiesterases: unity in diversity.", Trends Biochem Sci. 30(10), Oct. 2005, 542-550.
Terkeltaub , "Physiologic and pathologic functions of the NPP nucleotide pyrophosphatase/phosphodiesterase family focusing on NPP1 in calcification.", Purinergic Signal. 2(2), Jun. 2, 2006, 371-377.
Tsai , et al., "The Ectoenzyme E-NPP3 Negatively Regulates ATP-Dependent Chronic Allergic Responses by Basophils and Mast Cells", Immunity 42, Feb. 2015, 279-293.
Whisstock , et al., "Prediction of proteinfunction fromprotein sequence and structure", Quarterly Reviews of Biophysics 36, 3 (2003), pp. 2003, 307-340.
Witkowski , et al., "Conversion of a Beta-Ketoacyl Synthase to a Malonyl Decarboxylase by Replacement of the Active-Site Cysteine With Glutamine", Biochemistry 38(36), Sep. 1999, 11643-11650.
Zhang , et al., "The interaction of cationic polymers and their bisphosphonate derivatives with hydroxyapatite", Macromol Biosci. 7(5), May 10, 2007, 656-670 (Abstract Only).

* cited by examiner

Comparison of partially purified ENPP3 to crude starting material: SDS-PAGE

SEQUENCE LISTING

```
<160> NUMBER OF SEQ ID NOS: 76

<210> SEQ ID NO 1
<211> LENGTH: 925
<212> TYPE: PRT
<213> ORGANISM: Homo sapiens

<400> SEQUENCE: 1

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Val Leu Ser Leu
65                  70                  75                  80

Val Leu Ser Val Cys Val Leu Thr Thr Ile Leu Gly Cys Ile Phe Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365
```

```
Thr Leu Tyr Leu Glu Glu Pro Asp Ser Ser Gly His Ser Tyr Gly Pro
    370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
```

```
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
        835                 840                 845

Glu Asn Leu Asp Thr Leu Ala Phe Ile Leu Pro His Arg Thr Asp Asn
    850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp
        915                 920                 925


<210> SEQ ID NO 2
<211> LENGTH: 888
<212> TYPE: PRT
<213> ORGANISM: Homo sapiens

<400> SEQUENCE: 2

Met Ala Arg Arg Ser Ser Phe Gln Ser Cys Gln Ile Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Gly Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
            180                 185                 190

Arg Ser Cys Gly Thr His Ser Pro Tyr Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240
```

```
Thr Phe His Leu Arg Gly Arg Glu Lys Phe Asn His Arg Trp Trp Gly
                245                 250                 255

Gly Gln Pro Leu Trp Ile Thr Ala Thr Lys Gln Gly Val Lys Ala Gly
            260                 265                 270

Thr Phe Phe Trp Ser Val Val Ile Pro His Glu Arg Arg Ile Leu Thr
        275                 280                 285

Ile Leu Gln Trp Leu Thr Leu Pro Asp His Glu Arg Pro Ser Val Tyr
    290                 295                 300

Ala Phe Tyr Ser Glu Gln Pro Asp Phe Ser Gly His Lys Tyr Gly Pro
305                 310                 315                 320

Phe Gly Pro Glu Met Thr Asn Pro Leu Arg Glu Ile Asp Lys Ile Val
                325                 330                 335

Gly Gln Leu Met Asp Gly Leu Lys Gln Leu Lys Leu His Arg Cys Val
            340                 345                 350

Asn Val Ile Phe Val Gly Asp His Gly Met Glu Asp Val Thr Cys Asp
        355                 360                 365

Arg Thr Glu Phe Leu Ser Asn Tyr Leu Thr Asn Val Asp Asp Ile Thr
    370                 375                 380

Leu Val Pro Gly Thr Leu Gly Arg Ile Arg Ser Lys Phe Ser Asn Asn
385                 390                 395                 400

Ala Lys Tyr Asp Pro Lys Ala Ile Ile Ala Asn Leu Thr Cys Lys Lys
                405                 410                 415

Pro Asp Gln His Phe Lys Pro Tyr Leu Lys Gln His Leu Pro Lys Arg
            420                 425                 430

Leu His Tyr Ala Asn Asn Arg Arg Ile Glu Asp Ile His Leu Leu Val
        435                 440                 445

Glu Arg Arg Trp His Val Ala Arg Lys Pro Leu Asp Val Tyr Lys Lys
    450                 455                 460

Pro Ser Gly Lys Cys Phe Phe Gln Gly Asp His Gly Phe Asp Asn Lys
465                 470                 475                 480

Val Asn Ser Met Gln Thr Val Phe Val Gly Tyr Gly Ser Thr Phe Lys
                485                 490                 495

Tyr Lys Thr Lys Val Pro Pro Phe Glu Asn Ile Glu Leu Tyr Asn Val
            500                 505                 510

Met Cys Asp Leu Leu Gly Leu Lys Pro Ala Pro Asn Asn Gly Thr His
        515                 520                 525

Gly Ser Leu Asn His Leu Leu Arg Thr Asn Thr Phe Arg Pro Thr Met
    530                 535                 540

Pro Glu Glu Val Thr Arg Pro Asn Tyr Pro Gly Ile Met Tyr Leu Gln
545                 550                 555                 560

Ser Asp Phe Asp Leu Gly Cys Thr Cys Asp Asp Lys Val Glu Pro Lys
                565                 570                 575

Asn Lys Leu Asp Glu Leu Asn Lys Arg Leu His Thr Lys Gly Ser Thr
            580                 585                 590

Glu Ala Glu Thr Arg Lys Phe Arg Gly Ser Arg Asn Glu Asn Lys Glu
        595                 600                 605

Asn Ile Asn Gly Asn Phe Glu Pro Arg Lys Glu Arg His Leu Leu Tyr
    610                 615                 620

Gly Arg Pro Ala Val Leu Tyr Arg Thr Arg Tyr Asp Ile Leu Tyr His
625                 630                 635                 640

Thr Asp Phe Glu Ser Gly Tyr Ser Glu Ile Phe Leu Met Pro Leu Trp
                645                 650                 655

Thr Ser Tyr Thr Val Ser Lys Gln Ala Glu Val Ser Ser Val Pro Asp
```

```
            660                 665                 670

His Leu Thr Ser Cys Val Arg Pro Asp Val Arg Val Ser Pro Ser Phe
        675                 680                 685

Ser Gln Asn Cys Leu Ala Tyr Lys Asn Asp Lys Gln Met Ser Tyr Gly
    690                 695                 700

Phe Leu Phe Pro Pro Tyr Leu Ser Ser Ser Pro Glu Ala Lys Tyr Asp
705                 710                 715                 720

Ala Phe Leu Val Thr Asn Met Val Pro Met Tyr Pro Ala Phe Lys Arg
                725                 730                 735

Val Trp Asn Tyr Phe Gln Arg Val Leu Val Lys Lys Tyr Ala Ser Glu
            740                 745                 750

Arg Asn Gly Val Asn Val Ile Ser Gly Pro Ile Phe Asp Tyr Asp Tyr
        755                 760                 765

Asp Gly Leu His Asp Thr Glu Asp Lys Ile Lys Gln Tyr Val Glu Gly
    770                 775                 780

Ser Ser Ile Pro Val Pro Thr His Tyr Tyr Ser Ile Ile Thr Ser Cys
785                 790                 795                 800

Leu Asp Phe Thr Gln Pro Ala Asp Lys Cys Asp Gly Pro Leu Ser Val
                805                 810                 815

Ser Ser Phe Ile Leu Pro His Arg Pro Asp Asn Glu Glu Ser Cys Asn
            820                 825                 830

Ser Ser Glu Asp Glu Ser Lys Trp Val Glu Glu Leu Met Lys Met His
        835                 840                 845

Thr Ala Arg Val Arg Asp Ile Glu His Leu Thr Ser Leu Asp Phe Phe
    850                 855                 860

Arg Lys Thr Ser Arg Ser Tyr Pro Glu Ile Leu Thr Leu Lys Thr Tyr
865                 870                 875                 880

Leu His Thr Tyr Glu Ser Glu Ile
                885
```

```
<210> SEQ ID NO 3
<211> LENGTH: 1
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(1)
<223> OTHER INFORMATION: sequence can be repeated 1-15 times

<400> SEQUENCE: 3

Asp
1


<210> SEQ ID NO 4
<211> LENGTH: 3
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(3)
<223> OTHER INFORMATION: sequence can be repeated 1-10 times

<400> SEQUENCE: 4

Asp Ser Ser
1
```

<210> SEQ ID NO 5
<211> LENGTH: 3
<212> TYPE: PRT
<213> ORGANISM: Artificial Sequence
<220> FEATURE:
<223> OTHER INFORMATION: chemically synsthesized
<220> FEATURE:
<221> NAME/KEY: REPEAT
<222> LOCATION: (1)..(3)
<223> OTHER INFORMATION: sequence can be repeated 1-10 times

<400> SEQUENCE: 5

Glu Ser Ser
1

<210> SEQ ID NO 6
<211> LENGTH: 3
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(3)
<223> OTHER INFORMATION: sequence can be repeated 1-10 times

<400> SEQUENCE: 6

Arg Gln Gln
1

<210> SEQ ID NO 7
<211> LENGTH: 2
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(2)
<223> OTHER INFORMATION: sequence can be repeated 1-10 times

<400> SEQUENCE: 7

Lys Arg
1

<210> SEQ ID NO 8
<211> LENGTH: 1
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(1)
<223> OTHER INFORMATION: sequence can be repeated 1-15 times

<400> SEQUENCE: 8

Arg
1

<210> SEQ ID NO 9
<211> LENGTH: 16
<212> TYPE: PRT
<213> ORGANISM: Artificial Sequence
<220> FEATURE:
<223> OTHER INFORMATION: chemically synthesized

<400> SEQUENCE: 9

Asp Ser Ser Ser Glu Glu Lys Phe Leu Arg Arg Ile Gly Arg Phe Gly
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: chemically synthesized

<400> SEQUENCE: 10

Glu Glu Glu Glu Glu Glu Glu Pro Arg Gly Asp Thr
1 5 10

<210> SEQ ID NO 11
<211> LENGTH: 12
<212> TYPE: PRT
<213> ORGANISM: Artificial Sequence
<220> FEATURE:
<223> OTHER INFORMATION: chemically synthesized

<400> SEQUENCE: 11

Ala Pro Trp His Leu Ser Ser Gln Tyr Ser Arg Thr
1 5 10

<210> SEQ ID NO 12
<211> LENGTH: 12
<212> TYPE: PRT
<213> ORGANISM: Artificial Sequence
<220> FEATURE:
<223> OTHER INFORMATION: chemically synthesized

<400> SEQUENCE: 12

Ser Thr Leu Pro Ile Pro His Glu Phe Ser Arg Glu
1 5 10

<210> SEQ ID NO 13
<211> LENGTH: 12
<212> TYPE: PRT
<213> ORGANISM: Artificial Sequence
<220> FEATURE:
<223> OTHER INFORMATION: chemically synthesized

<400> SEQUENCE: 13

Val Thr Lys His Leu Asn Gln Ile Ser Gln Ser Tyr
1 5 10

<210> SEQ ID NO 14
<211> LENGTH: 1
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(1)
<223> OTHER INFORMATION: sequence can be repeated 1-15 times

<400> SEQUENCE: 14

Glu
1

<210> SEQ ID NO 15
<211> LENGTH: 925
<212> TYPE: PRT
<213> ORGANISM: Artificial Sequence
<220> FEATURE:
<223> OTHER INFORMATION: ENPP121

<400> SEQUENCE: 15

```
Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
    370                 375                 380

Val Ser Ser Glu Val Ile Lys Ala Leu Gln Arg Val Asp Gly Met Val
```

```
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815
```

```
Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
        835                 840                 845

Glu Asn Leu Asp Thr Leu Ala Phe Ile Leu Pro His Arg Thr Asp Asn
    850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp
        915                 920                 925


<210> SEQ ID NO 16
<211> LENGTH: 1155
<212> TYPE: PRT
<213> ORGANISM: Artificial Sequence
<220> FEATURE:
<223> OTHER INFORMATION: ENPP121 Fc

<400> SEQUENCE: 16

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255
```

```
Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
    370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670
```

```
Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
        835                 840                 845

Glu Asn Leu Asp Thr Leu Ala Phe Ile Leu Pro His Arg Thr Asp Asn
    850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp Leu Ile Asn
        915                 920                 925

Asp Lys Thr His Thr Cys Pro Pro Cys Pro Ala Pro Glu Leu Leu Gly
    930                 935                 940

Gly Pro Ser Val Phe Leu Phe Pro Pro Lys Pro Lys Asp Thr Leu Met
945                 950                 955                 960

Ile Ser Arg Thr Pro Glu Val Thr Cys Val Val Val Asp Val Ser His
                965                 970                 975

Glu Asp Pro Glu Val Lys Phe Asn Trp Tyr Val Asp Gly Val Glu Val
            980                 985                 990

His Asn Ala Lys Thr Lys Pro Arg  Glu Glu Gln Tyr Asn  Ser Thr Tyr
        995                 1000                 1005

Arg Val  Val Ser Val Leu Thr  Val Leu His Gln Asp  Trp Leu Asn
    1010                 1015                 1020

Gly Lys  Glu Tyr Lys Cys Lys  Val Ser Asn Lys Ala  Leu Pro Ala
    1025                 1030                 1035

Pro Ile  Glu Lys Thr Ile Ser  Lys Ala Lys Gly Gln  Pro Arg Glu
    1040                 1045                 1050

Pro Gln  Val Tyr Thr Leu Pro  Pro Ser Arg Glu Glu  Met Thr Lys
    1055                 1060                 1065

Asn Gln  Val Ser Leu Thr Cys  Leu Val Lys Gly Phe  Tyr Pro Ser
    1070                 1075                 1080

Asp Ile  Ala Val Glu Trp Glu  Ser Asn Gly Gln Pro  Glu Asn Asn
```

```
    1085                1090                1095

Tyr Lys  Thr Thr Pro Pro Val  Leu Asp Ser Asp Gly  Ser Phe Phe
    1100                1105                1110

Leu Tyr  Ser Lys Leu Thr Val  Asp Lys Ser Arg Trp  Gln Gln Gly
    1115                1120                1125

Asn Val  Phe Ser Cys Ser Val  Met His Glu Ala Leu  His Asn His
    1130                1135                1140

Tyr Thr  Gln Lys Ser Leu Ser  Leu Ser Pro Gly Lys
    1145                1150                1155


<210> SEQ ID NO 17
<211> LENGTH: 852
<212> TYPE: PRT
<213> ORGANISM: Artificial Sequence
<220> FEATURE:
<223> OTHER INFORMATION: ENNP71

<400> SEQUENCE: 17

Met Arg Gly Pro Ala Val Leu Leu Thr Val Ala Leu Ala Thr Leu Leu
1               5                   10                  15

Ala Pro Gly Ala Gly Ala Gly Leu Lys Pro Ser Cys Ala Lys Glu Val
            20                  25                  30

Lys Ser Cys Lys Gly Arg Cys Phe Glu Arg Thr Phe Gly Asn Cys Arg
        35                  40                  45

Cys Asp Ala Ala Cys Val Glu Leu Gly Asn Cys Cys Leu Asp Tyr Gln
    50                  55                  60

Glu Thr Cys Ile Glu Pro Glu His Ile Trp Thr Cys Asn Lys Phe Arg
65                  70                  75                  80

Cys Gly Glu Lys Arg Leu Thr Arg Ser Leu Cys Ala Cys Ser Asp Asp
                85                  90                  95

Cys Lys Asp Lys Gly Asp Cys Cys Ile Asn Tyr Ser Ser Val Cys Gln
            100                 105                 110

Gly Glu Lys Ser Trp Val Glu Glu Pro Cys Glu Ser Ile Asn Glu Pro
        115                 120                 125

Gln Cys Pro Ala Gly Phe Glu Thr Pro Pro Thr Leu Leu Phe Ser Leu
    130                 135                 140

Asp Gly Phe Arg Ala Glu Tyr Leu His Thr Trp Gly Gly Leu Leu Pro
145                 150                 155                 160

Val Ile Ser Lys Leu Lys Lys Cys Gly Thr Tyr Thr Lys Asn Met Arg
                165                 170                 175

Pro Val Tyr Pro Thr Lys Thr Phe Pro Asn His Tyr Ser Ile Val Thr
            180                 185                 190

Gly Leu Tyr Pro Glu Ser His Gly Ile Ile Asp Asn Lys Met Tyr Asp
        195                 200                 205

Pro Lys Met Asn Ala Ser Phe Ser Leu Lys Ser Lys Glu Lys Phe Asn
    210                 215                 220

Pro Glu Trp Tyr Lys Gly Glu Pro Ile Trp Val Thr Ala Lys Tyr Gln
225                 230                 235                 240

Gly Leu Lys Ser Gly Thr Phe Phe Trp Pro Gly Ser Asp Val Glu Ile
                245                 250                 255

Asn Gly Ile Phe Pro Asp Ile Tyr Lys Met Tyr Asn Gly Ser Val Pro
            260                 265                 270

Phe Glu Glu Arg Ile Leu Ala Val Leu Gln Trp Leu Gln Leu Pro Lys
        275                 280                 285

Asp Glu Arg Pro His Phe Tyr Thr Leu Tyr Leu Glu Glu Pro Asp Ser
```

```
    290                 295                 300

Ser Gly His Ser Tyr Gly Pro Val Ser Ser Glu Val Ile Lys Ala Leu
305                 310                 315                 320

Gln Arg Val Asp Gly Met Val Gly Met Leu Met Asp Gly Leu Lys Glu
                325                 330                 335

Leu Asn Leu His Arg Cys Leu Asn Leu Ile Leu Ile Ser Asp His Gly
            340                 345                 350

Met Glu Gln Gly Ser Cys Lys Lys Tyr Ile Tyr Leu Asn Lys Tyr Leu
        355                 360                 365

Gly Asp Val Lys Asn Ile Lys Val Ile Tyr Gly Pro Ala Ala Arg Leu
    370                 375                 380

Arg Pro Ser Asp Val Pro Asp Lys Tyr Tyr Ser Phe Asn Tyr Glu Gly
385                 390                 395                 400

Ile Ala Arg Asn Leu Ser Cys Arg Glu Pro Asn Gln His Phe Lys Pro
                405                 410                 415

Tyr Leu Lys His Phe Leu Pro Lys Arg Leu His Phe Ala Lys Ser Asp
            420                 425                 430

Arg Ile Glu Pro Leu Thr Phe Tyr Leu Asp Pro Gln Trp Gln Leu Ala
        435                 440                 445

Leu Asn Pro Ser Glu Arg Lys Tyr Cys Gly Ser Gly Phe His Gly Ser
    450                 455                 460

Asp Asn Val Phe Ser Asn Met Gln Ala Leu Phe Val Gly Tyr Gly Pro
465                 470                 475                 480

Gly Phe Lys His Gly Ile Glu Ala Asp Thr Phe Glu Asn Ile Glu Val
                485                 490                 495

Tyr Asn Leu Met Cys Asp Leu Leu Asn Leu Thr Pro Ala Pro Asn Asn
            500                 505                 510

Gly Thr His Gly Ser Leu Asn His Leu Leu Lys Asn Pro Val Tyr Thr
        515                 520                 525

Pro Lys His Pro Lys Glu Val His Pro Leu Val Gln Cys Pro Phe Thr
    530                 535                 540

Arg Asn Pro Arg Asp Asn Leu Gly Cys Ser Cys Asn Pro Ser Ile Leu
545                 550                 555                 560

Pro Ile Glu Asp Phe Gln Thr Gln Phe Asn Leu Thr Val Ala Glu Glu
                565                 570                 575

Lys Ile Ile Lys His Glu Thr Leu Pro Tyr Gly Arg Pro Arg Val Leu
            580                 585                 590

Gln Lys Glu Asn Thr Ile Cys Leu Leu Ser Gln His Gln Phe Met Ser
        595                 600                 605

Gly Tyr Ser Gln Asp Ile Leu Met Pro Leu Trp Thr Ser Tyr Thr Val
    610                 615                 620

Asp Arg Asn Asp Ser Phe Ser Thr Glu Asp Phe Ser Asn Cys Leu Tyr
625                 630                 635                 640

Gln Asp Phe Arg Ile Pro Leu Ser Pro Val His Lys Cys Ser Phe Tyr
                645                 650                 655

Lys Asn Asn Thr Lys Val Ser Tyr Gly Phe Leu Ser Pro Pro Gln Leu
            660                 665                 670

Asn Lys Asn Ser Ser Gly Ile Tyr Ser Glu Ala Leu Leu Thr Thr Asn
        675                 680                 685

Ile Val Pro Met Tyr Gln Ser Phe Gln Val Ile Trp Arg Tyr Phe His
    690                 695                 700

Asp Thr Leu Leu Arg Lys Tyr Ala Glu Glu Arg Asn Gly Val Asn Val
705                 710                 715                 720
```

```
Val Ser Gly Pro Val Phe Asp Phe Asp Tyr Asp Gly Arg Cys Asp Ser
                725                 730                 735

Leu Glu Asn Leu Arg Gln Lys Arg Arg Val Ile Arg Asn Gln Glu Ile
            740                 745                 750

Leu Ile Pro Thr His Phe Phe Ile Val Leu Thr Ser Cys Lys Asp Thr
        755                 760                 765

Ser Gln Thr Pro Leu His Cys Glu Asn Leu Asp Thr Leu Ala Phe Ile
    770                 775                 780

Leu Pro His Arg Thr Asp Asn Ser Glu Ser Cys Val His Gly Lys His
785                 790                 795                 800

Asp Ser Ser Trp Val Glu Glu Leu Leu Met Leu His Arg Ala Arg Ile
                805                 810                 815

Thr Asp Val Glu His Ile Thr Gly Leu Ser Phe Tyr Gln Gln Arg Lys
            820                 825                 830

Glu Pro Val Ser Asp Ile Leu Lys Leu Lys Thr His Leu Pro Thr Phe
        835                 840                 845

Ser Gln Glu Asp
    850


<210> SEQ ID NO 18
<211> LENGTH: 1082
<212> TYPE: PRT
<213> ORGANISM: Artificial Sequence
<220> FEATURE:
<223> OTHER INFORMATION: ENPP71 Fc

<400> SEQUENCE: 18

Met Arg Gly Pro Ala Val Leu Leu Thr Val Ala Leu Ala Thr Leu Leu
1               5                   10                  15

Ala Pro Gly Ala Gly Ala Gly Leu Lys Pro Ser Cys Ala Lys Glu Val
            20                  25                  30

Lys Ser Cys Lys Gly Arg Cys Phe Glu Arg Thr Phe Gly Asn Cys Arg
        35                  40                  45

Cys Asp Ala Ala Cys Val Glu Leu Gly Asn Cys Cys Leu Asp Tyr Gln
    50                  55                  60

Glu Thr Cys Ile Glu Pro Glu His Ile Trp Thr Cys Asn Lys Phe Arg
65                  70                  75                  80

Cys Gly Glu Lys Arg Leu Thr Arg Ser Leu Cys Ala Cys Ser Asp Asp
                85                  90                  95

Cys Lys Asp Lys Gly Asp Cys Cys Ile Asn Tyr Ser Ser Val Cys Gln
            100                 105                 110

Gly Glu Lys Ser Trp Val Glu Glu Pro Cys Glu Ser Ile Asn Glu Pro
        115                 120                 125

Gln Cys Pro Ala Gly Phe Glu Thr Pro Pro Thr Leu Leu Phe Ser Leu
    130                 135                 140

Asp Gly Phe Arg Ala Glu Tyr Leu His Thr Trp Gly Gly Leu Leu Pro
145                 150                 155                 160

Val Ile Ser Lys Leu Lys Lys Cys Gly Thr Tyr Thr Lys Asn Met Arg
                165                 170                 175

Pro Val Tyr Pro Thr Lys Thr Phe Pro Asn His Tyr Ser Ile Val Thr
            180                 185                 190

Gly Leu Tyr Pro Glu Ser His Gly Ile Ile Asp Asn Lys Met Tyr Asp
        195                 200                 205

Pro Lys Met Asn Ala Ser Phe Ser Leu Lys Ser Lys Glu Lys Phe Asn
    210                 215                 220
```

```
Pro Glu Trp Tyr Lys Gly Glu Pro Ile Trp Val Thr Ala Lys Tyr Gln
225                 230                 235                 240

Gly Leu Lys Ser Gly Thr Phe Phe Trp Pro Gly Ser Asp Val Glu Ile
                245                 250                 255

Asn Gly Ile Phe Pro Asp Ile Tyr Lys Met Tyr Asn Gly Ser Val Pro
            260                 265                 270

Phe Glu Glu Arg Ile Leu Ala Val Leu Gln Trp Leu Gln Leu Pro Lys
        275                 280                 285

Asp Glu Arg Pro His Phe Tyr Thr Leu Tyr Leu Glu Glu Pro Asp Ser
    290                 295                 300

Ser Gly His Ser Tyr Gly Pro Val Ser Ser Glu Val Ile Lys Ala Leu
305                 310                 315                 320

Gln Arg Val Asp Gly Met Val Gly Met Leu Met Asp Gly Leu Lys Glu
                325                 330                 335

Leu Asn Leu His Arg Cys Leu Asn Leu Ile Leu Ile Ser Asp His Gly
            340                 345                 350

Met Glu Gln Gly Ser Cys Lys Lys Tyr Ile Tyr Leu Asn Lys Tyr Leu
        355                 360                 365

Gly Asp Val Lys Asn Ile Lys Val Ile Tyr Gly Pro Ala Ala Arg Leu
    370                 375                 380

Arg Pro Ser Asp Val Pro Asp Lys Tyr Tyr Ser Phe Asn Tyr Glu Gly
385                 390                 395                 400

Ile Ala Arg Asn Leu Ser Cys Arg Glu Pro Asn Gln His Phe Lys Pro
                405                 410                 415

Tyr Leu Lys His Phe Leu Pro Lys Arg Leu His Phe Ala Lys Ser Asp
            420                 425                 430

Arg Ile Glu Pro Leu Thr Phe Tyr Leu Asp Pro Gln Trp Gln Leu Ala
        435                 440                 445

Leu Asn Pro Ser Glu Arg Lys Tyr Cys Gly Ser Gly Phe His Gly Ser
    450                 455                 460

Asp Asn Val Phe Ser Asn Met Gln Ala Leu Phe Val Gly Tyr Gly Pro
465                 470                 475                 480

Gly Phe Lys His Gly Ile Glu Ala Asp Thr Phe Glu Asn Ile Glu Val
                485                 490                 495

Tyr Asn Leu Met Cys Asp Leu Leu Asn Leu Thr Pro Ala Pro Asn Asn
            500                 505                 510

Gly Thr His Gly Ser Leu Asn His Leu Leu Lys Asn Pro Val Tyr Thr
        515                 520                 525

Pro Lys His Pro Lys Glu Val His Pro Leu Val Gln Cys Pro Phe Thr
    530                 535                 540

Arg Asn Pro Arg Asp Asn Leu Gly Cys Ser Cys Asn Pro Ser Ile Leu
545                 550                 555                 560

Pro Ile Glu Asp Phe Gln Thr Gln Phe Asn Leu Thr Val Ala Glu Glu
                565                 570                 575

Lys Ile Ile Lys His Glu Thr Leu Pro Tyr Gly Arg Pro Arg Val Leu
            580                 585                 590

Gln Lys Glu Asn Thr Ile Cys Leu Leu Ser Gln His Gln Phe Met Ser
        595                 600                 605

Gly Tyr Ser Gln Asp Ile Leu Met Pro Leu Trp Thr Ser Tyr Thr Val
    610                 615                 620

Asp Arg Asn Asp Ser Phe Ser Thr Glu Asp Phe Ser Asn Cys Leu Tyr
625                 630                 635                 640
```

```
Gln Asp Phe Arg Ile Pro Leu Ser Pro Val His Lys Cys Ser Phe Tyr
                645                 650                 655

Lys Asn Asn Thr Lys Val Ser Tyr Gly Phe Leu Ser Pro Pro Gln Leu
            660                 665                 670

Asn Lys Asn Ser Ser Gly Ile Tyr Ser Glu Ala Leu Leu Thr Thr Asn
        675                 680                 685

Ile Val Pro Met Tyr Gln Ser Phe Gln Val Ile Trp Arg Tyr Phe His
    690                 695                 700

Asp Thr Leu Leu Arg Lys Tyr Ala Glu Glu Arg Asn Gly Val Asn Val
705                 710                 715                 720

Val Ser Gly Pro Val Phe Asp Phe Asp Tyr Asp Gly Arg Cys Asp Ser
                725                 730                 735

Leu Glu Asn Leu Arg Gln Lys Arg Arg Val Ile Arg Asn Gln Glu Ile
            740                 745                 750

Leu Ile Pro Thr His Phe Phe Ile Val Leu Thr Ser Cys Lys Asp Thr
        755                 760                 765

Ser Gln Thr Pro Leu His Cys Glu Asn Leu Asp Thr Leu Ala Phe Ile
    770                 775                 780

Leu Pro His Arg Thr Asp Asn Ser Glu Ser Cys Val His Gly Lys His
785                 790                 795                 800

Asp Ser Ser Trp Val Glu Glu Leu Leu Met Leu His Arg Ala Arg Ile
                805                 810                 815

Thr Asp Val Glu His Ile Thr Gly Leu Ser Phe Tyr Gln Gln Arg Lys
            820                 825                 830

Glu Pro Val Ser Asp Ile Leu Lys Leu Lys Thr His Leu Pro Thr Phe
        835                 840                 845

Ser Gln Glu Asp Leu Ile Asn Asp Lys Thr His Thr Cys Pro Pro Cys
    850                 855                 860

Pro Ala Pro Glu Leu Leu Gly Gly Pro Ser Val Phe Leu Phe Pro Pro
865                 870                 875                 880

Lys Pro Lys Asp Thr Leu Met Ile Ser Arg Thr Pro Glu Val Thr Cys
                885                 890                 895

Val Val Val Asp Val Ser His Glu Asp Pro Glu Val Lys Phe Asn Trp
            900                 905                 910

Tyr Val Asp Gly Val Glu Val His Asn Ala Lys Thr Lys Pro Arg Glu
        915                 920                 925

Glu Gln Tyr Asn Ser Thr Tyr Arg Val Val Ser Val Leu Thr Val Leu
    930                 935                 940

His Gln Asp Trp Leu Asn Gly Lys Glu Tyr Lys Cys Lys Val Ser Asn
945                 950                 955                 960

Lys Ala Leu Pro Ala Pro Ile Glu Lys Thr Ile Ser Lys Ala Lys Gly
                965                 970                 975

Gln Pro Arg Glu Pro Gln Val Tyr Thr Leu Pro Pro Ser Arg Glu Glu
            980                 985                 990

Met Thr Lys Asn Gln Val Ser Leu  Thr Cys Leu Val Lys  Gly Phe Tyr
        995                 1000                1005

Pro Ser  Asp Ile Ala Val Glu  Trp Glu Ser Asn Gly  Gln Pro Glu
    1010                1015                1020

Asn Asn  Tyr Lys Thr Thr Pro  Pro Val Leu Asp Ser  Asp Gly Ser
    1025                1030                1035

Phe Phe  Leu Tyr Ser Lys Leu  Thr Val Asp Lys Ser  Arg Trp Gln
    1040                1045                1050

Gln Gly  Asn Val Phe Ser Cys  Ser Val Met His Glu  Ala Leu His
```

```
    1055                1060                1065

Asn His  Tyr Thr Gln Lys Ser  Leu Ser Leu Ser Pro  Gly Lys
    1070                1075                1080


<210> SEQ ID NO 19
<211> LENGTH: 849
<212> TYPE: PRT
<213> ORGANISM: Artificial Sequence
<220> FEATURE:
<223> OTHER INFORMATION: ENPP71 lacking ENPP1 N-Terminus GLK

<400> SEQUENCE: 19

Met Arg Gly Pro Ala Val Leu Leu Thr Val Ala Leu Ala Thr Leu Leu
1               5                   10                  15

Ala Pro Gly Ala Gly Ala Pro Ser Cys Ala Lys Glu Val Lys Ser Cys
            20                  25                  30

Lys Gly Arg Cys Phe Glu Arg Thr Phe Gly Asn Cys Arg Cys Asp Ala
        35                  40                  45

Ala Cys Val Glu Leu Gly Asn Cys Cys Leu Asp Tyr Gln Glu Thr Cys
    50                  55                  60

Ile Glu Pro Glu His Ile Trp Thr Cys Asn Lys Phe Arg Cys Gly Glu
65                  70                  75                  80

Lys Arg Leu Thr Arg Ser Leu Cys Ala Cys Ser Asp Asp Cys Lys Asp
                85                  90                  95

Lys Gly Asp Cys Cys Ile Asn Tyr Ser Ser Val Cys Gln Gly Glu Lys
            100                 105                 110

Ser Trp Val Glu Glu Pro Cys Glu Ser Ile Asn Glu Pro Gln Cys Pro
        115                 120                 125

Ala Gly Phe Glu Thr Pro Pro Thr Leu Leu Phe Ser Leu Asp Gly Phe
    130                 135                 140

Arg Ala Glu Tyr Leu His Thr Trp Gly Gly Leu Leu Pro Val Ile Ser
145                 150                 155                 160

Lys Leu Lys Lys Cys Gly Thr Tyr Thr Lys Asn Met Arg Pro Val Tyr
                165                 170                 175

Pro Thr Lys Thr Phe Pro Asn His Tyr Ser Ile Val Thr Gly Leu Tyr
            180                 185                 190

Pro Glu Ser His Gly Ile Ile Asp Asn Lys Met Tyr Asp Pro Lys Met
        195                 200                 205

Asn Ala Ser Phe Ser Leu Lys Ser Lys Glu Lys Phe Asn Pro Glu Trp
    210                 215                 220

Tyr Lys Gly Glu Pro Ile Trp Val Thr Ala Lys Tyr Gln Gly Leu Lys
225                 230                 235                 240

Ser Gly Thr Phe Phe Trp Pro Gly Ser Asp Val Glu Ile Asn Gly Ile
                245                 250                 255

Phe Pro Asp Ile Tyr Lys Met Tyr Asn Gly Ser Val Pro Phe Glu Glu
            260                 265                 270

Arg Ile Leu Ala Val Leu Gln Trp Leu Gln Leu Pro Lys Asp Glu Arg
        275                 280                 285

Pro His Phe Tyr Thr Leu Tyr Leu Glu Glu Pro Asp Ser Ser Gly His
    290                 295                 300

Ser Tyr Gly Pro Val Ser Ser Glu Val Ile Lys Ala Leu Gln Arg Val
305                 310                 315                 320

Asp Gly Met Val Gly Met Leu Met Asp Gly Leu Lys Glu Leu Asn Leu
                325                 330                 335

His Arg Cys Leu Asn Leu Ile Leu Ile Ser Asp His Gly Met Glu Gln
```

```
            340                 345                 350

Gly Ser Cys Lys Lys Tyr Ile Tyr Leu Asn Lys Tyr Leu Gly Asp Val
        355                 360                 365

Lys Asn Ile Lys Val Ile Tyr Gly Pro Ala Ala Arg Leu Arg Pro Ser
    370                 375                 380

Asp Val Pro Asp Lys Tyr Tyr Ser Phe Asn Tyr Glu Gly Ile Ala Arg
385                 390                 395                 400

Asn Leu Ser Cys Arg Glu Pro Asn Gln His Phe Lys Pro Tyr Leu Lys
                405                 410                 415

His Phe Leu Pro Lys Arg Leu His Phe Ala Lys Ser Asp Arg Ile Glu
            420                 425                 430

Pro Leu Thr Phe Tyr Leu Asp Pro Gln Trp Gln Leu Ala Leu Asn Pro
        435                 440                 445

Ser Glu Arg Lys Tyr Cys Gly Ser Gly Phe His Gly Ser Asp Asn Val
    450                 455                 460

Phe Ser Asn Met Gln Ala Leu Phe Val Gly Tyr Gly Pro Gly Phe Lys
465                 470                 475                 480

His Gly Ile Glu Ala Asp Thr Phe Glu Asn Ile Glu Val Tyr Asn Leu
                485                 490                 495

Met Cys Asp Leu Leu Asn Leu Thr Pro Ala Pro Asn Asn Gly Thr His
            500                 505                 510

Gly Ser Leu Asn His Leu Leu Lys Asn Pro Val Tyr Thr Pro Lys His
        515                 520                 525

Pro Lys Glu Val His Pro Leu Val Gln Cys Pro Phe Thr Arg Asn Pro
    530                 535                 540

Arg Asp Asn Leu Gly Cys Ser Cys Asn Pro Ser Ile Leu Pro Ile Glu
545                 550                 555                 560

Asp Phe Gln Thr Gln Phe Asn Leu Thr Val Ala Glu Glu Lys Ile Ile
                565                 570                 575

Lys His Glu Thr Leu Pro Tyr Gly Arg Pro Arg Val Leu Gln Lys Glu
            580                 585                 590

Asn Thr Ile Cys Leu Leu Ser Gln His Gln Phe Met Ser Gly Tyr Ser
        595                 600                 605

Gln Asp Ile Leu Met Pro Leu Trp Thr Ser Tyr Thr Val Asp Arg Asn
    610                 615                 620

Asp Ser Phe Ser Thr Glu Asp Phe Ser Asn Cys Leu Tyr Gln Asp Phe
625                 630                 635                 640

Arg Ile Pro Leu Ser Pro Val His Lys Cys Ser Phe Tyr Lys Asn Asn
                645                 650                 655

Thr Lys Val Ser Tyr Gly Phe Leu Ser Pro Pro Gln Leu Asn Lys Asn
            660                 665                 670

Ser Ser Gly Ile Tyr Ser Glu Ala Leu Leu Thr Thr Asn Ile Val Pro
        675                 680                 685

Met Tyr Gln Ser Phe Gln Val Ile Trp Arg Tyr Phe His Asp Thr Leu
    690                 695                 700

Leu Arg Lys Tyr Ala Glu Glu Arg Asn Gly Val Asn Val Val Ser Gly
705                 710                 715                 720

Pro Val Phe Asp Phe Asp Tyr Asp Gly Arg Cys Asp Ser Leu Glu Asn
                725                 730                 735

Leu Arg Gln Lys Arg Arg Val Ile Arg Asn Gln Glu Ile Leu Ile Pro
            740                 745                 750

Thr His Phe Phe Ile Val Leu Thr Ser Cys Lys Asp Thr Ser Gln Thr
        755                 760                 765
```

```
Pro Leu His Cys Glu Asn Leu Asp Thr Leu Ala Phe Ile Leu Pro His
    770                 775                 780

Arg Thr Asp Asn Ser Glu Ser Cys Val His Gly Lys His Asp Ser Ser
785                 790                 795                 800

Trp Val Glu Glu Leu Leu Met Leu His Arg Ala Arg Ile Thr Asp Val
                805                 810                 815

Glu His Ile Thr Gly Leu Ser Phe Tyr Gln Gln Arg Lys Glu Pro Val
            820                 825                 830

Ser Asp Ile Leu Lys Leu Lys Thr His Leu Pro Thr Phe Ser Gln Glu
        835                 840                 845

Asp


<210> SEQ ID NO 20
<211> LENGTH: 1079
<212> TYPE: PRT
<213> ORGANISM: Artificial Sequence
<220> FEATURE:
<223> OTHER INFORMATION: (ENPP71 lacking ENPP1 N-Terminus GLK)-Fc

<400> SEQUENCE: 20

Met Arg Gly Pro Ala Val Leu Leu Thr Val Ala Leu Ala Thr Leu Leu
1               5                   10                  15

Ala Pro Gly Ala Gly Ala Pro Ser Cys Ala Lys Glu Val Lys Ser Cys
            20                  25                  30

Lys Gly Arg Cys Phe Glu Arg Thr Phe Gly Asn Cys Arg Cys Asp Ala
        35                  40                  45

Ala Cys Val Glu Leu Gly Asn Cys Cys Leu Asp Tyr Gln Glu Thr Cys
    50                  55                  60

Ile Glu Pro Glu His Ile Trp Thr Cys Asn Lys Phe Arg Cys Gly Glu
65                  70                  75                  80

Lys Arg Leu Thr Arg Ser Leu Cys Ala Cys Ser Asp Asp Cys Lys Asp
                85                  90                  95

Lys Gly Asp Cys Cys Ile Asn Tyr Ser Ser Val Cys Gln Gly Glu Lys
            100                 105                 110

Ser Trp Val Glu Glu Pro Cys Glu Ser Ile Asn Glu Pro Gln Cys Pro
        115                 120                 125

Ala Gly Phe Glu Thr Pro Pro Thr Leu Leu Phe Ser Leu Asp Gly Phe
    130                 135                 140

Arg Ala Glu Tyr Leu His Thr Trp Gly Gly Leu Leu Pro Val Ile Ser
145                 150                 155                 160

Lys Leu Lys Lys Cys Gly Thr Tyr Thr Lys Asn Met Arg Pro Val Tyr
                165                 170                 175

Pro Thr Lys Thr Phe Pro Asn His Tyr Ser Ile Val Thr Gly Leu Tyr
            180                 185                 190

Pro Glu Ser His Gly Ile Ile Asp Asn Lys Met Tyr Asp Pro Lys Met
        195                 200                 205

Asn Ala Ser Phe Ser Leu Lys Ser Lys Glu Lys Phe Asn Pro Glu Trp
    210                 215                 220

Tyr Lys Gly Glu Pro Ile Trp Val Thr Ala Lys Tyr Gln Gly Leu Lys
225                 230                 235                 240

Ser Gly Thr Phe Phe Trp Pro Gly Ser Asp Val Glu Ile Asn Gly Ile
                245                 250                 255

Phe Pro Asp Ile Tyr Lys Met Tyr Asn Gly Ser Val Pro Phe Glu Glu
            260                 265                 270
```

-continued

```
Arg Ile Leu Ala Val Leu Gln Trp Leu Gln Leu Pro Lys Asp Glu Arg
        275                 280                 285

Pro His Phe Tyr Thr Leu Tyr Leu Glu Glu Pro Asp Ser Ser Gly His
    290                 295                 300

Ser Tyr Gly Pro Val Ser Ser Glu Val Ile Lys Ala Leu Gln Arg Val
305                 310                 315                 320

Asp Gly Met Val Gly Met Leu Met Asp Gly Leu Lys Glu Leu Asn Leu
                325                 330                 335

His Arg Cys Leu Asn Leu Ile Leu Ile Ser Asp His Gly Met Glu Gln
            340                 345                 350

Gly Ser Cys Lys Lys Tyr Ile Tyr Leu Asn Lys Tyr Leu Gly Asp Val
        355                 360                 365

Lys Asn Ile Lys Val Ile Tyr Gly Pro Ala Ala Arg Leu Arg Pro Ser
    370                 375                 380

Asp Val Pro Asp Lys Tyr Tyr Ser Phe Asn Tyr Glu Gly Ile Ala Arg
385                 390                 395                 400

Asn Leu Ser Cys Arg Glu Pro Asn Gln His Phe Lys Pro Tyr Leu Lys
                405                 410                 415

His Phe Leu Pro Lys Arg Leu His Phe Ala Lys Ser Asp Arg Ile Glu
            420                 425                 430

Pro Leu Thr Phe Tyr Leu Asp Pro Gln Trp Gln Leu Ala Leu Asn Pro
        435                 440                 445

Ser Glu Arg Lys Tyr Cys Gly Ser Gly Phe His Gly Ser Asp Asn Val
    450                 455                 460

Phe Ser Asn Met Gln Ala Leu Phe Val Gly Tyr Gly Pro Gly Phe Lys
465                 470                 475                 480

His Gly Ile Glu Ala Asp Thr Phe Glu Asn Ile Glu Val Tyr Asn Leu
                485                 490                 495

Met Cys Asp Leu Leu Asn Leu Thr Pro Ala Pro Asn Asn Gly Thr His
            500                 505                 510

Gly Ser Leu Asn His Leu Leu Lys Asn Pro Val Tyr Thr Pro Lys His
        515                 520                 525

Pro Lys Glu Val His Pro Leu Val Gln Cys Pro Phe Thr Arg Asn Pro
    530                 535                 540

Arg Asp Asn Leu Gly Cys Ser Cys Asn Pro Ser Ile Leu Pro Ile Glu
545                 550                 555                 560

Asp Phe Gln Thr Gln Phe Asn Leu Thr Val Ala Glu Glu Lys Ile Ile
                565                 570                 575

Lys His Glu Thr Leu Pro Tyr Gly Arg Pro Arg Val Leu Gln Lys Glu
            580                 585                 590

Asn Thr Ile Cys Leu Leu Ser Gln His Gln Phe Met Ser Gly Tyr Ser
        595                 600                 605

Gln Asp Ile Leu Met Pro Leu Trp Thr Ser Tyr Thr Val Asp Arg Asn
    610                 615                 620

Asp Ser Phe Ser Thr Glu Asp Phe Ser Asn Cys Leu Tyr Gln Asp Phe
625                 630                 635                 640

Arg Ile Pro Leu Ser Pro Val His Lys Cys Ser Phe Tyr Lys Asn Asn
                645                 650                 655

Thr Lys Val Ser Tyr Gly Phe Leu Ser Pro Pro Gln Leu Asn Lys Asn
            660                 665                 670

Ser Ser Gly Ile Tyr Ser Glu Ala Leu Leu Thr Thr Asn Ile Val Pro
        675                 680                 685

Met Tyr Gln Ser Phe Gln Val Ile Trp Arg Tyr Phe His Asp Thr Leu
```

```
    690                 695                 700

Leu Arg Lys Tyr Ala Glu Glu Arg Asn Gly Val Asn Val Val Ser Gly
705                 710                 715                 720

Pro Val Phe Asp Phe Asp Tyr Asp Gly Arg Cys Asp Ser Leu Glu Asn
                725                 730                 735

Leu Arg Gln Lys Arg Arg Val Ile Arg Asn Gln Glu Ile Leu Ile Pro
            740                 745                 750

Thr His Phe Phe Ile Val Leu Thr Ser Cys Lys Asp Thr Ser Gln Thr
        755                 760                 765

Pro Leu His Cys Glu Asn Leu Asp Thr Leu Ala Phe Ile Leu Pro His
    770                 775                 780

Arg Thr Asp Asn Ser Glu Ser Cys Val His Gly Lys His Asp Ser Ser
785                 790                 795                 800

Trp Val Glu Glu Leu Leu Met Leu His Arg Ala Arg Ile Thr Asp Val
                805                 810                 815

Glu His Ile Thr Gly Leu Ser Phe Tyr Gln Gln Arg Lys Glu Pro Val
            820                 825                 830

Ser Asp Ile Leu Lys Leu Lys Thr His Leu Pro Thr Phe Ser Gln Glu
        835                 840                 845

Asp Leu Ile Asn Asp Lys Thr His Thr Cys Pro Pro Cys Pro Ala Pro
    850                 855                 860

Glu Leu Leu Gly Gly Pro Ser Val Phe Leu Phe Pro Pro Lys Pro Lys
865                 870                 875                 880

Asp Thr Leu Met Ile Ser Arg Thr Pro Glu Val Thr Cys Val Val Val
                885                 890                 895

Asp Val Ser His Glu Asp Pro Glu Val Lys Phe Asn Trp Tyr Val Asp
            900                 905                 910

Gly Val Glu Val His Asn Ala Lys Thr Lys Pro Arg Glu Glu Gln Tyr
        915                 920                 925

Asn Ser Thr Tyr Arg Val Val Ser Val Leu Thr Val Leu His Gln Asp
    930                 935                 940

Trp Leu Asn Gly Lys Glu Tyr Lys Cys Lys Val Ser Asn Lys Ala Leu
945                 950                 955                 960

Pro Ala Pro Ile Glu Lys Thr Ile Ser Lys Ala Lys Gly Gln Pro Arg
                965                 970                 975

Glu Pro Gln Val Tyr Thr Leu Pro Pro Ser Arg Glu Glu Met Thr Lys
            980                 985                 990

Asn Gln Val Ser Leu Thr Cys Leu  Val Lys Gly Phe Tyr  Pro Ser Asp
        995                 1000                1005

Ile Ala  Val Glu Trp Glu Ser  Asn Gly Gln Pro Glu  Asn Asn Tyr
    1010                1015                1020

Lys Thr  Thr Pro Pro Val Leu  Asp Ser Asp Gly Ser  Phe Phe Leu
    1025                1030                1035

Tyr Ser  Lys Leu Thr Val Asp  Lys Ser Arg Trp Gln  Gln Gly Asn
    1040                1045                1050

Val Phe  Ser Cys Ser Val Met  His Glu Ala Leu His  Asn His Tyr
    1055                1060                1065

Thr Gln  Lys Ser Leu Ser Leu  Ser Pro Gly Lys
    1070                1075
```

<210> SEQ ID NO 21
<211> LENGTH: 1550
<212> TYPE: PRT
<213> ORGANISM: Artificial Sequence

<220> FEATURE:
<223> OTHER INFORMATION: ENPP121-ALB

<400> SEQUENCE: 21

Met Glu Arg Asp Gly Cys Ala Gly Gly Gly Ser Arg Gly Gly Glu Gly
1 5 10 15

Gly Arg Ala Pro Arg Glu Gly Pro Ala Gly Asn Gly Arg Asp Arg Gly
20 25 30

Arg Ser His Ala Ala Glu Ala Pro Gly Asp Pro Gln Ala Ala Ala Ser
35 40 45

Leu Leu Ala Pro Met Asp Val Gly Glu Glu Pro Leu Glu Lys Ala Ala
50 55 60

Arg Ala Arg Thr Ala Lys Asp Pro Asn Thr Tyr Lys Ile Ile Ser Leu
65 70 75 80

Phe Thr Phe Ala Val Gly Val Asn Ile Cys Leu Gly Phe Thr Ala Gly
85 90 95

Leu Lys Pro Ser Cys Ala Lys Glu Val Lys Ser Cys Lys Gly Arg Cys
100 105 110

Phe Glu Arg Thr Phe Gly Asn Cys Arg Cys Asp Ala Ala Cys Val Glu
115 120 125

Leu Gly Asn Cys Cys Leu Asp Tyr Gln Glu Thr Cys Ile Glu Pro Glu
130 135 140

His Ile Trp Thr Cys Asn Lys Phe Arg Cys Gly Glu Lys Arg Leu Thr
145 150 155 160

Arg Ser Leu Cys Ala Cys Ser Asp Asp Cys Lys Asp Lys Gly Asp Cys
165 170 175

Cys Ile Asn Tyr Ser Ser Val Cys Gln Gly Glu Lys Ser Trp Val Glu
180 185 190

Glu Pro Cys Glu Ser Ile Asn Glu Pro Gln Cys Pro Ala Gly Phe Glu
195 200 205

Thr Pro Pro Thr Leu Leu Phe Ser Leu Asp Gly Phe Arg Ala Glu Tyr
210 215 220

Leu His Thr Trp Gly Gly Leu Leu Pro Val Ile Ser Lys Leu Lys Lys
225 230 235 240

Cys Gly Thr Tyr Thr Lys Asn Met Arg Pro Val Tyr Pro Thr Lys Thr
245 250 255

Phe Pro Asn His Tyr Ser Ile Val Thr Gly Leu Tyr Pro Glu Ser His
260 265 270

Gly Ile Ile Asp Asn Lys Met Tyr Asp Pro Lys Met Asn Ala Ser Phe
275 280 285

Ser Leu Lys Ser Lys Glu Lys Phe Asn Pro Glu Trp Tyr Lys Gly Glu
290 295 300

Pro Ile Trp Val Thr Ala Lys Tyr Gln Gly Leu Lys Ser Gly Thr Phe
305 310 315 320

Phe Trp Pro Gly Ser Asp Val Glu Ile Asn Gly Ile Phe Pro Asp Ile
325 330 335

Tyr Lys Met Tyr Asn Gly Ser Val Pro Phe Glu Glu Arg Ile Leu Ala
340 345 350

Val Leu Gln Trp Leu Gln Leu Pro Lys Asp Glu Arg Pro His Phe Tyr
355 360 365

Thr Leu Tyr Leu Glu Glu Pro Asp Ser Ser Gly His Ser Tyr Gly Pro
370 375 380

Val Ser Ser Glu Val Ile Lys Ala Leu Gln Arg Val Asp Gly Met Val
385 390 395 400

```
Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815
```

```
Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
        835                 840                 845

Glu Asn Leu Asp Thr Leu Ala Phe Ile Leu Pro His Arg Thr Asp Asn
    850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp Arg Ser Gly
        915                 920                 925

Ser Gly Gly Ser Met Lys Trp Val Thr Phe Leu Leu Leu Leu Phe Val
    930                 935                 940

Ser Gly Ser Ala Phe Ser Arg Gly Val Phe Arg Arg Glu Ala His Lys
945                 950                 955                 960

Ser Glu Ile Ala His Arg Tyr Asn Asp Leu Gly Glu Gln His Phe Lys
                965                 970                 975

Gly Leu Val Leu Ile Ala Phe Ser Gln Tyr Leu Gln Lys Cys Ser Tyr
            980                 985                 990

Asp Glu His Ala Lys Leu Val Gln  Glu Val Thr Asp Phe  Ala Lys Thr
        995                 1000                1005

Cys Val  Ala Asp Glu Ser Ala  Ala Asn Cys Asp Lys  Ser Leu His
    1010                1015                1020

Thr Leu  Phe Gly Asp Lys Leu  Cys Ala Ile Pro Asn  Leu Arg Glu
    1025                1030                1035

Asn Tyr  Gly Glu Leu Ala Asp  Cys Cys Thr Lys Gln  Glu Pro Glu
    1040                1045                1050

Arg Asn  Glu Cys Phe Leu Gln  His Lys Asp Asp Asn  Pro Ser Leu
    1055                1060                1065

Pro Pro  Phe Glu Arg Pro Glu  Ala Glu Ala Met Cys  Thr Ser Phe
    1070                1075                1080

Lys Glu  Asn Pro Thr Thr Phe  Met Gly His Tyr Leu  His Glu Val
    1085                1090                1095

Ala Arg  Arg His Pro Tyr Phe  Tyr Ala Pro Glu Leu  Leu Tyr Tyr
    1100                1105                1110

Ala Glu  Gln Tyr Asn Glu Ile  Leu Thr Gln Cys Cys  Ala Glu Ala
    1115                1120                1125

Asp Lys  Glu Ser Cys Leu Thr  Pro Lys Leu Asp Gly  Val Lys Glu
    1130                1135                1140

Lys Ala  Leu Val Ser Ser Val  Arg Gln Arg Met Lys  Cys Ser Ser
    1145                1150                1155

Met Gln  Lys Phe Gly Glu Arg  Ala Phe Lys Ala Trp  Ala Val Ala
    1160                1165                1170

Arg Leu  Ser Gln Thr Phe Pro  Asn Ala Asp Phe Ala  Glu Ile Thr
    1175                1180                1185

Lys Leu  Ala Thr Asp Leu Thr  Lys Val Asn Lys Glu  Cys Cys His
    1190                1195                1200

Gly Asp  Leu Leu Glu Cys Ala  Asp Asp Arg Ala Glu  Leu Ala Lys
    1205                1210                1215

Tyr Met  Cys Glu Asn Gln Ala  Thr Ile Ser Ser Lys  Leu Gln Thr
```

```
    1220                1225                1230

Cys Cys  Asp Lys Pro Leu Leu  Lys Lys Ala His Cys  Leu Ser Glu
    1235                1240                1245

Val Glu  His Asp Thr Met Pro  Ala Asp Leu Pro Ala  Ile Ala Ala
    1250                1255                1260

Asp Phe  Val Glu Asp Gln Glu  Val Cys Lys Asn Tyr  Ala Glu Ala
    1265                1270                1275

Lys Asp  Val Phe Leu Gly Thr  Phe Leu Tyr Glu Tyr  Ser Arg Arg
    1280                1285                1290

His Pro  Asp Tyr Ser Val Ser  Leu Leu Leu Arg Leu  Ala Lys Lys
    1295                1300                1305

Tyr Glu  Ala Thr Leu Glu Lys  Cys Cys Ala Glu Ala  Asn Pro Pro
    1310                1315                1320

Ala Cys  Tyr Gly Thr Val Leu  Ala Glu Phe Gln Pro  Leu Val Glu
    1325                1330                1335

Glu Pro  Lys Asn Leu Val Lys  Thr Asn Cys Asp Leu  Tyr Glu Lys
    1340                1345                1350

Leu Gly  Glu Tyr Gly Phe Gln  Asn Ala Ile Leu Val  Arg Tyr Thr
    1355                1360                1365

Gln Lys  Ala Pro Gln Val Ser  Thr Pro Thr Leu Val  Glu Ala Ala
    1370                1375                1380

Arg Asn  Leu Gly Arg Val Gly  Thr Lys Cys Cys Thr  Leu Pro Glu
    1385                1390                1395

Asp Gln  Arg Leu Pro Cys Val  Glu Asp Tyr Leu Ser  Ala Ile Leu
    1400                1405                1410

Asn Arg  Val Cys Leu Leu His  Glu Lys Thr Pro Val  Ser Glu His
    1415                1420                1425

Val Thr  Lys Cys Cys Ser Gly  Ser Leu Val Glu Arg  Arg Pro Cys
    1430                1435                1440

Phe Ser  Ala Leu Thr Val Asp  Glu Thr Tyr Val Pro  Lys Glu Phe
    1445                1450                1455

Lys Ala  Glu Thr Phe Thr Phe  His Ser Asp Ile Cys  Thr Leu Pro
    1460                1465                1470

Glu Lys  Glu Lys Gln Ile Lys  Lys Gln Thr Ala Leu  Ala Glu Leu
    1475                1480                1485

Val Lys  His Lys Pro Lys Ala  Thr Ala Glu Gln Leu  Lys Thr Val
    1490                1495                1500

Met Asp  Asp Phe Ala Gln Phe  Leu Asp Thr Cys Cys  Lys Ala Ala
    1505                1510                1515

Asp Lys  Asp Thr Cys Phe Ser  Thr Glu Gly Pro Asn  Leu Val Thr
    1520                1525                1530

Arg Cys  Lys Asp Ala Leu Ala  Arg Ser Trp Ser His  Pro Gln Phe
    1535                1540                1545

Glu Lys
    1550
```

<210> SEQ ID NO 22
<211> LENGTH: 1474
<212> TYPE: PRT
<213> ORGANISM: Artificial Sequence
<220> FEATURE:
<223> OTHER INFORMATION: (ENPP71 lacking ENPP1 N-Terminus GLK)-ALB

<400> SEQUENCE: 22

Met Arg Gly Pro Ala Val Leu Leu Thr Val Ala Leu Ala Thr Leu Leu

```
1               5                   10                  15

Ala Pro Gly Ala Gly Ala Pro Ser Cys Ala Lys Glu Val Lys Ser Cys
            20                  25                  30

Lys Gly Arg Cys Phe Glu Arg Thr Phe Gly Asn Cys Arg Cys Asp Ala
        35                  40                  45

Ala Cys Val Glu Leu Gly Asn Cys Cys Leu Asp Tyr Gln Glu Thr Cys
    50                  55                  60

Ile Glu Pro Glu His Ile Trp Thr Cys Asn Lys Phe Arg Cys Gly Glu
65                  70                  75                  80

Lys Arg Leu Thr Arg Ser Leu Cys Ala Cys Ser Asp Asp Cys Lys Asp
                85                  90                  95

Lys Gly Asp Cys Cys Ile Asn Tyr Ser Ser Val Cys Gln Gly Glu Lys
            100                 105                 110

Ser Trp Val Glu Glu Pro Cys Glu Ser Ile Asn Glu Pro Gln Cys Pro
        115                 120                 125

Ala Gly Phe Glu Thr Pro Pro Thr Leu Leu Phe Ser Leu Asp Gly Phe
    130                 135                 140

Arg Ala Glu Tyr Leu His Thr Trp Gly Gly Leu Leu Pro Val Ile Ser
145                 150                 155                 160

Lys Leu Lys Lys Cys Gly Thr Tyr Thr Lys Asn Met Arg Pro Val Tyr
                165                 170                 175

Pro Thr Lys Thr Phe Pro Asn His Tyr Ser Ile Val Thr Gly Leu Tyr
            180                 185                 190

Pro Glu Ser His Gly Ile Ile Asp Asn Lys Met Tyr Asp Pro Lys Met
        195                 200                 205

Asn Ala Ser Phe Ser Leu Lys Ser Lys Glu Lys Phe Asn Pro Glu Trp
    210                 215                 220

Tyr Lys Gly Glu Pro Ile Trp Val Thr Ala Lys Tyr Gln Gly Leu Lys
225                 230                 235                 240

Ser Gly Thr Phe Phe Trp Pro Gly Ser Asp Val Glu Ile Asn Gly Ile
                245                 250                 255

Phe Pro Asp Ile Tyr Lys Met Tyr Asn Gly Ser Val Pro Phe Glu Glu
            260                 265                 270

Arg Ile Leu Ala Val Leu Gln Trp Leu Gln Leu Pro Lys Asp Glu Arg
        275                 280                 285

Pro His Phe Tyr Thr Leu Tyr Leu Glu Glu Pro Asp Ser Ser Gly His
    290                 295                 300

Ser Tyr Gly Pro Val Ser Ser Glu Val Ile Lys Ala Leu Gln Arg Val
305                 310                 315                 320

Asp Gly Met Val Gly Met Leu Met Asp Gly Leu Lys Glu Leu Asn Leu
                325                 330                 335

His Arg Cys Leu Asn Leu Ile Leu Ile Ser Asp His Gly Met Glu Gln
            340                 345                 350

Gly Ser Cys Lys Lys Tyr Ile Tyr Leu Asn Lys Tyr Leu Gly Asp Val
        355                 360                 365

Lys Asn Ile Lys Val Ile Tyr Gly Pro Ala Ala Arg Leu Arg Pro Ser
    370                 375                 380

Asp Val Pro Asp Lys Tyr Tyr Ser Phe Asn Tyr Glu Gly Ile Ala Arg
385                 390                 395                 400

Asn Leu Ser Cys Arg Glu Pro Asn Gln His Phe Lys Pro Tyr Leu Lys
                405                 410                 415

His Phe Leu Pro Lys Arg Leu His Phe Ala Lys Ser Asp Arg Ile Glu
            420                 425                 430
```

```
Pro Leu Thr Phe Tyr Leu Asp Pro Gln Trp Gln Leu Ala Leu Asn Pro
        435                 440                 445

Ser Glu Arg Lys Tyr Cys Gly Ser Gly Phe His Gly Ser Asp Asn Val
    450                 455                 460

Phe Ser Asn Met Gln Ala Leu Phe Val Gly Tyr Gly Pro Gly Phe Lys
465                 470                 475                 480

His Gly Ile Glu Ala Asp Thr Phe Glu Asn Ile Glu Val Tyr Asn Leu
                485                 490                 495

Met Cys Asp Leu Leu Asn Leu Thr Pro Ala Pro Asn Asn Gly Thr His
            500                 505                 510

Gly Ser Leu Asn His Leu Leu Lys Asn Pro Val Tyr Thr Pro Lys His
        515                 520                 525

Pro Lys Glu Val His Pro Leu Val Gln Cys Pro Phe Thr Arg Asn Pro
    530                 535                 540

Arg Asp Asn Leu Gly Cys Ser Cys Asn Pro Ser Ile Leu Pro Ile Glu
545                 550                 555                 560

Asp Phe Gln Thr Gln Phe Asn Leu Thr Val Ala Glu Glu Lys Ile Ile
                565                 570                 575

Lys His Glu Thr Leu Pro Tyr Gly Arg Pro Arg Val Leu Gln Lys Glu
            580                 585                 590

Asn Thr Ile Cys Leu Leu Ser Gln His Gln Phe Met Ser Gly Tyr Ser
        595                 600                 605

Gln Asp Ile Leu Met Pro Leu Trp Thr Ser Tyr Thr Val Asp Arg Asn
    610                 615                 620

Asp Ser Phe Ser Thr Glu Asp Phe Ser Asn Cys Leu Tyr Gln Asp Phe
625                 630                 635                 640

Arg Ile Pro Leu Ser Pro Val His Lys Cys Ser Phe Tyr Lys Asn Asn
                645                 650                 655

Thr Lys Val Ser Tyr Gly Phe Leu Ser Pro Pro Gln Leu Asn Lys Asn
            660                 665                 670

Ser Ser Gly Ile Tyr Ser Glu Ala Leu Leu Thr Thr Asn Ile Val Pro
        675                 680                 685

Met Tyr Gln Ser Phe Gln Val Ile Trp Arg Tyr Phe His Asp Thr Leu
    690                 695                 700

Leu Arg Lys Tyr Ala Glu Glu Arg Asn Gly Val Asn Val Val Ser Gly
705                 710                 715                 720

Pro Val Phe Asp Phe Asp Tyr Asp Gly Arg Cys Asp Ser Leu Glu Asn
                725                 730                 735

Leu Arg Gln Lys Arg Arg Val Ile Arg Asn Gln Glu Ile Leu Ile Pro
            740                 745                 750

Thr His Phe Phe Ile Val Leu Thr Ser Cys Lys Asp Thr Ser Gln Thr
        755                 760                 765

Pro Leu His Cys Glu Asn Leu Asp Thr Leu Ala Phe Ile Leu Pro His
    770                 775                 780

Arg Thr Asp Asn Ser Glu Ser Cys Val His Gly Lys His Asp Ser Ser
785                 790                 795                 800

Trp Val Glu Glu Leu Leu Met Leu His Arg Ala Arg Ile Thr Asp Val
                805                 810                 815

Glu His Ile Thr Gly Leu Ser Phe Tyr Gln Gln Arg Lys Glu Pro Val
            820                 825                 830

Ser Asp Ile Leu Lys Leu Lys Thr His Leu Pro Thr Phe Ser Gln Glu
        835                 840                 845
```

```
Asp Arg Ser Gly Ser Gly Gly Ser Met Lys Trp Val Thr Phe Leu Leu
    850                 855                 860

Leu Leu Phe Val Ser Gly Ser Ala Phe Ser Arg Gly Val Phe Arg Arg
865                 870                 875                 880

Glu Ala His Lys Ser Glu Ile Ala His Arg Tyr Asn Asp Leu Gly Glu
                885                 890                 895

Gln His Phe Lys Gly Leu Val Leu Ile Ala Phe Ser Gln Tyr Leu Gln
            900                 905                 910

Lys Cys Ser Tyr Asp Glu His Ala Lys Leu Val Gln Glu Val Thr Asp
        915                 920                 925

Phe Ala Lys Thr Cys Val Ala Asp Glu Ser Ala Ala Asn Cys Asp Lys
    930                 935                 940

Ser Leu His Thr Leu Phe Gly Asp Lys Leu Cys Ala Ile Pro Asn Leu
945                 950                 955                 960

Arg Glu Asn Tyr Gly Glu Leu Ala Asp Cys Cys Thr Lys Gln Glu Pro
                965                 970                 975

Glu Arg Asn Glu Cys Phe Leu Gln His Lys Asp Asp Asn Pro Ser Leu
            980                 985                 990

Pro Pro Phe Glu Arg Pro Glu Ala  Glu Ala Met Cys Thr  Ser Phe Lys
        995                 1000                1005

Glu Asn  Pro Thr Thr Phe Met  Gly His Tyr Leu His  Glu Val Ala
    1010                1015                1020

Arg Arg  His Pro Tyr Phe Tyr  Ala Pro Glu Leu Leu  Tyr Tyr Ala
    1025                1030                1035

Glu Gln  Tyr Asn Glu Ile Leu  Thr Gln Cys Cys Ala  Glu Ala Asp
    1040                1045                1050

Lys Glu  Ser Cys Leu Thr Pro  Lys Leu Asp Gly Val  Lys Glu Lys
    1055                1060                1065

Ala Leu  Val Ser Ser Val Arg  Gln Arg Met Lys Cys  Ser Ser Met
    1070                1075                1080

Gln Lys  Phe Gly Glu Arg Ala  Phe Lys Ala Trp Ala  Val Ala Arg
    1085                1090                1095

Leu Ser  Gln Thr Phe Pro Asn  Ala Asp Phe Ala Glu  Ile Thr Lys
    1100                1105                1110

Leu Ala  Thr Asp Leu Thr Lys  Val Asn Lys Glu Cys  Cys His Gly
    1115                1120                1125

Asp Leu  Leu Glu Cys Ala Asp  Asp Arg Ala Glu Leu  Ala Lys Tyr
    1130                1135                1140

Met Cys  Glu Asn Gln Ala Thr  Ile Ser Ser Lys Leu  Gln Thr Cys
    1145                1150                1155

Cys Asp  Lys Pro Leu Leu Lys  Lys Ala His Cys Leu  Ser Glu Val
    1160                1165                1170

Glu His  Asp Thr Met Pro Ala  Asp Leu Pro Ala Ile  Ala Ala Asp
    1175                1180                1185

Phe Val  Glu Asp Gln Glu Val  Cys Lys Asn Tyr Ala  Glu Ala Lys
    1190                1195                1200

Asp Val  Phe Leu Gly Thr Phe  Leu Tyr Glu Tyr Ser  Arg Arg His
    1205                1210                1215

Pro Asp  Tyr Ser Val Ser Leu  Leu Leu Arg Leu Ala  Lys Lys Tyr
    1220                1225                1230

Glu Ala  Thr Leu Glu Lys Cys  Cys Ala Glu Ala Asn  Pro Pro Ala
    1235                1240                1245

Cys Tyr  Gly Thr Val Leu Ala  Glu Phe Gln Pro Leu  Val Glu Glu
```

```
    1250                1255                1260

Pro Lys  Asn Leu Val Lys Thr  Asn Cys Asp Leu Tyr  Glu Lys Leu
    1265                1270                1275

Gly Glu  Tyr Gly Phe Gln Asn  Ala Ile Leu Val Arg  Tyr Thr Gln
    1280                1285                1290

Lys Ala  Pro Gln Val Ser Thr  Pro Thr Leu Val Glu  Ala Ala Arg
    1295                1300                1305

Asn Leu  Gly Arg Val Gly Thr  Lys Cys Cys Thr Leu  Pro Glu Asp
    1310                1315                1320

Gln Arg  Leu Pro Cys Val Glu  Asp Tyr Leu Ser Ala  Ile Leu Asn
    1325                1330                1335

Arg Val  Cys Leu Leu His Glu  Lys Thr Pro Val Ser  Glu His Val
    1340                1345                1350

Thr Lys  Cys Cys Ser Gly Ser  Leu Val Glu Arg Arg  Pro Cys Phe
    1355                1360                1365

Ser Ala  Leu Thr Val Asp Glu  Thr Tyr Val Pro Lys  Glu Phe Lys
    1370                1375                1380

Ala Glu  Thr Phe Thr Phe His  Ser Asp Ile Cys Thr  Leu Pro Glu
    1385                1390                1395

Lys Glu  Lys Gln Ile Lys Lys  Gln Thr Ala Leu Ala  Glu Leu Val
    1400                1405                1410

Lys His  Lys Pro Lys Ala Thr  Ala Glu Gln Leu Lys  Thr Val Met
    1415                1420                1425

Asp Asp  Phe Ala Gln Phe Leu  Asp Thr Cys Cys Lys  Ala Ala Asp
    1430                1435                1440

Lys Asp  Thr Cys Phe Ser Thr  Glu Gly Pro Asn Leu  Val Thr Arg
    1445                1450                1455

Cys Lys  Asp Ala Leu Ala Arg  Ser Trp Ser His Pro  Gln Phe Glu
    1460                1465                1470

Lys


<210> SEQ ID NO 23
<211> LENGTH: 19
<212> TYPE: PRT
<213> ORGANISM: Artificial Sequence
<220> FEATURE:
<223> OTHER INFORMATION: chemically synthesized

<400> SEQUENCE: 23

Ile Ile Ser Leu Phe Thr Phe Ala Val Gly Val Asn Ile Cys Leu Gly
1               5                   10                  15

Phe Thr Ala


<210> SEQ ID NO 24
<211> LENGTH: 850
<212> TYPE: PRT
<213> ORGANISM: Artificial Sequence
<220> FEATURE:
<223> OTHER INFORMATION: ENPP51

<400> SEQUENCE: 24

Met Thr Ser Lys Phe Leu Leu Val Ser Phe Ile Leu Ala Ala Leu Ser
1               5                   10                  15

Leu Ser Thr Thr Phe Ser Leu Gln Pro Ser Cys Ala Lys Glu Val Lys
            20                  25                  30

Ser Cys Lys Gly Arg Cys Phe Glu Arg Thr Phe Ser Asn Cys Arg Cys
        35                  40                  45
```

```
Asp Ala Ala Cys Val Ser Leu Gly Asn Cys Cys Leu Asp Phe Gln Glu
    50                  55                  60

Thr Cys Val Glu Pro Thr His Ile Trp Thr Cys Asn Lys Phe Arg Cys
65                  70                  75                  80

Gly Glu Lys Arg Leu Ser Arg Phe Val Cys Ser Cys Ala Asp Asp Cys
                85                  90                  95

Lys Thr His Asn Asp Cys Cys Ile Asn Tyr Ser Ser Val Cys Gln Asp
            100                 105                 110

Lys Lys Ser Trp Val Glu Glu Thr Cys Glu Ser Ile Asp Thr Pro Glu
        115                 120                 125

Cys Pro Ala Glu Phe Glu Ser Pro Pro Thr Leu Leu Phe Ser Leu Asp
    130                 135                 140

Gly Phe Arg Ala Glu Tyr Leu His Thr Trp Gly Gly Leu Leu Pro Val
145                 150                 155                 160

Ile Ser Lys Leu Lys Asn Cys Gly Thr Tyr Thr Lys Asn Met Arg Pro
                165                 170                 175

Met Tyr Pro Thr Lys Thr Phe Pro Asn His Tyr Ser Ile Val Thr Gly
            180                 185                 190

Leu Tyr Pro Glu Ser His Gly Ile Ile Asp Asn Lys Met Tyr Asp Pro
        195                 200                 205

Lys Met Asn Ala Ser Phe Ser Leu Lys Ser Lys Glu Lys Phe Asn Pro
    210                 215                 220

Leu Trp Tyr Lys Gly Gln Pro Ile Trp Val Thr Ala Asn His Gln Glu
225                 230                 235                 240

Val Lys Ser Gly Thr Tyr Phe Trp Pro Gly Ser Asp Val Glu Ile Asp
                245                 250                 255

Gly Ile Leu Pro Asp Ile Tyr Lys Val Tyr Asn Gly Ser Val Pro Phe
            260                 265                 270

Glu Glu Arg Ile Leu Ala Val Leu Glu Trp Leu Gln Leu Pro Ser His
        275                 280                 285

Glu Arg Pro His Phe Tyr Thr Leu Tyr Leu Glu Glu Pro Asp Ser Ser
    290                 295                 300

Gly His Ser His Gly Pro Val Ser Ser Glu Val Ile Lys Ala Leu Gln
305                 310                 315                 320

Lys Val Asp Arg Leu Val Gly Met Leu Met Asp Gly Leu Lys Asp Leu
                325                 330                 335

Gly Leu Asp Lys Cys Leu Asn Leu Ile Leu Ile Ser Asp His Gly Met
            340                 345                 350

Glu Gln Gly Ser Cys Lys Lys Tyr Val Tyr Leu Asn Lys Tyr Leu Gly
        355                 360                 365

Asp Val Asn Asn Val Lys Val Val Tyr Gly Pro Ala Ala Arg Leu Arg
    370                 375                 380

Pro Thr Asp Val Pro Glu Thr Tyr Tyr Ser Phe Asn Tyr Glu Ala Leu
385                 390                 395                 400

Ala Lys Asn Leu Ser Cys Arg Glu Pro Asn Gln His Phe Arg Pro Tyr
                405                 410                 415

Leu Lys Pro Phe Leu Pro Lys Arg Leu His Phe Ala Lys Ser Asp Arg
            420                 425                 430

Ile Glu Pro Leu Thr Phe Tyr Leu Asp Pro Gln Trp Gln Leu Ala Leu
        435                 440                 445

Asn Pro Ser Glu Arg Lys Tyr Cys Gly Ser Gly Phe His Gly Ser Asp
    450                 455                 460
```

```
Asn Leu Phe Ser Asn Met Gln Ala Leu Phe Ile Gly Tyr Gly Pro Ala
465                 470                 475                 480

Phe Lys His Gly Ala Glu Val Asp Ser Phe Glu Asn Ile Glu Val Tyr
                485                 490                 495

Asn Leu Met Cys Asp Leu Leu Gly Leu Ile Pro Ala Pro Asn Asn Gly
            500                 505                 510

Ser His Gly Ser Leu Asn His Leu Leu Lys Lys Pro Ile Tyr Asn Pro
        515                 520                 525

Ser His Pro Lys Glu Glu Gly Phe Leu Ser Gln Cys Pro Ile Lys Ser
    530                 535                 540

Thr Ser Asn Asp Leu Gly Cys Thr Cys Asp Pro Trp Ile Val Pro Ile
545                 550                 555                 560

Lys Asp Phe Glu Lys Gln Leu Asn Leu Thr Thr Glu Asp Val Asp Asp
                565                 570                 575

Ile Tyr His Met Thr Val Pro Tyr Gly Arg Pro Arg Ile Leu Leu Lys
            580                 585                 590

Gln His Arg Val Cys Leu Leu Gln Gln Gln Gln Phe Leu Thr Gly Tyr
        595                 600                 605

Ser Leu Asp Leu Leu Met Pro Leu Trp Ala Ser Tyr Thr Phe Leu Ser
    610                 615                 620

Asn Asp Gln Phe Ser Arg Asp Asp Phe Ser Asn Cys Leu Tyr Gln Asp
625                 630                 635                 640

Leu Arg Ile Pro Leu Ser Pro Val His Lys Cys Ser Tyr Tyr Lys Ser
                645                 650                 655

Asn Ser Lys Leu Ser Tyr Gly Phe Leu Thr Pro Pro Arg Leu Asn Arg
            660                 665                 670

Val Ser Asn His Ile Tyr Ser Glu Ala Leu Leu Thr Ser Asn Ile Val
        675                 680                 685

Pro Met Tyr Gln Ser Phe Gln Val Ile Trp His Tyr Leu His Asp Thr
    690                 695                 700

Leu Leu Gln Arg Tyr Ala His Glu Arg Asn Gly Ile Asn Val Val Ser
705                 710                 715                 720

Gly Pro Val Phe Asp Phe Asp Tyr Asp Gly Arg Tyr Asp Ser Leu Glu
                725                 730                 735

Ile Leu Lys Gln Asn Ser Arg Val Ile Arg Ser Gln Glu Ile Leu Ile
            740                 745                 750

Pro Thr His Phe Phe Ile Val Leu Thr Ser Cys Lys Gln Leu Ser Glu
        755                 760                 765

Thr Pro Leu Glu Cys Ser Ala Leu Glu Ser Ser Ala Tyr Ile Leu Pro
    770                 775                 780

His Arg Pro Asp Asn Ile Glu Ser Cys Thr His Gly Lys Arg Glu Ser
785                 790                 795                 800

Ser Trp Val Glu Glu Leu Leu Thr Leu His Arg Ala Arg Val Thr Asp
                805                 810                 815

Val Glu Leu Ile Thr Gly Leu Ser Phe Tyr Gln Asp Arg Gln Glu Ser
            820                 825                 830

Val Ser Glu Leu Leu Arg Leu Lys Thr His Leu Pro Ile Phe Ser Gln
        835                 840                 845

Glu Asp
    850
```

<210> SEQ ID NO 25
<211> LENGTH: 1474
<212> TYPE: PRT

```
<213> ORGANISM: Artificial Sequence
<220> FEATURE:
<223> OTHER INFORMATION: ENPP51-ALB

<400> SEQUENCE: 25

Met Thr Ser Lys Phe Leu Leu Val Ser Phe Ile Leu Ala Ala Leu Ser
1               5                   10                  15

Leu Ser Thr Thr Phe Ser Leu Gln Pro Ser Cys Ala Lys Glu Val Lys
            20                  25                  30

Ser Cys Lys Gly Arg Cys Phe Glu Arg Thr Phe Ser Asn Cys Arg Cys
        35                  40                  45

Asp Ala Ala Cys Val Ser Leu Gly Asn Cys Cys Leu Asp Phe Gln Glu
    50                  55                  60

Thr Cys Val Glu Pro Thr His Ile Trp Thr Cys Asn Lys Phe Arg Cys
65                  70                  75                  80

Gly Glu Lys Arg Leu Ser Arg Phe Val Cys Ser Cys Ala Asp Asp Cys
                85                  90                  95

Lys Thr His Asn Asp Cys Cys Ile Asn Tyr Ser Ser Val Cys Gln Asp
            100                 105                 110

Lys Lys Ser Trp Val Glu Glu Thr Cys Glu Ser Ile Asp Thr Pro Glu
        115                 120                 125

Cys Pro Ala Glu Phe Glu Ser Pro Pro Thr Leu Leu Phe Ser Leu Asp
    130                 135                 140

Gly Phe Arg Ala Glu Tyr Leu His Thr Trp Gly Gly Leu Leu Pro Val
145                 150                 155                 160

Ile Ser Lys Leu Lys Asn Cys Gly Thr Tyr Thr Lys Asn Met Arg Pro
                165                 170                 175

Met Tyr Pro Thr Lys Thr Phe Pro Asn His Tyr Ser Ile Val Thr Gly
            180                 185                 190

Leu Tyr Pro Glu Ser His Gly Ile Ile Asp Asn Lys Met Tyr Asp Pro
        195                 200                 205

Lys Met Asn Ala Ser Phe Ser Leu Lys Ser Lys Glu Lys Phe Asn Pro
    210                 215                 220

Leu Trp Tyr Lys Gly Gln Pro Ile Trp Val Thr Ala Asn His Gln Glu
225                 230                 235                 240

Val Lys Ser Gly Thr Tyr Phe Trp Pro Gly Ser Asp Val Glu Ile Asp
                245                 250                 255

Gly Ile Leu Pro Asp Ile Tyr Lys Val Tyr Asn Gly Ser Val Pro Phe
            260                 265                 270

Glu Glu Arg Ile Leu Ala Val Leu Glu Trp Leu Gln Leu Pro Ser His
        275                 280                 285

Glu Arg Pro His Phe Tyr Thr Leu Tyr Leu Glu Glu Pro Asp Ser Ser
    290                 295                 300

Gly His Ser His Gly Pro Val Ser Ser Glu Val Ile Lys Ala Leu Gln
305                 310                 315                 320

Lys Val Asp Arg Leu Val Gly Met Leu Met Asp Gly Leu Lys Asp Leu
                325                 330                 335

Gly Leu Asp Lys Cys Leu Asn Leu Ile Leu Ile Ser Asp His Gly Met
            340                 345                 350

Glu Gln Gly Ser Cys Lys Lys Tyr Val Tyr Leu Asn Lys Tyr Leu Gly
        355                 360                 365

Asp Val Asn Asn Val Lys Val Val Tyr Gly Pro Ala Ala Arg Leu Arg
    370                 375                 380

Pro Thr Asp Val Pro Glu Thr Tyr Tyr Ser Phe Asn Tyr Glu Ala Leu
```

```
385                 390                 395                 400

Ala Lys Asn Leu Ser Cys Arg Glu Pro Asn Gln His Phe Arg Pro Tyr
                405                 410                 415

Leu Lys Pro Phe Leu Pro Lys Arg Leu His Phe Ala Lys Ser Asp Arg
            420                 425                 430

Ile Glu Pro Leu Thr Phe Tyr Leu Asp Pro Gln Trp Gln Leu Ala Leu
        435                 440                 445

Asn Pro Ser Glu Arg Lys Tyr Cys Gly Ser Gly Phe His Gly Ser Asp
    450                 455                 460

Asn Leu Phe Ser Asn Met Gln Ala Leu Phe Ile Gly Tyr Gly Pro Ala
465                 470                 475                 480

Phe Lys His Gly Ala Glu Val Asp Ser Phe Glu Asn Ile Glu Val Tyr
                485                 490                 495

Asn Leu Met Cys Asp Leu Leu Gly Leu Ile Pro Ala Pro Asn Asn Gly
            500                 505                 510

Ser His Gly Ser Leu Asn His Leu Leu Lys Lys Pro Ile Tyr Asn Pro
        515                 520                 525

Ser His Pro Lys Glu Glu Gly Phe Leu Ser Gln Cys Pro Ile Lys Ser
    530                 535                 540

Thr Ser Asn Asp Leu Gly Cys Thr Cys Asp Pro Trp Ile Val Pro Ile
545                 550                 555                 560

Lys Asp Phe Glu Lys Gln Leu Asn Leu Thr Thr Glu Asp Val Asp Asp
                565                 570                 575

Ile Tyr His Met Thr Val Pro Tyr Gly Arg Pro Arg Ile Leu Leu Lys
            580                 585                 590

Gln His Arg Val Cys Leu Leu Gln Gln Gln Gln Phe Leu Thr Gly Tyr
        595                 600                 605

Ser Leu Asp Leu Leu Met Pro Leu Trp Ala Ser Tyr Thr Phe Leu Ser
    610                 615                 620

Asn Asp Gln Phe Ser Arg Asp Asp Phe Ser Asn Cys Leu Tyr Gln Asp
625                 630                 635                 640

Leu Arg Ile Pro Leu Ser Pro Val His Lys Cys Ser Tyr Tyr Lys Ser
                645                 650                 655

Asn Ser Lys Leu Ser Tyr Gly Phe Leu Thr Pro Pro Arg Leu Asn Arg
            660                 665                 670

Val Ser Asn His Ile Tyr Ser Glu Ala Leu Leu Thr Ser Asn Ile Val
        675                 680                 685

Pro Met Tyr Gln Ser Phe Gln Val Ile Trp His Tyr Leu His Asp Thr
    690                 695                 700

Leu Leu Gln Arg Tyr Ala His Glu Arg Asn Gly Ile Asn Val Val Ser
705                 710                 715                 720

Gly Pro Val Phe Asp Phe Asp Tyr Asp Gly Arg Tyr Asp Ser Leu Glu
                725                 730                 735

Ile Leu Lys Gln Asn Ser Arg Val Ile Arg Ser Gln Glu Ile Leu Ile
            740                 745                 750

Pro Thr His Phe Phe Ile Val Leu Thr Ser Cys Lys Gln Leu Ser Glu
        755                 760                 765

Thr Pro Leu Glu Cys Ser Ala Leu Glu Ser Ser Ala Tyr Ile Leu Pro
    770                 775                 780

His Arg Pro Asp Asn Ile Glu Ser Cys Thr His Gly Lys Arg Glu Ser
785                 790                 795                 800

Ser Trp Val Glu Glu Leu Leu Thr Leu His Arg Ala Arg Val Thr Asp
                805                 810                 815
```

```
Val Glu Leu Ile Thr Gly Leu Ser Phe Tyr Gln Asp Arg Gln Glu Ser
            820                 825                 830

Val Ser Glu Leu Leu Arg Leu Lys Thr His Leu Pro Ile Phe Ser Gln
        835                 840                 845

Glu Asp Gly Gly Ser Gly Gly Ser Met Lys Trp Val Thr Phe Leu Leu
    850                 855                 860

Leu Leu Phe Val Ser Gly Ser Ala Phe Ser Arg Gly Val Phe Arg Arg
865                 870                 875                 880

Glu Ala His Lys Ser Glu Ile Ala His Arg Tyr Asn Asp Leu Gly Glu
                885                 890                 895

Gln His Phe Lys Gly Leu Val Leu Ile Ala Phe Ser Gln Tyr Leu Gln
            900                 905                 910

Lys Cys Ser Tyr Asp Glu His Ala Lys Leu Val Gln Glu Val Thr Asp
        915                 920                 925

Phe Ala Lys Thr Cys Val Ala Asp Glu Ser Ala Ala Asn Cys Asp Lys
    930                 935                 940

Ser Leu His Thr Leu Phe Gly Asp Lys Leu Cys Ala Ile Pro Asn Leu
945                 950                 955                 960

Arg Glu Asn Tyr Gly Glu Leu Ala Asp Cys Cys Thr Lys Gln Glu Pro
                965                 970                 975

Glu Arg Asn Glu Cys Phe Leu Gln His Lys Asp Asp Asn Pro Ser Leu
            980                 985                 990

Pro Pro Phe Glu Arg Pro Glu Ala  Glu Ala Met Cys Thr  Ser Phe Lys
        995                 1000                 1005

Glu Asn  Pro Thr Thr Phe Met  Gly His Tyr Leu His  Glu Val Ala
    1010                 1015                 1020

Arg Arg  His Pro Tyr Phe Tyr  Ala Pro Glu Leu Leu  Tyr Tyr Ala
    1025                 1030                 1035

Glu Gln  Tyr Asn Glu Ile Leu  Thr Gln Cys Cys Ala  Glu Ala Asp
    1040                 1045                 1050

Lys Glu  Ser Cys Leu Thr Pro  Lys Leu Asp Gly Val  Lys Glu Lys
    1055                 1060                 1065

Ala Leu  Val Ser Ser Val Arg  Gln Arg Met Lys Cys  Ser Ser Met
    1070                 1075                 1080

Gln Lys  Phe Gly Glu Arg Ala  Phe Lys Ala Trp Ala  Val Ala Arg
    1085                 1090                 1095

Leu Ser  Gln Thr Phe Pro Asn  Ala Asp Phe Ala Glu  Ile Thr Lys
    1100                 1105                 1110

Leu Ala  Thr Asp Leu Thr Lys  Val Asn Lys Glu Cys  Cys His Gly
    1115                 1120                 1125

Asp Leu  Leu Glu Cys Ala Asp  Asp Arg Ala Glu Leu  Ala Lys Tyr
    1130                 1135                 1140

Met Cys  Glu Asn Gln Ala Thr  Ile Ser Ser Lys Leu  Gln Thr Cys
    1145                 1150                 1155

Cys Asp  Lys Pro Leu Leu Lys  Lys Ala His Cys Leu  Ser Glu Val
    1160                 1165                 1170

Glu His  Asp Thr Met Pro Ala  Asp Leu Pro Ala Ile  Ala Ala Asp
    1175                 1180                 1185

Phe Val  Glu Asp Gln Glu Val  Cys Lys Asn Tyr Ala  Glu Ala Lys
    1190                 1195                 1200

Asp Val  Phe Leu Gly Thr Phe  Leu Tyr Glu Tyr Ser  Arg Arg His
    1205                 1210                 1215
```

```
Pro Asp  Tyr Ser Val Ser Leu  Leu Leu Arg Leu Ala  Lys Lys Tyr
    1220                 1225                 1230

Glu Ala  Thr Leu Glu Lys Cys  Cys Ala Glu Ala Asn  Pro Pro Ala
    1235                 1240                 1245

Cys Tyr  Gly Thr Val Leu Ala  Glu Phe Gln Pro Leu  Val Glu Glu
    1250                 1255                 1260

Pro Lys  Asn Leu Val Lys Thr  Asn Cys Asp Leu Tyr  Glu Lys Leu
    1265                 1270                 1275

Gly Glu  Tyr Gly Phe Gln Asn  Ala Ile Leu Val Arg  Tyr Thr Gln
    1280                 1285                 1290

Lys Ala  Pro Gln Val Ser Thr  Pro Thr Leu Val Glu  Ala Ala Arg
    1295                 1300                 1305

Asn Leu  Gly Arg Val Gly Thr  Lys Cys Cys Thr Leu  Pro Glu Asp
    1310                 1315                 1320

Gln Arg  Leu Pro Cys Val Glu  Asp Tyr Leu Ser Ala  Ile Leu Asn
    1325                 1330                 1335

Arg Val  Cys Leu Leu His Glu  Lys Thr Pro Val Ser  Glu His Val
    1340                 1345                 1350

Thr Lys  Cys Cys Ser Gly Ser  Leu Val Glu Arg Arg  Pro Cys Phe
    1355                 1360                 1365

Ser Ala  Leu Thr Val Asp Glu  Thr Tyr Val Pro Lys  Glu Phe Lys
    1370                 1375                 1380

Ala Glu  Thr Phe Thr Phe His  Ser Asp Ile Cys Thr  Leu Pro Glu
    1385                 1390                 1395

Lys Glu  Lys Gln Ile Lys Lys  Gln Thr Ala Leu Ala  Glu Leu Val
    1400                 1405                 1410

Lys His  Lys Pro Lys Ala Thr  Ala Glu Gln Leu Lys  Thr Val Met
    1415                 1420                 1425

Asp Asp  Phe Ala Gln Phe Leu  Asp Thr Cys Cys Lys  Ala Ala Asp
    1430                 1435                 1440

Lys Asp  Thr Cys Phe Ser Thr  Glu Gly Pro Asn Leu  Val Thr Arg
    1445                 1450                 1455

Cys Lys  Asp Ala Leu Ala Arg  Ser Trp Ser His Pro  Gln Phe Glu
    1460                 1465                 1470

Lys


<210> SEQ ID NO 26
<211> LENGTH: 227
<212> TYPE: PRT
<213> ORGANISM: Artificial Sequence
<220> FEATURE:
<223> OTHER INFORMATION: Human IgG Fc domain, Fc

<400> SEQUENCE: 26

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
```

```
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 27
<211> LENGTH: 618
<212> TYPE: PRT
<213> ORGANISM: Artificial Sequence
<220> FEATURE:
<223> OTHER INFORMATION: ALB

<400> SEQUENCE: 27

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45

Ile Ala Phe Ser Gln Tyr Leu Gln Lys Cys Ser Tyr Asp Glu His Ala
    50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
                85                  90                  95

Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
        115                 120                 125

His Lys Asp Asp Asn Pro Ser Leu Pro Pro Phe Glu Arg Pro Glu Ala
    130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
        195                 200                 205

Val Lys Glu Lys Ala Leu Val Ser Ser Val Arg Gln Arg Met Lys Cys
```

```
    210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
                245                 250                 255

Lys Leu Ala Thr Asp Leu Thr Lys Val Asn Lys Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Thr Ile Ser Ser Lys Leu Gln Thr Cys Cys Asp
    290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
                325                 330                 335

Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
    370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Asp Leu Tyr Glu Lys Leu Gly Glu Tyr Gly Phe Gln Asn Ala Ile Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
    450                 455                 460

Pro Glu Asp Gln Arg Leu Pro Cys Val Glu Asp Tyr Leu Ser Ala Ile
465                 470                 475                 480

Leu Asn Arg Val Cys Leu Leu His Glu Lys Thr Pro Val Ser Glu His
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Glu Lys Glu
    530                 535                 540

Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
                565                 570                 575

Gln Phe Leu Asp Thr Cys Cys Lys Ala Ala Asp Lys Asp Thr Cys Phe
            580                 585                 590

Ser Thr Glu Gly Pro Asn Leu Val Thr Arg Cys Lys Asp Ala Leu Ala
        595                 600                 605

Arg Ser Trp Ser His Pro Gln Phe Glu Lys
    610                 615
```

<210> SEQ ID NO 28

```
<211> LENGTH: 3
<212> TYPE: PRT
<213> ORGANISM: Artificial Sequence
<220> FEATURE:
<223> OTHER INFORMATION: chemically synthesized

<400> SEQUENCE: 28

Leu Ile Asn
1


<210> SEQ ID NO 29
<211> LENGTH: 6
<212> TYPE: PRT
<213> ORGANISM: Artificial Sequence
<220> FEATURE:
<223> OTHER INFORMATION: chemically synthesized

<400> SEQUENCE: 29

Gly Gly Ser Gly Gly Ser
1               5


<210> SEQ ID NO 30
<211> LENGTH: 7
<212> TYPE: PRT
<213> ORGANISM: Artificial Sequence
<220> FEATURE:
<223> OTHER INFORMATION: chemically synthesized

<400> SEQUENCE: 30

Arg Ser Gly Ser Gly Gly Ser
1               5


<210> SEQ ID NO 31
<211> LENGTH: 875
<212> TYPE: PRT
<213> ORGANISM: Homo sapiens

<400> SEQUENCE: 31

Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
            20                  25                  30

Val Ile Met Ser Leu Gly Leu Gly Leu Gly Leu Gly Leu Arg Lys Leu
        35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Arg Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
```

```
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
    290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
            340                 345                 350

Met Glu Gly Leu Lys Gln Arg Asn Leu His Asn Cys Val Asn Ile Ile
        355                 360                 365

Leu Leu Ala Asp His Gly Met Asp Gln Thr Tyr Cys Asn Lys Met Glu
    370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                405                 410                 415

Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
    450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
    530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
        595                 600                 605
```

```
Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875


<210> SEQ ID NO 32
<211> LENGTH: 827
<212> TYPE: PRT
<213> ORGANISM: Artificial Sequence
<220> FEATURE:
<223> OTHER INFORMATION: Extracellular domain of ENPP3

<400> SEQUENCE: 32

Glu Lys Gln Gly Ser Cys Arg Lys Lys Cys Phe Asp Ala Ser Phe Arg
1               5                   10                  15

Gly Leu Glu Asn Cys Arg Cys Asp Val Ala Cys Lys Asp Arg Gly Asp
            20                  25                  30

Cys Cys Trp Asp Phe Glu Asp Thr Cys Val Glu Ser Thr Arg Ile Trp
        35                  40                  45

Met Cys Asn Lys Phe Arg Cys Gly Glu Thr Arg Leu Glu Ala Ser Leu
    50                  55                  60

Cys Ser Cys Ser Asp Asp Cys Leu Gln Arg Lys Asp Cys Cys Ala Asp
65                  70                  75                  80

Tyr Lys Ser Val Cys Gln Gly Glu Thr Ser Trp Leu Glu Glu Asn Cys
                85                  90                  95
```

```
Asp Thr Ala Gln Gln Ser Gln Cys Pro Glu Gly Phe Asp Leu Pro Pro
            100                 105                 110

Val Ile Leu Phe Ser Met Asp Gly Phe Arg Ala Glu Tyr Leu Tyr Thr
        115                 120                 125

Trp Asp Thr Leu Met Pro Asn Ile Asn Lys Leu Lys Thr Cys Gly Ile
    130                 135                 140

His Ser Lys Tyr Met Arg Ala Met Tyr Pro Thr Lys Thr Phe Pro Asn
145                 150                 155                 160

His Tyr Thr Ile Val Thr Gly Leu Tyr Pro Glu Ser His Gly Ile Ile
                165                 170                 175

Asp Asn Asn Met Tyr Asp Val Asn Leu Asn Lys Asn Phe Ser Leu Ser
            180                 185                 190

Ser Lys Glu Gln Asn Asn Pro Ala Trp Trp His Gly Gln Pro Met Trp
        195                 200                 205

Leu Thr Ala Met Tyr Gln Gly Leu Lys Ala Ala Thr Tyr Phe Trp Pro
    210                 215                 220

Gly Ser Glu Val Ala Ile Asn Gly Ser Phe Pro Ser Ile Tyr Met Pro
225                 230                 235                 240

Tyr Asn Gly Ser Val Pro Phe Glu Glu Arg Ile Ser Thr Leu Leu Lys
                245                 250                 255

Trp Leu Asp Leu Pro Lys Ala Glu Arg Pro Arg Phe Tyr Thr Met Tyr
            260                 265                 270

Phe Glu Glu Pro Asp Ser Ser Gly His Ala Gly Gly Pro Val Ser Ala
        275                 280                 285

Arg Val Ile Lys Ala Leu Gln Val Val Asp His Ala Phe Gly Met Leu
    290                 295                 300

Met Glu Gly Leu Lys Gln Arg Asn Leu His Asn Cys Val Asn Ile Ile
305                 310                 315                 320

Leu Leu Ala Asp His Gly Met Asp Gln Thr Tyr Cys Asn Lys Met Glu
                325                 330                 335

Tyr Met Thr Asp Tyr Phe Pro Arg Ile Asn Phe Phe Tyr Met Tyr Glu
            340                 345                 350

Gly Pro Ala Pro Arg Ile Arg Ala His Asn Ile Pro His Asp Phe Phe
        355                 360                 365

Ser Phe Asn Ser Glu Glu Ile Val Arg Asn Leu Ser Cys Arg Lys Pro
    370                 375                 380

Asp Gln His Phe Lys Pro Tyr Leu Thr Pro Asp Leu Pro Lys Arg Leu
385                 390                 395                 400

His Tyr Ala Lys Asn Val Arg Ile Asp Lys Val His Leu Phe Val Asp
                405                 410                 415

Gln Gln Trp Leu Ala Val Arg Ser Lys Ser Asn Thr Asn Cys Gly Gly
            420                 425                 430

Gly Asn His Gly Tyr Asn Asn Glu Phe Arg Ser Met Glu Ala Ile Phe
        435                 440                 445

Leu Ala His Gly Pro Ser Phe Lys Glu Lys Thr Glu Val Glu Pro Phe
    450                 455                 460

Glu Asn Ile Glu Val Tyr Asn Leu Met Cys Asp Leu Leu Arg Ile Gln
465                 470                 475                 480

Pro Ala Pro Asn Asn Gly Thr His Gly Ser Leu Asn His Leu Leu Lys
                485                 490                 495

Val Pro Phe Tyr Glu Pro Ser His Ala Glu Glu Val Ser Lys Phe Ser
            500                 505                 510
```

```
Val Cys Gly Phe Ala Asn Pro Leu Pro Thr Glu Ser Leu Asp Cys Phe
        515                 520                 525

Cys Pro His Leu Gln Asn Ser Thr Gln Leu Glu Gln Val Asn Gln Met
    530                 535                 540

Leu Asn Leu Thr Gln Glu Glu Ile Thr Ala Thr Val Lys Val Asn Leu
545                 550                 555                 560

Pro Phe Gly Arg Pro Arg Val Leu Gln Lys Asn Val Asp His Cys Leu
                565                 570                 575

Leu Tyr His Arg Glu Tyr Val Ser Gly Phe Gly Lys Ala Met Arg Met
            580                 585                 590

Pro Met Trp Ser Ser Tyr Thr Val Pro Gln Leu Gly Asp Thr Ser Pro
        595                 600                 605

Leu Pro Pro Thr Val Pro Asp Cys Leu Arg Ala Asp Val Arg Val Pro
    610                 615                 620

Pro Ser Glu Ser Gln Lys Cys Ser Phe Tyr Leu Ala Asp Lys Asn Ile
625                 630                 635                 640

Thr His Gly Phe Leu Tyr Pro Pro Ala Ser Asn Arg Thr Ser Asp Ser
                645                 650                 655

Gln Tyr Asp Ala Leu Ile Thr Ser Asn Leu Val Pro Met Tyr Glu Glu
            660                 665                 670

Phe Arg Lys Met Trp Asp Tyr Phe His Ser Val Leu Leu Ile Lys His
        675                 680                 685

Ala Thr Glu Arg Asn Gly Val Asn Val Val Ser Gly Pro Ile Phe Asp
    690                 695                 700

Tyr Asn Tyr Asp Gly His Phe Asp Ala Pro Asp Glu Ile Thr Lys His
705                 710                 715                 720

Leu Ala Asn Thr Asp Val Pro Ile Pro Thr His Tyr Phe Val Val Leu
                725                 730                 735

Thr Ser Cys Lys Asn Lys Ser His Thr Pro Glu Asn Cys Pro Gly Trp
            740                 745                 750

Leu Asp Val Leu Pro Phe Ile Ile Pro His Arg Pro Thr Asn Val Glu
        755                 760                 765

Ser Cys Pro Glu Gly Lys Pro Glu Ala Leu Trp Val Glu Glu Arg Phe
    770                 775                 780

Thr Ala His Ile Ala Arg Val Arg Asp Val Glu Leu Leu Thr Gly Leu
785                 790                 795                 800

Asp Phe Tyr Gln Asp Lys Val Gln Pro Val Ser Glu Ile Leu Gln Leu
                805                 810                 815

Lys Thr Tyr Leu Pro Thr Phe Glu Thr Thr Ile
            820                 825


<210> SEQ ID NO 33
<211> LENGTH: 17
<212> TYPE: PRT
<213> ORGANISM: Artificial Sequence
<220> FEATURE:
<223> OTHER INFORMATION: exENPP3

<400> SEQUENCE: 33

Leu Leu Val Ile Met Ser Leu Gly Leu Gly Leu Gly Leu Gly Leu Arg
1               5                   10                  15

Lys


<210> SEQ ID NO 34
<211> LENGTH: 22
<212> TYPE: PRT
```

<213> ORGANISM: Artificial Sequence
<220> FEATURE:
<223> OTHER INFORMATION: ENPP7 protein export signal sequence

<400> SEQUENCE: 34

Met Arg Gly Pro Ala Val Leu Leu Thr Val Ala Leu Ala Thr Leu Leu
1               5                   10                  15

Ala Pro Gly Ala Gly Ala
            20

<210> SEQ ID NO 35
<211> LENGTH: 98
<212> TYPE: PRT
<213> ORGANISM: Artificial Sequence
<220> FEATURE:
<223> OTHER INFORMATION: ENPP121GLK protein export signal sequence

<400> SEQUENCE: 35

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys

<210> SEQ ID NO 36
<211> LENGTH: 95
<212> TYPE: PRT
<213> ORGANISM: Artificial Sequence
<220> FEATURE:
<223> OTHER INFORMATION: ENPP121 protein export signal sequence

<400> SEQUENCE: 36

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala
                85                  90                  95

<210> SEQ ID NO 37
<211> LENGTH: 23
<212> TYPE: PRT
<213> ORGANISM: Artificial Sequence
<220> FEATURE:
<223> OTHER INFORMATION: ENPP5 protein export signal sequence
<220> FEATURE:
<221> NAME/KEY: MOD_RES

```
<222> LOCATION: (23)..(23)
<223> OTHER INFORMATION: residue can be absent, L, or LQ

<400> SEQUENCE: 37

Met Thr Ser Lys Phe Leu Leu Val Ser Phe Ile Leu Ala Ala Leu Ser
1               5                   10                  15

Leu Ser Thr Thr Phe Ser Xaa
            20


<210> SEQ ID NO 38
<211> LENGTH: 20
<212> TYPE: PRT
<213> ORGANISM: Artificial Sequence
<220> FEATURE:
<223> OTHER INFORMATION: ENPP7 signal sequence

<400> SEQUENCE: 38

Met Arg Gly Pro Ala Val Leu Leu Thr Val Ala Leu Ala Thr Leu Leu
1               5                   10                  15

Ala Pro Gly Ala
            20


<210> SEQ ID NO 39
<211> LENGTH: 22
<212> TYPE: PRT
<213> ORGANISM: Artificial Sequence
<220> FEATURE:
<223> OTHER INFORMATION: ENPP7 signal sequence

<400> SEQUENCE: 39

Met Arg Gly Pro Ala Val Leu Leu Thr Val Ala Leu Ala Thr Leu Leu
1               5                   10                  15

Ala Pro Gly Ala Gly Ala
            20


<210> SEQ ID NO 40
<211> LENGTH: 16
<212> TYPE: PRT
<213> ORGANISM: Artificial Sequence
<220> FEATURE:
<223> OTHER INFORMATION: chemically synthesized

<400> SEQUENCE: 40

Leu Val Ile Met Ser Leu Gly Leu Gly Leu Gly Leu Gly Leu Arg Lys
1               5                   10                  15


<210> SEQ ID NO 41
<211> LENGTH: 15
<212> TYPE: PRT
<213> ORGANISM: Artificial Sequence
<220> FEATURE:
<223> OTHER INFORMATION: chemically synthesized

<400> SEQUENCE: 41

Val Ile Met Ser Leu Gly Leu Gly Leu Gly Leu Gly Leu Arg Lys
1               5                   10                  15


<210> SEQ ID NO 42
<211> LENGTH: 14
<212> TYPE: PRT
<213> ORGANISM: Artificial Sequence
<220> FEATURE:
<223> OTHER INFORMATION: chemically synthesized

<400> SEQUENCE: 42
```

```
Ile Met Ser Leu Gly Leu Gly Leu Gly Leu Gly Leu Arg Lys
1               5                   10


<210> SEQ ID NO 43
<211> LENGTH: 13
<212> TYPE: PRT
<213> ORGANISM: Artificial Sequence
<220> FEATURE:
<223> OTHER INFORMATION: chemically synthesized

<400> SEQUENCE: 43

Met Ser Leu Gly Leu Gly Leu Gly Leu Gly Leu Arg Lys
1               5                   10


<210> SEQ ID NO 44
<211> LENGTH: 12
<212> TYPE: PRT
<213> ORGANISM: Artificial Sequence
<220> FEATURE:
<223> OTHER INFORMATION: chemically synthesized

<400> SEQUENCE: 44

Ser Leu Gly Leu Gly Leu Gly Leu Gly Leu Arg Lys
1               5                   10


<210> SEQ ID NO 45
<211> LENGTH: 11
<212> TYPE: PRT
<213> ORGANISM: Artificial Sequence
<220> FEATURE:
<223> OTHER INFORMATION: chemically synthesized

<400> SEQUENCE: 45

Leu Gly Leu Gly Leu Gly Leu Gly Leu Arg Lys
1               5                   10


<210> SEQ ID NO 46
<211> LENGTH: 10
<212> TYPE: PRT
<213> ORGANISM: Artificial Sequence
<220> FEATURE:
<223> OTHER INFORMATION: chemically synthesized

<400> SEQUENCE: 46

Gly Leu Gly Leu Gly Leu Gly Leu Arg Lys
1               5                   10


<210> SEQ ID NO 47
<211> LENGTH: 9
<212> TYPE: PRT
<213> ORGANISM: Artificial Sequence
<220> FEATURE:
<223> OTHER INFORMATION: chemically synthesized

<400> SEQUENCE: 47

Leu Gly Leu Gly Leu Gly Leu Arg Lys
1               5


<210> SEQ ID NO 48
<211> LENGTH: 8
<212> TYPE: PRT
<213> ORGANISM: Artificial Sequence
<220> FEATURE:
<223> OTHER INFORMATION: chemically synthesized

<400> SEQUENCE: 48

Gly Leu Gly Leu Gly Leu Arg Lys
```

1 5

<210> SEQ ID NO 49
<211> LENGTH: 7
<212> TYPE: PRT
<213> ORGANISM: Artificial Sequence
<220> FEATURE:
<223> OTHER INFORMATION: chemically synthesized

<400> SEQUENCE: 49

Leu Gly Leu Gly Leu Arg Lys
1 5

<210> SEQ ID NO 50
<211> LENGTH: 6
<212> TYPE: PRT
<213> ORGANISM: Artificial Sequence
<220> FEATURE:
<223> OTHER INFORMATION: chemically synthesized

<400> SEQUENCE: 50

Gly Leu Gly Leu Arg Lys
1 5

<210> SEQ ID NO 51
<211> LENGTH: 5
<212> TYPE: PRT
<213> ORGANISM: Artificial Sequence
<220> FEATURE:
<223> OTHER INFORMATION: chemically synthesized

<400> SEQUENCE: 51

Leu Gly Leu Arg Lys
1 5

<210> SEQ ID NO 52
<211> LENGTH: 4
<212> TYPE: PRT
<213> ORGANISM: Artificial Sequence
<220> FEATURE:
<223> OTHER INFORMATION: chemically synthesized

<400> SEQUENCE: 52

Gly Leu Arg Lys
1

<210> SEQ ID NO 53
<211> LENGTH: 3
<212> TYPE: PRT
<213> ORGANISM: Artificial Sequence
<220> FEATURE:
<223> OTHER INFORMATION: chemically synthesized

<400> SEQUENCE: 53

Leu Arg Lys
1

<210> SEQ ID NO 54
<211> LENGTH: 2
<212> TYPE: PRT
<213> ORGANISM: Artificial Sequence
<220> FEATURE:
<223> OTHER INFORMATION: chemically synthesized

<400> SEQUENCE: 54

Arg Lys
1

<210> SEQ ID NO 55
<211> LENGTH: 1
<212> TYPE: PRT
<213> ORGANISM: Artificial Sequence
<220> FEATURE:
<223> OTHER INFORMATION: chemically synthesized

<400> SEQUENCE: 55

Lys
1

<210> SEQ ID NO 56
<211> LENGTH: 1147
<212> TYPE: PRT
<213> ORGANISM: Artificial Sequence
<220> FEATURE:
<223> OTHER INFORMATION: ENPP121-NPP3-Fc

<400> SEQUENCE: 56

```
Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Lys
                85                  90                  95

Gln Gly Ser Cys Arg Lys Lys Cys Phe Asp Ala Ser Phe Arg Gly Leu
            100                 105                 110

Glu Asn Cys Arg Cys Asp Val Ala Cys Lys Asp Arg Gly Asp Cys Cys
        115                 120                 125

Trp Asp Phe Glu Asp Thr Cys Val Glu Ser Thr Arg Ile Trp Met Cys
    130                 135                 140

Asn Lys Phe Arg Cys Gly Glu Arg Leu Glu Ala Ser Leu Cys Ser Cys
145                 150                 155                 160

Ser Asp Asp Cys Leu Gln Arg Lys Asp Cys Cys Ala Asp Tyr Lys Ser
                165                 170                 175

Val Cys Gln Gly Glu Thr Ser Trp Leu Glu Glu Asn Cys Asp Thr Ala
            180                 185                 190

Gln Gln Ser Gln Cys Pro Glu Gly Phe Asp Leu Pro Pro Val Ile Leu
        195                 200                 205

Phe Ser Met Asp Gly Phe Arg Ala Glu Tyr Leu Tyr Thr Trp Asp Thr
    210                 215                 220

Leu Met Pro Asn Ile Asn Lys Leu Lys Thr Cys Gly Ile His Ser Lys
225                 230                 235                 240

Tyr Met Arg Ala Met Tyr Pro Thr Lys Thr Phe Pro Asn His Tyr Thr
                245                 250                 255

Ile Val Thr Gly Leu Tyr Pro Glu Ser His Gly Ile Ile Asp Asn Asn
            260                 265                 270

Met Tyr Asp Val Asn Leu Asn Lys Asn Phe Ser Leu Ser Ser Lys Glu
        275                 280                 285

Gln Asn Asn Pro Ala Trp Trp His Gly Gln Pro Met Trp Leu Thr Ala
```

```
    290                 295                 300

Met Tyr Gln Gly Leu Lys Ala Ala Thr Tyr Phe Trp Pro Gly Ser Glu
305                 310                 315                 320

Val Ala Ile Asn Gly Ser Phe Pro Ser Ile Tyr Met Pro Tyr Asn Gly
                325                 330                 335

Ser Val Pro Phe Glu Glu Arg Ile Ser Thr Leu Leu Lys Trp Leu Asp
            340                 345                 350

Leu Pro Lys Ala Glu Arg Pro Arg Phe Tyr Thr Met Tyr Phe Glu Glu
        355                 360                 365

Pro Asp Ser Ser Gly His Ala Gly Gly Pro Val Ser Ala Arg Val Ile
    370                 375                 380

Lys Ala Leu Gln Val Val Asp His Ala Phe Gly Met Leu Met Glu Gly
385                 390                 395                 400

Leu Lys Gln Arg Asn Leu His Asn Cys Val Asn Ile Ile Leu Leu Ala
                405                 410                 415

Asp His Gly Met Asp Gln Thr Tyr Cys Asn Lys Met Glu Tyr Met Thr
            420                 425                 430

Asp Tyr Phe Pro Arg Ile Asn Phe Phe Tyr Met Tyr Glu Gly Pro Ala
        435                 440                 445

Pro Arg Ile Arg Ala His Asn Ile Pro His Asp Phe Phe Ser Phe Asn
    450                 455                 460

Ser Glu Glu Ile Val Arg Asn Leu Ser Cys Arg Lys Pro Asp Gln His
465                 470                 475                 480

Phe Lys Pro Tyr Leu Thr Pro Asp Leu Pro Lys Arg Leu His Tyr Ala
                485                 490                 495

Lys Asn Val Arg Ile Asp Lys Val His Leu Phe Val Asp Gln Gln Trp
            500                 505                 510

Leu Ala Val Arg Ser Lys Ser Asn Thr Asn Cys Gly Gly Gly Asn His
        515                 520                 525

Gly Tyr Asn Asn Glu Phe Arg Ser Met Glu Ala Ile Phe Leu Ala His
    530                 535                 540

Gly Pro Ser Phe Lys Glu Lys Thr Glu Val Glu Pro Phe Glu Asn Ile
545                 550                 555                 560

Glu Val Tyr Asn Leu Met Cys Asp Leu Leu Arg Ile Gln Pro Ala Pro
                565                 570                 575

Asn Asn Gly Thr His Gly Ser Leu Asn His Leu Leu Lys Val Pro Phe
            580                 585                 590

Tyr Glu Pro Ser His Ala Glu Glu Val Ser Lys Phe Ser Val Cys Gly
        595                 600                 605

Phe Ala Asn Pro Leu Pro Thr Glu Ser Leu Asp Cys Phe Cys Pro His
    610                 615                 620

Leu Gln Asn Ser Thr Gln Leu Glu Gln Val Asn Gln Met Leu Asn Leu
625                 630                 635                 640

Thr Gln Glu Glu Ile Thr Ala Thr Val Lys Val Asn Leu Pro Phe Gly
                645                 650                 655

Arg Pro Arg Val Leu Gln Lys Asn Val Asp His Cys Leu Leu Tyr His
            660                 665                 670

Arg Glu Tyr Val Ser Gly Phe Gly Lys Ala Met Arg Met Pro Met Trp
        675                 680                 685

Ser Ser Tyr Thr Val Pro Gln Leu Gly Asp Thr Ser Pro Leu Pro Pro
    690                 695                 700

Thr Val Pro Asp Cys Leu Arg Ala Asp Val Arg Val Pro Pro Ser Glu
705                 710                 715                 720
```

```
Ser Gln Lys Cys Ser Phe Tyr Leu Ala Asp Lys Asn Ile Thr His Gly
                725                 730                 735

Phe Leu Tyr Pro Pro Ala Ser Asn Arg Thr Ser Asp Ser Gln Tyr Asp
            740                 745                 750

Ala Leu Ile Thr Ser Asn Leu Val Pro Met Tyr Glu Glu Phe Arg Lys
        755                 760                 765

Met Trp Asp Tyr Phe His Ser Val Leu Leu Ile Lys His Ala Thr Glu
    770                 775                 780

Arg Asn Gly Val Asn Val Val Ser Gly Pro Ile Phe Asp Tyr Asn Tyr
785                 790                 795                 800

Asp Gly His Phe Asp Ala Pro Asp Glu Ile Thr Lys His Leu Ala Asn
                805                 810                 815

Thr Asp Val Pro Ile Pro Thr His Tyr Phe Val Val Leu Thr Ser Cys
            820                 825                 830

Lys Asn Lys Ser His Thr Pro Glu Asn Cys Pro Gly Trp Leu Asp Val
        835                 840                 845

Leu Pro Phe Ile Ile Pro His Arg Pro Thr Asn Val Glu Ser Cys Pro
    850                 855                 860

Glu Gly Lys Pro Glu Ala Leu Trp Val Glu Glu Arg Phe Thr Ala His
865                 870                 875                 880

Ile Ala Arg Val Arg Asp Val Glu Leu Leu Thr Gly Leu Asp Phe Tyr
                885                 890                 895

Gln Asp Lys Val Gln Pro Val Ser Glu Ile Leu Gln Leu Lys Thr Tyr
            900                 905                 910

Leu Pro Thr Phe Glu Thr Thr Ile Asp Lys Thr His Thr Cys Pro Pro
        915                 920                 925

Cys Pro Ala Pro Glu Leu Leu Gly Gly Pro Ser Val Phe Leu Phe Pro
    930                 935                 940

Pro Lys Pro Lys Asp Thr Leu Met Ile Ser Arg Thr Pro Glu Val Thr
945                 950                 955                 960

Cys Val Val Val Asp Val Ser His Glu Asp Pro Glu Val Lys Phe Asn
                965                 970                 975

Trp Tyr Val Asp Gly Val Glu Val His Asn Ala Lys Thr Lys Pro Arg
            980                 985                 990

Glu Glu Gln Tyr Asn Ser Thr Tyr  Arg Val Val Ser Val  Leu Thr Val
        995                 1000                1005

Leu His  Gln Asp Trp Leu Asn  Gly Lys Glu Tyr Lys  Cys Lys Val
    1010                1015                1020

Ser Asn  Lys Ala Leu Pro Ala  Pro Ile Glu Lys Thr  Ile Ser Lys
    1025                1030                1035

Ala Lys  Gly Gln Pro Arg Glu  Pro Gln Val Tyr Thr  Leu Pro Pro
    1040                1045                1050

Ser Arg  Glu Glu Met Thr Lys  Asn Gln Val Ser Leu  Thr Cys Leu
    1055                1060                1065

Val Lys  Gly Phe Tyr Pro Ser  Asp Ile Ala Val Glu  Trp Glu Ser
    1070                1075                1080

Asn Gly  Gln Pro Glu Asn Asn  Tyr Lys Thr Thr Pro  Pro Val Leu
    1085                1090                1095

Asp Ser  Asp Gly Ser Phe Phe  Leu Tyr Ser Lys Leu  Thr Val Asp
    1100                1105                1110

Lys Ser  Arg Trp Gln Gln Gly  Asn Val Phe Ser Cys  Ser Val Met
    1115                1120                1125
```

```
His Glu  Ala Leu His Asn His  Tyr Thr Gln Lys Ser  Leu Ser Leu
    1130                 1135                 1140

Ser Pro  Gly Lys
    1145


<210> SEQ ID NO 57
<211> LENGTH: 1072
<212> TYPE: PRT
<213> ORGANISM: Artificial Sequence
<220> FEATURE:
<223> OTHER INFORMATION: ENPP7-ENPP3-Fc

<400> SEQUENCE: 57

Met Arg Gly Pro Ala Val Leu Leu Thr Val Ala Leu Ala Thr Leu Leu
1               5                   10                  15

Ala Pro Gly Ala Lys Gln Gly Ser Cys Arg Lys Lys Cys Phe Asp Ala
            20                  25                  30

Ser Phe Arg Gly Leu Glu Asn Cys Arg Cys Asp Val Ala Cys Lys Asp
        35                  40                  45

Arg Gly Asp Cys Cys Trp Asp Phe Glu Asp Thr Cys Val Glu Ser Thr
    50                  55                  60

Arg Ile Trp Met Cys Asn Lys Phe Arg Cys Gly Glu Arg Leu Glu Ala
65                  70                  75                  80

Ser Leu Cys Ser Cys Ser Asp Asp Cys Leu Gln Arg Lys Asp Cys Cys
                85                  90                  95

Ala Asp Tyr Lys Ser Val Cys Gln Gly Glu Thr Ser Trp Leu Glu Glu
            100                 105                 110

Asn Cys Asp Thr Ala Gln Gln Ser Gln Cys Pro Glu Gly Phe Asp Leu
        115                 120                 125

Pro Pro Val Ile Leu Phe Ser Met Asp Gly Phe Arg Ala Glu Tyr Leu
    130                 135                 140

Tyr Thr Trp Asp Thr Leu Met Pro Asn Ile Asn Lys Leu Lys Thr Cys
145                 150                 155                 160

Gly Ile His Ser Lys Tyr Met Arg Ala Met Tyr Pro Thr Lys Thr Phe
                165                 170                 175

Pro Asn His Tyr Thr Ile Val Thr Gly Leu Tyr Pro Glu Ser His Gly
            180                 185                 190

Ile Ile Asp Asn Asn Met Tyr Asp Val Asn Leu Asn Lys Asn Phe Ser
        195                 200                 205

Leu Ser Ser Lys Glu Gln Asn Asn Pro Ala Trp Trp His Gly Gln Pro
    210                 215                 220

Met Trp Leu Thr Ala Met Tyr Gln Gly Leu Lys Ala Ala Thr Tyr Phe
225                 230                 235                 240

Trp Pro Gly Ser Glu Val Ala Ile Asn Gly Ser Phe Pro Ser Ile Tyr
                245                 250                 255

Met Pro Tyr Asn Gly Ser Val Pro Phe Glu Glu Arg Ile Ser Thr Leu
            260                 265                 270

Leu Lys Trp Leu Asp Leu Pro Lys Ala Glu Arg Pro Arg Phe Tyr Thr
        275                 280                 285

Met Tyr Phe Glu Glu Pro Asp Ser Ser Gly His Ala Gly Gly Pro Val
    290                 295                 300

Ser Ala Arg Val Ile Lys Ala Leu Gln Val Val Asp His Ala Phe Gly
305                 310                 315                 320

Met Leu Met Glu Gly Leu Lys Gln Arg Asn Leu His Asn Cys Val Asn
                325                 330                 335
```

```
Ile Ile Leu Leu Ala Asp His Gly Met Asp Gln Thr Tyr Cys Asn Lys
            340                 345                 350

Met Glu Tyr Met Thr Asp Tyr Phe Pro Arg Ile Asn Phe Phe Tyr Met
        355                 360                 365

Tyr Glu Gly Pro Ala Pro Arg Ile Arg Ala His Asn Ile Pro His Asp
    370                 375                 380

Phe Phe Ser Phe Asn Ser Glu Glu Ile Val Arg Asn Leu Ser Cys Arg
385                 390                 395                 400

Lys Pro Asp Gln His Phe Lys Pro Tyr Leu Thr Pro Asp Leu Pro Lys
                405                 410                 415

Arg Leu His Tyr Ala Lys Asn Val Arg Ile Asp Lys Val His Leu Phe
            420                 425                 430

Val Asp Gln Gln Trp Leu Ala Val Arg Ser Lys Ser Asn Thr Asn Cys
        435                 440                 445

Gly Gly Gly Asn His Gly Tyr Asn Asn Glu Phe Arg Ser Met Glu Ala
    450                 455                 460

Ile Phe Leu Ala His Gly Pro Ser Phe Lys Glu Lys Thr Glu Val Glu
465                 470                 475                 480

Pro Phe Glu Asn Ile Glu Val Tyr Asn Leu Met Cys Asp Leu Leu Arg
                485                 490                 495

Ile Gln Pro Ala Pro Asn Asn Gly Thr His Gly Ser Leu Asn His Leu
            500                 505                 510

Leu Lys Val Pro Phe Tyr Glu Pro Ser His Ala Glu Glu Val Ser Lys
        515                 520                 525

Phe Ser Val Cys Gly Phe Ala Asn Pro Leu Pro Thr Glu Ser Leu Asp
    530                 535                 540

Cys Phe Cys Pro His Leu Gln Asn Ser Thr Gln Leu Glu Gln Val Asn
545                 550                 555                 560

Gln Met Leu Asn Leu Thr Gln Glu Glu Ile Thr Ala Thr Val Lys Val
                565                 570                 575

Asn Leu Pro Phe Gly Arg Pro Arg Val Leu Gln Lys Asn Val Asp His
            580                 585                 590

Cys Leu Leu Tyr His Arg Glu Tyr Val Ser Gly Phe Gly Lys Ala Met
        595                 600                 605

Arg Met Pro Met Trp Ser Ser Tyr Thr Val Pro Gln Leu Gly Asp Thr
    610                 615                 620

Ser Pro Leu Pro Pro Thr Val Pro Asp Cys Leu Arg Ala Asp Val Arg
625                 630                 635                 640

Val Pro Pro Ser Glu Ser Gln Lys Cys Ser Phe Tyr Leu Ala Asp Lys
                645                 650                 655

Asn Ile Thr His Gly Phe Leu Tyr Pro Pro Ala Ser Asn Arg Thr Ser
            660                 665                 670

Asp Ser Gln Tyr Asp Ala Leu Ile Thr Ser Asn Leu Val Pro Met Tyr
        675                 680                 685

Glu Glu Phe Arg Lys Met Trp Asp Tyr Phe His Ser Val Leu Leu Ile
    690                 695                 700

Lys His Ala Thr Glu Arg Asn Gly Val Asn Val Val Ser Gly Pro Ile
705                 710                 715                 720

Phe Asp Tyr Asn Tyr Asp Gly His Phe Asp Ala Pro Asp Glu Ile Thr
                725                 730                 735

Lys His Leu Ala Asn Thr Asp Val Pro Ile Pro Thr His Tyr Phe Val
            740                 745                 750

Val Leu Thr Ser Cys Lys Asn Lys Ser His Thr Pro Glu Asn Cys Pro
```

```
        755                 760                 765

Gly Trp Leu Asp Val Leu Pro Phe Ile Ile Pro His Arg Pro Thr Asn
    770                 775                 780

Val Glu Ser Cys Pro Glu Gly Lys Pro Glu Ala Leu Trp Val Glu Glu
785                 790                 795                 800

Arg Phe Thr Ala His Ile Ala Arg Val Arg Asp Val Glu Leu Leu Thr
                805                 810                 815

Gly Leu Asp Phe Tyr Gln Asp Lys Val Gln Pro Val Ser Glu Ile Leu
            820                 825                 830

Gln Leu Lys Thr Tyr Leu Pro Thr Phe Glu Thr Thr Ile Asp Lys Thr
        835                 840                 845

His Thr Cys Pro Pro Cys Pro Ala Pro Glu Leu Leu Gly Gly Pro Ser
    850                 855                 860

Val Phe Leu Phe Pro Pro Lys Pro Lys Asp Thr Leu Met Ile Ser Arg
865                 870                 875                 880

Thr Pro Glu Val Thr Cys Val Val Val Asp Val Ser His Glu Asp Pro
                885                 890                 895

Glu Val Lys Phe Asn Trp Tyr Val Asp Gly Val Glu Val His Asn Ala
            900                 905                 910

Lys Thr Lys Pro Arg Glu Glu Gln Tyr Asn Ser Thr Tyr Arg Val Val
        915                 920                 925

Ser Val Leu Thr Val Leu His Gln Asp Trp Leu Asn Gly Lys Glu Tyr
    930                 935                 940

Lys Cys Lys Val Ser Asn Lys Ala Leu Pro Ala Pro Ile Glu Lys Thr
945                 950                 955                 960

Ile Ser Lys Ala Lys Gly Gln Pro Arg Glu Pro Gln Val Tyr Thr Leu
                965                 970                 975

Pro Pro Ser Arg Glu Glu Met Thr Lys Asn Gln Val Ser Leu Thr Cys
            980                 985                 990

Leu Val Lys Gly Phe Tyr Pro Ser  Asp Ile Ala Val Glu  Trp Glu Ser
        995                 1000                1005

Asn Gly  Gln Pro Glu Asn Asn  Tyr Lys Thr Thr Pro  Pro Val Leu
    1010                1015                1020

Asp Ser  Asp Gly Ser Phe Phe  Leu Tyr Ser Lys Leu  Thr Val Asp
    1025                1030                1035

Lys Ser  Arg Trp Gln Gln Gly  Asn Val Phe Ser Cys  Ser Val Met
    1040                1045                1050

His Glu  Ala Leu His Asn His  Tyr Thr Gln Lys Ser  Leu Ser Leu
    1055                1060                1065

Ser Pro  Gly Lys
    1070


<210> SEQ ID NO 58
<211> LENGTH: 1074
<212> TYPE: PRT
<213> ORGANISM: Artificial Sequence
<220> FEATURE:
<223> OTHER INFORMATION: ENPP5-ENPP3-Fc

<400> SEQUENCE: 58

Met Thr Ser Lys Phe Leu Leu Val Ser Phe Ile Leu Ala Ala Leu Ser
1               5                   10                  15

Leu Ser Thr Thr Phe Ser Lys Gln Gly Ser Cys Arg Lys Lys Cys Phe
            20                  25                  30

Asp Ala Ser Phe Arg Gly Leu Glu Asn Cys Arg Cys Asp Val Ala Cys
```

```
        35                  40                  45

Lys Asp Arg Gly Asp Cys Cys Trp Asp Phe Glu Asp Thr Cys Val Glu
    50                  55                  60

Ser Thr Arg Ile Trp Met Cys Asn Lys Phe Arg Cys Gly Glu Arg Leu
65                  70                  75                  80

Glu Ala Ser Leu Cys Ser Cys Ser Asp Asp Cys Leu Gln Arg Lys Asp
                85                  90                  95

Cys Cys Ala Asp Tyr Lys Ser Val Cys Gln Gly Glu Thr Ser Trp Leu
            100                 105                 110

Glu Glu Asn Cys Asp Thr Ala Gln Gln Ser Gln Cys Pro Glu Gly Phe
        115                 120                 125

Asp Leu Pro Pro Val Ile Leu Phe Ser Met Asp Gly Phe Arg Ala Glu
    130                 135                 140

Tyr Leu Tyr Thr Trp Asp Thr Leu Met Pro Asn Ile Asn Lys Leu Lys
145                 150                 155                 160

Thr Cys Gly Ile His Ser Lys Tyr Met Arg Ala Met Tyr Pro Thr Lys
                165                 170                 175

Thr Phe Pro Asn His Tyr Thr Ile Val Thr Gly Leu Tyr Pro Glu Ser
            180                 185                 190

His Gly Ile Ile Asp Asn Asn Met Tyr Asp Val Asn Leu Asn Lys Asn
        195                 200                 205

Phe Ser Leu Ser Ser Lys Glu Gln Asn Asn Pro Ala Trp Trp His Gly
    210                 215                 220

Gln Pro Met Trp Leu Thr Ala Met Tyr Gln Gly Leu Lys Ala Ala Thr
225                 230                 235                 240

Tyr Phe Trp Pro Gly Ser Glu Val Ala Ile Asn Gly Ser Phe Pro Ser
                245                 250                 255

Ile Tyr Met Pro Tyr Asn Gly Ser Val Pro Phe Glu Glu Arg Ile Ser
            260                 265                 270

Thr Leu Leu Lys Trp Leu Asp Leu Pro Lys Ala Glu Arg Pro Arg Phe
        275                 280                 285

Tyr Thr Met Tyr Phe Glu Glu Pro Asp Ser Ser Gly His Ala Gly Gly
    290                 295                 300

Pro Val Ser Ala Arg Val Ile Lys Ala Leu Gln Val Val Asp His Ala
305                 310                 315                 320

Phe Gly Met Leu Met Glu Gly Leu Lys Gln Arg Asn Leu His Asn Cys
                325                 330                 335

Val Asn Ile Ile Leu Leu Ala Asp His Gly Met Asp Gln Thr Tyr Cys
            340                 345                 350

Asn Lys Met Glu Tyr Met Thr Asp Tyr Phe Pro Arg Ile Asn Phe Phe
        355                 360                 365

Tyr Met Tyr Glu Gly Pro Ala Pro Arg Ile Arg Ala His Asn Ile Pro
    370                 375                 380

His Asp Phe Phe Ser Phe Asn Ser Glu Glu Ile Val Arg Asn Leu Ser
385                 390                 395                 400

Cys Arg Lys Pro Asp Gln His Phe Lys Pro Tyr Leu Thr Pro Asp Leu
                405                 410                 415

Pro Lys Arg Leu His Tyr Ala Lys Asn Val Arg Ile Asp Lys Val His
            420                 425                 430

Leu Phe Val Asp Gln Gln Trp Leu Ala Val Arg Ser Lys Ser Asn Thr
        435                 440                 445

Asn Cys Gly Gly Gly Asn His Gly Tyr Asn Asn Glu Phe Arg Ser Met
    450                 455                 460
```

```
Glu Ala Ile Phe Leu Ala His Gly Pro Ser Phe Lys Glu Lys Thr Glu
465                 470                 475                 480

Val Glu Pro Phe Glu Asn Ile Glu Val Tyr Asn Leu Met Cys Asp Leu
                485                 490                 495

Leu Arg Ile Gln Pro Ala Pro Asn Asn Gly Thr His Gly Ser Leu Asn
            500                 505                 510

His Leu Leu Lys Val Pro Phe Tyr Glu Pro Ser His Ala Glu Glu Val
        515                 520                 525

Ser Lys Phe Ser Val Cys Gly Phe Ala Asn Pro Leu Pro Thr Glu Ser
    530                 535                 540

Leu Asp Cys Phe Cys Pro His Leu Gln Asn Ser Thr Gln Leu Glu Gln
545                 550                 555                 560

Val Asn Gln Met Leu Asn Leu Thr Gln Glu Glu Ile Thr Ala Thr Val
                565                 570                 575

Lys Val Asn Leu Pro Phe Gly Arg Pro Arg Val Leu Gln Lys Asn Val
            580                 585                 590

Asp His Cys Leu Leu Tyr His Arg Glu Tyr Val Ser Gly Phe Gly Lys
        595                 600                 605

Ala Met Arg Met Pro Met Trp Ser Ser Tyr Thr Val Pro Gln Leu Gly
    610                 615                 620

Asp Thr Ser Pro Leu Pro Pro Thr Val Pro Asp Cys Leu Arg Ala Asp
625                 630                 635                 640

Val Arg Val Pro Pro Ser Glu Ser Gln Lys Cys Ser Phe Tyr Leu Ala
                645                 650                 655

Asp Lys Asn Ile Thr His Gly Phe Leu Tyr Pro Pro Ala Ser Asn Arg
            660                 665                 670

Thr Ser Asp Ser Gln Tyr Asp Ala Leu Ile Thr Ser Asn Leu Val Pro
        675                 680                 685

Met Tyr Glu Glu Phe Arg Lys Met Trp Asp Tyr Phe His Ser Val Leu
    690                 695                 700

Leu Ile Lys His Ala Thr Glu Arg Asn Gly Val Asn Val Val Ser Gly
705                 710                 715                 720

Pro Ile Phe Asp Tyr Asn Tyr Asp Gly His Phe Asp Ala Pro Asp Glu
                725                 730                 735

Ile Thr Lys His Leu Ala Asn Thr Asp Val Pro Ile Pro Thr His Tyr
            740                 745                 750

Phe Val Val Leu Thr Ser Cys Lys Asn Lys Ser His Thr Pro Glu Asn
        755                 760                 765

Cys Pro Gly Trp Leu Asp Val Leu Pro Phe Ile Ile Pro His Arg Pro
    770                 775                 780

Thr Asn Val Glu Ser Cys Pro Glu Gly Lys Pro Glu Ala Leu Trp Val
785                 790                 795                 800

Glu Glu Arg Phe Thr Ala His Ile Ala Arg Val Arg Asp Val Glu Leu
                805                 810                 815

Leu Thr Gly Leu Asp Phe Tyr Gln Asp Lys Val Gln Pro Val Ser Glu
            820                 825                 830

Ile Leu Gln Leu Lys Thr Tyr Leu Pro Thr Phe Glu Thr Thr Ile Asp
        835                 840                 845

Lys Thr His Thr Cys Pro Pro Cys Pro Ala Pro Glu Leu Leu Gly Gly
    850                 855                 860

Pro Ser Val Phe Leu Phe Pro Pro Lys Pro Lys Asp Thr Leu Met Ile
865                 870                 875                 880
```

```
Ser Arg Thr Pro Glu Val Thr Cys Val Val Val Asp Val Ser His Glu
                885                 890                 895

Asp Pro Glu Val Lys Phe Asn Trp Tyr Val Asp Gly Val Glu Val His
            900                 905                 910

Asn Ala Lys Thr Lys Pro Arg Glu Glu Gln Tyr Asn Ser Thr Tyr Arg
        915                 920                 925

Val Val Ser Val Leu Thr Val Leu His Gln Asp Trp Leu Asn Gly Lys
    930                 935                 940

Glu Tyr Lys Cys Lys Val Ser Asn Lys Ala Leu Pro Ala Pro Ile Glu
945                 950                 955                 960

Lys Thr Ile Ser Lys Ala Lys Gly Gln Pro Arg Glu Pro Gln Val Tyr
                965                 970                 975

Thr Leu Pro Pro Ser Arg Glu Glu Met Thr Lys Asn Gln Val Ser Leu
            980                 985                 990

Thr Cys Leu Val Lys Gly Phe Tyr  Pro Ser Asp Ile Ala  Val Glu Trp
        995                 1000                1005

Glu Ser  Asn Gly Gln Pro Glu  Asn Asn Tyr Lys Thr  Thr Pro Pro
    1010                1015                1020

Val Leu  Asp Ser Asp Gly Ser  Phe Phe Leu Tyr Ser  Lys Leu Thr
    1025                1030                1035

Val Asp  Lys Ser Arg Trp Gln  Gln Gly Asn Val Phe  Ser Cys Ser
    1040                1045                1050

Val Met  His Glu Ala Leu His  Asn His Tyr Thr Gln  Lys Ser Leu
    1055                1060                1065

Ser Leu  Ser Pro Gly Lys
    1070


<210> SEQ ID NO 59
<211> LENGTH: 623
<212> TYPE: PRT
<213> ORGANISM: Homo sapiens

<400> SEQUENCE: 59

Gly Gly Gly Gly Ser Gly Gly Gly Gly Ser Gly Gly Gly Gly Ser Met
1               5                   10                  15

Lys Trp Val Thr Phe Leu Leu Leu Leu Phe Val Ser Gly Ser Ala Phe
            20                  25                  30

Ser Arg Gly Val Phe Arg Arg Glu Ala His Lys Ser Glu Ile Ala His
        35                  40                  45

Arg Tyr Asn Asp Leu Gly Glu Gln His Phe Lys Gly Leu Val Leu Ile
    50                  55                  60

Ala Phe Ser Gln Tyr Leu Gln Lys Cys Ser Tyr Asp Glu His Ala Lys
65                  70                  75                  80

Leu Val Gln Glu Val Thr Asp Phe Ala Lys Thr Cys Val Ala Asp Glu
                85                  90                  95

Ser Ala Ala Asn Cys Asp Lys Ser Leu His Thr Leu Phe Gly Asp Lys
            100                 105                 110

Leu Cys Ala Ile Pro Asn Leu Arg Glu Asn Tyr Gly Glu Leu Ala Asp
        115                 120                 125

Cys Cys Thr Lys Gln Glu Pro Glu Arg Asn Glu Cys Phe Leu Gln His
    130                 135                 140

Lys Asp Asp Asn Pro Ser Leu Pro Pro Phe Glu Arg Pro Glu Ala Glu
145                 150                 155                 160

Ala Met Cys Thr Ser Phe Lys Glu Asn Pro Thr Thr Phe Met Gly His
                165                 170                 175
```

```
Tyr Leu His Glu Val Ala Arg Arg His Pro Tyr Phe Tyr Ala Pro Glu
            180                 185                 190

Leu Leu Tyr Tyr Ala Glu Gln Tyr Asn Glu Ile Leu Thr Gln Cys Cys
        195                 200                 205

Ala Glu Ala Asp Lys Glu Ser Cys Leu Thr Pro Lys Leu Asp Gly Val
    210                 215                 220

Lys Glu Lys Ala Leu Val Ser Ser Val Arg Gln Arg Met Lys Cys Ser
225                 230                 235                 240

Ser Met Gln Lys Phe Gly Glu Arg Ala Phe Lys Ala Trp Ala Val Ala
                245                 250                 255

Arg Leu Ser Gln Thr Phe Pro Asn Ala Asp Phe Ala Glu Ile Thr Lys
            260                 265                 270

Leu Ala Thr Asp Leu Thr Lys Val Asn Lys Glu Cys Cys His Gly Asp
        275                 280                 285

Leu Leu Glu Cys Ala Asp Asp Arg Ala Glu Leu Ala Lys Tyr Met Cys
    290                 295                 300

Glu Asn Gln Ala Thr Ile Ser Ser Lys Leu Gln Thr Cys Cys Asp Lys
305                 310                 315                 320

Pro Leu Leu Lys Lys Ala His Cys Leu Ser Glu Val Glu His Asp Thr
                325                 330                 335

Met Pro Ala Asp Leu Pro Ala Ile Ala Ala Asp Phe Val Glu Asp Gln
            340                 345                 350

Glu Val Cys Lys Asn Tyr Ala Glu Ala Lys Asp Val Phe Leu Gly Thr
        355                 360                 365

Phe Leu Tyr Glu Tyr Ser Arg Arg His Pro Asp Tyr Ser Val Ser Leu
    370                 375                 380

Leu Leu Arg Leu Ala Lys Lys Tyr Glu Ala Thr Leu Glu Lys Cys Cys
385                 390                 395                 400

Ala Glu Ala Asn Pro Pro Ala Cys Tyr Gly Thr Val Leu Ala Glu Phe
                405                 410                 415

Gln Pro Leu Val Glu Glu Pro Lys Asn Leu Val Lys Thr Asn Cys Asp
            420                 425                 430

Leu Tyr Glu Lys Leu Gly Glu Tyr Gly Phe Gln Asn Ala Ile Leu Val
        435                 440                 445

Arg Tyr Thr Gln Lys Ala Pro Gln Val Ser Thr Pro Thr Leu Val Glu
    450                 455                 460

Ala Ala Arg Asn Leu Gly Arg Val Gly Thr Lys Cys Cys Thr Leu Pro
465                 470                 475                 480

Glu Asp Gln Arg Leu Pro Cys Val Glu Asp Tyr Leu Ser Ala Ile Leu
                485                 490                 495

Asn Arg Val Cys Leu Leu His Glu Lys Thr Pro Val Ser Glu His Val
            500                 505                 510

Thr Lys Cys Cys Ser Gly Ser Leu Val Glu Arg Arg Pro Cys Phe Ser
        515                 520                 525

Ala Leu Thr Val Asp Glu Thr Tyr Val Pro Lys Glu Phe Lys Ala Glu
    530                 535                 540

Thr Phe Thr Phe His Ser Asp Ile Cys Thr Leu Pro Glu Lys Glu Lys
545                 550                 555                 560

Gln Ile Lys Lys Gln Thr Ala Leu Ala Glu Leu Val Lys His Lys Pro
                565                 570                 575

Lys Ala Thr Ala Glu Gln Leu Lys Thr Val Met Asp Asp Phe Ala Gln
            580                 585                 590
```

```
Phe Leu Asp Thr Cys Cys Lys Ala Ala Asp Lys Asp Thr Cys Phe Ser
        595                 600                 605

Thr Glu Gly Pro Asn Leu Val Thr Arg Cys Lys Asp Ala Leu Ala
    610                 615                 620


<210> SEQ ID NO 60
<211> LENGTH: 1582
<212> TYPE: PRT
<213> ORGANISM: Artificial Sequence
<220> FEATURE:
<223> OTHER INFORMATION: ENPP121-ENPP3-Albumin

<400> SEQUENCE: 60

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Lys
                85                  90                  95

Gln Gly Ser Cys Arg Lys Lys Cys Phe Asp Ala Ser Phe Arg Gly Leu
            100                 105                 110

Glu Asn Cys Arg Cys Asp Val Ala Cys Lys Asp Arg Gly Asp Cys Cys
        115                 120                 125

Trp Asp Phe Glu Asp Thr Cys Val Glu Ser Thr Arg Ile Trp Met Cys
    130                 135                 140

Asn Lys Phe Arg Cys Gly Glu Arg Leu Glu Ala Ser Leu Cys Ser Cys
145                 150                 155                 160

Ser Asp Asp Cys Leu Gln Arg Lys Asp Cys Cys Ala Asp Tyr Lys Ser
                165                 170                 175

Val Cys Gln Gly Glu Thr Ser Trp Leu Glu Glu Asn Cys Asp Thr Ala
            180                 185                 190

Gln Gln Ser Gln Cys Pro Glu Gly Phe Asp Leu Pro Pro Val Ile Leu
        195                 200                 205

Phe Ser Met Asp Gly Phe Arg Ala Glu Tyr Leu Tyr Thr Trp Asp Thr
    210                 215                 220

Leu Met Pro Asn Ile Asn Lys Leu Lys Thr Cys Gly Ile His Ser Lys
225                 230                 235                 240

Tyr Met Arg Ala Met Tyr Pro Thr Lys Thr Phe Pro Asn His Tyr Thr
                245                 250                 255

Ile Val Thr Gly Leu Tyr Pro Glu Ser His Gly Ile Ile Asp Asn Asn
            260                 265                 270

Met Tyr Asp Val Asn Leu Asn Lys Asn Phe Ser Leu Ser Ser Lys Glu
        275                 280                 285

Gln Asn Asn Pro Ala Trp Trp His Gly Gln Pro Met Trp Leu Thr Ala
    290                 295                 300

Met Tyr Gln Gly Leu Lys Ala Ala Thr Tyr Phe Trp Pro Gly Ser Glu
305                 310                 315                 320

Val Ala Ile Asn Gly Ser Phe Pro Ser Ile Tyr Met Pro Tyr Asn Gly
                325                 330                 335
```

```
Ser Val Pro Phe Glu Glu Arg Ile Ser Thr Leu Leu Lys Trp Leu Asp
            340                 345                 350

Leu Pro Lys Ala Glu Arg Pro Arg Phe Tyr Thr Met Tyr Phe Glu Glu
        355                 360                 365

Pro Asp Ser Ser Gly His Ala Gly Gly Pro Val Ser Ala Arg Val Ile
    370                 375                 380

Lys Ala Leu Gln Val Val Asp His Ala Phe Gly Met Leu Met Glu Gly
385                 390                 395                 400

Leu Lys Gln Arg Asn Leu His Asn Cys Val Asn Ile Ile Leu Leu Ala
                405                 410                 415

Asp His Gly Met Asp Gln Thr Tyr Cys Asn Lys Met Glu Tyr Met Thr
            420                 425                 430

Asp Tyr Phe Pro Arg Ile Asn Phe Phe Tyr Met Tyr Glu Gly Pro Ala
        435                 440                 445

Pro Arg Ile Arg Ala His Asn Ile Pro His Asp Phe Phe Ser Phe Asn
    450                 455                 460

Ser Glu Glu Ile Val Arg Asn Leu Ser Cys Arg Lys Pro Asp Gln His
465                 470                 475                 480

Phe Lys Pro Tyr Leu Thr Pro Asp Leu Pro Lys Arg Leu His Tyr Ala
                485                 490                 495

Lys Asn Val Arg Ile Asp Lys Val His Leu Phe Val Asp Gln Gln Trp
            500                 505                 510

Leu Ala Val Arg Ser Lys Ser Asn Thr Asn Cys Gly Gly Gly Asn His
        515                 520                 525

Gly Tyr Asn Asn Glu Phe Arg Ser Met Glu Ala Ile Phe Leu Ala His
    530                 535                 540

Gly Pro Ser Phe Lys Glu Lys Thr Glu Val Glu Pro Phe Glu Asn Ile
545                 550                 555                 560

Glu Val Tyr Asn Leu Met Cys Asp Leu Leu Arg Ile Gln Pro Ala Pro
                565                 570                 575

Asn Asn Gly Thr His Gly Ser Leu Asn His Leu Leu Lys Val Pro Phe
            580                 585                 590

Tyr Glu Pro Ser His Ala Glu Glu Val Ser Lys Phe Ser Val Cys Gly
        595                 600                 605

Phe Ala Asn Pro Leu Pro Thr Glu Ser Leu Asp Cys Phe Cys Pro His
    610                 615                 620

Leu Gln Asn Ser Thr Gln Leu Glu Gln Val Asn Gln Met Leu Asn Leu
625                 630                 635                 640

Thr Gln Glu Glu Ile Thr Ala Thr Val Lys Val Asn Leu Pro Phe Gly
                645                 650                 655

Arg Pro Arg Val Leu Gln Lys Asn Val Asp His Cys Leu Leu Tyr His
            660                 665                 670

Arg Glu Tyr Val Ser Gly Phe Gly Lys Ala Met Arg Met Pro Met Trp
        675                 680                 685

Ser Ser Tyr Thr Val Pro Gln Leu Gly Asp Thr Ser Pro Leu Pro Pro
    690                 695                 700

Thr Val Pro Asp Cys Leu Arg Ala Asp Val Arg Val Pro Pro Ser Glu
705                 710                 715                 720

Ser Gln Lys Cys Ser Phe Tyr Leu Ala Asp Lys Asn Ile Thr His Gly
                725                 730                 735

Phe Leu Tyr Pro Pro Ala Ser Asn Arg Thr Ser Asp Ser Gln Tyr Asp
            740                 745                 750

Ala Leu Ile Thr Ser Asn Leu Val Pro Met Tyr Glu Glu Phe Arg Lys
```

```
        755                 760                 765

Met Trp Asp Tyr Phe His Ser Val Leu Leu Ile Lys His Ala Thr Glu
    770                 775                 780

Arg Asn Gly Val Asn Val Val Ser Gly Pro Ile Phe Asp Tyr Asn Tyr
785                 790                 795                 800

Asp Gly His Phe Asp Ala Pro Asp Glu Ile Thr Lys His Leu Ala Asn
                805                 810                 815

Thr Asp Val Pro Ile Pro Thr His Tyr Phe Val Val Leu Thr Ser Cys
            820                 825                 830

Lys Asn Lys Ser His Thr Pro Glu Asn Cys Pro Gly Trp Leu Asp Val
        835                 840                 845

Leu Pro Phe Ile Ile Pro His Arg Pro Thr Asn Val Glu Ser Cys Pro
    850                 855                 860

Glu Gly Lys Pro Glu Ala Leu Trp Val Glu Glu Arg Phe Thr Ala His
865                 870                 875                 880

Ile Ala Arg Val Arg Asp Val Glu Leu Leu Thr Gly Leu Asp Phe Tyr
                885                 890                 895

Gln Asp Lys Val Gln Pro Val Ser Glu Ile Leu Gln Leu Lys Thr Tyr
            900                 905                 910

Leu Pro Thr Phe Glu Thr Thr Ile Asp Lys Thr His Thr Cys Pro Pro
        915                 920                 925

Cys Pro Ala Pro Glu Leu Leu Gly Gly Pro Ser Val Phe Leu Phe Pro
    930                 935                 940

Pro Lys Pro Lys Asp Thr Leu Met Ile Ser Arg Thr Pro Glu Val Thr
945                 950                 955                 960

Gly Gly Gly Ser Gly Gly Gly Gly Ser Gly Gly Gly Gly Ser Met Lys
                965                 970                 975

Trp Val Thr Phe Leu Leu Leu Leu Phe Val Ser Gly Ser Ala Phe Ser
            980                 985                 990

Arg Gly Val Phe Arg Arg Glu Ala  His Lys Ser Glu Ile  Ala His Arg
        995                 1000                1005

Tyr Asn  Asp Leu Gly Glu Gln  His Phe Lys Gly Leu  Val Leu Ile
    1010                1015                1020

Ala Phe  Ser Gln Tyr Leu Gln  Lys Cys Ser Tyr Asp  Glu His Ala
    1025                1030                1035

Lys Leu  Val Gln Glu Val Thr  Asp Phe Ala Lys Thr  Cys Val Ala
    1040                1045                1050

Asp Glu  Ser Ala Ala Asn Cys  Asp Lys Ser Leu His  Thr Leu Phe
    1055                1060                1065

Gly Asp  Lys Leu Cys Ala Ile  Pro Asn Leu Arg Glu  Asn Tyr Gly
    1070                1075                1080

Glu Leu  Ala Asp Cys Cys Thr  Lys Gln Glu Pro Glu  Arg Asn Glu
    1085                1090                1095

Cys Phe  Leu Gln His Lys Asp  Asp Asn Pro Ser Leu  Pro Pro Phe
    1100                1105                1110

Glu Arg  Pro Glu Ala Glu Ala  Met Cys Thr Ser Phe  Lys Glu Asn
    1115                1120                1125

Pro Thr  Thr Phe Met Gly His  Tyr Leu His Glu Val  Ala Arg Arg
    1130                1135                1140

His Pro  Tyr Phe Tyr Ala Pro  Glu Leu Leu Tyr Tyr  Ala Glu Gln
    1145                1150                1155

Tyr Asn  Glu Ile Leu Thr Gln  Cys Cys Ala Glu Ala  Asp Lys Glu
    1160                1165                1170
```

```
Ser Cys  Leu Thr Pro Lys Leu  Asp Gly Val Lys Glu  Lys Ala Leu
    1175                 1180                 1185

Val Ser  Ser Val Arg Gln Arg  Met Lys Cys Ser Ser  Met Gln Lys
    1190                 1195                 1200

Phe Gly  Glu Arg Ala Phe Lys  Ala Trp Ala Val Ala  Arg Leu Ser
    1205                 1210                 1215

Gln Thr  Phe Pro Asn Ala Asp  Phe Ala Glu Ile Thr  Lys Leu Ala
    1220                 1225                 1230

Thr Asp  Leu Thr Lys Val Asn  Lys Glu Cys Cys His  Gly Asp Leu
    1235                 1240                 1245

Leu Glu  Cys Ala Asp Asp Arg  Ala Glu Leu Ala Lys  Tyr Met Cys
    1250                 1255                 1260

Glu Asn  Gln Ala Thr Ile Ser  Ser Lys Leu Gln Thr  Cys Cys Asp
    1265                 1270                 1275

Lys Pro  Leu Leu Lys Lys Ala  His Cys Leu Ser Glu  Val Glu His
    1280                 1285                 1290

Asp Thr  Met Pro Ala Asp Leu  Pro Ala Ile Ala Ala  Asp Phe Val
    1295                 1300                 1305

Glu Asp  Gln Glu Val Cys Lys  Asn Tyr Ala Glu Ala  Lys Asp Val
    1310                 1315                 1320

Phe Leu  Gly Thr Phe Leu Tyr  Glu Tyr Ser Arg Arg  His Pro Asp
    1325                 1330                 1335

Tyr Ser  Val Ser Leu Leu Leu  Arg Leu Ala Lys Lys  Tyr Glu Ala
    1340                 1345                 1350

Thr Leu  Glu Lys Cys Cys Ala  Glu Ala Asn Pro Pro  Ala Cys Tyr
    1355                 1360                 1365

Gly Thr  Val Leu Ala Glu Phe  Gln Pro Leu Val Glu  Glu Pro Lys
    1370                 1375                 1380

Asn Leu  Val Lys Thr Asn Cys  Asp Leu Tyr Glu Lys  Leu Gly Glu
    1385                 1390                 1395

Tyr Gly  Phe Gln Asn Ala Ile  Leu Val Arg Tyr Thr  Gln Lys Ala
    1400                 1405                 1410

Pro Gln  Val Ser Thr Pro Thr  Leu Val Glu Ala Ala  Arg Asn Leu
    1415                 1420                 1425

Gly Arg  Val Gly Thr Lys Cys  Cys Thr Leu Pro Glu  Asp Gln Arg
    1430                 1435                 1440

Leu Pro  Cys Val Glu Asp Tyr  Leu Ser Ala Ile Leu  Asn Arg Val
    1445                 1450                 1455

Cys Leu  Leu His Glu Lys Thr  Pro Val Ser Glu His  Val Thr Lys
    1460                 1465                 1470

Cys Cys  Ser Gly Ser Leu Val  Glu Arg Arg Pro Cys  Phe Ser Ala
    1475                 1480                 1485

Leu Thr  Val Asp Glu Thr Tyr  Val Pro Lys Glu Phe  Lys Ala Glu
    1490                 1495                 1500

Thr Phe  Thr Phe His Ser Asp  Ile Cys Thr Leu Pro  Glu Lys Glu
    1505                 1510                 1515

Lys Gln  Ile Lys Lys Gln Thr  Ala Leu Ala Glu Leu  Val Lys His
    1520                 1525                 1530

Lys Pro  Lys Ala Thr Ala Glu  Gln Leu Lys Thr Val  Met Asp Asp
    1535                 1540                 1545

Phe Ala  Gln Phe Leu Asp Thr  Cys Cys Lys Ala Ala  Asp Lys Asp
    1550                 1555                 1560
```

```
Thr Cys  Phe Ser Thr Glu Gly  Pro Asn Leu Val Thr  Arg Cys Lys
    1565                 1570                 1575

Asp Ala  Leu Ala
    1580


<210> SEQ ID NO 61
<211> LENGTH: 1507
<212> TYPE: PRT
<213> ORGANISM: Artificial Sequence
<220> FEATURE:
<223> OTHER INFORMATION: ENPP7-ENPP3-Albumin

<400> SEQUENCE: 61

Met Arg Gly Pro Ala Val Leu Leu Thr Val Ala Leu Ala Thr Leu Leu
1               5                   10                  15

Ala Pro Gly Ala Lys Gln Gly Ser Cys Arg Lys Lys Cys Phe Asp Ala
            20                  25                  30

Ser Phe Arg Gly Leu Glu Asn Cys Arg Cys Asp Val Ala Cys Lys Asp
        35                  40                  45

Arg Gly Asp Cys Cys Trp Asp Phe Glu Asp Thr Cys Val Glu Ser Thr
    50                  55                  60

Arg Ile Trp Met Cys Asn Lys Phe Arg Cys Gly Glu Arg Leu Glu Ala
65                  70                  75                  80

Ser Leu Cys Ser Cys Ser Asp Asp Cys Leu Gln Arg Lys Asp Cys Cys
                85                  90                  95

Ala Asp Tyr Lys Ser Val Cys Gln Gly Glu Thr Ser Trp Leu Glu Glu
            100                 105                 110

Asn Cys Asp Thr Ala Gln Gln Ser Gln Cys Pro Glu Gly Phe Asp Leu
        115                 120                 125

Pro Pro Val Ile Leu Phe Ser Met Asp Gly Phe Arg Ala Glu Tyr Leu
    130                 135                 140

Tyr Thr Trp Asp Thr Leu Met Pro Asn Ile Asn Lys Leu Lys Thr Cys
145                 150                 155                 160

Gly Ile His Ser Lys Tyr Met Arg Ala Met Tyr Pro Thr Lys Thr Phe
                165                 170                 175

Pro Asn His Tyr Thr Ile Val Thr Gly Leu Tyr Pro Glu Ser His Gly
            180                 185                 190

Ile Ile Asp Asn Asn Met Tyr Asp Val Asn Leu Asn Lys Asn Phe Ser
        195                 200                 205

Leu Ser Ser Lys Glu Gln Asn Asn Pro Ala Trp Trp His Gly Gln Pro
    210                 215                 220

Met Trp Leu Thr Ala Met Tyr Gln Gly Leu Lys Ala Ala Thr Tyr Phe
225                 230                 235                 240

Trp Pro Gly Ser Glu Val Ala Ile Asn Gly Ser Phe Pro Ser Ile Tyr
                245                 250                 255

Met Pro Tyr Asn Gly Ser Val Pro Phe Glu Glu Arg Ile Ser Thr Leu
            260                 265                 270

Leu Lys Trp Leu Asp Leu Pro Lys Ala Glu Arg Pro Arg Phe Tyr Thr
        275                 280                 285

Met Tyr Phe Glu Glu Pro Asp Ser Ser Gly His Ala Gly Gly Pro Val
    290                 295                 300

Ser Ala Arg Val Ile Lys Ala Leu Gln Val Val Asp His Ala Phe Gly
305                 310                 315                 320

Met Leu Met Glu Gly Leu Lys Gln Arg Asn Leu His Asn Cys Val Asn
                325                 330                 335
```

```
Ile Ile Leu Leu Ala Asp His Gly Met Asp Gln Thr Tyr Cys Asn Lys
            340                 345                 350

Met Glu Tyr Met Thr Asp Tyr Phe Pro Arg Ile Asn Phe Phe Tyr Met
        355                 360                 365

Tyr Glu Gly Pro Ala Pro Arg Ile Arg Ala His Asn Ile Pro His Asp
    370                 375                 380

Phe Phe Ser Phe Asn Ser Glu Glu Ile Val Arg Asn Leu Ser Cys Arg
385                 390                 395                 400

Lys Pro Asp Gln His Phe Lys Pro Tyr Leu Thr Pro Asp Leu Pro Lys
                405                 410                 415

Arg Leu His Tyr Ala Lys Asn Val Arg Ile Asp Lys Val His Leu Phe
            420                 425                 430

Val Asp Gln Gln Trp Leu Ala Val Arg Ser Lys Ser Asn Thr Asn Cys
        435                 440                 445

Gly Gly Gly Asn His Gly Tyr Asn Asn Glu Phe Arg Ser Met Glu Ala
    450                 455                 460

Ile Phe Leu Ala His Gly Pro Ser Phe Lys Glu Lys Thr Glu Val Glu
465                 470                 475                 480

Pro Phe Glu Asn Ile Glu Val Tyr Asn Leu Met Cys Asp Leu Leu Arg
                485                 490                 495

Ile Gln Pro Ala Pro Asn Asn Gly Thr His Gly Ser Leu Asn His Leu
            500                 505                 510

Leu Lys Val Pro Phe Tyr Glu Pro Ser His Ala Glu Glu Val Ser Lys
        515                 520                 525

Phe Ser Val Cys Gly Phe Ala Asn Pro Leu Pro Thr Glu Ser Leu Asp
    530                 535                 540

Cys Phe Cys Pro His Leu Gln Asn Ser Thr Gln Leu Glu Gln Val Asn
545                 550                 555                 560

Gln Met Leu Asn Leu Thr Gln Glu Glu Ile Thr Ala Thr Val Lys Val
                565                 570                 575

Asn Leu Pro Phe Gly Arg Pro Arg Val Leu Gln Lys Asn Val Asp His
            580                 585                 590

Cys Leu Leu Tyr His Arg Glu Tyr Val Ser Gly Phe Gly Lys Ala Met
        595                 600                 605

Arg Met Pro Met Trp Ser Ser Tyr Thr Val Pro Gln Leu Gly Asp Thr
    610                 615                 620

Ser Pro Leu Pro Pro Thr Val Pro Asp Cys Leu Arg Ala Asp Val Arg
625                 630                 635                 640

Val Pro Pro Ser Glu Ser Gln Lys Cys Ser Phe Tyr Leu Ala Asp Lys
                645                 650                 655

Asn Ile Thr His Gly Phe Leu Tyr Pro Pro Ala Ser Asn Arg Thr Ser
            660                 665                 670

Asp Ser Gln Tyr Asp Ala Leu Ile Thr Ser Asn Leu Val Pro Met Tyr
        675                 680                 685

Glu Glu Phe Arg Lys Met Trp Asp Tyr Phe His Ser Val Leu Leu Ile
    690                 695                 700

Lys His Ala Thr Glu Arg Asn Gly Val Asn Val Val Ser Gly Pro Ile
705                 710                 715                 720

Phe Asp Tyr Asn Tyr Asp Gly His Phe Asp Ala Pro Asp Glu Ile Thr
                725                 730                 735

Lys His Leu Ala Asn Thr Asp Val Pro Ile Pro Thr His Tyr Phe Val
            740                 745                 750

Val Leu Thr Ser Cys Lys Asn Lys Ser His Thr Pro Glu Asn Cys Pro
```

```
        755                 760                 765

Gly Trp Leu Asp Val Leu Pro Phe Ile Ile Pro His Arg Pro Thr Asn
    770                 775                 780

Val Glu Ser Cys Pro Glu Gly Lys Pro Glu Ala Leu Trp Val Glu Glu
785                 790                 795                 800

Arg Phe Thr Ala His Ile Ala Arg Val Arg Asp Val Glu Leu Leu Thr
                805                 810                 815

Gly Leu Asp Phe Tyr Gln Asp Lys Val Gln Pro Val Ser Glu Ile Leu
            820                 825                 830

Gln Leu Lys Thr Tyr Leu Pro Thr Phe Glu Thr Thr Ile Asp Lys Thr
        835                 840                 845

His Thr Cys Pro Pro Cys Pro Ala Pro Glu Leu Leu Gly Gly Pro Ser
    850                 855                 860

Val Phe Leu Phe Pro Pro Lys Pro Lys Asp Thr Leu Met Ile Ser Arg
865                 870                 875                 880

Thr Pro Glu Val Thr Gly Gly Gly Ser Gly Gly Gly Gly Ser Gly Gly
                885                 890                 895

Gly Gly Ser Met Lys Trp Val Thr Phe Leu Leu Leu Leu Phe Val Ser
            900                 905                 910

Gly Ser Ala Phe Ser Arg Gly Val Phe Arg Arg Glu Ala His Lys Ser
        915                 920                 925

Glu Ile Ala His Arg Tyr Asn Asp Leu Gly Glu Gln His Phe Lys Gly
    930                 935                 940

Leu Val Leu Ile Ala Phe Ser Gln Tyr Leu Gln Lys Cys Ser Tyr Asp
945                 950                 955                 960

Glu His Ala Lys Leu Val Gln Glu Val Thr Asp Phe Ala Lys Thr Cys
                965                 970                 975

Val Ala Asp Glu Ser Ala Ala Asn Cys Asp Lys Ser Leu His Thr Leu
            980                 985                 990

Phe Gly Asp Lys Leu Cys Ala Ile  Pro Asn Leu Arg Glu  Asn Tyr Gly
        995                 1000                1005

Glu Leu  Ala Asp Cys Cys Thr  Lys Gln Glu Pro Glu  Arg Asn Glu
    1010                1015                1020

Cys Phe  Leu Gln His Lys Asp  Asp Asn Pro Ser Leu  Pro Pro Phe
    1025                1030                1035

Glu Arg  Pro Glu Ala Glu Ala  Met Cys Thr Ser Phe  Lys Glu Asn
    1040                1045                1050

Pro Thr  Thr Phe Met Gly His  Tyr Leu His Glu Val  Ala Arg Arg
    1055                1060                1065

His Pro  Tyr Phe Tyr Ala Pro  Glu Leu Leu Tyr Tyr  Ala Glu Gln
    1070                1075                1080

Tyr Asn  Glu Ile Leu Thr Gln  Cys Cys Ala Glu Ala  Asp Lys Glu
    1085                1090                1095

Ser Cys  Leu Thr Pro Lys Leu  Asp Gly Val Lys Glu  Lys Ala Leu
    1100                1105                1110

Val Ser  Ser Val Arg Gln Arg  Met Lys Cys Ser Ser  Met Gln Lys
    1115                1120                1125

Phe Gly  Glu Arg Ala Phe Lys  Ala Trp Ala Val Ala  Arg Leu Ser
    1130                1135                1140

Gln Thr  Phe Pro Asn Ala Asp  Phe Ala Glu Ile Thr  Lys Leu Ala
    1145                1150                1155

Thr Asp  Leu Thr Lys Val Asn  Lys Glu Cys Cys His  Gly Asp Leu
    1160                1165                1170
```

```
Leu Glu  Cys Ala Asp Asp Arg  Ala Glu Leu Ala Lys  Tyr Met Cys
    1175                 1180                 1185

Glu Asn  Gln Ala Thr Ile Ser  Ser Lys Leu Gln Thr  Cys Cys Asp
    1190                 1195                 1200

Lys Pro  Leu Leu Lys Lys Ala  His Cys Leu Ser Glu  Val Glu His
    1205                 1210                 1215

Asp Thr  Met Pro Ala Asp Leu  Pro Ala Ile Ala Ala  Asp Phe Val
    1220                 1225                 1230

Glu Asp  Gln Glu Val Cys Lys  Asn Tyr Ala Glu Ala  Lys Asp Val
    1235                 1240                 1245

Phe Leu  Gly Thr Phe Leu Tyr  Glu Tyr Ser Arg Arg  His Pro Asp
    1250                 1255                 1260

Tyr Ser  Val Ser Leu Leu Leu  Arg Leu Ala Lys Lys  Tyr Glu Ala
    1265                 1270                 1275

Thr Leu  Glu Lys Cys Cys Ala  Glu Ala Asn Pro Pro  Ala Cys Tyr
    1280                 1285                 1290

Gly Thr  Val Leu Ala Glu Phe  Gln Pro Leu Val Glu  Glu Pro Lys
    1295                 1300                 1305

Asn Leu  Val Lys Thr Asn Cys  Asp Leu Tyr Glu Lys  Leu Gly Glu
    1310                 1315                 1320

Tyr Gly  Phe Gln Asn Ala Ile  Leu Val Arg Tyr Thr  Gln Lys Ala
    1325                 1330                 1335

Pro Gln  Val Ser Thr Pro Thr  Leu Val Glu Ala Ala  Arg Asn Leu
    1340                 1345                 1350

Gly Arg  Val Gly Thr Lys Cys  Cys Thr Leu Pro Glu  Asp Gln Arg
    1355                 1360                 1365

Leu Pro  Cys Val Glu Asp Tyr  Leu Ser Ala Ile Leu  Asn Arg Val
    1370                 1375                 1380

Cys Leu  Leu His Glu Lys Thr  Pro Val Ser Glu His  Val Thr Lys
    1385                 1390                 1395

Cys Cys  Ser Gly Ser Leu Val  Glu Arg Arg Pro Cys  Phe Ser Ala
    1400                 1405                 1410

Leu Thr  Val Asp Glu Thr Tyr  Val Pro Lys Glu Phe  Lys Ala Glu
    1415                 1420                 1425

Thr Phe  Thr Phe His Ser Asp  Ile Cys Thr Leu Pro  Glu Lys Glu
    1430                 1435                 1440

Lys Gln  Ile Lys Lys Gln Thr  Ala Leu Ala Glu Leu  Val Lys His
    1445                 1450                 1455

Lys Pro  Lys Ala Thr Ala Glu  Gln Leu Lys Thr Val  Met Asp Asp
    1460                 1465                 1470

Phe Ala  Gln Phe Leu Asp Thr  Cys Cys Lys Ala Ala  Asp Lys Asp
    1475                 1480                 1485

Thr Cys  Phe Ser Thr Glu Gly  Pro Asn Leu Val Thr  Arg Cys Lys
    1490                 1495                 1500

Asp Ala  Leu Ala
    1505
```

<210> SEQ ID NO 62
<211> LENGTH: 1509
<212> TYPE: PRT
<213> ORGANISM: Artificial Sequence
<220> FEATURE:
<223> OTHER INFORMATION: ENPP5-ENPP3-Albumin

<400> SEQUENCE: 62

```
Met Thr Ser Lys Phe Leu Leu Val Ser Phe Ile Leu Ala Ala Leu Ser
1               5                   10                  15

Leu Ser Thr Thr Phe Ser Lys Gln Gly Ser Cys Arg Lys Lys Cys Phe
            20                  25                  30

Asp Ala Ser Phe Arg Gly Leu Glu Asn Cys Arg Cys Asp Val Ala Cys
        35                  40                  45

Lys Asp Arg Gly Asp Cys Cys Trp Asp Phe Glu Asp Thr Cys Val Glu
    50                  55                  60

Ser Thr Arg Ile Trp Met Cys Asn Lys Phe Arg Cys Gly Glu Arg Leu
65                  70                  75                  80

Glu Ala Ser Leu Cys Ser Cys Ser Asp Asp Cys Leu Gln Arg Lys Asp
                85                  90                  95

Cys Cys Ala Asp Tyr Lys Ser Val Cys Gln Gly Glu Thr Ser Trp Leu
            100                 105                 110

Glu Glu Asn Cys Asp Thr Ala Gln Gln Ser Gln Cys Pro Glu Gly Phe
        115                 120                 125

Asp Leu Pro Pro Val Ile Leu Phe Ser Met Asp Gly Phe Arg Ala Glu
    130                 135                 140

Tyr Leu Tyr Thr Trp Asp Thr Leu Met Pro Asn Ile Asn Lys Leu Lys
145                 150                 155                 160

Thr Cys Gly Ile His Ser Lys Tyr Met Arg Ala Met Tyr Pro Thr Lys
                165                 170                 175

Thr Phe Pro Asn His Tyr Thr Ile Val Thr Gly Leu Tyr Pro Glu Ser
            180                 185                 190

His Gly Ile Ile Asp Asn Asn Met Tyr Asp Val Asn Leu Asn Lys Asn
        195                 200                 205

Phe Ser Leu Ser Ser Lys Glu Gln Asn Asn Pro Ala Trp Trp His Gly
    210                 215                 220

Gln Pro Met Trp Leu Thr Ala Met Tyr Gln Gly Leu Lys Ala Ala Thr
225                 230                 235                 240

Tyr Phe Trp Pro Gly Ser Glu Val Ala Ile Asn Gly Ser Phe Pro Ser
                245                 250                 255

Ile Tyr Met Pro Tyr Asn Gly Ser Val Pro Phe Glu Glu Arg Ile Ser
            260                 265                 270

Thr Leu Leu Lys Trp Leu Asp Leu Pro Lys Ala Glu Arg Pro Arg Phe
        275                 280                 285

Tyr Thr Met Tyr Phe Glu Glu Pro Asp Ser Ser Gly His Ala Gly Gly
    290                 295                 300

Pro Val Ser Ala Arg Val Ile Lys Ala Leu Gln Val Val Asp His Ala
305                 310                 315                 320

Phe Gly Met Leu Met Glu Gly Leu Lys Gln Arg Asn Leu His Asn Cys
                325                 330                 335

Val Asn Ile Ile Leu Leu Ala Asp His Gly Met Asp Gln Thr Tyr Cys
            340                 345                 350

Asn Lys Met Glu Tyr Met Thr Asp Tyr Phe Pro Arg Ile Asn Phe Phe
        355                 360                 365

Tyr Met Tyr Glu Gly Pro Ala Pro Arg Ile Arg Ala His Asn Ile Pro
    370                 375                 380

His Asp Phe Phe Ser Phe Asn Ser Glu Glu Ile Val Arg Asn Leu Ser
385                 390                 395                 400

Cys Arg Lys Pro Asp Gln His Phe Lys Pro Tyr Leu Thr Pro Asp Leu
                405                 410                 415
```

-continued

```
Pro Lys Arg Leu His Tyr Ala Lys Asn Val Arg Ile Asp Lys Val His
            420                 425                 430

Leu Phe Val Asp Gln Gln Trp Leu Ala Val Arg Ser Lys Ser Asn Thr
        435                 440                 445

Asn Cys Gly Gly Gly Asn His Gly Tyr Asn Asn Glu Phe Arg Ser Met
    450                 455                 460

Glu Ala Ile Phe Leu Ala His Gly Pro Ser Phe Lys Glu Lys Thr Glu
465                 470                 475                 480

Val Glu Pro Phe Glu Asn Ile Glu Val Tyr Asn Leu Met Cys Asp Leu
                485                 490                 495

Leu Arg Ile Gln Pro Ala Pro Asn Asn Gly Thr His Gly Ser Leu Asn
            500                 505                 510

His Leu Leu Lys Val Pro Phe Tyr Glu Pro Ser His Ala Glu Glu Val
        515                 520                 525

Ser Lys Phe Ser Val Cys Gly Phe Ala Asn Pro Leu Pro Thr Glu Ser
    530                 535                 540

Leu Asp Cys Phe Cys Pro His Leu Gln Asn Ser Thr Gln Leu Glu Gln
545                 550                 555                 560

Val Asn Gln Met Leu Asn Leu Thr Gln Glu Glu Ile Thr Ala Thr Val
                565                 570                 575

Lys Val Asn Leu Pro Phe Gly Arg Pro Arg Val Leu Gln Lys Asn Val
            580                 585                 590

Asp His Cys Leu Leu Tyr His Arg Glu Tyr Val Ser Gly Phe Gly Lys
        595                 600                 605

Ala Met Arg Met Pro Met Trp Ser Ser Tyr Thr Val Pro Gln Leu Gly
    610                 615                 620

Asp Thr Ser Pro Leu Pro Pro Thr Val Pro Asp Cys Leu Arg Ala Asp
625                 630                 635                 640

Val Arg Val Pro Pro Ser Glu Ser Gln Lys Cys Ser Phe Tyr Leu Ala
                645                 650                 655

Asp Lys Asn Ile Thr His Gly Phe Leu Tyr Pro Pro Ala Ser Asn Arg
            660                 665                 670

Thr Ser Asp Ser Gln Tyr Asp Ala Leu Ile Thr Ser Asn Leu Val Pro
        675                 680                 685

Met Tyr Glu Glu Phe Arg Lys Met Trp Asp Tyr Phe His Ser Val Leu
    690                 695                 700

Leu Ile Lys His Ala Thr Glu Arg Asn Gly Val Asn Val Val Ser Gly
705                 710                 715                 720

Pro Ile Phe Asp Tyr Asn Tyr Asp Gly His Phe Asp Ala Pro Asp Glu
                725                 730                 735

Ile Thr Lys His Leu Ala Asn Thr Asp Val Pro Ile Pro Thr His Tyr
            740                 745                 750

Phe Val Val Leu Thr Ser Cys Lys Asn Lys Ser His Thr Pro Glu Asn
        755                 760                 765

Cys Pro Gly Trp Leu Asp Val Leu Pro Phe Ile Ile Pro His Arg Pro
    770                 775                 780

Thr Asn Val Glu Ser Cys Pro Glu Gly Lys Pro Glu Ala Leu Trp Val
785                 790                 795                 800

Glu Glu Arg Phe Thr Ala His Ile Ala Arg Val Arg Asp Val Glu Leu
                805                 810                 815

Leu Thr Gly Leu Asp Phe Tyr Gln Asp Lys Val Gln Pro Val Ser Glu
            820                 825                 830

Ile Leu Gln Leu Lys Thr Tyr Leu Pro Thr Phe Glu Thr Thr Ile Asp
```

```
        835                 840                 845

Lys Thr His Thr Cys Pro Pro Cys Pro Ala Pro Glu Leu Leu Gly Gly
    850                 855                 860

Pro Ser Val Phe Leu Phe Pro Pro Lys Pro Lys Asp Thr Leu Met Ile
865                 870                 875                 880

Ser Arg Thr Pro Glu Val Thr Gly Gly Gly Ser Gly Gly Gly Gly Ser
                885                 890                 895

Gly Gly Gly Gly Ser Met Lys Trp Val Thr Phe Leu Leu Leu Leu Phe
            900                 905                 910

Val Ser Gly Ser Ala Phe Ser Arg Gly Val Phe Arg Arg Glu Ala His
        915                 920                 925

Lys Ser Glu Ile Ala His Arg Tyr Asn Asp Leu Gly Glu Gln His Phe
    930                 935                 940

Lys Gly Leu Val Leu Ile Ala Phe Ser Gln Tyr Leu Gln Lys Cys Ser
945                 950                 955                 960

Tyr Asp Glu His Ala Lys Leu Val Gln Glu Val Thr Asp Phe Ala Lys
                965                 970                 975

Thr Cys Val Ala Asp Glu Ser Ala Ala Asn Cys Asp Lys Ser Leu His
            980                 985                 990

Thr Leu Phe Gly Asp Lys Leu Cys  Ala Ile Pro Asn Leu  Arg Glu Asn
        995                 1000                1005

Tyr Gly  Glu Leu Ala Asp Cys  Cys Thr Lys Gln Glu  Pro Glu Arg
    1010                1015                1020

Asn Glu  Cys Phe Leu Gln His  Lys Asp Asp Asn Pro  Ser Leu Pro
    1025                1030                1035

Pro Phe  Glu Arg Pro Glu Ala  Glu Ala Met Cys Thr  Ser Phe Lys
    1040                1045                1050

Glu Asn  Pro Thr Thr Phe Met  Gly His Tyr Leu His  Glu Val Ala
    1055                1060                1065

Arg Arg  His Pro Tyr Phe Tyr  Ala Pro Glu Leu Leu  Tyr Tyr Ala
    1070                1075                1080

Glu Gln  Tyr Asn Glu Ile Leu  Thr Gln Cys Cys Ala  Glu Ala Asp
    1085                1090                1095

Lys Glu  Ser Cys Leu Thr Pro  Lys Leu Asp Gly Val  Lys Glu Lys
    1100                1105                1110

Ala Leu  Val Ser Ser Val Arg  Gln Arg Met Lys Cys  Ser Ser Met
    1115                1120                1125

Gln Lys  Phe Gly Glu Arg Ala  Phe Lys Ala Trp Ala  Val Ala Arg
    1130                1135                1140

Leu Ser  Gln Thr Phe Pro Asn  Ala Asp Phe Ala Glu  Ile Thr Lys
    1145                1150                1155

Leu Ala  Thr Asp Leu Thr Lys  Val Asn Lys Glu Cys  Cys His Gly
    1160                1165                1170

Asp Leu  Leu Glu Cys Ala Asp  Asp Arg Ala Glu Leu  Ala Lys Tyr
    1175                1180                1185

Met Cys  Glu Asn Gln Ala Thr  Ile Ser Ser Lys Leu  Gln Thr Cys
    1190                1195                1200

Cys Asp  Lys Pro Leu Leu Lys  Lys Ala His Cys Leu  Ser Glu Val
    1205                1210                1215

Glu His  Asp Thr Met Pro Ala  Asp Leu Pro Ala Ile  Ala Ala Asp
    1220                1225                1230

Phe Val  Glu Asp Gln Glu Val  Cys Lys Asn Tyr Ala  Glu Ala Lys
    1235                1240                1245
```

```
Asp Val  Phe Leu Gly Thr Phe  Leu Tyr Glu Tyr Ser  Arg Arg His
    1250                 1255                 1260

Pro Asp  Tyr Ser Val Ser Leu  Leu Leu Arg Leu Ala  Lys Lys Tyr
    1265                 1270                 1275

Glu Ala  Thr Leu Glu Lys Cys  Cys Ala Glu Ala Asn  Pro Pro Ala
    1280                 1285                 1290

Cys Tyr  Gly Thr Val Leu Ala  Glu Phe Gln Pro Leu  Val Glu Glu
    1295                 1300                 1305

Pro Lys  Asn Leu Val Lys Thr  Asn Cys Asp Leu Tyr  Glu Lys Leu
    1310                 1315                 1320

Gly Glu  Tyr Gly Phe Gln Asn  Ala Ile Leu Val Arg  Tyr Thr Gln
    1325                 1330                 1335

Lys Ala  Pro Gln Val Ser Thr  Pro Thr Leu Val Glu  Ala Ala Arg
    1340                 1345                 1350

Asn Leu  Gly Arg Val Gly Thr  Lys Cys Cys Thr Leu  Pro Glu Asp
    1355                 1360                 1365

Gln Arg  Leu Pro Cys Val Glu  Asp Tyr Leu Ser Ala  Ile Leu Asn
    1370                 1375                 1380

Arg Val  Cys Leu Leu His Glu  Lys Thr Pro Val Ser  Glu His Val
    1385                 1390                 1395

Thr Lys  Cys Cys Ser Gly Ser  Leu Val Glu Arg Arg  Pro Cys Phe
    1400                 1405                 1410

Ser Ala  Leu Thr Val Asp Glu  Thr Tyr Val Pro Lys  Glu Phe Lys
    1415                 1420                 1425

Ala Glu  Thr Phe Thr Phe His  Ser Asp Ile Cys Thr  Leu Pro Glu
    1430                 1435                 1440

Lys Glu  Lys Gln Ile Lys Lys  Gln Thr Ala Leu Ala  Glu Leu Val
    1445                 1450                 1455

Lys His  Lys Pro Lys Ala Thr  Ala Glu Gln Leu Lys  Thr Val Met
    1460                 1465                 1470

Asp Asp  Phe Ala Gln Phe Leu  Asp Thr Cys Cys Lys  Ala Ala Asp
    1475                 1480                 1485

Lys Asp  Thr Cys Phe Ser Thr  Glu Gly Pro Asn Leu  Val Thr Arg
    1490                 1495                 1500

Cys Lys  Asp Ala Leu Ala
    1505
```

<210> SEQ ID NO 63
<211> LENGTH: 3447
<212> TYPE: DNA
<213> ORGANISM: Artificial Sequence
<220> FEATURE:
<223> OTHER INFORMATION: ENPP121-ENPP3-Fc nucleotide sequence

<400> SEQUENCE: 63

```
atggaaaggg acggatgcgc cggtggtgga tctcgcggag gcgaaggtgg aagggcccct     60

agggaaggac ctgccggaaa cggaagggac aggggacgct ctcacgccgc tgaagctcca    120

ggcgaccctc aggccgctgc ctctctgctg gctcctatgg acgtcggaga agaacccctg    180

gaaaaggccg ccagggccag gactgccaag gaccccaaca cctacaagat catctccctc    240

ttcactttcg ccgtcggagt caacatctgc ctgggattca ccgccgaaaa gcaaggcagc    300

tgcaggaaga agtgctttga tgcatcattt agaggactgg agaactgccg gtgtgatgtg    360

gcatgtaaag accgaggtga ttgctgctgg gattttgaag acacctgtgt ggaatcaact    420
```

```
cgaatatgga tgtgcaataa atttcgttgt ggagagacca gattagaggc cagcctttgc    480
tcttgttcag atgactgttt gcagaggaaa gattgctgtg ctgactataa gagtgtttgc    540
caaggagaaa cctcatggct ggaagaaaac tgtgacacag cccagcagtc tcagtgccca    600
gaagggtttg acctgccacc agttatcttg ttttctatgg atggatttag agctgaatat    660
ttatacacat gggatacttt aatgccaaat atcaataaac tgaaaacatg tggaattcat    720
tcaaaataca tgagagctat gtatcctacc aaaaccttcc caaatcatta caccattgtc    780
acgggcttgt atccagagtc acatggcatc attgacaata atatgtatga tgtaaatctc    840
aacaagaatt tttcactttc ttcaaaggaa caaaataatc cagcctggtg gcatgggcaa    900
ccaatgtggc tgacagcaat gtatcaaggt ttaaaagccg ctacctactt ttggcccgga    960
tcagaagtgg ctataaatgg ctcctttcct tccatataca tgccttacaa cggaagtgtc   1020
ccatttgaag agaggatttc tacactgtta aaatggctgg acctgcccaa agctgaaaga   1080
cccaggtttt ataccatgta ttttgaagaa cctgattcct ctggacatgc aggtggacca   1140
gtcagtgcca gagtaattaa agccttacag gtagtagatc atgcttttgg gatgttgatg   1200
gaaggcctga agcagcggaa tttgcacaac tgtgtcaata tcatccttct ggctgaccat   1260
ggaatggacc agacttattg taacaagatg gaatacatga ctgattattt tcccagaata   1320
aacttcttct acatgtacga agggcctgcc ccccgcatcc gagctcataa tatacctcat   1380
gacttttta gttttaattc tgaggaaatt gttagaaacc tcagttgccg aaaacctgat    1440
cagcatttca agccctattt gactcctgat ttgccaaagc gactgcacta tgccaagaac   1500
gtcagaatcg acaaagttca tctctttgtg gatcaacagt ggctggctgt taggagtaaa   1560
tcaaatacaa attgtggagg aggcaaccat ggttataaca atgagtttag gagcatggag   1620
gctatctttc tggcacatgg acccagtttt aaagagaaga ctgaagttga accatttgaa   1680
aatattgaag tctataacct aatgtgtgat cttctacgca ttcaaccagc accaaacaat   1740
ggaacccatg gtagtttaaa ccatcttctg aaggtgcctt tttatgagcc atcccatgca   1800
gaggaggtgt caaagttttc tgtttgtggc tttgctaatc cattgcccac agagtctctt   1860
gactgtttct gccctcacct acaaaatagt actcagctgg aacaagtgaa tcagatgcta   1920
aatctcaccc aagaagaaat aacagcaaca gtgaaagtaa atttgccatt tgggaggcct   1980
agggtactgc agaagaacgt ggaccactgt ctcctttacc acagggaata tgtcagtgga   2040
tttggaaaag ctatgaggat gcccatgtgg agttcataca cagtccccca gttgggagac   2100
acatcgcctc tgcctcccac tgtcccagac tgtctgcggg ctgatgtcag ggttcctcct   2160
tctgagagcc aaaaatgttc cttctattta gcagacaaga atatcaccca cggcttcctc   2220
tatcctcctg ccagcaatag aacatcagat agccaatatg atgctttaat tactagcaat   2280
ttggtaccta tgtatgaaga attcagaaaa atgtgggact acttccacag tgttcttctt   2340
ataaaacatg ccacagaaag aaatggagta aatgtggtta gtggaccaat atttgattat   2400
aattatgatg gccattttga tgctccagat gaaattacca aacatttagc caacactgat   2460
gttcccatcc caacacacta ctttgtggtg ctgaccagtt gtaaaaacaa gagccacaca   2520
ccggaaaact gccctgggtg gctggatgtc ctacccttta tcatccctca ccgacctacc   2580
aacgtggaga gctgtcctga aggtaaacca gaagctcttt gggttgaaga aagatttaca   2640
gctcacattg cccgggtccg tgatgtagaa cttctcactg ggcttgactt ctatcaggat   2700
aaagtgcagc ctgtctctga aattttgcaa ctaaagacat atttaccaac atttgaaacc   2760
actattgaca aaactcacac atgcccaccg tgcccagcac ctgaactcct ggggggaccg   2820
```

tcagtcttcc tcttcccccc aaaacccaag gacaccctca tgatctcccg gacccctgag 2880
gtcacatgcg tggtggtgga cgtgagccac gaagaccctg aggtcaagtt caactggtac 2940
gtggacggcg tggaggtgca taatgccaag acaaagccgc gggaggagca gtacaacagc 3000
acgtaccgtg tggtcagcgt cctcaccgtc ctgcaccagg actggctgaa tggcaaggag 3060
tacaagtgca aggtctccaa caaagccctc ccagccccca tcgagaaaac catctccaaa 3120
gccaaagggc agccccgaga accacaggtg tacaccctgc ccccatcccg ggaggagatg 3180
accaagaacc aggtcagcct gacctgcctg gtcaaaggct tctatcccag cgacatcgcc 3240
gtggagtggg agagcaatgg gcagccggag aacaactaca agaccacgcc tcccgtgctg 3300
gactccgacg gctccttctt cctctatagc aagctcaccg tggacaagag caggtggcag 3360
caggggaacg tcttctcatg ctccgtgatg catgaggctc tgcacaacca ctacacgcag 3420
aagagcctct ccctgtcccc gggtaaa 3447

<210> SEQ ID NO 64
<211> LENGTH: 4638
<212> TYPE: DNA
<213> ORGANISM: Artificial Sequence
<220> FEATURE:
<223> OTHER INFORMATION: ENPP121-ENPP3-Albumin nucleotide sequence

<400> SEQUENCE: 64
atggaaaggg acggatgcgc cggtggtgga tctcgcggag gcgaaggtgg aagggcccct 60
agggaaggac ctgccggaaa cggaagggac aggggacgct ctcacgccgc tgaagctcca 120
ggcgaccctc aggccgctgc ctctctgctg gctcctatgg acgtcggaga agaacccctg 180
gaaaaggccg ccagggccag gactgccaag gaccccaaca cctacaagat catctccctc 240
ttcactttcg ccgtcggagt caacatctgc ctgggattca ccgccgaaaa gcaaggcagc 300
tgcaggaaga agtgctttga tgcatcattt agaggactgg agaactgccg gtgtgatgtg 360
gcatgtaaag accgaggtga ttgctgctgg gattttgaag acacctgtgt ggaatcaact 420
cgaatatgga tgtgcaataa atttcgttgt ggagagacca gattagaggc cagccttttgc 480 tcttgttcag atgactgttt gcagaggaaa gattgctgtg ctgactataa gagtgtttgc 540
caaggagaaa cctcatggct ggaagaaaac tgtgacacag cccagcagtc tcagtgccca 600
gaagggtttg acctgccacc agttatcttg ttttctatgg atggatttag agctgaatat 660
ttatacacat gggatacttt aatgccaaat atcaataaac tgaaaacatg tggaattcat 720
tcaaaataca tgagagctat gtatcctacc aaaaccttcc caaatcatta caccattgtc 780
acgggcttgt atccagagtc acatggcatc attgacaata atatgtatga tgtaaatctc 840
aacaagaatt tttcactttc ttcaaaggaa caaaataatc cagcctggtg gcatgggcaa 900
ccaatgtggc tgacagcaat gtatcaaggt ttaaaagccg ctacctactt ttggcccgga 960
tcagaagtgg ctataaatgg ctcctttcct tccatataca tgccttacaa cggaagtgtc 1020
ccatttgaag agaggatttc tacactgtta aaatggctgg acctgcccaa agctgaaaga 1080
cccaggtttt ataccatgta ttttgaagaa cctgattcct ctggacatgc aggtggacca 1140
gtcagtgcca gagtaattaa agccttacag gtagtagatc atgcttttgg gatgttgatg 1200
gaaggcctga agcagcggaa tttgcacaac tgtgtcaata tcatccttct ggctgaccat 1260
ggaatggacc agacttattg taacaagatg gaatacatga ctgattattt tcccagaata 1320
aacttcttct acatgtacga agggcctgcc ccccgcatcc gagctcataa tatacctcat 1380

```
gactttttta gttttaattc tgaggaaatt gttagaaacc tcagttgccg aaaacctgat   1440
cagcatttca agccctattt gactcctgat ttgccaaagc gactgcacta tgccaagaac   1500
gtcagaatcg acaaagttca tctctttgtg gatcaacagt ggctggctgt taggagtaaa   1560
tcaaatacaa attgtggagg aggcaaccat ggttataaca atgagtttag gagcatggag   1620
gctatctttc tggcacatgg acccagtttt aaagagaaga ctgaagttga accatttgaa   1680
aatattgaag tctataacct aatgtgtgat cttctacgca ttcaaccagc accaaacaat   1740
ggaacccatg gtagtttaaa ccatcttctg aaggtgcctt tttatgagcc atcccatgca   1800
gaggaggtgt caaagttttc tgtttgtggc tttgctaatc cattgcccac agagtctctt   1860
gactgtttct gccctcacct acaaaatagt actcagctgg aacaagtgaa tcagatgcta   1920
aatctcaccc aagaagaaat aacagcaaca gtgaaagtaa atttgccatt tgggaggcct   1980
agggtactgc agaagaacgt ggaccactgt ctcctttacc acagggaata tgtcagtgga   2040
tttggaaaag ctatgaggat gcccatgtgg agttcataca cagtccccca gttgggagac   2100
acatcgcctc tgcctcccac tgtcccagac tgtctgcggg ctgatgtcag ggttcctcct   2160
tctgagagcc aaaaatgttc cttctattta gcagacaaga atatcaccca cggcttcctc   2220
tatcctcctg ccagcaatag aacatcagat agccaatatg atgctttaat tactagcaat   2280
ttggtaccta tgtatgaaga attcagaaaa atgtgggact acttccacag tgttcttctt   2340
ataaaacatg ccacagaaag aaatggagta aatgtggtta gtggaccaat atttgattat   2400
aattatgatg gccattttga tgctccagat gaaattacca aacatttagc caacactgat   2460
gttcccatcc caacacacta ctttgtggtg ctgaccagtt gtaaaaacaa gagccacaca   2520
ccggaaaact gccctgggtg gctggatgtc ctacccttta tcatccctca ccgacctacc   2580
aacgtggaga gctgtcctga aggtaaacca gaagctcttt gggttgaaga aagatttaca   2640
gctcacattg cccgggtccg tgatgtagaa cttctcactg ggcttgactt ctatcaggat   2700
aaagtgcagc ctgtctctga aattttgcaa ctaaagacat atttaccaac atttgaaacc   2760
actattggtg gaggaggctc tggtggaggc ggtagcggag gcggagggtc gatgaagtgg   2820
gtaaccttta tttcccttct tttctcttt agctcggctt attccagggg tgtgtttcgt    2880
cgagatgcac acaagagtga ggttgctcat cggtttaaag atttgggaga agaaaatttc   2940
aaagccttgg tgttgattgc ctttgctcag tatcttcagc agtgtccatt tgaagatcat   3000
gtaaaattag tgaatgaagt aactgaattt gcaaaaacat gtgttgctga tgagtcagct   3060
gaaaattgtg acaaatcact tcataccctt tttggagaca aattatgcac agttgcaact   3120
cttcgtgaaa cctatggtga aatggctgac tgctgtgcaa aacaagaacc tgagagaaat   3180
gaatgcttct tgcaacacaa agatgacaac ccaaacctcc cccgattggt gagaccagag   3240
gttgatgtga tgtgcactgc ttttcatgac aatgaagaga catttttgaa aaaatactta   3300
tatgaaattg ccagaagaca tccttacttt tatgccccgg aactcctttt ctttgctaaa   3360
aggtataaag ctgcttttac agaatgttgc caagctgctg ataaagctgc ctgcctgttg   3420
ccaaagctcg atgaacttcg ggatgaaggg aaggcttcgt ctgccaaaca gagactcaag   3480
tgtgccagtc tccaaaaatt tggagaaaga gctttcaaag catgggcagt agctcgcctg   3540
agccagagat ttcccaaagc tgagtttgca gaagtttcca agttagtgac agatcttacc   3600
aaagtccaca cggaatgctg ccatggagat ctgcttgaat gtgctgatga cagggcggac   3660
cttgccaagt atatctgtga aaatcaagat tcgatctcca gtaaactgaa ggaatgctgt   3720
gaaaaacctc tgttggaaaa atcccactgc attgccgaag tggaaaatga tgagatgcct   3780
```

gctgacttgc cttcattagc tgctgatttt gttgaaagta aggatgtttg caaaaactat 3840
gctgaggcaa aggatgtctt cctgggcatg tttttgtatg aatatgcaag aaggcatcct 3900
gattactctg tcgtgctgct gctgagactt gccaagacat atgaaaccac tctagagaag 3960
tgctgtgccg ctgcagatcc tcatgaatgc tatgccaaag tgttcgatga atttaaacct 4020
cttgtggaag agcctcagaa tttaatcaaa caaaattgtg agctttttga gcagcttgga 4080
gagtacaaat tccagaatgc gctattagtt cgttacacca agaaagtacc ccaagtgtca 4140
actccaactc ttgtagaggt ctcaagaaac ctaggaaaag tgggcagcaa atgttgtaaa 4200
catcctgaag caaaaagaat gccctgtgca gaagactatc tatccgtggt cctgaaccag 4260
ttatgtgtgt tgcatgagaa aacgccagta agtgacagag tcaccaaatg ctgcacagaa 4320
tccttggtga acaggcgacc atgcttttca gctctggaag tcgatgaaac atacgttccc 4380
aaagagttta atgctgaaac attcaccttc catgcagata tatgcacact ttctgagaag 4440
gagagacaaa tcaagaaaca aactgcactt gttgagctcg tgaaacacaa gcccaaggca 4500
acaaaagagc aactgaaagc tgttatggat gatttcgcag cttttgtaga gaagtgctgc 4560
aaggctgacg ataaggagac ctgctttgcc gaggagggta aaaaacttgt tgctgcaagt 4620
caagctgcct taggctta 4638

<210> SEQ ID NO 65
<211> LENGTH: 8852
<212> TYPE: DNA
<213> ORGANISM: Artificial Sequence
<220> FEATURE:
<223> OTHER INFORMATION: hNPP3-hFc-pcDNA3 nucleotide sequence

<400> SEQUENCE: 65
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttatggaa 900
agggacggat gcgccggtgg tggatctcgc ggaggcgaag gtggaagggc ccctagggaa 960
ggacctgccg gaaacggaag ggacagggga cgctctcacg ccgctgaagc tccaggcgac 1020
cctcaggccg ctgcctctct gctggctcct atggacgtcg gagaagaacc cctggaaaag 1080
gccgccaggg ccaggactgc caaggacccc aacacctaca agatcatctc cctcttcact 1140

-continued

```
ttcgccgtcg gagtcaacat ctgcctggga ttcaccgccg aaaagcaagg cagctgcagg   1200
aagaagtgct ttgatgcatc atttagagga ctggagaact gccggtgtga tgtggcatgt   1260
aaagaccgag gtgattgctg ctgggatttt gaagacacct gtgtggaatc aactcgaata   1320
tggatgtgca ataaatttcg ttgtggagag accagattag aggccagcct ttgctcttgt   1380
tcagatgact gtttgcagag gaaagattgc tgtgctgact ataagagtgt ttgccaagga   1440
gaaacctcat ggctggaaga aaactgtgac acagcccagc agtctcagtg cccagaaggg   1500
tttgacctgc caccagttat cttgttttct atggatggat ttagagctga atatttatac   1560
acatgggata ctttaatgcc aaatatcaat aaactgaaaa catgtggaat tcattcaaaa   1620
tacatgagag ctatgtatcc taccaaaacc ttcccaaatc attacaccat tgtcacgggc   1680
ttgtatccag agtcacatgg catcattgac aataatatgt atgatgtaaa tctcaacaag   1740
aatttttcac tttcttcaaa ggaacaaaat aatccagcct ggtggcatgg gcaaccaatg   1800
tggctgacag caatgtatca aggtttaaaa gccgctacct acttttggcc cggatcagaa   1860
gtggctataa atggctcctt tccttccata tacatgcctt acaacggaag tgtcccattt   1920
gaagagagga tttctacact gttaaaatgg ctggacctgc ccaaagctga aagacccagg   1980
ttttatacca tgtattttga agaacctgat tcctctggac atgcaggtgg accagtcagt   2040
gccagagtaa ttaaagcctt acaggtagta gatcatgctt ttgggatgtt gatggaaggc   2100
ctgaagcagc ggaatttgca caactgtgtc aatatcatcc ttctggctga ccatggaatg   2160
gaccagactt attgtaacaa gatggaatac atgactgatt attttcccag aataaacttc   2220
ttctacatgt acgaagggcc tgccccccgc atccgagctc ataatatacc tcatgacttt   2280
tttagtttta attctgagga aattgttaga aacctcagtt gccgaaaacc tgatcagcat   2340
ttcaagccct atttgactcc tgatttgcca aagcgactgc actatgccaa gaacgtcaga   2400
atcgacaaag ttcatctctt tgtggatcaa cagtggctgg ctgttaggag taaatcaaat   2460
acaaattgtg gaggaggcaa ccatggttat aacaatgagt ttaggagcat ggaggctatc   2520
tttctggcac atggacccag ttttaaagag aagactgaag ttgaaccatt tgaaaatatt   2580
gaagtctata acctaatgtg tgatcttcta cgcattcaac cagcaccaaa caatggaacc   2640
catggtagtt taaaccatct tctgaaggtg cctttttatg agccatccca tgcagaggag   2700
gtgtcaaagt tttctgtttg tggctttgct aatccattgc ccacagagtc tcttgactgt   2760
ttctgccctc acctacaaaa tagtactcag ctggaacaag tgaatcagat gctaaatctc   2820
acccaagaag aaataacagc aacagtgaaa gtaaatttgc catttgggag gcctagggta   2880
ctgcagaaga acgtggacca ctgtctcctt taccacaggg aatatgtcag tggatttgga   2940
aaagctatga ggatgcccat gtggagttca tacacagtcc cccagttggg agacacatcg   3000
cctctgcctc ccactgtccc agactgtctg cgggctgatg tcagggttcc tccttctgag   3060
agccaaaaat gttccttcta tttagcagac aagaatatca cccacggctt cctctatcct   3120
cctgccagca atagaacatc agatagccaa tatgatgctt taattactag caatttggta   3180
cctatgtatg aagaattcag aaaaatgtgg gactacttcc acagtgttct tcttataaaa   3240
catgccacag aaagaaatgg agtaaatgtg gttagtggac caatatttga ttataattat   3300
gatggccatt ttgatgctcc agatgaaatt accaaacatt tagccaacac tgatgttccc   3360
atcccaacac actactttgt ggtgctgacc agttgtaaaa acaagagcca cacaccggaa   3420
aactgccctg ggtggctgga tgtcctaccc tttatcatcc ctcaccgacc taccaacgtg   3480
gagagctgtc ctgaaggtaa accagaagct ctttgggttg aagaaagatt tacagctcac   3540
```

```
attgcccggg tccgtgatgt agaacttctc actgggcttg acttctatca ggataaagtg   3600
cagcctgtct ctgaaatttt gcaactaaag acatatttac caacatttga aaccactatt   3660
gacaaaactc acacatgccc accgtgccca gcacctgaac tcctgggggg accgtcagtc   3720
ttcctcttcc ccccaaaacc caaggacacc ctcatgatct cccggacccc tgaggtcaca   3780
tgcgtggtgg tggacgtgag ccacgaagac cctgaggtca agttcaactg gtacgtggac   3840
ggcgtggagg tgcataatgc caagacaaag ccgcgggagg agcagtacaa cagcacgtac   3900
cgtgtggtca gcgtcctcac cgtcctgcac caggactggc tgaatggcaa ggagtacaag   3960
tgcaaggtct ccaacaaagc cctcccagcc cccatcgaga aaaccatctc caaagccaaa   4020
gggcagcccc gagaaccaca ggtgtacacc ctgcccccat cccgggagga gatgaccaag   4080
aaccaggtca gcctgacctg cctggtcaaa ggcttctatc ccagcgacat cgccgtggag   4140
tgggagagca atgggcagcc ggagaacaac tacaagacca cgcctcccgt gctggactcc   4200
gacggctcct tcttcctcta tagcaagctc accgtggaca agagcaggtg gcagcagggg   4260
aacgtcttct catgctccgt gatgcatgag gctctgcaca accactacac gcagaagagc   4320
ctctccctgt ccccgggtaa atgaaattct gcagatatcc atcacactgg cggccgctcg   4380
agcatgcatc tagagggccc tattctatag tgtcacctaa atgctagagc tcgctgatca   4440
gcctcgactg tgccttctag ttgccagcca tctgttgttt gcccctcccc cgtgccttcc   4500
ttgaccctgg aaggtgccac tcccactgtc ctttcctaat aaaatgagga aattgcatcg   4560
cattgtctga gtaggtgtca ttctattctg gggggtgggg tggggcagga cagcaagggg   4620
gaggattggg aagacaatag caggcatgct ggggatgcgg tgggctctat ggcttctgag   4680
gcggaaagaa ccagctgggg ctctaggggg tatccccacg cgccctgtag cggcgcatta   4740
agcgcggcgg gtgtggtggt tacgcgcagc gtgaccgcta cacttgccag cgccctagcg   4800
cccgctcctt tcgctttctt cccttccttt ctcgccacgt tcgccggctt tccccgtcaa   4860
gctctaaatc ggggcatccc tttagggttc cgatttagtg ctttacggca cctcgacccc   4920
aaaaaacttg attagggtga tggttcacgt agtgggccat cgccctgata gacggttttt   4980
cgccctttga cgttggagtc cacgttcttt aatagtggac tcttgttcca aactggaaca   5040
acactcaacc ctatctcggt ctattctttt gatttataag ggattttggg gatttcggcc   5100
tattggttaa aaaatgagct gatttaacaa aaatttaacg cgaattaatt ctgtggaatg   5160
tgtgtcagtt agggtgtgga aagtccccag gctccccagg caggcagaag tatgcaaagc   5220
atgcatctca attagtcagc aaccaggtgt ggaaagtccc caggctcccc agcaggcaga   5280
agtatgcaaa gcatgcatct caattagtca gcaaccatag tcccgcccct aactccgccc   5340
atcccgcccc taactccgcc cagttccgcc cattctccgc cccatggctg actaattttt   5400
tttatttatg cagaggccga ggccgcctct gcctctgagc tattccagaa gtagtgagga   5460
ggcttttttg gaggcctagg cttttgcaaa aagctcccgg gagcttgtat atccattttc   5520
ggatctgatc aagagacagg atgaggatcg tttcgcatga ttgaacaaga tggattgcac   5580
gcaggttctc cggccgcttg ggtggagagg ctattcggct atgactgggc acaacagaca   5640
atcggctgct ctgatgccgc cgtgttccgg ctgtcagcgc aggggcgccc ggttcttttt   5700
gtcaagaccg acctgtccgg tgccctgaat gaactgcagg acgaggcagc gcggctatcg   5760
tggctggcca cgacgggcgt tccttgcgca gctgtgctcg acgttgtcac tgaagcggga   5820
agggactggc tgctattggg cgaagtgccg ggcaggatc tcctgtcatc tcaccttgct   5880
```

```
cctgccgaga aagtatccat catggctgat gcaatgcggc ggctgcatac gcttgatccg   5940

gctacctgcc cattcgacca ccaagcgaaa catcgcatcg agcgagcacg tactcggatg   6000

gaagccggtc ttgtcgatca ggatgatctg gacgaagagc atcaggggct cgcgccagcc   6060

gaactgttcg ccaggctcaa ggcgcgcatg cccgacggcg aggatctcgt cgtgacccat   6120

ggcgatgcct gcttgccgaa tatcatggtg gaaaatggcc gcttttctgg attcatcgac   6180

tgtggccggc tgggtgtggc ggaccgctat caggacatag cgttggctac ccgtgatatt   6240

gctgaagagc ttggcggcga atgggctgac cgcttcctcg tgctttacgg tatcgccgct   6300

cccgattcgc agcgcatcgc cttctatcgc cttcttgacg agttcttctg agcgggactc   6360

tggggttcga aatgaccgac caagcgacgc ccaacctgcc atcacgagat ttcgattcca   6420

ccgccgcctt ctatgaaagg ttgggcttcg gaatcgtttt ccgggacgcc ggctggatga   6480

tcctccagcg cggggatctc atgctggagt tcttcgccca ccccaacttg tttattgcag   6540

cttataatgg ttacaaataa agcaatagca tcacaaattt cacaaataaa gcattttttt   6600

cactgcattc tagttgtggt ttgtccaaac tcatcaatgt atcttatcat gtctgtatac   6660

cgtcgacctc tagctagagc ttggcgtaat catggtcata gctgtttcct gtgtgaaatt   6720

gttatccgct cacaattcca cacaacatac gagccggaag cataaagtgt aaagcctggg   6780

gtgcctaatg agtgagctaa ctcacattaa ttgcgttgcg ctcactgccc gctttccagt   6840

cgggaaacct gtcgtgccag ctgcattaat gaatcggcca acgcgcgggg agaggcggtt   6900

tgcgtattgg gcgctcttcc gcttcctcgc tcactgactc gctgcgctcg gtcgttcggc   6960

tgcggcgagc ggtatcagct cactcaaagg cggtaatacg gttatccaca gaatcagggg   7020

ataacgcagg aaagaacatg tgagcaaaag gccagcaaaa ggccaggaac cgtaaaaagg   7080

ccgcgttgct ggcgtttttc cataggctcc gcccccctga cgagcatcac aaaaatcgac   7140

gctcaagtca gaggtggcga aacccgacag gactataaag ataccaggcg tttccccctg   7200

gaagctccct cgtgcgctct cctgttccga ccctgccgct taccggatac ctgtccgcct   7260

ttctcccttc gggaagcgtg gcgctttctc aatgctcacg ctgtaggtat ctcagttcgg   7320

tgtaggtcgt tcgctccaag ctgggctgtg tgcacgaacc ccccgttcag cccgaccgct   7380

gcgccttatc cggtaactat cgtcttgagt ccaacccggt aagacacgac ttatcgccac   7440

tggcagcagc cactggtaac aggattagca gagcgaggta tgtaggcggt gctacagagt   7500

tcttgaagtg gtggcctaac tacggctaca ctagaaggac agtatttggt atctgcgctc   7560

tgctgaagcc agttaccttc ggaaaaagag ttggtagctc ttgatccggc aaacaaacca   7620

ccgctggtag cggtggtttt tttgtttgca agcagcagat tacgcgcaga aaaaaaggat   7680

ctcaagaaga tcctttgatc ttttctacgg ggtctgacgc tcagtggaac gaaaactcac   7740

gttaagggat tttggtcatg agattatcaa aaaggatctt cacctagatc cttttaaatt   7800

aaaaatgaag ttttaaatca atctaaagta tatatgagta aacttggtct gacagttacc   7860

aatgcttaat cagtgaggca cctatctcag cgatctgtct atttcgttca tccatagttg   7920

cctgactccc cgtcgtgtag ataactacga tacgggaggg cttaccatct ggccccagtg   7980

ctgcaatgat accgcgagac ccacgctcac cggctccaga tttatcagca ataaaccagc   8040

cagccggaag ggccgagcgc agaagtggtc ctgcaacttt atccgcctcc atccagtcta   8100

ttaattgttg ccgggaagct agagtaagta gttcgccagt taatagtttg cgcaacgttg   8160

ttgccattgc tacaggcatc gtggtgtcac gctcgtcgtt tggtatggct tcattcagct   8220

ccggttccca acgatcaagg cgagttacat gatcccccat gttgtgcaaa aaagcggtta   8280
```

```
gctccttcgg tcctccgatc gttgtcagaa gtaagttggc cgcagtgtta tcactcatgg   8340

ttatggcagc actgcataat tctcttactg tcatgccatc cgtaagatgc ttttctgtga   8400

ctggtgagta ctcaaccaag tcattctgag aatagtgtat gcggcgaccg agttgctctt   8460

gcccggcgtc aatacgggat aataccgcgc cacatagcag aactttaaaa gtgctcatca   8520

ttggaaaacg ttcttcgggg cgaaaactct caaggatctt accgctgttg agatccagtt   8580

cgatgtaacc cactcgtgca cccaactgat cttcagcatc ttttactttc accagcgttt   8640

ctgggtgagc aaaaacagga aggcaaaatg ccgcaaaaaa gggaataagg gcgacacgga   8700

aatgttgaat actcatactc ttcctttttc aatattattg aagcatttat cagggttatt   8760

gtctcatgag cggatacata tttgaatgta tttagaaaaa taaacaaata ggggttccgc   8820

gcacatttcc ccgaaaagtg ccacctgacg tc                                 8852
```

<210> SEQ ID NO 66
<211> LENGTH: 1152
<212> TYPE: PRT
<213> ORGANISM: Artificial Sequence
<220> FEATURE:
<223> OTHER INFORMATION: ENPP121-Fc

<400> SEQUENCE: 66

```
Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255
```

```
Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
    370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
```

```
        675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
        835                 840                 845

Glu Asn Leu Asp Thr Leu Ala Phe Ile Leu Pro His Arg Thr Asp Asn
    850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp Asp Lys Thr
        915                 920                 925

His Thr Cys Pro Pro Cys Pro Ala Pro Glu Leu Leu Gly Gly Pro Ser
    930                 935                 940

Val Phe Leu Phe Pro Pro Lys Pro Lys Asp Thr Leu Met Ile Ser Arg
945                 950                 955                 960

Thr Pro Glu Val Thr Cys Val Val Val Asp Val Ser His Glu Asp Pro
                965                 970                 975

Glu Val Lys Phe Asn Trp Tyr Val Asp Gly Val Glu Val His Asn Ala
            980                 985                 990

Lys Thr Lys Pro Arg Glu Glu Gln  Tyr Asn Ser Thr Tyr  Arg Val Val
        995                 1000                1005

Ser Val  Leu Thr Val Leu His  Gln Asp Trp Leu Asn  Gly Lys Glu
    1010                1015                1020

Tyr Lys  Cys Lys Val Ser Asn  Lys Ala Leu Pro Ala  Pro Ile Glu
    1025                1030                1035

Lys Thr  Ile Ser Lys Ala Lys  Gly Gln Pro Arg Glu  Pro Gln Val
    1040                1045                1050

Tyr Thr  Leu Pro Pro Ser Arg  Glu Glu Met Thr Lys  Asn Gln Val
    1055                1060                1065

Ser Leu  Thr Cys Leu Val Lys  Gly Phe Tyr Pro Ser  Asp Ile Ala
    1070                1075                1080

Val Glu  Trp Glu Ser Asn Gly  Gln Pro Glu Asn Asn  Tyr Lys Thr
    1085                1090                1095
```

```
Thr Pro  Pro Val Leu Asp Ser  Asp Gly Ser Phe Phe  Leu Tyr Ser
    1100                 1105                 1110

Lys Leu  Thr Val Asp Lys Ser  Arg Trp Gln Gln Gly  Asn Val Phe
    1115                 1120                 1125

Ser Cys  Ser Val Met His Glu  Ala Leu His Asn His  Tyr Thr Gln
    1130                 1135                 1140

Lys Ser  Leu Ser Leu Ser Pro  Gly Lys
    1145                 1150
```

<210> SEQ ID NO 67
<211> LENGTH: 1077
<212> TYPE: PRT
<213> ORGANISM: Artificial Sequence
<220> FEATURE:
<223> OTHER INFORMATION: ENPP71-Fc

<400> SEQUENCE: 67

```
Met Arg Gly Pro Ala Val Leu Leu Thr Val Ala Leu Ala Thr Leu Leu
1               5                   10                  15

Ala Pro Gly Ala Gly Leu Lys Pro Ser Cys Ala Lys Glu Val Lys Ser
            20                  25                  30

Cys Lys Gly Arg Cys Phe Glu Arg Thr Phe Gly Asn Cys Arg Cys Asp
        35                  40                  45

Ala Ala Cys Val Glu Leu Gly Asn Cys Cys Leu Asp Tyr Gln Glu Thr
    50                  55                  60

Cys Ile Glu Pro Glu His Ile Trp Thr Cys Asn Lys Phe Arg Cys Gly
65                  70                  75                  80

Glu Lys Arg Leu Thr Arg Ser Leu Cys Ala Cys Ser Asp Asp Cys Lys
                85                  90                  95

Asp Lys Gly Asp Cys Cys Ile Asn Tyr Ser Ser Val Cys Gln Gly Glu
            100                 105                 110

Lys Ser Trp Val Glu Glu Pro Cys Glu Ser Ile Asn Glu Pro Gln Cys
        115                 120                 125

Pro Ala Gly Phe Glu Thr Pro Pro Thr Leu Leu Phe Ser Leu Asp Gly
    130                 135                 140

Phe Arg Ala Glu Tyr Leu His Thr Trp Gly Gly Leu Leu Pro Val Ile
145                 150                 155                 160

Ser Lys Leu Lys Lys Cys Gly Thr Tyr Thr Lys Asn Met Arg Pro Val
                165                 170                 175

Tyr Pro Thr Lys Thr Phe Pro Asn His Tyr Ser Ile Val Thr Gly Leu
            180                 185                 190

Tyr Pro Glu Ser His Gly Ile Ile Asp Asn Lys Met Tyr Asp Pro Lys
        195                 200                 205

Met Asn Ala Ser Phe Ser Leu Lys Ser Lys Glu Lys Phe Asn Pro Glu
    210                 215                 220

Trp Tyr Lys Gly Glu Pro Ile Trp Val Thr Ala Lys Tyr Gln Gly Leu
225                 230                 235                 240

Lys Ser Gly Thr Phe Phe Trp Pro Gly Ser Asp Val Glu Ile Asn Gly
                245                 250                 255

Ile Phe Pro Asp Ile Tyr Lys Met Tyr Asn Gly Ser Val Pro Phe Glu
            260                 265                 270

Glu Arg Ile Leu Ala Val Leu Gln Trp Leu Gln Leu Pro Lys Asp Glu
        275                 280                 285

Arg Pro His Phe Tyr Thr Leu Tyr Leu Glu Glu Pro Asp Ser Ser Gly
    290                 295                 300
```

```
His Ser Tyr Gly Pro Val Ser Ser Glu Val Ile Lys Ala Leu Gln Arg
305                 310                 315                 320

Val Asp Gly Met Val Gly Met Leu Met Asp Gly Leu Lys Glu Leu Asn
                325                 330                 335

Leu His Arg Cys Leu Asn Leu Ile Leu Ile Ser Asp His Gly Met Glu
            340                 345                 350

Gln Gly Ser Cys Lys Lys Tyr Ile Tyr Leu Asn Lys Tyr Leu Gly Asp
        355                 360                 365

Val Lys Asn Ile Lys Val Ile Tyr Gly Pro Ala Ala Arg Leu Arg Pro
    370                 375                 380

Ser Asp Val Pro Asp Lys Tyr Tyr Ser Phe Asn Tyr Glu Gly Ile Ala
385                 390                 395                 400

Arg Asn Leu Ser Cys Arg Glu Pro Asn Gln His Phe Lys Pro Tyr Leu
                405                 410                 415

Lys His Phe Leu Pro Lys Arg Leu His Phe Ala Lys Ser Asp Arg Ile
            420                 425                 430

Glu Pro Leu Thr Phe Tyr Leu Asp Pro Gln Trp Gln Leu Ala Leu Asn
        435                 440                 445

Pro Ser Glu Arg Lys Tyr Cys Gly Ser Gly Phe His Gly Ser Asp Asn
    450                 455                 460

Val Phe Ser Asn Met Gln Ala Leu Phe Val Gly Tyr Gly Pro Gly Phe
465                 470                 475                 480

Lys His Gly Ile Glu Ala Asp Thr Phe Glu Asn Ile Glu Val Tyr Asn
                485                 490                 495

Leu Met Cys Asp Leu Leu Asn Leu Thr Pro Ala Pro Asn Asn Gly Thr
            500                 505                 510

His Gly Ser Leu Asn His Leu Leu Lys Asn Pro Val Tyr Thr Pro Lys
        515                 520                 525

His Pro Lys Glu Val His Pro Leu Val Gln Cys Pro Phe Thr Arg Asn
    530                 535                 540

Pro Arg Asp Asn Leu Gly Cys Ser Cys Asn Pro Ser Ile Leu Pro Ile
545                 550                 555                 560

Glu Asp Phe Gln Thr Gln Phe Asn Leu Thr Val Ala Glu Glu Lys Ile
                565                 570                 575

Ile Lys His Glu Thr Leu Pro Tyr Gly Arg Pro Arg Val Leu Gln Lys
            580                 585                 590

Glu Asn Thr Ile Cys Leu Leu Ser Gln His Gln Phe Met Ser Gly Tyr
        595                 600                 605

Ser Gln Asp Ile Leu Met Pro Leu Trp Thr Ser Tyr Thr Val Asp Arg
    610                 615                 620

Asn Asp Ser Phe Ser Thr Glu Asp Phe Ser Asn Cys Leu Tyr Gln Asp
625                 630                 635                 640

Phe Arg Ile Pro Leu Ser Pro Val His Lys Cys Ser Phe Tyr Lys Asn
                645                 650                 655

Asn Thr Lys Val Ser Tyr Gly Phe Leu Ser Pro Pro Gln Leu Asn Lys
            660                 665                 670

Asn Ser Ser Gly Ile Tyr Ser Glu Ala Leu Leu Thr Thr Asn Ile Val
        675                 680                 685

Pro Met Tyr Gln Ser Phe Gln Val Ile Trp Arg Tyr Phe His Asp Thr
    690                 695                 700

Leu Leu Arg Lys Tyr Ala Glu Glu Arg Asn Gly Val Asn Val Val Ser
705                 710                 715                 720
```

```
Gly Pro Val Phe Asp Phe Asp Tyr Asp Gly Arg Cys Asp Ser Leu Glu
                725                 730                 735

Asn Leu Arg Gln Lys Arg Arg Val Ile Arg Asn Gln Glu Ile Leu Ile
            740                 745                 750

Pro Thr His Phe Phe Ile Val Leu Thr Ser Cys Lys Asp Thr Ser Gln
        755                 760                 765

Thr Pro Leu His Cys Glu Asn Leu Asp Thr Leu Ala Phe Ile Leu Pro
    770                 775                 780

His Arg Thr Asp Asn Ser Glu Ser Cys Val His Gly Lys His Asp Ser
785                 790                 795                 800

Ser Trp Val Glu Glu Leu Leu Met Leu His Arg Ala Arg Ile Thr Asp
                805                 810                 815

Val Glu His Ile Thr Gly Leu Ser Phe Tyr Gln Gln Arg Lys Glu Pro
            820                 825                 830

Val Ser Asp Ile Leu Lys Leu Lys Thr His Leu Pro Thr Phe Ser Gln
        835                 840                 845

Glu Asp Asp Lys Thr His Thr Cys Pro Pro Cys Pro Ala Pro Glu Leu
    850                 855                 860

Leu Gly Gly Pro Ser Val Phe Leu Phe Pro Pro Lys Pro Lys Asp Thr
865                 870                 875                 880

Leu Met Ile Ser Arg Thr Pro Glu Val Thr Cys Val Val Val Asp Val
                885                 890                 895

Ser His Glu Asp Pro Glu Val Lys Phe Asn Trp Tyr Val Asp Gly Val
            900                 905                 910

Glu Val His Asn Ala Lys Thr Lys Pro Arg Glu Glu Gln Tyr Asn Ser
        915                 920                 925

Thr Tyr Arg Val Val Ser Val Leu Thr Val Leu His Gln Asp Trp Leu
    930                 935                 940

Asn Gly Lys Glu Tyr Lys Cys Lys Val Ser Asn Lys Ala Leu Pro Ala
945                 950                 955                 960

Pro Ile Glu Lys Thr Ile Ser Lys Ala Lys Gly Gln Pro Arg Glu Pro
                965                 970                 975

Gln Val Tyr Thr Leu Pro Pro Ser Arg Glu Glu Met Thr Lys Asn Gln
            980                 985                 990

Val Ser Leu Thr Cys Leu Val Lys  Gly Phe Tyr Pro Ser  Asp Ile Ala
        995                 1000                1005

Val Glu  Trp Glu Ser Asn Gly  Gln Pro Glu Asn Asn  Tyr Lys Thr
    1010                1015                1020

Thr Pro  Pro Val Leu Asp Ser  Asp Gly Ser Phe Phe  Leu Tyr Ser
    1025                1030                1035

Lys Leu  Thr Val Asp Lys Ser  Arg Trp Gln Gln Gly  Asn Val Phe
    1040                1045                1050

Ser Cys  Ser Val Met His Glu  Ala Leu His Asn His  Tyr Thr Gln
    1055                1060                1065

Lys Ser  Leu Ser Leu Ser Pro  Gly Lys
    1070                1075
```

```
<210> SEQ ID NO 68
<211> LENGTH: 1079
<212> TYPE: PRT
<213> ORGANISM: Artificial Sequence
<220> FEATURE:
<223> OTHER INFORMATION: ENPP51-Fc

<400> SEQUENCE: 68
```

```
Met Thr Ser Lys Phe Leu Leu Val Ser Phe Ile Leu Ala Ala Leu Ser
1               5                   10                  15

Leu Ser Thr Thr Phe Ser Gly Leu Lys Pro Ser Cys Ala Lys Glu Val
            20                  25                  30

Lys Ser Cys Lys Gly Arg Cys Phe Glu Arg Thr Phe Gly Asn Cys Arg
        35                  40                  45

Cys Asp Ala Ala Cys Val Glu Leu Gly Asn Cys Cys Leu Asp Tyr Gln
    50                  55                  60

Glu Thr Cys Ile Glu Pro Glu His Ile Trp Thr Cys Asn Lys Phe Arg
65                  70                  75                  80

Cys Gly Glu Lys Arg Leu Thr Arg Ser Leu Cys Ala Cys Ser Asp Asp
                85                  90                  95

Cys Lys Asp Lys Gly Asp Cys Cys Ile Asn Tyr Ser Ser Val Cys Gln
            100                 105                 110

Gly Glu Lys Ser Trp Val Glu Glu Pro Cys Glu Ser Ile Asn Glu Pro
        115                 120                 125

Gln Cys Pro Ala Gly Phe Glu Thr Pro Pro Thr Leu Leu Phe Ser Leu
    130                 135                 140

Asp Gly Phe Arg Ala Glu Tyr Leu His Thr Trp Gly Gly Leu Leu Pro
145                 150                 155                 160

Val Ile Ser Lys Leu Lys Lys Cys Gly Thr Tyr Thr Lys Asn Met Arg
                165                 170                 175

Pro Val Tyr Pro Thr Lys Thr Phe Pro Asn His Tyr Ser Ile Val Thr
            180                 185                 190

Gly Leu Tyr Pro Glu Ser His Gly Ile Ile Asp Asn Lys Met Tyr Asp
        195                 200                 205

Pro Lys Met Asn Ala Ser Phe Ser Leu Lys Ser Lys Glu Lys Phe Asn
    210                 215                 220

Pro Glu Trp Tyr Lys Gly Glu Pro Ile Trp Val Thr Ala Lys Tyr Gln
225                 230                 235                 240

Gly Leu Lys Ser Gly Thr Phe Phe Trp Pro Gly Ser Asp Val Glu Ile
                245                 250                 255

Asn Gly Ile Phe Pro Asp Ile Tyr Lys Met Tyr Asn Gly Ser Val Pro
            260                 265                 270

Phe Glu Glu Arg Ile Leu Ala Val Leu Gln Trp Leu Gln Leu Pro Lys
        275                 280                 285

Asp Glu Arg Pro His Phe Tyr Thr Leu Tyr Leu Glu Glu Pro Asp Ser
    290                 295                 300

Ser Gly His Ser Tyr Gly Pro Val Ser Ser Glu Val Ile Lys Ala Leu
305                 310                 315                 320

Gln Arg Val Asp Gly Met Val Gly Met Leu Met Asp Gly Leu Lys Glu
                325                 330                 335

Leu Asn Leu His Arg Cys Leu Asn Leu Ile Leu Ile Ser Asp His Gly
            340                 345                 350

Met Glu Gln Gly Ser Cys Lys Lys Tyr Ile Tyr Leu Asn Lys Tyr Leu
        355                 360                 365

Gly Asp Val Lys Asn Ile Lys Val Ile Tyr Gly Pro Ala Ala Arg Leu
    370                 375                 380

Arg Pro Ser Asp Val Pro Asp Lys Tyr Tyr Ser Phe Asn Tyr Glu Gly
385                 390                 395                 400

Ile Ala Arg Asn Leu Ser Cys Arg Glu Pro Asn Gln His Phe Lys Pro
                405                 410                 415

Tyr Leu Lys His Phe Leu Pro Lys Arg Leu His Phe Ala Lys Ser Asp
```

```
            420                 425                 430

Arg Ile Glu Pro Leu Thr Phe Tyr Leu Asp Pro Gln Trp Gln Leu Ala
        435                 440                 445

Leu Asn Pro Ser Glu Arg Lys Tyr Cys Gly Ser Gly Phe His Gly Ser
    450                 455                 460

Asp Asn Val Phe Ser Asn Met Gln Ala Leu Phe Val Gly Tyr Gly Pro
465                 470                 475                 480

Gly Phe Lys His Gly Ile Glu Ala Asp Thr Phe Glu Asn Ile Glu Val
                485                 490                 495

Tyr Asn Leu Met Cys Asp Leu Leu Asn Leu Thr Pro Ala Pro Asn Asn
            500                 505                 510

Gly Thr His Gly Ser Leu Asn His Leu Leu Lys Asn Pro Val Tyr Thr
        515                 520                 525

Pro Lys His Pro Lys Glu Val His Pro Leu Val Gln Cys Pro Phe Thr
    530                 535                 540

Arg Asn Pro Arg Asp Asn Leu Gly Cys Ser Cys Asn Pro Ser Ile Leu
545                 550                 555                 560

Pro Ile Glu Asp Phe Gln Thr Gln Phe Asn Leu Thr Val Ala Glu Glu
                565                 570                 575

Lys Ile Ile Lys His Glu Thr Leu Pro Tyr Gly Arg Pro Arg Val Leu
            580                 585                 590

Gln Lys Glu Asn Thr Ile Cys Leu Leu Ser Gln His Gln Phe Met Ser
        595                 600                 605

Gly Tyr Ser Gln Asp Ile Leu Met Pro Leu Trp Thr Ser Tyr Thr Val
    610                 615                 620

Asp Arg Asn Asp Ser Phe Ser Thr Glu Asp Phe Ser Asn Cys Leu Tyr
625                 630                 635                 640

Gln Asp Phe Arg Ile Pro Leu Ser Pro Val His Lys Cys Ser Phe Tyr
                645                 650                 655

Lys Asn Asn Thr Lys Val Ser Tyr Gly Phe Leu Ser Pro Pro Gln Leu
            660                 665                 670

Asn Lys Asn Ser Ser Gly Ile Tyr Ser Glu Ala Leu Leu Thr Thr Asn
        675                 680                 685

Ile Val Pro Met Tyr Gln Ser Phe Gln Val Ile Trp Arg Tyr Phe His
    690                 695                 700

Asp Thr Leu Leu Arg Lys Tyr Ala Glu Glu Arg Asn Gly Val Asn Val
705                 710                 715                 720

Val Ser Gly Pro Val Phe Asp Phe Asp Tyr Asp Gly Arg Cys Asp Ser
                725                 730                 735

Leu Glu Asn Leu Arg Gln Lys Arg Arg Val Ile Arg Asn Gln Glu Ile
            740                 745                 750

Leu Ile Pro Thr His Phe Phe Ile Val Leu Thr Ser Cys Lys Asp Thr
        755                 760                 765

Ser Gln Thr Pro Leu His Cys Glu Asn Leu Asp Thr Leu Ala Phe Ile
    770                 775                 780

Leu Pro His Arg Thr Asp Asn Ser Glu Ser Cys Val His Gly Lys His
785                 790                 795                 800

Asp Ser Ser Trp Val Glu Glu Leu Leu Met Leu His Arg Ala Arg Ile
                805                 810                 815

Thr Asp Val Glu His Ile Thr Gly Leu Ser Phe Tyr Gln Gln Arg Lys
            820                 825                 830

Glu Pro Val Ser Asp Ile Leu Lys Leu Lys Thr His Leu Pro Thr Phe
        835                 840                 845
```

```
Ser Gln Glu Asp Asp Lys Thr His Thr Cys Pro Pro Cys Pro Ala Pro
    850                 855                 860

Glu Leu Leu Gly Gly Pro Ser Val Phe Leu Phe Pro Pro Lys Pro Lys
865                 870                 875                 880

Asp Thr Leu Met Ile Ser Arg Thr Pro Glu Val Thr Cys Val Val Val
                885                 890                 895

Asp Val Ser His Glu Asp Pro Glu Val Lys Phe Asn Trp Tyr Val Asp
            900                 905                 910

Gly Val Glu Val His Asn Ala Lys Thr Lys Pro Arg Glu Glu Gln Tyr
        915                 920                 925

Asn Ser Thr Tyr Arg Val Val Ser Val Leu Thr Val Leu His Gln Asp
    930                 935                 940

Trp Leu Asn Gly Lys Glu Tyr Lys Cys Lys Val Ser Asn Lys Ala Leu
945                 950                 955                 960

Pro Ala Pro Ile Glu Lys Thr Ile Ser Lys Ala Lys Gly Gln Pro Arg
                965                 970                 975

Glu Pro Gln Val Tyr Thr Leu Pro Pro Ser Arg Glu Glu Met Thr Lys
            980                 985                 990

Asn Gln Val Ser Leu Thr Cys Leu  Val Lys Gly Phe Tyr  Pro Ser Asp
        995                 1000                1005

Ile Ala  Val Glu Trp Glu Ser  Asn Gly Gln Pro Glu  Asn Asn Tyr
    1010                1015                1020

Lys Thr  Thr Pro Pro Val Leu  Asp Ser Asp Gly Ser  Phe Phe Leu
    1025                1030                1035

Tyr Ser  Lys Leu Thr Val Asp  Lys Ser Arg Trp Gln  Gln Gly Asn
    1040                1045                1050

Val Phe  Ser Cys Ser Val Met  His Glu Ala Leu His  Asn His Tyr
    1055                1060                1065

Thr Gln  Lys Ser Leu Ser Leu  Ser Pro Gly Lys
    1070                1075
```

<210> SEQ ID NO 69
<211> LENGTH: 1472
<212> TYPE: PRT
<213> ORGANISM: Artificial Sequence
<220> FEATURE:
<223> OTHER INFORMATION: ENPP121-ALB

<400> SEQUENCE: 69

```
Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125
```

```
Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
    370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540
```

```
Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
        835                 840                 845

Glu Asn Leu Asp Thr Leu Ala Phe Ile Leu Pro His Arg Thr Asp Asn
    850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp Arg Ser Gly
        915                 920                 925

Ser Gly Gly Ser Met Lys Trp Val Thr Phe Leu Leu Leu Leu Phe Val
    930                 935                 940

Ser Gly Ser Ala Phe Ser Arg Gly Val Phe Arg Arg Glu Ala His Lys
945                 950                 955                 960

Ser Glu Ile Ala His Arg Tyr Asn Asp Leu Gly Glu Gln His Phe Lys
```

```
                965                 970                 975

Gly Leu Val Leu Ile Ala Phe Ser Gln Tyr Leu Gln Lys Cys Ser Tyr
            980                 985                 990

Asp Glu His Ala Lys Leu Val Gln  Glu Val Thr Asp Phe  Ala Lys Thr
        995                 1000                1005

Cys Val  Ala Asp Glu Ser Ala  Ala Asn Cys Asp Lys  Ser Leu His
    1010                 1015                 1020

Thr Leu  Phe Gly Asp Lys Leu  Cys Ala Ile Pro Asn  Leu Arg Glu
    1025                 1030                 1035

Asn Tyr  Gly Glu Leu Ala Asp  Cys Cys Thr Lys Gln  Glu Pro Glu
    1040                 1045                 1050

Arg Asn  Glu Cys Phe Leu Gln  His Lys Asp Asp Asn  Pro Ser Leu
    1055                 1060                 1065

Pro Pro  Phe Glu Arg Pro Glu  Ala Glu Ala Met Cys  Thr Ser Phe
    1070                 1075                 1080

Lys Glu  Asn Pro Thr Thr Phe  Met Gly His Tyr Leu  His Glu Val
    1085                 1090                 1095

Ala Arg  Arg His Pro Tyr Phe  Tyr Ala Pro Glu Leu  Leu Tyr Tyr
    1100                 1105                 1110

Ala Glu  Gln Tyr Asn Glu Ile  Leu Thr Gln Cys Cys  Ala Glu Ala
    1115                 1120                 1125

Asp Lys  Glu Ser Cys Leu Thr  Pro Lys Leu Asp Gly  Val Lys Glu
    1130                 1135                 1140

Lys Ala  Leu Val Ser Ser Val  Arg Gln Arg Met Lys  Cys Ser Ser
    1145                 1150                 1155

Met Gln  Lys Phe Gly Glu Arg  Ala Phe Lys Ala Trp  Ala Val Ala
    1160                 1165                 1170

Arg Leu  Ser Gln Thr Phe Pro  Asn Ala Asp Phe Ala  Glu Ile Thr
    1175                 1180                 1185

Lys Leu  Ala Thr Asp Leu Thr  Lys Val Asn Lys Glu  Cys Cys His
    1190                 1195                 1200

Gly Asp  Leu Leu Glu Cys Ala  Asp Asp Arg Ala Glu  Leu Ala Lys
    1205                 1210                 1215

Tyr Met  Cys Glu Asn Gln Ala  Thr Ile Ser Ser Lys  Leu Gln Thr
    1220                 1225                 1230

Cys Cys  Asp Lys Pro Leu Leu  Lys Lys Ala His Cys  Leu Ser Glu
    1235                 1240                 1245

Val Glu  His Asp Thr Met Pro  Ala Asp Leu Pro Ala  Ile Ala Ala
    1250                 1255                 1260

Asp Phe  Val Glu Asp Gln Glu  Val Cys Lys Asn Tyr  Ala Glu Ala
    1265                 1270                 1275

Lys Asp  Val Phe Leu Gly Thr  Phe Leu Tyr Glu Tyr  Ser Arg Arg
    1280                 1285                 1290

His Pro  Asp Tyr Ser Val Ser  Leu Leu Leu Arg Leu  Ala Lys Lys
    1295                 1300                 1305

Tyr Glu  Ala Thr Leu Glu Lys  Cys Cys Ala Glu Ala  Asn Pro Pro
    1310                 1315                 1320

Ala Cys  Tyr Gly Thr Val Leu  Ala Glu Phe Gln Pro  Leu Val Glu
    1325                 1330                 1335

Glu Pro  Lys Asn Leu Val Lys  Thr Asn Cys Asp Leu  Tyr Glu Lys
    1340                 1345                 1350

Leu Gly  Glu Tyr Gly Phe Gln  Asn Ala Ile Leu Val  Arg Tyr Thr
    1355                 1360                 1365
```

```
Gln Lys  Ala Pro Gln Val Ser  Thr Pro Thr Leu Val  Glu Ala Ala
    1370                 1375                 1380

Arg Asn  Leu Gly Arg Val Gly  Thr Lys Cys Cys Thr  Leu Pro Glu
    1385                 1390                 1395

Asp Gln  Arg Leu Pro Cys Val  Glu Asp Tyr Leu Ser  Ala Ile Leu
    1400                 1405                 1410

Asn Arg  Val Cys Leu Leu His  Glu Lys Thr Pro Val  Ser Glu His
    1415                 1420                 1425

Val Thr  Lys Cys Cys Ser Gly  Ser Leu Val Glu Arg  Arg Pro Cys
    1430                 1435                 1440

Phe Ser  Ala Leu Thr Val Asp  Glu Thr Tyr Val Pro  Lys Glu Phe
    1445                 1450                 1455

Lys Ala  Glu Thr Phe Thr Phe  His Ser Asp Ile Cys  Thr Leu
    1460                 1465                 1470


<210> SEQ ID NO 70
<211> LENGTH: 1396
<212> TYPE: PRT
<213> ORGANISM: Artificial Sequence
<220> FEATURE:
<223> OTHER INFORMATION: NPP71-ALB

<400> SEQUENCE: 70

Met Arg Gly Pro Ala Val Leu Leu Thr Val Ala Leu Ala Thr Leu Leu
1               5                   10                  15

Ala Pro Gly Ala Gly Leu Lys Pro Ser Cys Ala Lys Glu Val Lys Ser
            20                  25                  30

Cys Lys Gly Arg Cys Phe Glu Arg Thr Phe Gly Asn Cys Arg Cys Asp
        35                  40                  45

Ala Ala Cys Val Glu Leu Gly Asn Cys Cys Leu Asp Tyr Gln Glu Thr
    50                  55                  60

Cys Ile Glu Pro Glu His Ile Trp Thr Cys Asn Lys Phe Arg Cys Gly
65                  70                  75                  80

Glu Lys Arg Leu Thr Arg Ser Leu Cys Ala Cys Ser Asp Asp Cys Lys
                85                  90                  95

Asp Lys Gly Asp Cys Cys Ile Asn Tyr Ser Ser Val Cys Gln Gly Glu
            100                 105                 110

Lys Ser Trp Val Glu Glu Pro Cys Glu Ser Ile Asn Glu Pro Gln Cys
        115                 120                 125

Pro Ala Gly Phe Glu Thr Pro Pro Thr Leu Leu Phe Ser Leu Asp Gly
    130                 135                 140

Phe Arg Ala Glu Tyr Leu His Thr Trp Gly Gly Leu Leu Pro Val Ile
145                 150                 155                 160

Ser Lys Leu Lys Lys Cys Gly Thr Tyr Thr Lys Asn Met Arg Pro Val
                165                 170                 175

Tyr Pro Thr Lys Thr Phe Pro Asn His Tyr Ser Ile Val Thr Gly Leu
            180                 185                 190

Tyr Pro Glu Ser His Gly Ile Ile Asp Asn Lys Met Tyr Asp Pro Lys
        195                 200                 205

Met Asn Ala Ser Phe Ser Leu Lys Ser Lys Glu Lys Phe Asn Pro Glu
    210                 215                 220

Trp Tyr Lys Gly Glu Pro Ile Trp Val Thr Ala Lys Tyr Gln Gly Leu
225                 230                 235                 240

Lys Ser Gly Thr Phe Phe Trp Pro Gly Ser Asp Val Glu Ile Asn Gly
                245                 250                 255
```

```
Ile Phe Pro Asp Ile Tyr Lys Met Tyr Asn Gly Ser Val Pro Phe Glu
            260                 265                 270

Glu Arg Ile Leu Ala Val Leu Gln Trp Leu Gln Leu Pro Lys Asp Glu
        275                 280                 285

Arg Pro His Phe Tyr Thr Leu Tyr Leu Glu Glu Pro Asp Ser Ser Gly
    290                 295                 300

His Ser Tyr Gly Pro Val Ser Ser Glu Val Ile Lys Ala Leu Gln Arg
305                 310                 315                 320

Val Asp Gly Met Val Gly Met Leu Met Asp Gly Leu Lys Glu Leu Asn
                325                 330                 335

Leu His Arg Cys Leu Asn Leu Ile Leu Ile Ser Asp His Gly Met Glu
            340                 345                 350

Gln Gly Ser Cys Lys Lys Tyr Ile Tyr Leu Asn Lys Tyr Leu Gly Asp
        355                 360                 365

Val Lys Asn Ile Lys Val Ile Tyr Gly Pro Ala Ala Arg Leu Arg Pro
    370                 375                 380

Ser Asp Val Pro Asp Lys Tyr Tyr Ser Phe Asn Tyr Glu Gly Ile Ala
385                 390                 395                 400

Arg Asn Leu Ser Cys Arg Glu Pro Asn Gln His Phe Lys Pro Tyr Leu
                405                 410                 415

Lys His Phe Leu Pro Lys Arg Leu His Phe Ala Lys Ser Asp Arg Ile
            420                 425                 430

Glu Pro Leu Thr Phe Tyr Leu Asp Pro Gln Trp Gln Leu Ala Leu Asn
        435                 440                 445

Pro Ser Glu Arg Lys Tyr Cys Gly Ser Gly Phe His Gly Ser Asp Asn
    450                 455                 460

Val Phe Ser Asn Met Gln Ala Leu Phe Val Gly Tyr Gly Pro Gly Phe
465                 470                 475                 480

Lys His Gly Ile Glu Ala Asp Thr Phe Glu Asn Ile Glu Val Tyr Asn
                485                 490                 495

Leu Met Cys Asp Leu Leu Asn Leu Thr Pro Ala Pro Asn Asn Gly Thr
            500                 505                 510

His Gly Ser Leu Asn His Leu Leu Lys Asn Pro Val Tyr Thr Pro Lys
        515                 520                 525

His Pro Lys Glu Val His Pro Leu Val Gln Cys Pro Phe Thr Arg Asn
    530                 535                 540

Pro Arg Asp Asn Leu Gly Cys Ser Cys Asn Pro Ser Ile Leu Pro Ile
545                 550                 555                 560

Glu Asp Phe Gln Thr Gln Phe Asn Leu Thr Val Ala Glu Glu Lys Ile
                565                 570                 575

Ile Lys His Glu Thr Leu Pro Tyr Gly Arg Pro Arg Val Leu Gln Lys
            580                 585                 590

Glu Asn Thr Ile Cys Leu Leu Ser Gln His Gln Phe Met Ser Gly Tyr
        595                 600                 605

Ser Gln Asp Ile Leu Met Pro Leu Trp Thr Ser Tyr Thr Val Asp Arg
    610                 615                 620

Asn Asp Ser Phe Ser Thr Glu Asp Phe Ser Asn Cys Leu Tyr Gln Asp
625                 630                 635                 640

Phe Arg Ile Pro Leu Ser Pro Val His Lys Cys Ser Phe Tyr Lys Asn
                645                 650                 655

Asn Thr Lys Val Ser Tyr Gly Phe Leu Ser Pro Pro Gln Leu Asn Lys
            660                 665                 670
```

```
Asn Ser Ser Gly Ile Tyr Ser Glu Ala Leu Leu Thr Thr Asn Ile Val
        675                 680                 685

Pro Met Tyr Gln Ser Phe Gln Val Ile Trp Arg Tyr Phe His Asp Thr
    690                 695                 700

Leu Leu Arg Lys Tyr Ala Glu Glu Arg Asn Gly Val Asn Val Val Ser
705                 710                 715                 720

Gly Pro Val Phe Asp Phe Asp Tyr Asp Gly Arg Cys Asp Ser Leu Glu
                725                 730                 735

Asn Leu Arg Gln Lys Arg Arg Val Ile Arg Asn Gln Glu Ile Leu Ile
            740                 745                 750

Pro Thr His Phe Phe Ile Val Leu Thr Ser Cys Lys Asp Thr Ser Gln
        755                 760                 765

Thr Pro Leu His Cys Glu Asn Leu Asp Thr Leu Ala Phe Ile Leu Pro
    770                 775                 780

His Arg Thr Asp Asn Ser Glu Ser Cys Val His Gly Lys His Asp Ser
785                 790                 795                 800

Ser Trp Val Glu Glu Leu Leu Met Leu His Arg Ala Arg Ile Thr Asp
                805                 810                 815

Val Glu His Ile Thr Gly Leu Ser Phe Tyr Gln Gln Arg Lys Glu Pro
            820                 825                 830

Val Ser Asp Ile Leu Lys Leu Lys Thr His Leu Pro Thr Phe Ser Gln
        835                 840                 845

Glu Asp Gly Gly Ser Gly Gly Ser Met Lys Trp Val Thr Phe Leu Leu
    850                 855                 860

Leu Leu Phe Val Ser Gly Ser Ala Phe Ser Arg Gly Val Phe Arg Arg
865                 870                 875                 880

Glu Ala His Lys Ser Glu Ile Ala His Arg Tyr Asn Asp Leu Gly Glu
                885                 890                 895

Gln His Phe Lys Gly Leu Val Leu Ile Ala Phe Ser Gln Tyr Leu Gln
            900                 905                 910

Lys Cys Ser Tyr Asp Glu His Ala Lys Leu Val Gln Glu Val Thr Asp
        915                 920                 925

Phe Ala Lys Thr Cys Val Ala Asp Glu Ser Ala Ala Asn Cys Asp Lys
    930                 935                 940

Ser Leu His Thr Leu Phe Gly Asp Lys Leu Cys Ala Ile Pro Asn Leu
945                 950                 955                 960

Arg Glu Asn Tyr Gly Glu Leu Ala Asp Cys Cys Thr Lys Gln Glu Pro
                965                 970                 975

Glu Arg Asn Glu Cys Phe Leu Gln His Lys Asp Asp Asn Pro Ser Leu
            980                 985                 990

Pro Pro Phe Glu Arg Pro Glu Ala  Glu Ala Met Cys Thr  Ser Phe Lys
        995                 1000                1005

Glu Asn  Pro Thr Thr Phe Met  Gly His Tyr Leu His  Glu Val Ala
    1010                1015                1020

Arg Arg  His Pro Tyr Phe Tyr  Ala Pro Glu Leu Leu  Tyr Tyr Ala
    1025                1030                1035

Glu Gln  Tyr Asn Glu Ile Leu  Thr Gln Cys Cys Ala  Glu Ala Asp
    1040                1045                1050

Lys Glu  Ser Cys Leu Thr Pro  Lys Leu Asp Gly Val  Lys Glu Lys
    1055                1060                1065

Ala Leu  Val Ser Ser Val Arg  Gln Arg Met Lys Cys  Ser Ser Met
    1070                1075                1080

Gln Lys  Phe Gly Glu Arg Ala  Phe Lys Ala Trp Ala  Val Ala Arg
```

```
    1085                1090                1095

Leu Ser  Gln Thr Phe Pro Asn  Ala Asp Phe Ala Glu  Ile Thr Lys
    1100                1105                1110

Leu Ala  Thr Asp Leu Thr Lys  Val Asn Lys Glu Cys  Cys His Gly
    1115                1120                1125

Asp Leu  Leu Glu Cys Ala Asp  Asp Arg Ala Glu Leu  Ala Lys Tyr
    1130                1135                1140

Met Cys  Glu Asn Gln Ala Thr  Ile Ser Ser Lys Leu  Gln Thr Cys
    1145                1150                1155

Cys Asp  Lys Pro Leu Leu Lys  Lys Ala His Cys Leu  Ser Glu Val
    1160                1165                1170

Glu His  Asp Thr Met Pro Ala  Asp Leu Pro Ala Ile  Ala Ala Asp
    1175                1180                1185

Phe Val  Glu Asp Gln Glu Val  Cys Lys Asn Tyr Ala  Glu Ala Lys
    1190                1195                1200

Asp Val  Phe Leu Gly Thr Phe  Leu Tyr Glu Tyr Ser  Arg Arg His
    1205                1210                1215

Pro Asp  Tyr Ser Val Ser Leu  Leu Leu Arg Leu Ala  Lys Lys Tyr
    1220                1225                1230

Glu Ala  Thr Leu Glu Lys Cys  Cys Ala Glu Ala Asn  Pro Pro Ala
    1235                1240                1245

Cys Tyr  Gly Thr Val Leu Ala  Glu Phe Gln Pro Leu  Val Glu Glu
    1250                1255                1260

Pro Lys  Asn Leu Val Lys Thr  Asn Cys Asp Leu Tyr  Glu Lys Leu
    1265                1270                1275

Gly Glu  Tyr Gly Phe Gln Asn  Ala Ile Leu Val Arg  Tyr Thr Gln
    1280                1285                1290

Lys Ala  Pro Gln Val Ser Thr  Pro Thr Leu Val Glu  Ala Ala Arg
    1295                1300                1305

Asn Leu  Gly Arg Val Gly Thr  Lys Cys Cys Thr Leu  Pro Glu Asp
    1310                1315                1320

Gln Arg  Leu Pro Cys Val Glu  Asp Tyr Leu Ser Ala  Ile Leu Asn
    1325                1330                1335

Arg Val  Cys Leu Leu His Glu  Lys Thr Pro Val Ser  Glu His Val
    1340                1345                1350

Thr Lys  Cys Cys Ser Gly Ser  Leu Val Glu Arg Arg  Pro Cys Phe
    1355                1360                1365

Ser Ala  Leu Thr Val Asp Glu  Thr Tyr Val Pro Lys  Glu Phe Lys
    1370                1375                1380

Ala Glu  Thr Phe Thr Phe His  Ser Asp Ile Cys Thr  Leu
    1385                1390                1395
```

<210> SEQ ID NO 71
<211> LENGTH: 3456
<212> TYPE: DNA
<213> ORGANISM: Artificial Sequence
<220> FEATURE:
<223> OTHER INFORMATION: ENPP121-Fc nucleotide sequence

<400> SEQUENCE: 71

```
atggaaaggg acggatgcgc cggtggtgga tctcgcggag gcgaaggtgg aagggcccct     60

agggaaggac ctgccggaaa cggaagggac aggggacgct ctcacgccgc tgaagctcca    120

ggcgaccctc aggccgctgc ctctctgctg gctcctatgg acgtcggaga agaacccctg    180

gaaaaggccg ccagggccag gactgccaag gaccccaaca cctacaagat catctccctc    240
```

```
ttcactttcg ccgtcggagt caacatctgc ctgggattca ccgccggact gaagcccagc    300
tgcgccaaag aagtgaagtc ctgcaagggc cggtgcttcg agcggacctt cggcaactgc    360
agatgcgacg ccgcctgtgt ggaactgggc aactgctgcc tggactacca ggaaacctgc    420
atcgagcccg agcacatctg gacctgcaac aagttcagat gcggcgagaa gcggctgacc    480
agatccctgt gtgcctgcag cgacgactgc aaggacaagg gcgactgctg catcaactac    540
agcagcgtgt gccagggcga gaagtcctgg gtggaagaac cctgcgagag catcaacgag    600
ccccagtgcc ctgccggctt cgagacacct cctaccctgc tgttcagcct ggacggcttt    660
cgggccgagt acctgcacac atggggaggc ctgctgcccg tgatcagcaa gctgaagaag    720
tgcggcacct acaccaagaa catgcggccc gtgtacccca ccaagacctt ccccaaccac    780
tactccatcg tgaccggcct gtaccccgag agccacggca tcatcgacaa caagatgtac    840
gaccccaaga tgaacgccag cttcagcctg aagtccaaag agaagttcaa ccccgagtgg    900
tataagggcg agcccatctg ggtcaccgcc aagtaccagg gcctgaaaag cggcacattc    960
ttttggcccg gcagcgacgt ggaaatcaac ggcatcttcc ccgacatcta taagatgtac   1020
aacggcagcg tgcccttcga ggaacggatc ctggctgtgc tgcagtggct gcagctgccc   1080
aaggatgagc ggccccactt ctacaccctg tacctggaag aacctgacag cagcggccac   1140
agctacggcc ctgtgtccag cgaagtgatc aaggccctgc agcgggtgga cggcatggtg   1200
ggaatgctga tggacggcct gaaagagctg aacctgcaca gatgcctgaa cctgatcctg   1260
atcagcgacc acggcatgga acagggatcc tgcaagaagt acatctacct gaacaagtac   1320
ctgggcgacg tgaagaacat caaagtgatc tacggcccag ccgccagact gaggcctagc   1380
gacgtgcccg acaagtacta cagcttcaac tacgagggaa tcgcccggaa cctgagctgc   1440
agagagccca accagcactt caagccctac ctgaagcact tcctgcccaa gcggctgcac   1500
ttcgccaaga gcgacagaat cgagcccctg accttctacc tggaccccca gtggcagctg   1560
gccctgaatc ccagcgagag aaagtactgc ggcagcggct tccacggctc cgacaacgtg   1620
ttcagcaaca tgcaggccct gttcgtgggc tacggacccg gctttaagca cggcatcgag   1680
gccgacacct tcgagaacat cgaggtgtac aatctgatgt gcgacctgct gaatctgacc   1740
cctgccccca acaatggcac ccacggcagc ctgaaccatc tgctgaagaa ccccgtgtac   1800
acccctaagc accccaaaga ggtgcacccc ctggtgcagt gccccttcac cagaaacccc   1860
agagacaacc tgggctgtag ctgcaacccc agcatcctgc ccatcgagga cttccagacc   1920
cagttcaacc tgaccgtggc cgaggaaaag atcatcaagc acgagacact gccctacggc   1980
agaccccggg tgctgcagaa agagaacacc atctgcctgc tgagccagca ccagttcatg   2040
agcggctact cccaggacat cctgatgccc ctgtggacca gctacaccgt ggaccggaac   2100
gacagcttct ccaccgagga tttcagcaac tgcctgtacc aggatttccg gatccccctg   2160
agccccgtgc acaagtgcag cttctacaag aacaacacca aggtgtccta cggcttcctg   2220
agccctcccc agctgaacaa gaacagctcc ggcatctaca gcgaggccct gctgactacc   2280
aacatcgtgc ccatgtacca gagcttccaa gtgatctggc ggtacttcca cgacaccctg   2340
ctgcggaagt acgccgaaga acggaacggc gtgaacgtgg tgtccggccc agtgttcgac   2400
ttcgactacg acggcagatg tgacagcctg gaaaatctgc ggcagaaaag aagagtgatc   2460
cggaaccagg aaattctgat ccctacccac ttctttatcg tgctgacaag ctgcaaggat   2520
accagccaga cccccctgca ctgcgagaac ctggataccc tggccttcat cctgcctcac   2580
```

cggaccgaca acagcgagag ctgtgtgcac ggcaagcacg acagctcttg ggtggaagaa 2640
ctgctgatgc tgcaccgggc cagaatcacc gatgtggaac acatcaccgg cctgagcttt 2700
taccagcagc ggaaagaacc cgtgtccgat atcctgaagc tgaaaaccca tctgcccacc 2760
ttcagccagg aagatgacaa gacccacact tgcccccccct gcccagctcc tgaactgctg 2820
ggaggaccct ctgtgttcct gttcccccca aagcccaagg acaccctgat gatctctagg 2880
acccccgaag tcacttgcgt cgtcgtcgac gtgtcccacg aggaccctga agtcaagttc 2940
aactggtacg tcgacggtgt cgaagtccac aacgccaaga ccaagcccag ggaagaacag 3000
tacaactcta cctaccgcgt cgtcagcgtc ctgaccgtcc tgcaccagga ctggctgaac 3060
ggaaaggaat acaagtgcaa ggtgtccaac aaggccctgc ctgcccccat cgaaaagacc 3120
atctctaagg ccaagggaca gccccgcgaa ccccaggtct acaccctgcc accctctagg 3180
gaagaaatga ccaagaacca ggtgtccctg acctgcctgg tcaagggatt ctacccctct 3240
gacatcgccg tcgaatggga atctaacgga cagcccgaaa acaactacaa gaccaccccc 3300
cctgtcctgg actctgacgg atcattcttc ctgtactcta agctgactgt cgacaagtct 3360
aggtggcagc agggaaacgt gttctcttgc tctgtcatgc acgaagccct gcacaaccac 3420
tacacccaga agtctctgtc tctgtccccc ggaaag 3456

<210> SEQ ID NO 72
<211> LENGTH: 4662
<212> TYPE: DNA
<213> ORGANISM: Artificial Sequence
<220> FEATURE:
<223> OTHER INFORMATION: ENPP121-Albumin nucleotide sequence

<400> SEQUENCE: 72
atggaaaggg acggatgcgc cggtggtgga tctcgcggag gcgaaggtgg aagggcccct 60
agggaaggac ctgccggaaa cggaagggac aggggacgct ctcacgccgc tgaagctcca 120
ggcgaccctc aggccgctgc ctctctgctg gctcctatgg acgtcggaga agaacccctg 180
gaaaaggccg ccagggccag gactgccaag gaccccaaca cctacaagat catctccctc 240
ttcactttcg ccgtcggagt caacatctgc ctgggattca ccgccggact gaagcccagc 300
tgcgccaaag aagtgaagtc ctgcaagggc cggtgcttcg agcggacctt cggcaactgc 360
agatgcgacg ccgcctgtgt ggaactgggc aactgctgcc tggactacca ggaaacctgc 420
atcgagcccg agcacatctg gacctgcaac aagttcagat gcggcgagaa gcggctgacc 480
agatccctgt gtgcctgcag cgacgactgc aaggacaagg gcgactgctg catcaactac 540
agcagcgtgt gccagggcga gaagtcctgg gtggaagaac cctgcgagag catcaacgag 600
ccccagtgcc ctgccggctt cgagacacct cctaccctgc tgttcagcct ggacggcttt 660
cgggccgagt acctgcacac atggggaggc ctgctgcccg tgatcagcaa gctgaagaag 720
tgcggcacct acaccaagaa catgcggccc gtgtacccca ccaagacctt ccccaaccac 780
tactccatcg tgaccggcct gtaccccgag agccacggca tcatcgacaa caagatgtac 840
gaccccaaga tgaacgccag cttcagcctg aagtccaaag agaagttcaa ccccgagtgg 900
tataagggcg agcccatctg ggtcaccgcc aagtaccagg gcctgaaaag cggcacattc 960
ttttggcccg gcagcgacgt ggaaatcaac ggcatcttcc ccgacatcta taagatgtac 1020
aacggcagcg tgcccttcga ggaacggatc ctggctgtgc tgcagtggct gcagctgccc 1080
aaggatgagc ggccccactt ctacaccctg tacctggaag aacctgacag cagcggccac 1140
agctacggcc ctgtgtccag cgaagtgatc aaggccctgc agcgggtgga cggcatggtg 1200

```
ggaatgctga tggacggcct gaaagagctg aacctgcaca gatgcctgaa cctgatcctg   1260
atcagcgacc acggcatgga acagggatcc tgcaagaagt acatctacct gaacaagtac   1320
ctgggcgacg tgaagaacat caaagtgatc tacggcccag ccgccagact gaggcctagc   1380
gacgtgcccg acaagtacta cagcttcaac tacgagggaa tcgcccggaa cctgagctgc   1440
agagagccca accagcactt caagccctac ctgaagcact tcctgcccaa gcggctgcac   1500
ttcgccaaga gcgacagaat cgagcccctg accttctacc tggacccccca gtggcagctg   1560
gccctgaatc ccagcgagag aaagtactgc ggcagcggct tccacggctc cgacaacgtg   1620
ttcagcaaca tgcaggccct gttcgtgggc tacggacccg gctttaagca cggcatcgag   1680
gccgacacct tcgagaacat cgaggtgtac aatctgatgt gcgacctgct gaatctgacc   1740
cctgccccca acaatggcac ccacggcagc ctgaaccatc tgctgaagaa ccccgtgtac   1800
acccctaagc accccaaaga ggtgcacccc ctggtgcagt gccccttcac cagaaacccc   1860
agagacaacc tgggctgtag ctgcaacccc agcatcctgc ccatcgagga cttccagacc   1920
cagttcaacc tgaccgtggc cgaggaaaag atcatcaagc acgagacact gccctacggc   1980
agaccccggg tgctgcagaa agagaacacc atctgcctgc tgagccagca ccagttcatg   2040
agcggctact cccaggacat cctgatgccc ctgtggacca gctacaccgt ggaccggaac   2100
gacagcttct ccaccgagga tttcagcaac tgcctgtacc aggatttccg gatccccctg   2160
agccccgtgc acaagtgcag cttctacaag aacaacacca aggtgtccta cggcttcctg   2220
agccctcccc agctgaacaa gaacagctcc ggcatctaca gcgaggccct gctgactacc   2280
aacatcgtgc ccatgtacca gagcttccaa gtgatctggc ggtacttcca cgacaccctg   2340
ctgcggaagt acgccgaaga acggaacggc gtgaacgtgg tgtccggccc agtgttcgac   2400
ttcgactacg acggcagatg tgacagcctg gaaaatctgc ggcagaaaag aagagtgatc   2460
cggaaccagg aaattctgat ccctacccac ttctttatcg tgctgacaag ctgcaaggat   2520
accagccaga ccccccctgca ctgcgagaac ctggataccc tggccttcat cctgcctcac   2580
cggaccgaca acagcgagag ctgtgtgcac ggcaagcacg acagctcttg ggtggaagaa   2640
ctgctgatgc tgcaccgggc cagaatcacc gatgtggaac acatcaccgg cctgagcttt   2700
taccagcagc ggaaagaacc cgtgtccgat atcctgaagc tgaaaaccca tctgcccacc   2760
ttcagccagg aagatggtgg aggaggctct ggtggaggcg gtagcggagg cggagggtcg   2820
ggaggttctg gatcaatgaa gtgggtaacc tttatttccc ttctttttct ctttagctcg   2880
gcttattcca ggggtgtgtt tcgtcgagat gcacacaaga gtgaggttgc tcatcggttt   2940
aaagatttgg gagaagaaaa tttcaaagcc ttggtgttga ttgcctttgc tcagtatctt   3000
cagcagtgtc catttgaaga tcatgtaaaa ttagtgaatg aagtaactga atttgcaaaa   3060
acatgtgttg ctgatgagtc agctgaaaat tgtgacaaat cacttcatac cctttttgga   3120
gacaaattat gcacagttgc aactcttcgt gaaacctatg gtgaaatggc tgactgctgt   3180
gcaaaacaag aacctgagag aaatgaatgc ttcttgcaac acaaagatga caacccaaac   3240
ctcccccgat tggtgagacc agaggttgat gtgatgtgca ctgcttttca tgacaatgaa   3300
gagacatttt tgaaaaaata cttatatgaa attgccagaa gacatcctta cttttatgcc   3360
ccggaactcc ttttctttgc taaaaggtat aaagctgctt ttacagaatg ttgccaagct   3420
gctgataaag ctgcctgcct gttgccaaag ctcgatgaac ttcgggatga agggaaggct   3480
tcgtctgcca aacagagact caagtgtgcc agtctccaaa aatttggaga aagagctttc   3540
```

```
aaagcatggg cagtagctcg cctgagccag agatttccca aagctgagtt tgcagaagtt   3600
tccaagttag tgacagatct taccaaagtc cacacggaat gctgccatgg agatctgctt   3660
gaatgtgctg atgacagggc ggaccttgcc aagtatatct gtgaaaatca agattcgatc   3720
tccagtaaac tgaaggaatg ctgtgaaaaa cctctgttgg aaaaatccca ctgcattgcc   3780
gaagtggaaa atgatgagat gcctgctgac ttgccttcat tagctgctga ttttgttgaa   3840
agtaaggatg tttgcaaaaa ctatgctgag gcaaaggatg tcttcctggg catgtttttg   3900
tatgaatatg caagaaggca tcctgattac tctgtcgtgc tgctgctgag acttgccaag   3960
acatatgaaa ccactctaga gaagtgctgt gccgctgcag atcctcatga atgctatgcc   4020
aaagtgttcg atgaatttaa acctcttgtg gaagagcctc agaatttaat caaacaaaat   4080
tgtgagcttt ttgagcagct tggagagtac aaattccaga atgcgctatt agttcgttac   4140
accaagaaag taccccaagt gtcaactcca actcttgtag aggtctcaag aaacctagga   4200
aaagtgggca gcaaatgttg taaacatcct gaagcaaaaa gaatgccctg tgcagaagac   4260
tatctatccg tggtcctgaa ccagttatgt gtgttgcatg agaaaacgcc agtaagtgac   4320
agagtcacca aatgctgcac agaatccttg gtgaacaggc gaccatgctt ttcagctctg   4380
gaagtcgatg aaacatacgt tcccaaagag tttaatgctg aaacattcac cttccatgca   4440
gatatatgca cactttctga gaaggagaga caaatcaaga aacaaactgc acttgttgag   4500
ctcgtgaaac acaagcccaa ggcaacaaaa gagcaactga aagctgttat ggatgatttc   4560
gcagcttttg tagagaagtg ctgcaaggct gacgataagg agacctgctt tgccgaggag   4620
ggtaaaaaac ttgttgctgc aagtcaagct gccttaggct ta                      4662
```

<210> SEQ ID NO 73
<211> LENGTH: 3228
<212> TYPE: DNA
<213> ORGANISM: Artificial Sequence
<220> FEATURE:
<223> OTHER INFORMATION: ENPP7-1-Fc nucleotide sequence

<400> SEQUENCE: 73

```
atgagaggac ctgccgtcct gctgaccgtc gccctggcta ccttgctggc ccctggtgct     60
ggtgcaccca gctgcgccaa agaagtgaag tcctgcaagg gccggtgctt cgagcggacc    120
ttcggcaact gcagatgcga cgccgcctgt gtggaactgg gcaactgctg cctggactac    180
caggaaacct gcatcgagcc cgagcacatc tggacctgca acaagttcag atgcggcgag    240
aagcggctga ccagatccct gtgtgcctgc agcgacgact gcaaggacaa gggcgactgc    300
tgcatcaact acagcagcgt gtgccagggc gagaagtcct gggtggaaga accctgcgag    360
agcatcaacg agccccagtg ccctgccggc ttcgagacac ctcctaccct gctgttcagc    420
ctggacggct ttcgggccga gtacctgcac acatggggag gcctgctgcc cgtgatcagc    480
aagctgaaga agtgcggcac ctacaccaag aacatgcggc ccgtgtaccc caccaagacc    540
ttccccaacc actactccat cgtgaccggc ctgtaccccg agagccacgg catcatcgac    600
aacaagatgt acgaccccaa gatgaacgcc agcttcagcc tgaagtccaa agagaagttc    660
aaccccgagt ggtataaggg cgagcccatc tgggtcaccg ccaagtacca gggcctgaaa    720
agcggcacat tcttttggcc cggcagcgac gtggaaatca acggcatctt ccccgacatc    780
tataagatgt acaacggcag cgtgcccttc gaggaacgga tcctggctgt gctgcagtgg    840
ctgcagctgc ccaaggatga gcggccccac ttctacaccc tgtacctgga agaacctgac    900
agcagcggcc acagctacgg ccctgtgtcc agcgaagtga tcaaggccct gcagcgggtg    960
```

```
gacggcatgg tgggaatgct gatggacggc ctgaaagagc tgaacctgca cagatgcctg   1020

aacctgatcc tgatcagcga ccacggcatg gaacagggat cctgcaagaa gtacatctac   1080

ctgaacaagt acctgggcga cgtgaagaac atcaaagtga tctacggccc agccgccaga   1140

ctgaggccta gcgacgtgcc cgacaagtac tacagcttca actacgaggg aatcgcccgg   1200

aacctgagct gcagagagcc caaccagcac ttcaagccct acctgaagca cttcctgccc   1260

aagcggctgc acttcgccaa gagcgacaga atcgagcccc tgaccttcta cctggacccc   1320

cagtggcagc tggccctgaa tcccagcgag agaaagtact gcggcagcgg cttccacggc   1380

tccgacaacg tgttcagcaa catgcaggcc ctgttcgtgg gctacggacc cggctttaag   1440

cacggcatcg aggccgacac cttcgagaac atcgaggtgt acaatctgat gtgcgacctg   1500

ctgaatctga cccctgcccc caacaatggc acccacggca gcctgaacca tctgctgaag   1560

aaccccgtgt acacccctaa gcaccccaaa gaggtgcacc ccctggtgca gtgccccttc   1620

accagaaacc ccagagacaa cctgggctgt agctgcaacc ccagcatcct gcccatcgag   1680

gacttccaga cccagttcaa cctgaccgtg gccgaggaaa agatcatcaa gcacgagaca   1740

ctgccctacg gcagaccccg ggtgctgcag aaagagaaca ccatctgcct gctgagccag   1800

caccagttca tgagcggcta ctcccaggac atcctgatgc ccctgtggac cagctacacc   1860

gtggaccgga acgacagctt ctccaccgag gatttcagca actgcctgta ccaggatttc   1920

cggatccccc tgagccccgt gcacaagtgc agcttctaca agaacaacac caaggtgtcc   1980

tacggcttcc tgagccctcc ccagctgaac aagaacagct ccggcatcta cagcgaggcc   2040

ctgctgacta ccaacatcgt gcccatgtac cagagcttcc aagtgatctg gcggtacttc   2100

cacgacaccc tgctgcggaa gtacgccgaa gaacggaacg gcgtgaacgt ggtgtccggc   2160

ccagtgttcg acttcgacta cgacggcaga tgtgacagcc tggaaaatct gcggcagaaa   2220

agaagagtga tccggaacca ggaaattctg atccctaccc acttctttat cgtgctgaca   2280

agctgcaagg ataccagcca gaccccccctg cactgcgaga acctggatac cctggccttc   2340

atcctgcctc accggaccga caacagcgag agctgtgtgc acggcaagca cgacagctct   2400

tgggtggaag aactgctgat gctgcaccgg gccagaatca ccgatgtgga acacatcacc   2460

ggcctgagct tttaccagca gcggaaagaa cccgtgtccg atatcctgaa gctgaaaacc   2520

catctgccca ccttcagcca ggaagatgac aagacccaca cttgcccccc ctgcccagct   2580

cctgaactgc tgggaggacc ctctgtgttc ctgttccccc caaagcccaa ggacaccctg   2640

atgatctcta ggacccccga agtcacttgc gtcgtcgtcg acgtgtccca cgaggaccct   2700

gaagtcaagt tcaactggta cgtcgacggt gtcgaagtcc acaacgccaa gaccaagccc   2760

agggaagaac agtacaactc tacctaccgc gtcgtcagcg tcctgaccgt cctgcaccag   2820

gactggctga acggaaagga atacaagtgc aaggtgtcca acaaggccct gcctgccccc   2880

atcgaaaaga ccatctctaa ggccaaggga cagccccgcg aaccccaggt ctacaccctg   2940

ccaccctcta gggaagaaat gaccaagaac caggtgtccc tgacctgcct ggtcaaggga   3000

ttctacccct ctgacatcgc cgtcgaatgg gaatctaacg gacagcccga aaacaactac   3060

aagaccaccc cccctgtcct ggactctgac ggatcattct tcctgtactc taagctgact   3120

gtcgacaagt ctaggtggca gcagggaaac gtgttctctt gctctgtcat gcacgaagcc   3180

ctgcacaacc actacaccca gaagtctctg tctctgtccc ccggaaag                3228
```

<210> SEQ ID NO 74

<211> LENGTH: 4434
<212> TYPE: DNA
<213> ORGANISM: Artificial Sequence
<220> FEATURE:
<223> OTHER INFORMATION: ENPP7-NPP1-Albumin nucleotide sequence

<400> SEQUENCE: 74

```
atgagaggac ctgccgtcct gctgaccgtc gccctggcta ccttgctggc ccctggtgct     60
ggtgcaccca gctgcgccaa agaagtgaag tcctgcaagg gccggtgctt cgagcggacc    120
ttcggcaact gcagatgcga cgccgcctgt gtggaactgg gcaactgctg cctggactac    180
caggaaacct gcatcgagcc cgagcacatc tggacctgca acaagttcag atgcggcgag    240
aagcggctga ccagatccct gtgtgcctgc agcgacgact gcaaggacaa gggcgactgc    300
tgcatcaact acagcagcgt gtgccagggc gagaagtcct gggtggaaga accctgcgag    360
agcatcaacg agccccagtg ccctgccggc ttcgagacac ctcctaccct gctgttcagc    420
ctggacggct ttcgggccga gtacctgcac acatggggag gcctgctgcc cgtgatcagc    480
aagctgaaga agtgcggcac ctacaccaag aacatgcggc ccgtgtaccc caccaagacc    540
ttccccaacc actactccat cgtgaccggc ctgtaccccg agagccacgg catcatcgac    600
aacaagatgt acgaccccaa gatgaacgcc agcttcagcc tgaagtccaa agagaagttc    660
aaccccgagt ggtataaggg cgagcccatc tgggtcaccg ccaagtacca gggcctgaaa    720
agcggcacat tcttttggcc cggcagcgac gtggaaatca acggcatctt ccccgacatc    780
tataagatgt acaacggcag cgtgcccttc gaggaacgga tcctggctgt gctgcagtgg    840
ctgcagctgc ccaaggatga gcggccccac ttctacaccc tgtacctgga agaacctgac    900
agcagcggcc acagctacgg ccctgtgtcc agcgaagtga tcaaggccct gcagcgggtg    960
gacggcatgg tgggaatgct gatggacggc ctgaaagagc tgaacctgca cagatgcctg   1020
aacctgatcc tgatcagcga ccacggcatg gaacagggat cctgcaagaa gtacatctac   1080
ctgaacaagt acctgggcga cgtgaagaac atcaaagtga tctacggccc agccgccaga   1140
ctgaggccta gcgacgtgcc cgacaagtac tacagcttca actacgaggg aatcgcccgg   1200
aacctgagct gcagagagcc caaccagcac ttcaagccct acctgaagca cttcctgccc   1260
aagcggctgc acttcgccaa gagcgacaga atcgagcccc tgaccttcta cctggacccc   1320
cagtggcagc tggccctgaa tcccagcgag agaaagtact gcggcagcgg cttccacggc   1380
tccgacaacg tgttcagcaa catgcaggcc ctgttcgtgg gctacggacc cggctttaag   1440
cacggcatcg aggccgacac cttcgagaac atcgaggtgt acaatctgat gtgcgacctg   1500
ctgaatctga cccctgcccc caacaatggc acccacggca gcctgaacca tctgctgaag   1560
aaccccgtgt acacccctaa gcaccccaaa gaggtgcacc ccctggtgca gtgcccctto   1620
accagaaacc ccagagacaa cctgggctgt agctgcaacc ccagcatcct gcccatcgag   1680
gacttccaga cccagttcaa cctgaccgtg gccgaggaaa agatcatcaa gcacgagaca   1740
ctgccctacg gcagaccccg ggtgctgcag aaagagaaca ccatctgcct gctgagccag   1800
caccagttca tgagcggcta ctcccaggac atcctgatgc ccctgtggac cagctacacc   1860
gtggaccgga acgacagctt ctccaccgag gatttcagca actgcctgta ccaggatttc   1920
cggatccccc tgagccccgt gcacaagtgc agcttctaca agaacaacac caaggtgtcc   1980
tacggcttcc tgagccctcc ccagctgaac aagaacagct ccggcatcta cagcgaggcc   2040
ctgctgacta ccaacatcgt gcccatgtac cagagcttcc aagtgatctg gcggtacttc   2100
cacgacaccc tgctgcggaa gtacgccgaa gaacggaacg gcgtgaacgt ggtgtccggc   2160
```

```
ccagtgttcg acttcgacta cgacggcaga tgtgacagcc tggaaaatct gcggcagaaa   2220

agaagagtga tccggaacca ggaaattctg atccctaccc acttctttat cgtgctgaca   2280

agctgcaagg ataccagcca gacccccctg cactgcgaga acctggatac cctggccttc   2340

atcctgcctc accggaccga caacagcgag agctgtgtgc acggcaagca cgacagctct   2400

tgggtggaag aactgctgat gctgcaccgg gccagaatca ccgatgtgga acacatcacc   2460

ggcctgagct tttaccagca gcggaaagaa cccgtgtccg atatcctgaa gctgaaaacc   2520

catctgccca ccttcagcca ggaagatggt ggaggaggct ctggtggagg cggtagcgga   2580

ggcggagggt cgggaggttc tggatcaatg aagtgggtaa cctttatttc ccttcttttt   2640

ctctttagct cggcttattc caggggtgtg tttcgtcgag atgcacacaa gagtgaggtt   2700

gctcatcggt ttaaagattt gggagaagaa aatttcaaag ccttggtgtt gattgccttt   2760

gctcagtatc ttcagcagtg tccatttgaa gatcatgtaa aattagtgaa tgaagtaact   2820

gaatttgcaa aaacatgtgt tgctgatgag tcagctgaaa attgtgacaa atcacttcat   2880

acccttttttg gagacaaatt atgcacagtt gcaactcttc gtgaaaccta tggtgaaatg   2940

gctgactgct gtgcaaaaca agaacctgag agaaatgaat gcttcttgca acacaaagat   3000

gacaacccaa acctcccccg attggtgaga ccagaggttg atgtgatgtg cactgctttt   3060

catgacaatg aagagacatt tttgaaaaaa tacttatatg aaattgccag aagacatcct   3120

tacttttatg ccccggaact ccttttcttt gctaaaaggt ataaagctgc ttttacagaa   3180

tgttgccaag ctgctgataa agctgcctgc ctgttgccaa agctcgatga acttcgggat   3240

gaagggaagg cttcgtctgc caaacagaga ctcaagtgtg ccagtctcca aaaatttgga   3300

gaaagagctt tcaaagcatg ggcagtagct cgcctgagcc agagatttcc caaagctgag   3360

tttgcagaag tttccaagtt agtgacagat cttaccaaag tccacacgga atgctgccat   3420

ggagatctgc ttgaatgtgc tgatgacagg gcggaccttg ccaagtatat ctgtgaaaat   3480

caagattcga tctccagtaa actgaaggaa tgctgtgaaa aacctctgtt ggaaaaatcc   3540

cactgcattg ccgaagtgga aaatgatgag atgcctgctg acttgccttc attagctgct   3600

gattttgttg aaagtaagga tgtttgcaaa aactatgctg aggcaaagga tgtcttcctg   3660

ggcatgtttt tgtatgaata tgcaagaagg catcctgatt actctgtcgt gctgctgctg   3720

agacttgcca agacatatga aaccactcta gagaagtgct gtgccgctgc agatcctcat   3780

gaatgctatg ccaaagtgtt cgatgaattt aaacctcttg tggaagagcc tcagaattta   3840

atcaaacaaa attgtgagct tttgagcag cttggagagt acaaattcca gaatgcgcta   3900

ttagttcgtt acaccaagaa agtaccccaa gtgtcaactc caactcttgt agaggtctca   3960

agaaacctag gaaaagtggg cagcaaatgt tgtaaacatc ctgaagcaaa aagaatgccc   4020

tgtgcagaag actatctatc cgtggtcctg aaccagttat gtgtgttgca tgagaaaacg   4080

ccagtaagtg acagagtcac caaatgctgc acagaatcct tggtgaacag gcgaccatgc   4140

ttttcagctc tggaagtcga tgaaacatac gttcccaaag agtttaatgc tgaaacattc   4200

accttccatg cagatatatg cacactttct gagaaggaga gacaaatcaa gaaacaaact   4260

gcacttgttg agctcgtgaa acacaagccc aaggcaacaa aagagcaact gaaagctgtt   4320

atggatgatt tcgcagcttt tgtagagaag tgctgcaagg ctgacgataa ggagacctgc   4380

tttgccgagg agggtaaaaa acttgttgct gcaagtcaag ctgccttagg ctta         4434
```

<210> SEQ ID NO 75

<211> LENGTH: 2625
<212> TYPE: DNA
<213> ORGANISM: Artificial Sequence
<220> FEATURE:
<223> OTHER INFORMATION: ENPP3 nucleotide sequence

<400> SEQUENCE: 75
atggaatcta cgttgacttt agcaacggaa caacctgtta agaagaacac tcttaagaaa 60
tataaaatag cttgcattgt tcttcttgct ttgctggtga tcatgtcact tggattaggc 120
ctggggcttg gactcaggaa actggaaaag caaggcagct gcaggaagaa gtgctttgat 180
gcatcattta gaggactgga gaactgccgg tgtgatgtgg catgtaaaga ccgaggtgat 240
tgctgctggg attttgaaga cacctgtgtg gaatcaactc gaatatggat gtgcaataaa 300
tttcgttgtg gagagaccag attagaggcc agcctttgct cttgttcaga tgactgtttg 360
cagaggaaag attgctgtgc tgactataag agtgtttgcc aaggagaaac ctcatggctg 420
gaagaaaact gtgacacagc ccagcagtct cagtgcccag aagggtttga cctgccacca 480
gttatcttgt tttctatgga tggatttaga gctgaatatt tatacacatg ggatacttta 540
atgccaaata tcaataaact gaaaacatgt ggaattcatt caaaatacat gagagctatg 600
tatcctacca aaaccttccc aaatcattac accattgtca cgggcttgta tccagagtca 660
catggcatca ttgacaataa tatgtatgat gtaaatctca acaagaattt ttcactttct 720
tcaaaggaac aaaataatcc agcctggtgg catgggcaac caatgtggct gacagcaatg 780
tatcaaggtt taaaagccgc tacctacttt tggcccggat cagaagtggc tataaatggc 840
tcctttcctt ccatatacat gccttacaac ggaagtgtcc catttgaaga gaggatttct 900
acactgttaa aatggctgga cctgcccaaa gctgaaagac ccaggtttta taccatgtat 960
tttgaagaac ctgattcctc tggacatgca ggtggaccag tcagtgccag agtaattaaa 1020
gccttacagg tagtagatca tgcttttggg atgttgatgg aaggcctgaa gcagcggaat 1080
ttgcacaact gtgtcaatat catccttctg gctgaccatg gaatggacca gacttattgt 1140
aacaagatgg aatacatgac tgattatttt cccagaataa acttcttcta catgtacgaa 1200
gggcctgccc cccgcatccg agctcataat atacctcatg actttttttag ttttaattct 1260 gaggaaattg ttagaaacct cagttgccga aaacctgatc agcatttcaa gccctatttg 1320
actcctgatt tgccaaagcg actgcactat gccaagaacg tcagaatcga caaagttcat 1380
ctctttgtgg atcaacagtg gctggctgtt aggagtaaat caaatacaaa ttgtggagga 1440
ggcaaccatg gttataacaa tgagtttagg agcatggagg ctatctttct ggcacatgga 1500
cccagtttta aagagaagac tgaagttgaa ccatttgaaa atattgaagt ctataaccta 1560
atgtgtgatc ttctacgcat tcaaccagca ccaaacaatg gaacccatgg tagtttaaac 1620
catcttctga aggtgccttt ttatgagcca tcccatgcag aggaggtgtc aaagttttct 1680
gtttgtggct ttgctaatcc attgcccaca gagtctcttg actgtttctg ccctcaccta 1740
caaaatagta ctcagctgga acaagtgaat cagatgctaa atctcaccca agaagaaata 1800
acagcaacag tgaaagtaaa tttgccattt gggaggccta gggtactgca gaagaacgtg 1860
gaccactgtc tcctttacca cagggaatat gtcagtggat ttggaaaagc tatgaggatg 1920
cccatgtgga gttcatacac agtcccccag ttgggagaca catcgcctct gcctcccact 1980
gtcccagact gtctgcgggc tgatgtcagg gttcctcctt ctgagagcca aaaatgttcc 2040
ttctatttag cagacaagaa tatcacccac ggcttcctct atcctcctgc cagcaataga 2100
acatcagata gccaatatga tgctttaatt actagcaatt tggtacctat gtatgaagaa 2160

```
ttcagaaaaa tgtgggacta cttccacagt gttcttctta taaaacatgc cacagaaaga   2220

aatggagtaa atgtggttag tggaccaata tttgattata attatgatgg ccattttgat   2280

gctccagatg aaattaccaa acatttagcc aacactgatg ttcccatccc aacacactac   2340

tttgtggtgc tgaccagttg taaaaacaag agccacacac cggaaaactg ccctgggtgg   2400

ctggatgtcc taccctttat catccctcac cgacctacca acgtggagag ctgtcctgaa   2460

ggtaaaccag aagctctttg ggttgaagaa agatttacag ctcacattgc ccgggtccgt   2520

gatgtagaac ttctcactgg gcttgacttc tatcaggata aagtgcagcc tgtctctgaa   2580

attttgcaac taaagacata tttaccaaca tttgaaacca ctatt                   2625
```

<210> SEQ ID NO 76
<211> LENGTH: 2775
<212> TYPE: DNA
<213> ORGANISM: Artificial Sequence
<220> FEATURE:
<223> OTHER INFORMATION: ENPP1 nucleotide sequence

<400> SEQUENCE: 76

```
atggaacggg acggctgtgc cggcggagga tcaagaggcg gagaaggcgg cagagcccct     60

agagaaggac ctgccggcaa cggcagagac agaggcagat ctcatgccgc cgaagcccct    120

ggcgatcctc aggctgctgc ttctctgctg gcccccatgg atgtgggcga ggaacctctg    180

gaaaaggccg ccagagccag aaccgccaag gaccccaaca cctacaaggt gctgagcctg    240

gtgctgtccg tgtgcgtgct gaccaccatc ctgggctgca tcttcggcct gaagcccagc    300

tgcgccaaag aagtgaagtc ctgcaagggc cggtgcttcg agcggacctt cggcaactgc    360

agatgcgacg ccgcctgtgt ggaactgggc aactgctgcc tggactacca ggaaacctgc    420

atcgagcccg agcacatctg gacctgcaac aagttcagat gcggcgagaa gcggctgacc    480

agatccctgt gtgcctgcag cgacgactgc aaggacaagg gcgactgctg catcaactac    540

agcagcgtgt gccagggcga gaagtcctgg gtggaagaac cctgcgagag catcaacgag    600

ccccagtgcc ctgccggctt cgagacacct cctaccctgc tgttcagcct ggacggcttt    660

cgggccgagt acctgcacac atggggaggc ctgctgcccg tgatcagcaa gctgaagaag    720

tgcggcacct acaccaagaa catgcggccc gtgtacccca ccaagacctt ccccaaccac    780

tactccatcg tgaccggcct gtaccccgag agccacggca tcatcgacaa caagatgtac    840

gaccccaaga tgaacgccag cttcagcctg aagtccaaag agaagttcaa ccccgagtgg    900

tataagggcg agcccatctg ggtcaccgcc aagtaccagg gcctgaaaag cggcacattc    960

ttttggcccg gcagcgacgt ggaaatcaac ggcatcttcc ccgacatcta taagatgtac   1020

aacggcagcg tgcccttcga ggaacggatc ctggctgtgc tgcagtggct gcagctgccc   1080

aaggatgagc ggccccactt ctacaccctg tacctggaag aacctgacag cagcggccac   1140

agctacggcc ctgtgtccag cgaagtgatc aaggccctgc agcgggtgga cggcatggtg   1200

ggaatgctga tggacggcct gaaagagctg aacctgcaca gatgcctgaa cctgatcctg   1260

atcagcgacc acggcatgga acagggatcc tgcaagaagt acatctacct gaacaagtac   1320

ctgggcgacg tgaagaacat caaagtgatc tacggcccag ccgccagact gaggcctagc   1380

gacgtgcccg acaagtacta cagcttcaac tacgagggaa tcgcccggaa cctgagctgc   1440

agagagccca accagcactt caagccctac ctgaagcact tcctgcccaa gcggctgcac   1500

ttcgccaaga gcgacagaat cgagcccctg accttctacc tggaccccca gtggcagctg   1560
```

-continued

```
gccctgaatc ccagcgagag aaagtactgc ggcagcggct tccacggctc cgacaacgtg   1620

ttcagcaaca tgcaggccct gttcgtgggc tacggacccg gctttaagca cggcatcgag   1680

gccgacacct tcgagaacat cgaggtgtac aatctgatgt gcgacctgct gaatctgacc   1740

cctgccccca acaatggcac ccacggcagc ctgaaccatc tgctgaagaa ccccgtgtac   1800

acccctaagc accccaaaga ggtgcacccc ctggtgcagt gcccccttcac cagaaacccc   1860

agagacaacc tgggctgtag ctgcaacccc agcatcctgc ccatcgagga cttccagacc   1920

cagttcaacc tgaccgtggc cgaggaaaag atcatcaagc acgagacact gccctacggc   1980

agaccccggg tgctgcagaa agagaacacc atctgcctgc tgagccagca ccagttcatg   2040

agcggctact cccaggacat cctgatgccc ctgtggacca gctacaccgt ggaccggaac   2100

gacagcttct ccaccgagga tttcagcaac tgcctgtacc aggatttccg gatccccctg   2160

agccccgtgc acaagtgcag cttctacaag aacaacacca aggtgtccta cggcttcctg   2220

agccctcccc agctgaacaa gaacagctcc ggcatctaca gcgaggccct gctgactacc   2280

aacatcgtgc ccatgtacca gagcttccaa gtgatctggc ggtacttcca cgacaccctg   2340

ctgcggaagt acgccgaaga acggaacggc gtgaacgtgg tgtccggccc agtgttcgac   2400

ttcgactacg acggcagatg tgacagcctg gaaaatctgc ggcagaaaag aagagtgatc   2460

cggaaccagg aaattctgat ccctacccac ttctttatcg tgctgacaag ctgcaaggat   2520

accagccaga ccccccctgca ctgcgagaac ctggataccc tggccttcat cctgcctcac   2580

cggaccgaca acagcgagag ctgtgtgcac ggcaagcacg acagctcttg ggtggaagaa   2640

ctgctgatgc tgcaccgggc cagaatcacc gatgtggaac acatcaccgg cctgagcttt   2700

taccagcagc ggaaagaacc cgtgtccgat atcctgaagc tgaaaaccca tctgcccacc   2760

ttcagccagg aagat                                                  2775
```

COMPOSITIONS AND METHODS FOR STROKE PREVENTION IN PEDIATRIC SICKLE CELL ANEMIA PATIENTS

CROSS-REFERENCE TO RELATED APPLICATIONS

This present application is a 35 U.S.C. § 371 national phase application from, and claims priority to, International Application No. PCT/US2017/045280, filed Aug. 3, 2017, and published under PCT Article 21(2) in English, which claims priority under 35 U.S.C. § 119(e) to U.S. Provisional Application No. 62/371,269, filed Aug. 5, 2016, all of which are incorporated herein by reference in their entireties.

BACKGROUND OF THE INVENTION

Stroke, also known as cerebrovascular accident (CVA) or cerebrovascular insult (CVI), takes place when less-than-optimal blood flow to the brain results in brain cell death. Signs and symptoms of a stroke may include an inability to move or feel on one side of the body, problems understanding or speaking, loss of equilibrium, or loss of vision to one side, among others. If symptoms last less than one or two hours it is known as a transient ischemic attack (TIA). The main risk factor for stroke is high blood pressure. Other risk factors include tobacco smoking, obesity, high blood cholesterol, diabetes mellitus, previous TIA occurrence(s), sickle cell anemia, and atrial fibrillation.

There are two main types of stroke: ischemic, due to lack of blood flow, and hemorrhagic, due to bleeding An ischemic stroke is typically caused by blockage of a blood vessel. A hemorrhagic stroke is caused by bleeding either directly into the brain or into the space surrounding the brain. Prevention of stroke includes decreasing risk factors, as well as possibly aspirin, statins, surgery to open up the arteries to the brain in those with problematic narrowing, and warfarin in those with atrial fibrillation.

In particular, stroke is a devastating complication for children suffering from sickle cell anemia (SCA). The causes of stroke in SCA are poorly understood, hampering effects to reduce its occurrence. The peak incidence of ischemic stroke is during childhood, but there is also a significant rate of ischemic stroke in adult SCA patients. The only established treatment to prevent primary or recurrent stroke in SCA patients is chronic transfusion treatment. However, SCA patients can still suffer cerebral vasculopathy despite this intervention. Discontinuation of transfusion quickly removes the protective effect of lowering sickle hemoglobin concentrations, and results in a reversion to high risk of cerebral vasculopathy and stroke.

There is thus a need in the art for novel compositions and methods for treating stroke in sickle cell anemia patients. The present invention fulfills this need.

BRIEF SUMMARY OF THE INVENTION

The invention provides a method of treating or preventing stroke in a sickle cell anemia (SCA) patient in need thereof The invention further provides a method of detecting whether a SCA patient is at risk for stroke. The invention further provides a method of treating or preventing stroke in a SCA patient in need thereof The invention further provides a composition comprising at least one anti-stroke treatment and a compound of the invention, or a salt or solvate thereof.

In certain embodiments, the method comprises administering to the patient a therapeutically effective amount of a compound of the invention. In other embodiments, the compound of the invention is a compound of formula (I), or a salt or solvate thereof:

PROTEIN-Z-DOMAIN-X-Y (I), wherein in (I):

PROTEIN is at least one selected from the group consisting of ENPP1 (SEQ ID NO:1), ENPP121 (SEQ ID NO:15), ENPP71 (SEQ ID NO:17), ENPP71 lacking ENPP1 N-terminus GLK (SEQ ID NO:19), ENPP51 (SEQ ID NO:24), and A-B-SEQ ID NO:32; A is a protein export sequence; B is absent or a sequence corresponding to residues $Xaa_p$-$Xaa_{17}$ in SEQ ID NO:33, wherein p is an integer ranging from 1 to 17; DOMAIN is absent or at least one selected from the group consisting of a human IgG Fc domain (Fc), human serum albumin protein (ALB) and a fragment thereof; X and Z are independently absent or a polypeptide comprising 1-20 amino acids; and, Y is absent or a sequence selected from the "bone targeting" sequence group consisting of: $D_m$ (SEQ ID NO:3), $(DSS)_n$ (SEQ ID NO:4), $(ESS)_n$ (SEQ ID NO:5), $(RQQ)_n$ (SEQ ID NO:6), $(KR)_n$ (SEQ ID NO:7), $R_m$ (SEQ ID NO:8), DSSSEEKFLRRIGRFG (SEQ ID NO:9), EEEEEEEPRGDT (SEQ ID NO:10), APWHLSSQYSRT (SEQ ID NO:11), STLPIPHEFSRE (SEQ ID NO:12), VTKHLNQISQSY (SEQ ID NO:13), and $E_m$ (SEQ ID NO:14), wherein m is an integer ranging from 1 to 15, and wherein n is an integer ranging from 1 to 10.

In certain embodiments, the risk of developing stroke, or the severity of the stroke, is minimized in the patient. In other embodiments, Y is absent. In yet other embodiments, the compound lacks a negatively-charged bone-targeting sequence.

In certain embodiments, the patient is administered the compound by at least one route selected from the group consisting of subcutaneous, oral, aerosol, inhalational, rectal, vaginal, transdermal, subcutaneous, intranasal, buccal, sublingual, parenteral, intrathecal, intragastrical, ophthalmic, pulmonary and topical. In other embodiments, the compound is intravenously or subcutaneously administered to the patient.

In certain embodiments, treating the patient with the compound increases, or prevents further decrease of, the patient's extracellular pyrophosphate concentrations.

In certain embodiments, the PROTEIN comprises an ecto-nucleotide pyrophosphate/phosphodiesterase-2 (ENPP2) transmembrane domain. In other embodiments, the ENPP2 transmembrane domain comprises residues 12-30 of SEQ ID NO:2, which corresponds to SEQ ID NO:23. In yet other embodiments, DOMAIN comprises ALB. In yet other embodiments, the compound of formula (I) lacks a polyaspartic acid domain. In yet other embodiments, the PROTEIN lacks the ENPP1 transmembrane domain. In yet other embodiments, DOMAIN comprises an IgG Fc domain. In yet other embodiments, A is selected from the group consisting of SEQ ID NOs:34-39.

In certain embodiments, the compound is administered to the patient as a pharmaceutical composition further comprising at least one pharmaceutically acceptable carrier. In other embodiments, the patient is further administered at least one additional anti-stroke treatment. In yet other embodiments, the additional anti-stroke treatment is selected from the group consisting of an anticoagulant medication, hydroxyurea, an antiplatelet medication, an antihypertensive medication, a tissue plasminogen activator (tPA), a surgical intervention, and an endovascular procedure. In yet other embodiments, the compound and the at least one additional anti-stroke treatment are co-administered to the patient. In yet other embodiments, the compound and the at least one additional anti-stroke treatment are co-formulated. In yet other embodiments, the compound is the only anti-stroke treatment administered to the patient. In yet other embodiments, the compound is the only anti-stroke treatment administered to the patient in an amount sufficient to treat or prevent stroke in the patient. In yet other embodiments, the patient is a mammal. In yet other embodiments, the mammal is a human.

In certain embodiments, the method comprises measuring the amount of pyrophosphate (PPi) in a sample from the SCA patient. In other embodiments, the method comprises comparing the amount of PPi in the sample from the SCA patient with the amount of PPi in a reference sample. In yet other embodiments, when the amount of PPi is lower in the sample from the SCA patient than in the reference sample, the patient is at risk for stroke.

In certain embodiments, the method comprises measuring the amount of pyrophosphate (PPi) in a sample from the SCA patient. In other embodiments, the method comprises comparing the amount of PPi in the sample from the SCA patient with the amount of PPi in a reference sample. In yet other embodiments, if the amount of PPi is lower in the sample from the SCA patient than in the reference sample, the patient is determined to be at risk for stroke. In yet other embodiments, the method further comprises administering to the patient at risk for stroke a therapeutically effective amount of a compound of the invention, or a salt or solvate thereof.

In certain embodiments, the composition is in a kit further comprising instructions for using the anti-stroke treatment and the compound for treating or preventing stroke in a sickle cell anemia patient.

BRIEF DESCRIPTION OF THE DRAWINGS

The following detailed description of illustrative embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

DETAILED DESCRIPTION OF THE INVENTION

Figure 1:
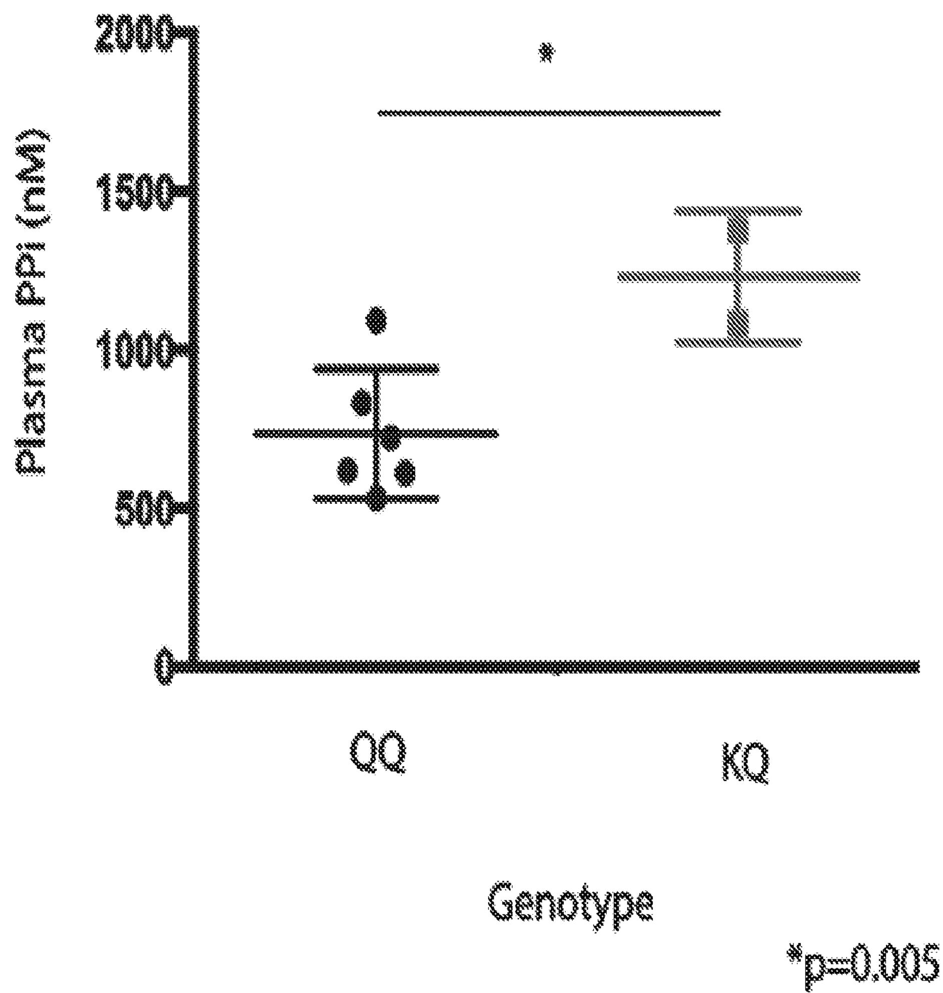
FIG. 1 is a graph showing plasma pyrophosphate (PPi) levels of sickle cell anemia patients with ENPP1 genotypes predictive of stroke risk (homoalleles Q/Q) compared with ENPP1 polymorphisms predictive of stroke protection (heteroalleles K/Q). The mean PPi levels in the at risk population is ≈0.8 nM, which is significantly lower than those patients with ENPP1 genotypes associated with stroke protection (p≈0.005, Student's two tailed T-test).

The present invention relates, in one aspect, to the unexpected discovery that sickle cell anemia (SCA) patients possessing a genotype associated with high risk for stroke have decreased levels of pyrophosphate (PPi). In another aspect, the invention relates to the discovery that certain ENPP1-containing or ENPP3-containing polypeptides, mutants, or mutant fragments thereof can be used to treat or prevent stroke in sickle cell anemia patients. Certain ENPP1- or ENPP3-derived polypeptides, mutants, or mutant fragments thereof have been previously disclosed in PCT Publications No. WO 2014/126965, WO 2016/187408, and WO 2017/087936, all of which are incorporated by reference in their entireties herein.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, illustrative methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The following notation conventions are applied to the present disclosure for the sake of clarity. In any case, any teaching herein that does not follow this convention is still part of the present disclosure, and can be fully understood in view of the context in which the teaching is disclosed. Protein symbols are disclosed in non-italicized capital letters. As non-limiting examples, 'ENPP1' or 'ENPP7' refer to the corresponding proteins. In certain embodiments, if the protein is a human protein, an 'h' is used before the protein symbol. In other embodiments, if the protein is a mouse protein, an 'm' is used before the symbol. Hence, human ENPP1 is referred to as 'hENPP1', and mouse ENPP1 is referred to as 'mENPP1'. Human gene symbols are disclosed in italicized capital letters. As a non-limiting example, the human gene corresponding to the protein hENPP1 is ENPP1. Mouse gene symbols are disclosed with the first letter in upper case and the remaining letters in lower case; further, the mouse gene symbol is italicized. As a non-limiting example, the mouse gene that makes the protein mEnpp 1 is Enpp1.

"About" as used herein when referring to a measurable value such as an amount, a temporal duration, and the like, is meant to encompass variations of ±20% or ±10%, in certain embodiments ±5%, in certain embodiments ±1%, in certain embodiments ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type, might be abnormal for a different cell or tissue type.

As used herein, the term "ALB" refers to a human serum albumin protein.

A disease or disorder is "alleviated" if the severity of a symptom of the disease or disorder, the frequency with which such a symptom is experienced by a patient, or both, is reduced.

As used herein the terms "alteration," "defect," "variation" or "mutation" refer to a mutation in a gene in a cell that affects the function, activity, expression (transcription or translation) or conformation of the polypeptide it encodes, including missense and nonsense mutations, insertions, deletions, frameshifts and premature terminations.

The term "amino acid sequence variant" refers to polypeptides having amino acid sequences that differ to some extent from a native sequence polypeptide. Ordinarily, amino acid sequence variants possess at least about 70% homology, at least about 80% homology, at least about 90% homology, or at least about 95% homology to the native polypeptide.

The term "antibody," as used herein, refers to an immunoglobulin molecule that is able to specifically bind to a specific epitope on an antigen. Antibodies can be intact immunoglobulins derived from natural sources or from recombinant sources and can be immunoreactive portions of intact immunoglobulins.

As used herein, the term "Ap3P" refers to adenosine-5'-triphospho-5'-adenosine or a salt thereof.

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine.

The term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "Fc" refers to a human IgG (immunoglobulin) Fc domain. Subtypes of IgG such as IgG1, IgG2, IgG3, and IgG4 are contemplated for usage as Fc domains.

As used herein, the term "fragment," as applied to a nucleic acid, refers to a subsequence of a larger nucleic acid. A "fragment" of a nucleic acid can be at least about 15, 50-100, 100-500, 500-1000, 1000-1500 nucleotides, 1500-2500, or 2500 nucleotides (and any integer value in between). As used herein, the term "fragment," as applied to a protein or peptide, refers to a subsequence of a larger protein or peptide, and can be at least about 20, 50, 100, 200, 300 or 400 amino acids in length (and any integer value in between).

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE.

"Instructional material," as that term is used herein, includes a publication, a recording, a diagram, or any other medium of expression that can be used to communicate the usefulness of the nucleic acid, peptide, and/or compound of the invention in the kit for identifying or alleviating or treating the various diseases or disorders recited herein.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment that has been separated from sequences that flank it in a naturally occurring state, e.g., a DNA fragment that has been removed from the sequences that are normally adjacent to the fragment, e.g., the sequences adjacent to the fragment in a genome in which it naturally occurs, and/or substantially purified from other components that naturally accompany the nucleic acid, e.g., RNA or DNA or proteins, which naturally accompany it in the cell. The term includes, for example, a recombinant DNA that is incorporated into a vector, into an autonomously replicating plasmid or virus, or into the genomic DNA of a prokaryote or eukaryote, or that exists as a separate molecule (e.g., as a cDNA or a genomic or cDNA fragment produced by PCR or restriction enzyme digestion) independent of other sequences. It also includes a recombinant DNA that is part of a hybrid gene encoding additional polypeptide sequence.

As used herein, the term "NPP" or "ENPP" refers to ectonucleotide pyrophosphatase/phosphodiesterase.

A "nucleic acid" refers to a polynucleotide and includes poly-ribonucleotides and poly-deoxyribonucleotides, any polymer or oligomer of pyrimidine and purine bases, preferably cytosine, thymine, and uracil, and adenine and guanine, respectively. See Albert L. Lehninger, Principles of Biochemistry, at 793-800 (Worth Pub. 1982) which is herein incorporated in its entirety for all purposes.

An "oligonucleotide" or "polynucleotide" is a nucleic acid ranging from at least 2, in certain embodiments at least 8, 15 or 25 nucleotides in length, but may be up to 50, 100, 1000, or 5000 nucleotides long or a compound that specifically hybridizes to a polynucleotide.

As used herein, the term "PPi" refers to plasma pyrophosphate.

As used herein, the term "patient," "individual" or "subject" refers to a human or a non-human mammal. Non-human mammals include, for example, livestock and pets, such as ovine, bovine, porcine, canine, feline and murine mammals. In certain embodiments, the patient, individual or subject is human.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "pharmaceutical composition" or "composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, inhalational, rectal, vaginal, transdermal, intranasal, buccal, sublingual, parenteral, intrathecal, intragastrical, ophthalmic, pulmonary and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Salts may be prepared from the corresponding compound by reacting the appropriate acid or base with the compound.

As used herein the term "plasma pyrophosphate (PPi) levels" refers to the amount of pyrophosphate present in plasma of animals. In certain embodiments, animals include rat, mouse, cat, dog, human, cow and horse. It is necessary to measure PPi in plasma rather than serum because of release from platelets. There are several ways to measure PPi, one of which is by enzymatic assay using uridine-diphosphoglucose (UDPG) pyrophosphorylase (Lust & Seegmiller, 1976, Clin. Chim. Acta 66: 241-249; Cheung & Suhadolnik, 1977, Anal. Biochem. 83: 61-63) with modifications.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases.

As used herein, the term "polypeptide" or "peptide" or "protein" refers to a polymer composed of amino acid residues, related naturally occurring structural variants, and synthetic non-naturally occurring analogs thereof linked via peptide bonds. Conventional notation is used herein to represent polypeptide sequences: the left-hand end of a polypeptide sequence is the amino-terminus, and the right-hand end of a polypeptide sequence is the carboxyl-terminus.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, the term "SCA" refers to sickle cell anemia.

By the term "specifically binds," as used herein with respect to an antibody, is meant an antibody that recognizes a specific antigen, but does not substantially recognize or bind other molecules in a sample. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally.

As used herein, "substantially purified" refers to being essentially free of other components. For example, a substantially purified polypeptide is a polypeptide that has been separated from other components with which it is normally associated in its naturally occurring state. Non-limiting embodiments include 95% purity, 99% purity, 99.5% purity, 99.9% purity and 100% purity.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

As used herein, the term "wild-type" refers to a gene or gene product isolated from a naturally occurring source. A wild-type gene is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. Naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Stroke is a devastating complication for children with sickle cell anemia (SCA). The causes of stroke in SCA are poorly understood and there is an urgent need to define the mechanisms that trigger stroke, so that medical specialists may design therapeutic approaches to avoid, or minimize the physiologic impact of, strokes. Polymorphisms in the coding region of ENPP1 are associated with the overall risk of stroke in patients with SCA: those polymorphisms associated with stroke risk and stroke protection in pediatric SCA are, respectively, Q173 (or Q121) and K173 (or K121). The numbering of the varying amino acid residue refers to the immature ENPP1 enzyme comprising the N-terminal signal sequence (position 173), or the same exact residue in the mature ENPP1 enzyme (position 121). At the time of the invention, the mechanism by which polymorphisms in ENPP1 modulated stroke risk in SCA patients was unknown.

In an unexpected finding demonstrated herein, pediatric patients at risk for stroke, possessing the ENPP1 homoallelic QQ genotype, had significantly lower plasma pyrophosphate (PPi) levels than individuals with the heteroallelic KQ polymorphism (FIG. 1). In fact, the level of PPi in SCA patients at risk for stroke is so low that they may be at risk for arterial wall vascular calcification, which may in certain embodiments provide a physiologic mechanism for the stroke risk in these patients. Without wishing to be bound by any specific theory, this provides a rational explanation for the stroke etiology.

The findings of the present invention establish a direct link between stroke in pediatric sickle cell patients, ENPP1 activity, and plasma PPi. This provides a surprising basis for the use of ENPP1- or ENPP3-derived polypeptides, mutants, or mutant fragments in pediatric sickle cell patients as a way to elevate their plasma PPi levels and reduce their risk for stroke.

Compositions

In certain embodiments, the compositions of the invention comprises at least one compound of formula (I), or a solvate or salt (such as a pharmaceutically acceptable salt) thereof:

PROTEIN-Z-DOMAIN-X-Y (I), wherein:

PROTEIN is at least one selected from the group consisting of ENPP1 (SEQ ID NO:1), ENPP121 (SEQ ID NO:15), ENPP71 (SEQ ID NO:17), ENPP71 lacking ENPP1 N-terminus GLK (SEQ ID NO:19), ENPP51 (SEQ ID NO:24), and A-B-SEQ ID NO:32; A is a protein export sequence; B is absent or a sequence corresponding to residues $Xaa_p$-$Xaa_{17}$ in SEQ ID NO:33, wherein p is an integer ranging from 1 to 17; DOMAIN is absent or at least one selected from the group consisting of a human IgG Fc domain (Fc) (such as but not limited to IgG1, IgG2, IgG3 and/or IgG4), human serum albumin protein (ALB) and a fragment thereof; X and Z are independently absent or a polypeptide comprising 1-20 amino acids; and, Y is absent or a sequence selected from the "bone targeting" sequence group consisting of: $D_m$ (SEQ ID NO:3), $(DSS)_n$ (SEQ ID NO:4), $(ESS)_n$ (SEQ ID NO:5), $(RQQ)_n$ (SEQ ID NO:6), $(KR)_n$ (SEQ ID NO:7), $R_m$ (SEQ ID NO:8), DSSSEEKFLRRIGRFG (SEQ ID NO:9), EEEEEEEPRGDT (SEQ ID NO:10), APWHLSSQYSRT (SEQ ID NO:11), STLPIPHEFSRE (SEQ ID NO:12), VTKHLNQISQSY (SEQ ID NO:13), and $E_m$ (SEQ ID NO:14), wherein m is an integer ranging from 1 to 15, and wherein n is an integer ranging from 1 to 10.

In certain embodiments, A is selected from the group consisting of SEQ ID NOs:34-39. In other embodiments, B is absent or selected from the group consisting of SEQ ID NOs:40-55.

In certain embodiments, DOMAIN comprises a human IgG Fc domain or fragment thereof. In other embodiments, DOMAIN consists essentially of a human IgG Fc domain or fragment thereof. In yet other embodiments, DOMAIN consists of a human IgG Fc domain or fragment thereof.

In certain embodiments, DOMAIN comprises a human serum albumin protein or fragment thereof. In other embodiments, DOMAIN consists essentially of a human serum albumin protein or fragment thereof. In yet other embodiments, DOMAIN consists of a human serum albumin protein or fragment thereof. In yet other embodiments, DOMAIN is absent.

In certain embodiments, Y is a negatively-charged bone-targeting sequence. In certain embodiments, Y is absent. In certain embodiments, Y is absent and the compound of formula (I) lacks a negatively-charged bone-targeting sequence. In yet other embodiments, a polyaspartic acid domain and SEQ ID NOs:3-14 are non-limiting examples of a negatively-charged bone-targeting sequence.

In certain embodiments, the PROTEIN or mutant thereof is truncated to remove the nuclease domain. In yet other embodiments, the PROTEIN or mutant thereof is truncated to remove the nuclease domain from about residue 524 to about residue 885 relative to SEQ ID NO:1, leaving only the catalytic domain from about residue 186 to about residue 586 relative to SEQ ID NO:1, which serves to preserve the catalytic activity of the protein.

In certain embodiments, in (I) PROTEIN-Z-DOMAIN comprises (SEQ ID NO:15)-Z-(Fc or fragment thereof). In other embodiments, Z is a tripeptide. In yet other embodiments, Z is L I N. In yet other embodiments, in (I) PROTEIN-Z-DOMAIN comprises SEQ ID NO:16.

In certain embodiments, in (I) PROTEIN-Z-DOMAIN comprises (SEQ ID NO:17)-Z-(Fc or fragment thereof). In other embodiments, Z is a tripeptide. In yet other embodiments, Z is L I N. In yet other embodiments, in (I) PROTEIN-Z-DOMAIN comprises SEQ ID NO:18.

In certain embodiments, in (I) PROTEIN-Z-DOMAIN comprises (SEQ ID NO:19)-Z-(Fc or fragment thereof). In other embodiments, Z is a tripeptide. In yet other embodiments, Z is L I N. In yet other embodiments, in (I) PROTEIN-Z-DOMAIN comprises SEQ ID NO:20.

In certain embodiments, in (I) PROTEIN-Z-DOMAIN comprises (SEQ ID NO:24)-Z-(Fc or fragment thereof). In other embodiments, Z is a tripeptide. In yet other embodiments, Z is L I N. In yet other embodiments, in (I) PROTEIN-Z-DOMAIN comprises (SEQ ID NO:24)-Z-(SEQ ID NO:26).

In certain embodiments, in (I) PROTEIN-Z-DOMAIN comprises (SEQ ID NO:15)-Z-(ALB or fragment thereof). In other embodiments, Z is a tripeptide. In yet other embodiments, Z is one selected from the group consisting of SEQ ID NOs:28-30. In yet other embodiments, in (I) PROTEIN-Z-DOMAIN comprises SEQ ID NO:21.

In certain embodiments, in (I) PROTEIN-Z-DOMAIN comprises (SEQ ID NO:17)-Z-(ALB or fragment thereof). In other embodiments, Z is a tripeptide. In yet other embodiments, Z is one selected from the group consisting of SEQ ID NOs:28-30. In yet other embodiments, in (I) PROTEIN-Z-DOMAIN comprises (SEQ ID NO:17)-Z-(SEQ ID NO:27), wherein Z is one selected from the group consisting of SEQ ID NOs:28-30.

In certain embodiments, in (I) PROTEIN-Z-DOMAIN comprises (SEQ ID NO:19)-Z-(ALB or fragment thereof). In other embodiments, Z is a tripeptide. In yet other embodiments, Z is one selected from the group consisting of SEQ ID NOs:28-30. In yet other embodiments, in (I) PROTEIN-Z-DOMAIN comprises SEQ ID NO:22.

In certain embodiments, in (I) PROTEIN-Z-DOMAIN comprises (SEQ ID NO:24)-Z-(ALB or fragment thereof). In other embodiments, Z is a tripeptide. In yet other embodiments, Z is one selected from the group consisting of SEQ ID NOs:28-30. In yet other embodiments, in (I) PROTEIN-Z-DOMAIN comprises SEQ ID NO:25.

In certain embodiments, X and Z are independently absent or a polypeptide comprising 1-18 amino acids. In other embodiments, X and Z are independently absent or a polypeptide comprising 1-16 amino acids. In yet other embodiments, X and Z are independently absent or a polypeptide comprising 1-14 amino acids. In yet other embodiments, X and Z are independently absent or a polypeptide comprising 1-12 amino acids. In yet other embodiments, X and Z are independently absent or a polypeptide comprising 1-10 amino acids. In yet other embodiments, X and Z are independently absent or a polypeptide comprising 1-8 amino acids. In yet other embodiments, X and Z are independently absent or a polypeptide comprising 1-6 amino acids. In yet other embodiments, X and Z are independently absent or a polypeptide comprising 1-5 amino acids. In yet other embodiments, X and Z are independently absent or a polypeptide comprising 1-4 amino acids. In yet other embodiments, X and Z are independently absent or a polypeptide comprising 1-3 amino acids. In yet other embodiments, X and Z are independently absent or a polypeptide comprising 1-2 amino acids. In yet other embodiments, X and Z are independently absent or a single amino acid.

In certain embodiments, m is 1. In other embodiments, m is 2. In yet other embodiments, m is 3. In yet other embodiments, m is 4. In yet other embodiments, m is 5. In yet other embodiments, m is 6. In yet other embodiments, m is 7. In yet other embodiments, m is 8. In yet other embodiments, m is 9. In yet other embodiments, m is 10. In yet other embodiments, m is 11. In yet other embodiments, m is 12. In yet other embodiments, m is 13. In yet other embodiments, m is 14. In yet other embodiments, m is 15. In yet other embodiments, each occurrence of m is independently selected from the group consisting of an integer ranging from 1 to 15, from 2 to 15, from 3 to 15, from 4 to 15, from 5 to 15, from 6 to 15, from 7 to 15, from 8 to 15, from 9 to 15, from 10 to 15, from 11 to 15, from 12 to 15, from 13 to 15, from 14 to 15, from 1 to 14, from 2 to 14, from 3 to 14, from 4 to 14, from 5 to 14, from 6 to 14, from 7 to 14, from 8 to 14, from 9 to 14, from 10 to 14, from 11 to 14, from 12 to 14, from 13 to 14, from 1 to 13, from 2 to 13, from 3 to 13, from 4 to 13, from 5 to 13, from 6 to 13, from 7 to 13, from 8 to 13, from 9 to 13, from 10 to 13, from 11 to 13, from 12 to 13, from 1 to 12, from 2 to 12, from 3 to 12, from 4 to 12, from 5 to 12, from 6 to 12, from 7 to 12, from 8 to 12, from 9 to 12, from 10 to 12, from 11 to 12, from 1 to 11, from 2 to 11, from 3 to 11, from 4 to 11, from 5 to 11, from 6 to 11, from 7 to 11, from 8 to 11, from 9 to 11, from 10 to 11, from 1 to 10, from 2 to 10, from 3 to 10, from 4 to 10, from 5 to 10, from 6 to 10, from 7 to 10, from 8 to 10, from 9 to 10, from 1 to 9, from 2 to 9, from 3 to 9, from 4 to 9, from 5 to 9, from 6 to 9, from 7 to 9, from 8 to 9, from 1 to 8, from 2 to 8, from 3 to 8, from 4 to 8, from 5 to 8, from 6 to 8, from 7 to 8, from 1 to 7, from 2 to 7, from 3 to 7, from 4 to 7, from 5 to 7, from 6 to 7, from 1 to 6, from 2to 6, from 3 to 6, from 4 to 6, from 5 to 6, from Ito 5, from 2 to 5, from 3 to 5, from 4 to 5, from 1 to 4, from 2 to 4, from 3 to 4, from 1 to 3, from 2 to 3, and from 1 to 2.

In certain embodiments, n is 1. In other embodiments, n is 2. In yet other embodiments, n is 3. In yet other embodiments, n is 4. In yet other embodiments, n is 5. In yet other embodiments, n is 6. In yet other embodiments, n is 7. In yet other embodiments, n is 8. In yet other embodiments, n is 9. In yet other embodiments, n is 10. In yet other embodiments, each occurrence of n is independently selected from the group consisting of an integer ranging from 1 to 10, from 2 to 10, from 3 to 10, from 4 to 10, from 5 to 10, from 6 to 10, from 7 to 10, from 8 to 10, from 9 to 10, from 1 to 9, from 2 to 9, from 3 to 9, from 4 to 9, from 5 to 9, from 6 to 9, from 7 to 9, from 8 to 9, from 1 to 8, from 2 to 8, from 3 to 8, from 4 to 8, from 5 to 8, from 6 to 8, from 7 to 8, from 1 to 7, from 2 to 7, from 3 to 7, from 4 to 7, from 5 to 7, from 6 to 7, from 1 to 6, from 2 to 6, from 3 to 6, from 4 to 6, from 5 to 6, from 1 to 5, from 2 to 5, from 3 to 5, from 4 to 5, from 1 to 4, from 2 to 4, from 3 to 4, from 1 to 3, from 2 to 3, and from 1 to 2.

In certain embodiments, the PROTEIN or mutant thereof is modified with a segment of the extracellular region of ENPP1 or ENPP3 containing a furin cleavage site between the transmembrane and extracellular domain, as compared to SEQ ID NO:1. In other embodiments, the PROTEIN or mutant thereof is not modified with a segment of the extracellular region of ENPP1 or ENPP3 containing a furin cleavage site between the transmembrane and extracellular domain, as compared to SEQ ID NO:1.

In certain embodiments, the PROTEIN or mutant thereof is modified with a segment of the extracellular region of ENPP2 containing a signal peptidase cleavage site, as compared to SEQ ID NO:1. In other embodiments, the PROTEIN or mutant thereof is not modified with a segment of the extracellular region of ENPP2 containing a signal peptidase cleavage site, as compared to SEQ ID NO:1.

In certain embodiments, the compound of the invention is soluble. In other embodiments, the compound of the invention is a recombinant polypeptide. In yet other embodiments, the compound of the invention includes an ENPP1 or ENPP3 polypeptide or mutant thereof that lacks the ENPP1 or ENPP3 transmembrane domain. In yet other embodiments, the compound of the invention includes an ENPP1 or ENPP3 polypeptide or mutant thereof, wherein the ENPP1 or ENPP3 transmembrane domain or mutant thereof has been removed (and/or truncated) and replaced with the transmembrane domain of another polypeptide, such as, by way of non-limiting example, ENPP2.

In certain embodiments, the compound of the invention comprises an ENPP1 or ENNP3 polypeptide or mutant thereof further comprising more than one transmembrane domain.

In certain embodiments, ENPP1 or ENNP3 is C-terminally fused to the Fc domain of human immunoglobulin 1 (IgG1), human immunoglobulin 2 (IgG2), human immunoglobulin 3 (IgG3), and/or human immunoglobulin 4 (IgG4).

In certain embodiments, ENPP1 or ENNP3 is C-terminally fused to human serum albumin.

In certain embodiments, a fragment and/or variant of ENPP1 or ENNP3 is fused with human serum albumin or variants and/or fragments thereof. Human serum albumin may be conjugated to ENPP1 or ENNP3 protein through a chemical linker, including but not limited to naturally occurring or engineered disulfide bonds, or by genetic fusion to ENPP1 or ENNP3, or a fragment and/or variant thereof.

In certain embodiment, the compound of the invention comprises an ENPP1 or ENNP3 polypeptide or mutant thereof comprising transmembrane domains of ENPP1 or ENNP3 and another polypeptide, such as, by way of non-limiting example, ENPP2. In other embodiments, the ENPP1 or ENNP3 polypeptide comprises a cleavage product of a precursor ENPP1 or ENNP3 polypeptide comprising an ENPP2 transmembrane domain. In yet other embodiments, the ENPP2 transmembrane domain comprises residues 12-30 of NCBI accession no. NP_001124335 (SEQ ID NO:2), which corresponds to IISLFTFAVGVNICLGFTA (SEQ ID NO:23).

In certain embodiments, the compound of the invention has a sequence selected from the group consisting of SEQ ID NOs:21, 22 and 25.

In certain embodiments, the compound of the invention has a sequence selected from the group consisting of SEQ ID NOs:21, 22, 25 and (SEQ ID NO:17)-Z-(SEQ ID NO:27).

In certain embodiments, the compound of the invention has a sequence selected from the group consisting of SEQ ID NOs:16, 18, 20 and (SEQ ID NO:24)-Z-(SEQ ID NO:26).

In certain embodiments, the compounds of the invention have more than one transmembrane domain. In other embodiments, the compounds of the invention are further pegylated. In yet other embodiments, the compounds of the invention have more than one transmembrane domain and are further pegylated.

In certain embodiments, the compound of the invention has a $k_{cat}$ value greater than or equal to about 3.4 (±0.4)$s^{-1}$ $enzyme^{-1}$, wherein the $k_{cat}$ is determined by measuring the rate of hydrolysis of ATP for the compound.

In certain embodiments, the compound of the invention has a $K_M$ value less than or equal to about 2 μM, wherein the $K_M$ is determined by measuring the rate of hydrolysis of ATP for the compound.

In certain embodiments, the compound of the invention is formulated as a liquid formulation.

In certain embodiments, the compound of the invention is formulated as a liquid formulation. In other embodiments, the invention provides a dry product form of a pharmaceutical composition comprising a therapeutic amount of a compound of the invention, whereby the dry product is reconstitutable to a solution of the compound in liquid form.

The invention provides a kit comprising at least one compound of the invention, or a salt or solvate thereof, and instructions for using the compound within the methods of the invention. The invention further provides a composition comprising at least one anti-stroke treatment and a compound of the invention, or a salt or solvate thereof.

Cloning, Expression and Purification of ENPP1

In certain embodiments, the ENPP1 polypeptide is soluble. In other embodiments, the ENPP1 polypeptide is a recombinant ENPP1 polypeptide. In yet other embodiments, the polypeptide of the invention comprises a ENPP1 polypeptide lacking the ENPP1 transmembrane domain. In yet other embodiments, the polypeptide of the invention comprises a ENPP1 polypeptide wherein the ENPP1 transmembrane domain has been removed and replaced with the transmembrane domain of another polypeptide, such as, by way of non-limiting example, ENPP2, ENPP5 or ENPP7.

In certain embodiments, the polypeptide of the invention comprises an IgG Fc domain. In other embodiments, the polypeptide of the invention comprises or lacks a polyaspartic acid domain, from about 2 to about 20 or more sequential aspartic acid residues. In yet other embodiments, the polypeptide of the invention comprises an IgG Fc domain and a polyaspartic acid domain comprising from about 2 to about 20 or more sequential aspartic acid residues. In yet other embodiments, the ENPP1 polypeptide is truncated and lacks a nuclease domain. In yet other embodiments, the ENPP1 polypeptide is truncated and lacks the nuclease domain from about residue 524 to about residue 885 relative to SEQ ID NO:1, leaving only a catalytic domain from about residue 186 to about residue 586 relative to SEQ ID NO:1, which preserves the catalytic activity of the protein.

In certain embodiments, the polypeptide of the invention comprises albumin or a portion thereof (an albumin domain). In other embodiments, the albumin domain is located at the C terminal region of the ENPP1 polypeptide. In other embodiments, the IgG Fc domain is located at the C terminal region of the ENPP1 polypeptide. In yet embodiments, the presence of IgFc domain or albumin domain improves half-life, solubility, reduces immunogenicity and increases the activity of the ENPP1 polypeptide.

In certain embodiments, the polypeptide of the invention comprises a signal peptide resulting in the secretion of a precursor of the ENPP1 polypeptide, which undergoes proteolytic processing to yield the ENPP1 polypeptide. In other embodiments, the signal peptide is selected from the group consisting of signal peptides of ENPP2, ENPP5 and ENPP7. In yet other embodiments, the signal peptide is selected from the group consisting of SEQ ID NOs:37-39.

In certain embodiments, the IgG Fc domain or the albumin domain is connected to the C terminal region of the ENPP1 polypeptide by a linker region. In other embodiments, the linker is selected from SEQ ID NOs:3-14, where n is an integer ranging from 1-20.

ENPP1, or a ENPP1 polypeptide, can be prepared as described in US 2015/0359858 A1, which is incorporated herein in its entirety by reference. ENPP1 is a transmembrane protein localized to the cell surface with distinct intramembrane domains. In order to express ENPP1 as a soluble extracellular protein, the transmembrane domain of ENPP1 may be swapped for the transmembrane domain of ENPP2, which results in the accumulation of soluble, recombinant ENPP1 in the extracellular fluid of the baculovirus cultures or is secreted from HEK cells and shall be purified as described in PCT Publications No. WO 2014/126965, WO 2016/187408, and WO 2017/087936, all of which are incorporated by reference in their entireties herein.

Cloning and Expression of ENPP3

In certain embodiments, the ENPP3 polypeptide is soluble. In other embodiments, the ENPP3 polypeptide is a recombinant ENPP3 polypeptide. In yet other embodiments, the polypeptide of the invention includes a ENPP3 polypeptide that lacks the ENPP3 transmembrane domain. In another embodiment, the polypeptide of the invention includes a ENPP3 polypeptide wherein the ENPP3 transmembrane domain has been removed and replaced with the transmembrane domain of another polypeptide, such as, by way of non-limiting example, ENPP2, ENPP5 or ENPP7.

In some embodiments, the polypeptide of the invention comprises an IgG Fc domain. In other embodiments, the polypeptide of the invention comprises or lacks a polyaspartic acid domain, from about 2 to about 20 or more sequential aspartic acid residues or 2 to about 20 sequential glutamic acid residues. In yet other embodiments, the polypeptide of the invention comprises an IgG Fc domain and a polyaspartic acid domain comprising from about 2 to about 20 or more sequential aspartic acid residues.

In certain embodiments, the polypeptide of the invention comprises an albumin domain. In other embodiments, the albumin domain is located at the C terminal region of the ENPP3 polypeptide. In yet other embodiments, the IgG Fc domain is located at the C terminal region of the ENPP3 polypeptide. In yet other embodiments, the presence of IgG Fc domain or albumin domain improves half-life, solubility, reduces immunogenicity and increases the activity of the ENPP3 polypeptide.

In certain embodiments, the polypeptide of the invention comprises a signal peptide resulting in the secretion of a precursor of the ENPP3 polypeptide, which undergoes proteolytic processing to yield the ENPP3 polypeptide. In other embodiments, the signal peptide is selected from the group consisting of signal peptides of ENPP2, ENPP5 and ENPP7. In yet other embodiments, the signal peptide is selected from the group consisting of SEQ ID NOs:37-39.

In certain embodiments, the IgG Fc domain or the albumin domain is connected to the C terminal region of the ENPP3 polypeptide by a linker region. In other embodiments, the linker is selected from SEQ ID NOs:3-14, where n is an integer ranging from 1-20.

ENPP3 is poorly exported to the cell surface. Soluble ENPP3 protein is constructed by replacing the signal sequence of ENPP3 with the native signal sequence of other ENPPs. Soluble ENPP3 constructs are prepared by using the signal export signal sequence of other ENPP enzymes, such as but not limited to ENPP7 and/or ENPP5. Soluble ENPP3 constructs are prepared using a signal sequence comprised of a combination of the signal sequences of ENPP1 and ENPP2 ("ENPP1-2-1" or "ENPP121" hereinafter). Signal sequences of any other known proteins may be used to target the extracellular domain of ENPP3 for secretion as well, such as but not limited to the signal sequence of the immunoglobulin kappa and lambda light chain proteins. Further, the invention should not be construed to be limited to the constructs described herein, but also includes constructs comprising any enzymatically active truncation of the ENPP3 extracellular domain.

Production and Purification of ENPP3 and ENPP3 Fusion Proteins

ENPP3 is produced by establishing stable transfections in either CHO or HEK293 mammalian cells. The protein may be produced in either adherent or suspension cells. To establish stable cell lines the nucleic acid sequence encoding ENPP3 fusion proteins (such as sequences disclosed elsewhere herein) into an appropriate vector for large scale protein production. There are a variety of these vectors available from commercial sources and any of those may be used.

Figure 4:
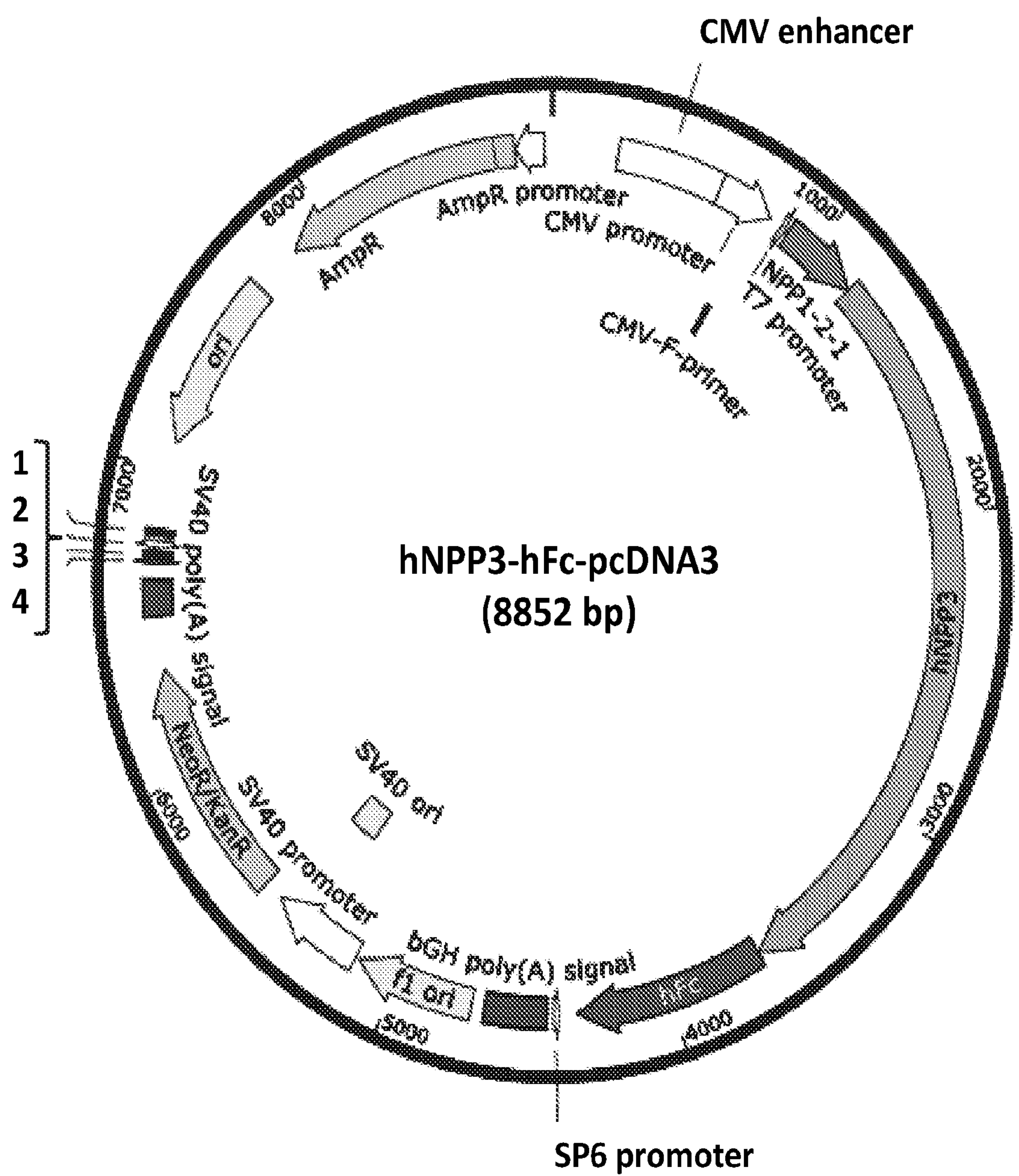
FIG. 4 illustrates a plasmid map of a non-limiting ENPP3-Fc construct contemplated within the invention.
Figure 5:
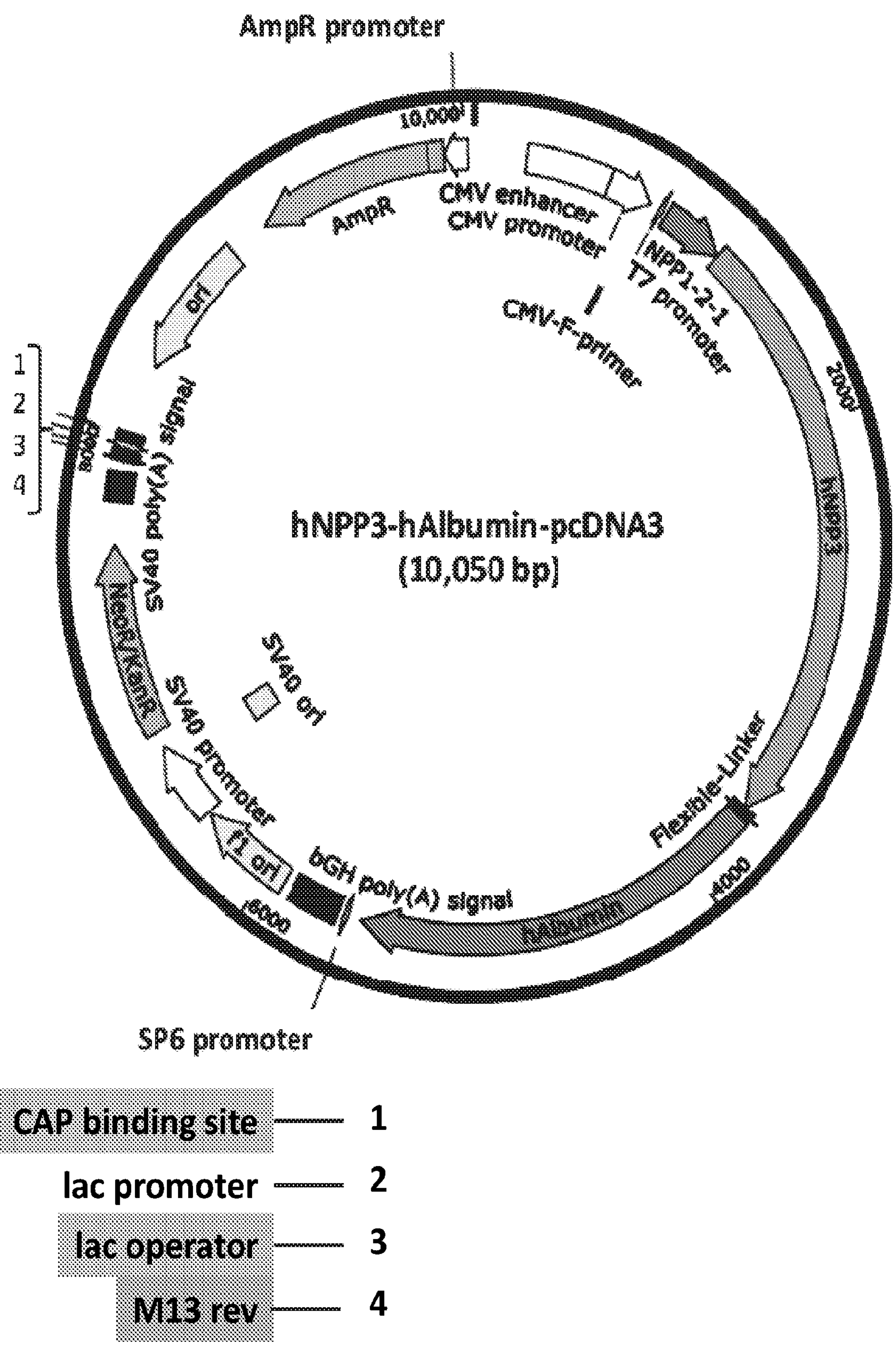
FIG. 5 illustrates a plasmid map of a non-limiting ENPP3-Albumin construct contemplated within the invention.

For example, FIG. 4 shows a plasmid map of ENPP121-exNPP3-Fc cloned into the pcDNA3 plasmid with appropriate endonuclease restriction sites. The protein subdomains are color coded to illustrate the signal sequence, extracellular domain of ENPP3, and Fc domains of the fusion protein. The amino acid sequence of the cloned protein is also displayed below the plasmid map and also color coded to illustrate the domains of the fusion protein. The pcDNA3 plasmid containing the desired protein constructs can be stably transfected into expression plasmid using established techniques such as electroporation or lipofectamine, and the cells can be grown under antibiotic selection to enhance for stably transfected cells.

Clones of single, stably transfected cells are then established and screened for high expressing clones of the desired fusion protein. Screening of the single cell clones for ENPP3 protein expression can be accomplished in a high-throughput manner in 96 well plates using the synthetic enzymatic substrate pNP-TMP as previously described for ENPP1 (Saunders, et al., 2008, Mol. Cancer Ther. 7(10): 3352-62; Albright, et al., 2015, Nat Commun. 6: 10006).

Upon identification of high expressing clones through screening, protein production can be accomplished in shaking flasks or bio-reactors are previously described for ENPP1 (Albright, et al., 2015, Nat Commun. 6: 10006).

Purification of ENPP3 can be accomplished using a combination of standard purification techniques known in the art. These techniques are well known in the art and are selected from techniques such as column chromatograph, ultracentrifugation, filtration, and precipitation. Column chromatographic purification is accomplished using affinity chromatography such as protein-A and protein-G resins, metal affinity resins such as nickel or copper, hydrophobic exchange chromatography, and reverse-phase high-pressure chromatography (HPLC) using C8-C14 resins. Ion exchange may also be employed such as anion and cation exchange chromatography using commercially available resins such as Q-sepharose (anion exchange) and SP-sepharose (cation exchange), blue sepharose resin and blue-sephadex resin, and hydroxyapatite resins. Size exclusion chromatography using commercially available S-75 and S200 Superdex resins may also be employed, as known in the art. Buffers used to solubilize the protein, and provide the selection media for the above described chromatographic steps, are standard biological buffers known to practitioners of the art and science of protein chemistry.

Some examples of buffers that are used in preparation include citrate, phosphate, acetate, tris(hydroxymethyl)aminomethane, saline buffers, glycine-HCL buffers, cacodylate buffers, and sodium barbital buffers which are well known in the art. Using a single techniques or a series of techniques in combination and the appropriate buffer systems adjusted to the appropriate pH one can purify the fusion proteins described to greater than 99% purity from crude material, as demonstrated in FIG. 1. This figure compares partially purified ENPP3 and the crude starting material side by side on a Coomasie stained polyacrylamide gel after a single purification step.

Figure 3:
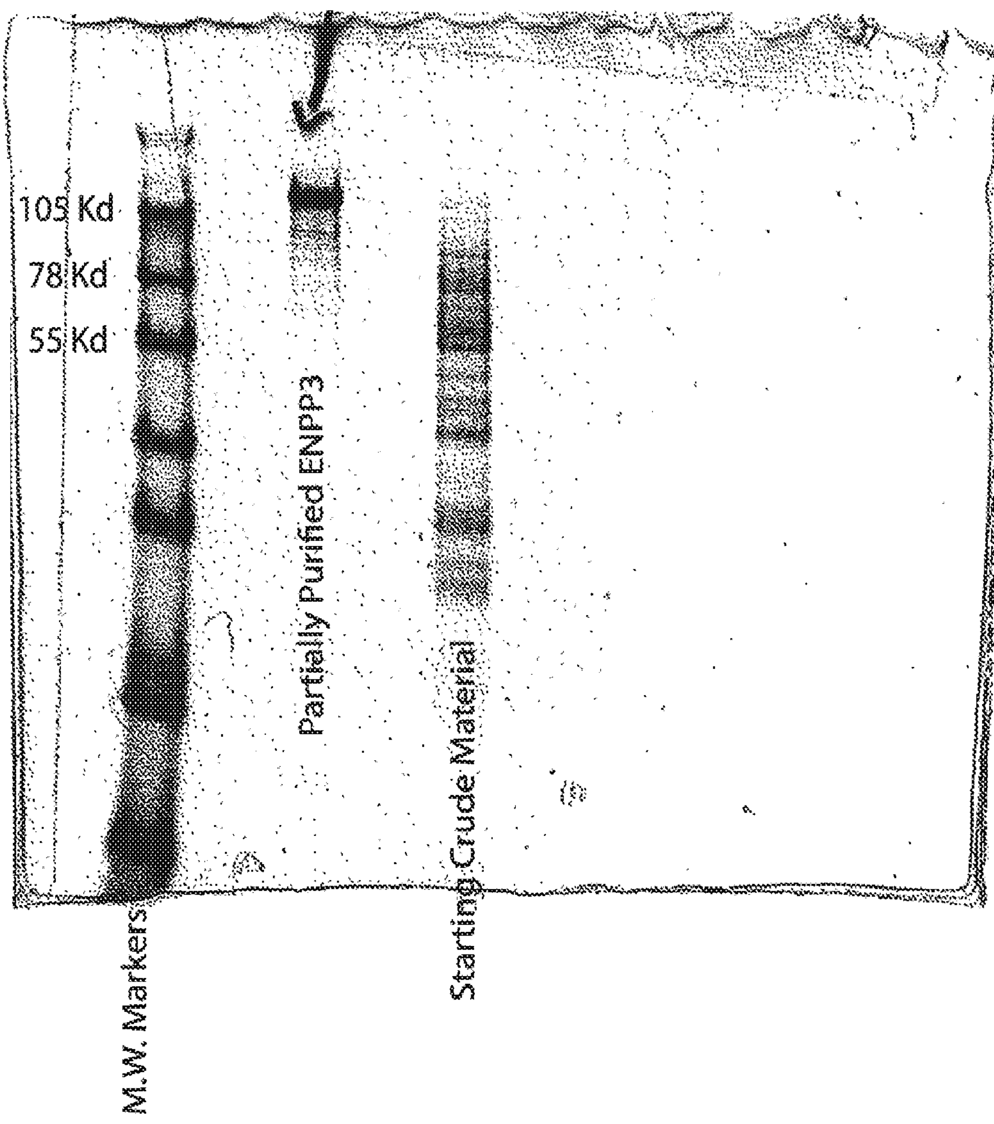
FIG. 3 illustrates a protein gel showing non-limiting expression and purification of a ENPP3 polypeptide.

As demonstrated in FIG. 3, a protein of molecular weight slightly greater than 105 kD corresponding to the appropriate molecular weight of ENPP3 is enriched from the crude starting material displayed in the right lane after a single purification step. This material may then be additionally purified using additional techniques and/or chromatographic steps as described above, to reach substantially higher purity such as ~99% purity.

SEQUENCES

ENPP1 Amino Acid Sequence (NCBI accession NP_006199) (SEQ ID NO: 1)
MERDGCAGGGSRGGEGGRAPREGPAGNGRDRGRSHAAEAPGDPQAAASLLAPMDVGEEPLEKAARART
AKDPNTYKVLSLVLSVCVLTTILGCIFGLKPSCAKEVKSCKGRCFERTFGNCRCDAACVELGNCCLDY
QETCIEPEHIWTCNKFRCGEKRLTRSLCACSDDCKDKGDCCINYSSVCQGEKSWVEEPCESINEPQCP
AGFETPPTLLFSLDGFRAEYLHTWGGLLPVISKLKKCGTYTKNMRPVYPTKTFPNHYSIVTGLYPESH
GIIDNKMYDPKMNASFSLKSKEKFNPEWYKGEPIWVTAKYQGLKSGTFFWPGSDVEINGIFPDIYKMY
NGSVPFEERILAVLQWLQLPKDERPHFYTLYLEEPDSSGHSYGPVSSEVIKALQRVDGMVGMLMDGLK
ELNLHRCLNLILISDHGMEQGSCKKYIYLNKYLGDVKNIKVIYGPAARLRPSDVPDKYYSFNYEGIAR
NLSCREPNQHFKPYLKHFLPKRLHFAKSDRIEPLTFYLDPQWQLALNPSERKYCGSGFHGSDNVFSNM
QALFVGYGPGFKHGIEADTFENIEVYNLMCDLLNLTPAPNNGTHGSLNHLLKNPVYTPKHPKEVHPLV
QCPFTRNPRDNLGCSCNPSILPIEDFQTQFNLTVAEEKIIKHETLPYGRPRVLQKENTICLLSQHQFM
SGYSQDILMPLWTSYTVDRNDSFSTEDFSNCLYQDFRIPLSPVHKCSFYKNNTKVSYGFLSPPQLNKN
SSGIYSEALLTTNIVPMYQSFQVIWRYFHDTLLRKYAEERNGVNVVSGPVFDFDYDGRCDSLENLRQK
RRVIRNQEILIPTHFFIVLTSCKDTSQTPLHCENLDTLAFILPHRTDNSESCVHGKHDSSWVEELLML
HRARITDVEHITGLSFYQQRKEPVSDILKLKTHLPTFSQED ENPP2 Amino Acid Sequence (NCBI accession NP_001124335) (SEQ ID NO: 2)
MARRSSFQSCQIISLFTFAVGVNICLGFTAHRIKRAEGWEEGPPTVLSDSPWTNISGSCKGRCFELQE
AGPPDCRCDNLCKSYTSCCHDFDELCLKTARGWECTKDRCGEVRNEENACHCSEDCLARGDCCTNYQV
VCKGESHWVDDDCEEIKAAECPAGFVRPPLIIFSVDGFRASYMKKGSKVMPNIEKLRSCGTHSPYMRP
VYPTKTFPNLYTLATGLYPESHGIVGNSMYDPVFDATFHLRGREKFNHRWWGGQPLWITATKQGVKAG
TFFWSVVIPHERRILTILQWLTLPDHERPSVYAFYSEQPDFSGHKYGPFGPEMTNPLREIDKIVGQLM
DGLKQLKLHRCVNVIFVGDHGMEDVTCDRTEFLSNYLTNVDDITLVPGTLGRIRSKFSNNAKYDPKAI
IANLTCKKPDQHFKPYLKQHLPKRLHYANNRRIEDIHLLVERRWHVARKPLDVYKKPSGKCFFQGDHG
FDNKVNSMQTVFVGYGSTFKYKTKVPPFENIELYNVMCDLLGLKPAPNNGTHGSLNHLLRTNTFRPTM
PEEVTRPNYPGIMYLQSDFDLGCTCDDKVEPKNKLDELNKRLHTKGSTEAETRKFRGSRNENKENING
NFEPRKERHLLYGRPAVLYRTRYDILYHTDFESGYSEIFLMPLWTSYTVSKQAEVSSVPDHLTSCVRP
DVRVSPSFSQNCLAYKNDKQMSYGFLFPPYLSSSPEAKYDAFLVTNMVPMYPAFKRVWNYFQRVLVKK
YASERNGVNVISGPIFDYDYDGLHDTEDKIKQYVEGSSIPVPTHYYSIITSCLDFTQPADKCDGPLSV
SSFILPHRPDNEESCNSSEDESKWVEELMKMHTARVRDIEHLTSLDFFRKTSRSYPEILTLKTYLHTY
ESEI $D_m$ wherein m is an integer ranging from 1 to 15 (SEQ ID NO: 3)

$(DSS)_n$ wherein n is an integer ranging from 1 to 10 (SEQ ID NO: 4)

$(ESS)_n$ wherein n is an integer ranging from 1 to 10 (SEQ ID NO: 5)

$(RQQ)_n$ wherein n is an integer ranging from 1 to 10 (SEQ ID NO: 6)

$(KR)_n$ wherein n is an integer ranging from 1 to 10 (SEQ ID NO: 7)

$R_m$ wherein m is an integer ranging from 1 to 15 (SEQ ID NO: 8)

DSSSEEKFLRRIGRFG (SEQ ID NO: 9)

-continued

| SEQUENCES |
| --- |

EEEEEEEPRGDT (SEQ ID NO: 10)

APWHLSSQYSRT (SEQ ID NO: 11)

STLPIPHEFSRE (SEQ ID NO: 12)

VTKHLNQISQSY (SEQ ID NO: 13)

$E_m$ wherein m is an integer ranging from 1 to 15 (SEQ ID NO: 14)

ENPP121 Amino Acid Sequence (SEQ ID NO: 15)

1 M E R D G C A G G G S R G G E G G R A P

21 R E G P A G N G R D R G R S H A A E A P

41 G D P Q A A A S L L A P M D V G E E P L

61 E K A A R A R T A K D P N T Y K I I S L

81 F T F A V G V N I C L G**F T A G L K P S

101 C A K E V K S C K G R C F E R T F G N C

121 R C D A A C V E L G N C C L D Y Q E T C

141 I E P E H I W T C N K F R C G E K R L T

161 R S L C A C S D D C K D K G D C C I N Y

181 S S V C Q G E K S W V E E P C E S I N E

201 P Q C P A G F E T P P T L L F S L D G F

221 R A E Y L H T W G G L L P V I S K L K K

241 C G T Y T K N M R P V Y P T K T F P N H

261 Y S I V T G L Y P E S H G I I D N K M Y

281 D P K M N A S F S L K S K E K F N P E W

301 Y K G E P I W V T A K Y Q G L K S G T F

321 F W P G S D V E I N G I F P D I Y K M Y

341 N G S V P F E E R I L A V L Q W L Q L P

361 K D E R P H F Y T L Y L E E P D S S G H

381 S Y G P V S S E V I K A L Q R V D G M V

401 G M L M D G L K E L N L H R C L N L I L

421 I S D H G M E Q G S C K K Y I Y L N K Y

441 L G D V K N I K V I Y G P A A R L R P S

461 D V P D K Y Y S F N Y E G I A R N L S C

481 R E P N Q H F K P Y L K H F L P K R L H

501 F A K S D R I E P L T F Y L D P Q W Q L

521 A L N P S E R K Y C G S G F H G S D N V

541 F S N M Q A L F V G Y G P G F K H G I E

561 A D T F E N I E V Y N L M C D L L N L T

581 P A P N N G T H G S L N H L L K N P V Y

601 T P K H P K E V H P L V Q C P F T R N P

621 R D N L G C S C N P S I L P I E D F Q T

641 Q F N L T V A E E K I I K H E T L P Y G

-continued

SEQUENCES

661 R P R V L Q K E N T I C L L S Q H Q F M

681 S G Y S Q D I L M P L W T S Y T V D R N

701 D S F S T E D F S N C L Y Q D F R I P L

721 S P V H K C S F Y K N N T K V S Y G F L

741 S P P Q L N K N S S G I Y S E A L L T T

761 N I V P M Y Q S F Q V I W R Y F H D T L

781 L R K Y A E E R N G V N V V S G P V F D

801 F D Y D G R C D S L E N L R Q K R R V I

821 R N Q E I L I P T H F F I V L T S C K D

841 T S Q T P L H C E N L D T L A F I L P H

861 R T D N S E S C V H G K H D S S W V E E

881 L L M L H R A R I T D V E H I T G L S F

901 Y Q Q R K E P V S D I L K L K T H L P T

921 F S Q E D

Singly Underlined: residues swapped with ENPP2 residues 1-27 to afford cleavage at transition position (**); Doubly Underlined: ENPP1 protein (beginning and end).

ENPP121-Fc Amino Acid Sequence (SEQ ID NO: 16)

1 M E R D G C A G G G S R G G E G G R A P

21 R E G P A G N G R D R G R S H A A E A P

41 G D P Q A A A S L L A P M D V G E E P L

61 E K A A R A R T A K D P N T Y K I I S L

81 F T F A V G V N I C L G**F T A G L K P S

101 C A K E V K S C K G R C F E R T F G N C

121 R C D A A C V E L G N C C L D Y Q E T C

141 I E P E H I W T C N K F R C G E K R K T

161 R S L C A C S D D C K D K G D C C I N Y

181 S S V C Q G E K S W V E E P C E S I N E

201 P Q C P A G F E T P P T L L F S L D G F

221 R A E Y L H T W G G L L P V I S L K K K

241 C G T Y T K N M R P V Y P T K T F P N H

261 Y S I V T G L Y P E S H G L L D N K M Y

281 D P K M N A S F S L K S K E K F N P E W

301 Y K G E P I W V T A K Y Q G L K S G T F

321 F W P G S D V E I N G I F P D I Y K M Y

341 N G S V P F E E R I L A V K Q W L Q L P

361 K D E R P H F Y T L Y L E E P D S S G H

381 S Y G P V S S E V I K A L Q R V D G M V

401 G M K M D G L K E L N K H R C L N L I L

421 I S D H G M E Q G S C K K Y I Y L N K Y

441 L G D V K N I K V I Y G P A A R L R P S

-continued

| SEQUENCES | |
|---|---|
| 461 | D V P D K Y Y S F N Y E G I A R N L S C |
| 481 | R E P N Q H F K P Y L K H F L P K R L H |
| 501 | F A K S D R I E P L T F Y L D P Q W Q L |
| 521 | A L N P S E R K Y C G S G F H G S D N V |
| 541 | F S N M Q A L F V G Y G P G F K H G I E |
| 561 | A D T F E N I E V Y N L M C D L L N L T |
| 581 | P A P N N G T H G S L N H L L K N P V Y |
| 601 | T P K H P K E V H P L V Q C P F T R N P |
| 621 | R D N L G C S C N P S I L P I E D F Q T |
| 641 | Q F N L T V A E E K I I K H E T L P Y G |
| 661 | R P R V L Q K E N T I C L L S Q H Q F M |
| 681 | S G Y S Q D I L M P L W T S Y T V D R N |
| 701 | D S F S T E D F S N C L Y Q D F R I P K |
| 721 | S P V H K C S F Y K N N T K V S Y G F L |
| 741 | S P P Q L N K N S S G I Y S E A L L T T |
| 761 | N I V P M Y Q S F Q V I W R Y F H D T L |
| 781 | L R K Y A E E R N G V N V V S G P V F D |
| 801 | F D Y D G R C D S L E N L R Q K R R V I |
| 821 | R N Q E I L I P T H F F I V L T S C K D |
| 841 | T S Q T P L H C E N L D L K A F I L P H |
| 861 | R T D N S E S C V H G K H D S S W V E E |
| 881 | L L M L H R A R I T D V E H I T G L S F |
| 901 | Y Q Q R K E P V S D I K L K K T H L P T |
| 921 | F S Q E D L I N **D K T H T C P P C A P** |
| 941 | **E L L G G P S V F L F P P K P K D T L M** |
| 961 | **I S R T P E V T C V V V D V S H E D P E** |
| 981 | **V K F N W Y V D G V E V H N A K T K P R** |
| 1001 | **E E Q Y N S T Y R V V S V K T V L H Q D** |
| 1021 | **W L N G K E Y K C K V S N K A L P A P I** |
| 1041 | **E K T I S K A K G Q P R E P Q V Y T K P** |
| 1061 | **P S R E E M T K N Q V S K T C K V K G F** |
| 1081 | **Y P S D I A V E W E S N G Q P E N N Y K** |
| 1101 | **T T P P V L D S D G S F F L Y S K L T V** |
| 1121 | **D K S R W Q Q G N V F S C S V M H E A L** |
| 1141 | **H N H Y T Q K S L S L S P G K** |

-continued

SEQUENCES

Singly Underlined: residues swapped with ENPP2 residues 1-27 to afford cleavage at transition position (**); Doubly Underlined: ENPP1 protein (beginning and end); Bold: hIgG1 (Fc)

ENPP71 Amino Acid Sequence (SEQ ID NO: 17)

```
  1   MRGPAVLLTV ALATLLAPGA GAGLKPSCAK EVKSCKGRCF ERTFGNCRCD
 51   AACVELGNCC LDYQETCIEP EHIWTCNKFR CGEKRLTRSL CACSDDCKDK
101   GDCCINYSSV CQGEKSWVEE PCESINEPQC PAGFETPPTL LFSLDGFRAE
151   YLHTWGGLLP VISKLKKCGT YTKNMRPVYP TKTFPNHYSI VTGLYPESHG
201   IIDNKMYDPK MNASFSLKSK EKFNPEWYKG EPIWVTAKYQ GLKSGTFFWP
251   GSDVEINGIF PDIYKMYNGS VPFEERILAV LQWLQLPKDE RPHFYTLYLE
301   EPDSSGHSYG PVSSEVIKAL QRVDGMVGML MDGLKELNLH RCLNLILISD
351   HGMEQGSCKK YIYLNKYLGD VKNIKVIYGP AARLRPSDVP DKYYSFNYEG
401   IARNLSCREP NQHFKPYLKH FLPKRLHFAK SDRIEPLTFY LDPQWQLALN
451   PSERKYCGSG FHGSDNVFSN MQALFVGYGP GFKHGIEADT FENIEVYNLM
501   CDLLNLTPAP NNGTHGSLNH LLKNPVYTPK HPKEVHPLVQ CPFTRNPRDN
551   LGCSCNPSIL PIEDFQTQFN LTVAEEKIIK HETLPYGRPR VLQKENTICL
601   LSQHQFMSGY SQDILMPLWT SYTVDRNDSF STEDFSNCLY QDFRIPLSPV
651   HKCSFYKNNT KVSYGFLSPP QLNKNSSGIY SEALLTTNIV PMYQSFQVIW
701   RYFHDTLLRK YAEERNGVNV VSGPVFDFDY DGRCDSLENL RQKRRVIRNQ
751   EILIPTHFFI VLTSCKDTSQ TPLHCENLDT LAFILPHRTD NSESCVHGKH
801   DSSWVEELLM LHRARITDVE HITGLSFYQQ RKEPVSDILK LKTHLPTFSQ
851   ED
```

Singly Underlined: ENPP7; Doubly Underlined: ENPP1 protein (beginning and end).

ENPP71-Fc Amino Acid Sequence (SEQ ID NO: 18)

```
  1   MRGPAVLLTV ALATLLAPGA GAGLKPSCAK EVKSCKGRCF ERTFGNCRCD
 51   AACVELGNCC LDYQETCIEP EHIWTCNKFR CGEKRLTRSL CACSDDCKDK
101   GDCCINYSSV CQGEKSWVEE PCESINEPQC PAGFETPPTL LFSLDGFRAE
151   YLHTWGGLLP VISKLKKCGT YTKNMRPVYP TKTFPNHYSI VTGLYPESHG
201   IIDNKMYDPK MNASFSLKSK EKFNPEWYKG EPIWVTAKYQ GLKSGTFFWP
251   GSDVEINGIF PDIYKMYNGS VPFEERILAV LQWLQLPKDE RPHFYTLYLE
301   EPDSSGHSYG PVSSEVIKAL QRVDGMVGML MDGLKELNLH RCLNLILISD
351   HGMEQGSCKK YIYLNKYLGD VKNIKVIYGP AARLRPSDVP DKYYSFNYEG
401   IARNLSCREP NQHFKPYLKH FLPKRLHFAK SDRIEPLTFY LDPQWQLALN
451   PSERKYCGSG FHGSDNVFSN MQALFVGYGP GFKHGIEADT FENIEVYNLM
501   CDLLNLTPAP NNGTHGSLNH LLKNPVYTPK HPKEVHPLVQ CPFTRNPRDN
551   LGCSCNPSIL PIEDFQTQFN LTVAEEKIIK HETLPYGRPR VLQKENTICL
601   LSQHQFMSGY SQDILMPLWT SYTVDRNDSF STEDFSNCLY QDFRIPLSPV
651   HKCSFYKNNT KVSYGFLSPP QLNKNSSGIY SEALLTTNIV PMYQSFQVIW
701   RYFHDTLLRK YAEERNGVNV VSGPVFDFDY DGRCDSLENL RQKRRVIRNQ
751   EILIPTHFFI VLTSCKDTSQ TPLHCENLDT LAFILPHRTD NSESCVHGKH
```

-continued

SEQUENCES

801 DSSWVEELLM LHRARITDVE HITGLSFYQQ RKEPVSDILK LKTHLPTFSQ

851 EDLINDKTHT CPPCPAPELL GGPSVFLFPP KPKDTLMISR TPEVTCVVVD

901 VSHEDPEVKF NWYVDGVEVH NAKTKPREEQ YNSTYRVVSV LTVLHQDWLN

951 GKEYKCKVSN KALPAPIEKT ISKAKGQPRE PQVYTLPPSR EEMTKNQVSL

1001 TCLVKGFYPS DIAVEWESNG QPENNYKTTP PVLDSDGSFF LYSKLTVDKS

1051 RWQQGNVFSC SVMHEALHNH YTQKSLSLSP GK

Singly Underlined: ENPP7; Doubly Underlined: ENPP1 protein (beginning and end); Bold: hIgG1 (Fc).

(ENPP71 lacking ENPP1 N-Terminus GLK) Amino Acid Sequence (SEQ ID NO: 19)

1 MRGPAVLLTV ALATLLAPGA GA PSCAK EVKSCKGRCF ERTFGNCRCD

51 AACVELGNCC LDYQETCIEP EHIWTCNKFR CGEKRLTRSL CACSDDCKDK

101 GDCCINYSSV CQGEKSWVEE PCESINEPQC PAGFETPPTL LFSLDGFRAE

151 YLHTWGGLLP VISKLKKCGT YTKNMRPVYP TKTFPNHYSI VTGLYPESHG

201 IIDNKMYDPK MNASFSLKSK EKFNPEWYKG EPIWVTAKYQ GLKSGTFFWP

251 GSDVEINGIF PDIYKMYNGS VPFEERILAV LQWLQLPKDE RPHFYTLYLE

301 EPDSSGHSYG PVSSEVIKAL QRVDGMVGML MDGLKELNLH RCLNLILISD

351 HGMEQGSCKK YIYLNKYLGD VKNIKVIYGP AARLRPSDVP DKYYSFNYEG

401 IARNLSCREP NQHFKPYLKH FLPKRLHFAK SDRIEPLTFY LDPQWQLALN

451 PSERKYCGSG FHGSDNVFSN MQALFVGYGP GFKHGIEADT FENIEVYNLM

501 CDLLNLTPAP NNGTHGSLNH LLKNPVYTPK HPKEVHPLVQ CPFTRNPRDN

551 LGCSCNPSIL PIEDFQTQFN LTVAEEKIIK HETLPYGRPR VLQKENTICL

601 LSQHQFMSGY SQDILMPLWT SYTVDRNDSF STEDFSNCLY QDFRIPLSPV

651 HKCSFYKNNT KVSYGFLSPP QLNKNSSGIY SEALLTTNIV PMYQSFQVIW

701 RYFHDTLLRK YAEERNGVNV VSGPVFDFDY DGRCDSLENL RQKRRVIRNQ

751 EILIPTHFFI VLTSCKDTSQ TPLHCENLDT LAFILPHRTD NSESCVHGKH

801 DSSWVEELLM LHRARITDVE HITGLSFYQQ RKEPVSDILK LKTHLPTFSQ

851 ED

Singly Underlined: ENPP7; Doubly Underlined: ENPP1 protein (beginning and end) (first 3-amino acids at the N-terminus of ENPP1, GLK, are omitted).

(ENPP71 lacking ENPP1 N-Terminus GLK)-Fc Amino Acid Sequence (SEQ ID NO: 20)

1 MRGPAVLLTV ALATLLAPGA GA PSCAK EVKSCKGRCF ERTFGNCRCD
51 AACVELGNCC LDYQETCIEP EHIWTCNKFR CGEKRLTRSL CACSDDCKDK
101 GDCCINYSSV CQGEKSWVEE PCESINEPQC PAGFETPPTL LFSLDGFRAE
151 YLHTWGGLLP VISKLKKCGT YTKNMRPVYP TKTFPNHYSI VTGLYPESHG
201 IIDNKMYDPK MNASFSLKSK EKFNPEWYKG EPIWVTAKYQ GLKSGTFFWP
251 GSDVEINGIF PDIYKMYNGS VPFEERILAV LQWLQLPKDE RPHFYTLYLE
301 EPDSSGHSYG PVSSEVIKAL QRVDGMVGML MDGLKELNLH RCLNLILISD
351 HGMEQGSCKK YIYLNKYLGD VKNIKVIYGP AARLRPSDVP DKYYSFNYEG
401 IARNLSCREP NQHFKPYLKH FLPKRLHFAK SDRIEPLTFY LDPQWQLALN
451 PSERKYCGSG FHGSDNVFSN MQALFVGYGP GFKHGIEADT FENIEVYNLM
501 CDLLNLTPAP NNGTHGSLNH LLKNPVYTPK HPKEVHPLVQ CPFTRNPRDN
551 LGCSCNPSIL PIEDFQTQFN LTVAEEKIIK HETLPYGRPR VLQKENTICL
601 LSQHQFMSGY SQDILMPLWT SYTVDRNDSF STEDFSNCLY QDFRIPLSPV
651 HKCSFYKNNT KVSYGFLSPP QLNKNSSGIY SEALLTTNIV PMYQSFQVIW
701 RYFHDTLLRK YAEERNGVNV VSGPVFDFDY DGRCDSLENL RQKRRVIRNQ
751 EILIPTHFFI VLTSCKDTSQ TPLHCENLDT LAFILPHRTD NSESCVHGKH
801 DSSWVEELLM LHRARITDVE HITGLSFYQQ RKEPVSDILK LKTHLPTFSQ

-continued

| SEQUENCES |
|---|
| 851 EDLIN**DKTHT CPPCPAPELL GGPSVFLFPP KPKDTLMISR TPEVTCVVVD** |
| 901 **VSHEDPEVKF NWYVDGVEVH NAKTKPREEQ YNSTYRVVSV LTVLHQDWLN** |
| 951 **GKEYKCKVSN KALPAPIEKT ISKAKGQPRE PQVYTLPPSR EEMTKNQVSL** |
| 1001 **TCLVKGFYPS DIAVEWESNG QPENNYKTTP PVLDSDGSFF LYSKLTVDKS** |
| 1051 **RWQQGNVFSC SVMHEALHNH YTQKSLSLSP GK** |

Singly Underlined: ENPP7; Doubly Underlined: ENPP1 protein (beginning and end) (first 3-amino acids at the N-terminus of ENPP1 are omitted); Bold: hIgG1 (Fc).

ENPP121-ALB Amino Acid Sequence (SEQ ID NO: 21)
*MERDGCAGGGSRGGEGGRAPREGPAGNGRDRGRSHAAEAPGDPQAAASLLAPMDVGEEPLEKAARART*
*AKDPNTYKIIS*LFTFAVGVNICLG**FTAGLKPSCAKEVKSCKGRCFERTFGNCRCDAACVELGNCCL
DYQETCIEPEHIWTCNKFRCGEKRLTRSLCACSDDCKDKGDCCINYSSVCQGEKSWVEEPCESINEPQ
CPAGFETPPTLLFSLDGFRAEYLHTWGGLLPVISKLKKCGTYTKNMRPVYPTKTFPNHYSIVTGLYPE
SHGIIDNKMYDPKMNASFSLKSKEKFNPEWYKGEPIWVTAKYQGLKSGTFFWPGSDVEINGIFPDIYK
MYNGSVPFEERILAVLQWLQLPKDERPHFYTLYLEEPDSSGHSYGPVSSEVIKALQRVDGMVGMLMDG
LKELNLHRCLNLILISDHGMEQGSCKKYIYLNKYLGDVKNIKVIYGPAARLRPSDVPDKYYSFNYEGI
ARNLSCREPNQHFKPYLKHFLPKRLHFAKSDRIEPLTFYLDPQWQLALNPSERKYCGSGFHGSDNVFS
NMQALFVGYGPGFKHGIEADTFENIEVYNLMCDLLNLTPAPNNGTHGSLNHLLKNPVYTPKHPKEVHP
LVQCPFTRNPRDNLGCSCNPSILPIEDFQTQFNLTVAEEKIIKHETLPYGRPRVLQKENTICLLSQHQ
FMSGYSQDILMPLWTSYTVDRNDSFSTEDFSNCLYQDFRIPLSPVHKCSFYKNNTKVSYGFLSPPQLN
KNSSGIYSEALLTTNIVPMYQSFQVIWRYFHDTLLRKYAEERNGVNVVSGPVFDFDYDGRCDSLENLR
QKRRVIRNQEILIPTHFFIVLTSCKDTSQTPLHCENLDTLAFILPHRTDNSESCVHGKHDSSWVEELL
MLHRARITDVEHITGLSFYQQRKEPVSDILKLKTHLPTFSQEDRSGSGGSMKWVTFLLLLFVSGSAFS
RGVFRREAHKSEIAHRYNDLGEQHFKGLVLIAFSQYLQKCSYDEHAKLVQEVTDFAKTCVADESAANC
DKSLHTLFGDKLCAIPNLRENYGELADCCTKQEPERNECFLQHKDDNPSLPPFERPEAEAMCTSFKEN
PTTFMGHYLHEVARRHPYFYAPELLYYAEQYNEILTQCCAEADKESCLTPKLDGVKEKALVSSVRQRM
KCSSMQKFGERAFKAWAVARLSQTFPNADFAEITKLATDLTKVNKECCHGDLLECADDRAELAKYMCE
NQATISSKLQTCCDKPLLKKAHCLSEVEHDTMPADLPAIAADFVEDQEVCKNYAEAKDVFLGTFLYEY
SRRHPDYSVSLLLRLAKKYEATLEKCCAEANPPACYGTVLAEFQPLVEEPKNLVKTNCDLYEKLGEYG
FQNAILVRYTQKAPQVSTPTLVEAARNLGRVGTKCCTLPEDQRLPCVEDYLSAILNRVCLLHEKTPVS
EHVTKCCSGSLVERRPCFSALTVDETYVPKEFKAETFTFHSDICTLPEKEKQIKKQTALAELVKHKPK
ATAEQLKTVMDDFAQFLDTCCKAADKDTCFSTEGPNLVTRCKDALARSWSHPQFEK

Bold Italics: ENPP1 cytoplasmic and transmembrane; Singly Underlined: Swapped residues with ENPP2 residues 1-27 to give cleavage at transition position (**); Doubly Underlined. ENPP1 transmembrane; Plain: ENPP1 Extracellular Domain; Bold Underlined: Linker; Bold: Albumin (ENPP71 lacking ENPP1 N-Terminus GLK)-ALB Amino Acid Sequence (SEQ ID NO: 22)
MRGPAVLLTVALATLLAPGAGAPSCAKEVKSCKGRCFERTFGNCRCDAACVELGNCCLDYQETCIEPE
HIWTCNKFRCGEKRLTRSLCACSDDCKDKGDCCINYSSVCQGEKSWVEEPCESINEPQCPAGFETPPT
LLFSLDGFRAEYLHTWGGLLPVISKLKKCGTYTKNMRPVYPTKTFPNHYSIVTGLYPESHGIIDNKMY
DPKMNASFSLKSKEKFNPEWYKGEPIWVTAKYQGLKSGTFFWPGSDVEINGIFPDIYKMYNGSVPFEE
RILAVLQWLQLPKDERPHFYTLYLEEPDSSGHSYGPVSSEVIKALQRVDGMVGMLMDGLKELNLHRCL
NLILISDHGMEQGSCKKYIYLNKYLGDVKNIKVIYGPAARLRPSDVPDKYYSFNYEGIARNLSCREPN
QHFKPYLKHFLPKRLHFAKSDRIEPLTFYLDPQWQLALNPSERKYCGSGFHGSDNVFSNMQALFVGYG
PGFKHGIEADTFENIEVYNLMCDLLNLTPAPNNGTHGSLNHLLKNPVYTPKHPKEVHPLVQCPFTRNP
RDNLGCSCNPSILPIEDFQTQFNLTVAEEKIIKHETLPYGRPRVLQKENTICLLSQHQFMSGYSQDIL
MPLWTSYTVDRNDSFSTEDFSNCLYQDFRIPLSPVHKCSFYKNNTKVSYGFLSPPQLNKNSSGIYSEA
LLTTNIVPMYQSFQVIWRYFHDTLLRKYAEERNGVNVVSGPVFDFDYDGRCDSLENLRQKRRVIRNQE
ILIPTHFFIVLTSCKDTSQTPLHCENLDTLAFILPHRTDNSESCVHGKHDSSWVEELLMLHRARITDV
EHITGLSFYQQRKEPVSDILKLKTHLPTFSQEDRSGSGGSMKWVTFLLLLFVSGSAFSRGVFRREAHK
SEIAHRYNDLGEQHFKGLVLIAFSQYLQKCSYDEHAKLVQEVTDFAKTCVADESAANCDKSLHTLFGD
KLCAIPNLRENYGELADCCTKQEPERNECFLQHKDDNPSLPPFERPEAEAMCTSFKENPTTFMGHYLH
EVARRHPYFYAPELLYYAEQYNEILTQCCAEADKESCLTPKLDGVKEKALVSSVRQRMKCSSMQKFGE
RAFKAWAVARLSQTFPNADFAEITKLATDLTKVNKECCHGDLLECADDRAELAKYMCENQATISSKLQ
TCCDKPLLKKAHCLSEVEHDTMPADLPAIAADFVEDQEVCKNYAEAKDVFLGTFLYEYSRRHPDYSVS
LLLRLAKKYEATLEKCCAEANPPACYGTVLAEFQPLVEEPKNLVKTNCDLYEKLGEYGFQNAILVRYT
QKAPQVSTPTLVEAARNLGRVGTKCCTLPEDQRLPCVEDYLSAILNRVCLLHEKTPVSEHVTKCCSGS
LVERRPCFSALTVDETYVPKEFKAETFTFHSDICTLPEKEKQIKKQTALAELVKHKPKATAEQLKTVM
DDFAQFLDTCCKAADKDTCFSTEGPNLVTRCKDALARSWSHPQFEK Doubly Underlined: ENPP7; Plain Text: ENPP1; Bold: spacer sequence; Singly Underlined: albumin

IISLFTFAVGVNICLGFTA (SEQ ID NO: 23)

ENPP51 Amino Acid Sequence (SEQ ID NO: 24)
MTSKFLLVSFILAALSLSTTFSLQPSCAKEVKSCKGRCFERTFSNCRCDAACVSLGNCCLDFQETCVE
PTHIWTCNKFRCGEKRLSRFVCSCADDCKTHNDCCINYSSVCQDKKSWVEETCESIDTPECPAEFESP
PTLLFSLDGFRAEYLHTWGGLLPVISKLKNCGTYTKNMRPMYPTKTFPNHYSIVTGLYPESHGIIDNK
MYDPKMNASFSLKSKEKFNPLWYKGQPIWVTANHQEVKSGTYFWPGSDVEIDGILPDIYKVYNGSVPF
EERILAVLEWLQLPSHERPHFYTLYLEEPDSSGHSHGPVSSEVIKALQKVDRLVGMLMDGLKDLGLDK
CLNLILISDHGMEQGSCKKYVYLNKYLGDVNNVKVVYGPAARLRPTDVPETYYSFNYEALAKNLSCRE
PNQHFRPYLKPFLPKRLHFAKSDRIEPLTFYLDPQWQLALNPSERKYCGSGFHGSDNLFSNMQALFIG
YGPAFKHGAEVDSFENIEVYNLMCDLLGLIPAPNNGSHGSLNHLLKKPIYNPSHPKEEGFLSQCPIKS -continued

| SEQUENCES |
|---|
| TSNDLGCTCDPWIVPIKDFEKQLNLTTEDVDDIYHMTVPYGRPRILLKQHRVCLLQQQQFLTGYSLDL<br>LMPLWASYTFLSNDQFSRDDFSNCLYQDLRIPLSPVHKCSYYKSNSKLSYGFLTPPRLNRVSNHIYSE<br>ALLTSNIVPMYQSFQVIWHYLHDTLLQRYAHERNGINVVSGPVFDFDYDGRYDSLEILKQNSRVIRSQ<br>EILIPTHFFIVLTSCKQLSETPLECSALESSAYILPHRPDNIESCTHGKRESSWVEELLTLHRARVTD<br>VELITGLSFYQDRQESVSELLRLKTHLPIFSQED |
| Underlined: ENPP5; Plain: ENPP1 |
| ENPP51-ALB Amino Acid Sequence (SEQ ID NO: 25)<br>MTSKFLLVSFILAALSLSTTFSLQPSCAKEVKSCKGRCFERTFSNCRCDAACVSLGNCCLDFQETCVE<br>PTHIWTCNKFRCGEKRLSRFVCSCADDCKTHNDCCINYSSVCQDKKSWVEETCESIDTPECPAEFESP<br>PTLLFSLDGFRAEYLHTWGGLLPVISKLKNCGTYTKNMRPMYPTKTFPNHYSIVTGLYPESHGIIDNK<br>MYDPKMNASFSLKSKEKFNPLWYKGQPIWVTANHQEVKSGTYFWPGSDVEIDGILPDIYKVYNGSVPF<br>EERILAVLEWLQLPSHERPHFYTLYLEEPDSSGHSHGPVSSEVIKALQKVDRLVGMLMDGLKDLGLDK<br>CLNLILISDHGMEQGSCKKYVYLNKYLGDVNNVKVVYGPAARLRPTDVPETYYSFNYEALAKNLSCRE<br>PNQHFRPYLKPFLPKRLHFAKSDRIEPLTFYLDPQWQLALNPSERKYCGSGFHGSDNLFSNMQALFIG<br>YGPAFKHGAEVDSFENIEVYNLMCDLLGLIPAPNNGSHGSLNHLLKKPIYNPSHPKEEGFLSQCPIKS<br>TSNDLGCTCDPWIVPIKDFEKQLNLTTEDVDDIYHMTVPYGRPRILLKQHRVCLLQQQQFLTGYSLDL<br>LMPLWASYTFLSNDQFSRDDFSNCLYQDLRIPLSPVHKCSYYKSNSKLSYGFLTPPRLNRVSNHIYSE<br>ALLTSNIVPMYQSFQVIWHYLHDTLLQRYAHERNGINVVSGPVFDFDYDGRYDSLEILKQNSRVIRSQ<br>EILIPTHFFIVLTSCKQLSETPLECSALESSAYILPHRPDNIESCTHGKRESSWVEELLTLHRARVTD<br>VELITGLSFYQDRQESVSELLRLKTHLPIFSQED**GGSGGS**MKWVTFLLLLFVSGSAFSRGVFRREAHK<br>SEIAHRYNDLGEQHFKGLVLIAFSQYLQKCSYDEHAKLVQEVTDFAKTCVADESAANCDKSLHTLFGD<br>KLCAIPNLRENYGELADCCTKQEPERNECFLQHKDDNPSLPPFERPEAEAMCTSFKENPTTFMGHYLH<br>EVARRHPYFYAPELLYYAEQYNEILTQCCAEADKESCLTPKLDGVKEKALVSSVRQRMKCSSMQKFGE<br>RAFKAWAVARLSQTFPNADFAEITKLATDLTKVNKECCHGDLLECADDRAELAKYMCENQATISSKLQ<br>TCCDKPLLKKAHCLSEVEHDTMPADLPAIAADFVEDQEVCKNYAEAKDVFLGTFLYEYSRRHPDYSVS<br>LLLRLAKKYEATLEKCCAEANPPACYGTVLAEFQPLVEEPKNLVKTNCDLYEKLGEYGFQNAILVRYT<br>QKAPQVSTPTLVEAARNLGRVGTKCCTLPEDQRLPCVEDYLSAILNRVCLLHEKTPVSEHVTKCCSGS<br>LVERRPCFSALTVDETYVPKEFKAETFTFHSDICTLPEKEKQIKKQTALAELVKHKPKATAEQLKTVM<br>DDFAQFLDTCCKAADKDTCFSTEGPNLVTRCKDALARSWSHPQFEK |
| Doubly Underlined: ENPP5; Plain: ENPP1; Bold: Spacer; Singly Underlined: Albumin |
| Human IgG Fc domain, Fc (SEQ ID NO: 26)<br>DKTHTCPPCPAPELLGGPSVFLFPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYTLPPSRE<br>EMTKNQVSLTCLVKGFYPSDIAVEWESNGQPENNYKTTPPVLDSDGSFFLYSKLTVDKSRWQQGNVFS<br>CSVMHEALHNHYTQKSLSLSPGK |
| ALB (SEQ ID NO: 27)<br>MKWVTFLLLLFVSGSAFSRGVFRREAHKSEIAHRYNDLGEQHFKGLVLIAFSQYLQKCSYDEHAKLVQ<br>EVTDFAKTCVADESAANCDKSLHTLFGDKLCAIPNLRENYGELADCCTKQEPERNECFLQHKDDNPSL<br>PPFERPEAEAMCTSFKENPTTFMGHYLHEVARRHPYFYAPELLYYAEQYNEILTQCCAEADKESCLTP<br>KLDGVKEKALVSSVRQRMKCSSMQKFGERAFKAWAVARLSQTFPNADFAEITKLATDLTKVNKECCHG<br>DLLECADDRAELAKYMCENQATISSKLQTCCDKPLLKKAHCLSEVEHDTMPADLPAIAADFVEDQEVC<br>KNYAEAKDVFLGTFLYEYSRRHPDYSVSLLLRLAKKYEATLEKCCAEANPPACYGTVLAEFQPLVEEP<br>KNLVKTNCDLYEKLGEYGFQNAILVRYTQKAPQVSTPTLVEAARNLGRVGTKCCTLPEDQRLPCVEDY<br>LSAILNRVCLLHEKTPVSEHVTKCCSGSLVERRPCFSALTVDETYVPKEFKAETFTFHSDICTLPEKE<br>KQIKKQTALAELVKHKPKATAEQLKTVMDDFAQFLDTCCKAADKDTCFSTEGPNLVTRCKDALARSWS<br>HPQFEK |
| LIN (SEQ ID NO: 28) |
| GGSGGS (SEQ ID NO: 29) |
| RSGSGGS (SEQ ID NO: 30) |
| ENPP3 Amino Acid Sequence (NCBI accession NP_ 014638-1) (SEQ ID NO: 31)<br>10 20 30 40 50<br>MESTLTLATE QPVKKNTLKK YKIACIVLLA LLVIMSLGLG LGLGLRKLEK<br><br>60 70 80 90 100<br>QGSCRKKCFD ASFRGLENCR CDVACKDRGD CCWDFEDTCV ESTRIWMCNK<br><br>110 120 130 140 150<br>FRCGETRLEA SLCSCSDDCL QRKDCCADYK SVCQGETSWL EENCDTAQQS<br><br>160 170 180 190 200<br>QCPEGFDLPP VILFSMDGFR AEYLYTWDTL MPNINKLKTC GIHSKYMRAM<br><br>210 220 230 240 250<br>YPTKTFPNHY TIVTGLYPES HGIIDNNMYD VNLNKNFSLS SKEQNNPAWW<br><br>260 270 280 290 300<br>HGQPMWLTAM YQGLKAATYF WPGSEVAING SFPSIYMPYN GSVPFEERIS |

-continued

SEQUENCES

```
       310        320        330        340        350
TLLKWLDLPK AERPRFYTMY FEEPDSSGHA GGPVSARVIK ALQVVDHAFG

       360        370        380        390        400
MLMEGLKQRN LHNCVNIILL ADHGMDQTYC NKMEYMTDYF PRINFFYMYE

       410        420        430        440        450
GPAPRIRAHN IPHDFFSFNS EEIVRNLSCR KPDQHFKPYL TPDLPKRLHY

       460        470        480        490        500
AKNVRIDKVH LFVDQQWLAV RSKSNTNCGG GNHGYNNEFR SMEAIFLAHG

       510        520        530        540        550
PSFKEKTEVE PFENIEVYNL MCDLLRIQPA PNNGTHGSLN HLLKVPFYEP

       560        570        580        590        600
SHAEEVSKFS VCGFANPLPT ESLDCFCPHL QNSTQLEQVN QMLNLTQEEI

       610        620        630        640        650
TATVKVNLPF GRPRVLQKNV DHCLLYHREY VSGFGKAMRM PMWSSYTVPQ

       660        670        680        690        700
LGDTSPLPPT VPDCLRADVR VPPSESQKCS FYLADKNITH GFLYPPASNR

       710        720        730        740        750
TSDSQYDALI TSNLVPMYEE FRKMWDYFHS VLLIKHATER NGVNVVSGPI

       760        770        780        790        800
FDYNYDGHFD APDEITKHLA NTDVPIPTHY FVVLTSCKNK SHTPENCPGW

       810        820        830        840        850
LDVLPFIIPH RPTNVESCPE GKPEALWVEE RFTAHIARVR DVELLTGLDF

       860        870
YQDKVQPVSE ILQLKTYLPT FETTI
```

Extracellular domain of ENPP3 (SEQ ID NO: 32)

```
            60         70         80         90        100
EK QGSCRKKCFD ASFRGLENCR CDVACKDRGD CCWDFEDTCV ESTRIWMCNK

       110        120        130        140        150
FRCGETRLEA SLCSCSDDCL QRKDCCADYK SVCQGETSWL EENCDTAQQS

       160        170        180        190        200
QCPEGFDLPP VILFSMDGFR AEYLYTWDTL MPNINKLKTC GIHSKYMRAM

       210        220        230        240        250
YPTKTFPNHY TIVTGLYPES HGIIDNNMYD VNLNKNFSLS SKEQNNPAWW

       260        270        280        290        300
HGQPMWLTAM YQGLKAATYF WPGSEVAING SFPSIYMPYN GSVPFEERIS

       310        320        330        340        350
TLLKWLDLPK AERPRFYTMY FEEPDSSGHA GGPVSARVIK ALQVVDHAFG

       360        370        380        390        400
MLMEGLKQRN LHNCVNIILL ADHGMDQTYC NKMEYMTDYF PRINFFYMYE

       410        420        430        440        450
GPAPRIRAHN IPHDFFSFNS EEIVRNLSCR KPDQHFKPYL TPDLPKRLHY

       460        470        480        490        500
AKNVRIDKVH LFVDQQWLAV RSKSNTNCGG GNHGYNNEFR SMEAIFLAHG

       510        520        530        540        550
PSFKEKTEVE PFENIEVYNL MCDLLRIQPA PNNGTHGSLN HLLKVPFYEP

       560        570        580        590        600
SHAEEVSKFS VCGFANPLPT ESLDCFCPHL QNSTQLEQVN QMLNLTQEEI

       610        620        630        640        650
TATVKVNLPF GRPRVLQKNV DHCLLYHREY VSGFGKAMRM PMWSSYTVPQ

       660        670        680        690        700
LGDTSPLPPT VPDCLRADVR VPPSESQKCS FYLADKNITH GFLYPPASNR

       710        720        730        740        750
```

-continued

| SEQUENCES |
|---|

TSDSQYDALI TSNLVPMYEE FRKMWDYFHS VLLIKHATER NGVNVVSGPI 760 770 780 790 800
FDYNYDGHFD APDEITKHLA NTDVPIPTHY FVVLTSCKNK SHTPENCPGW 810 820 830 840 850
LDVLPFIIPH RPTNVESCPE GKPEALWVEE RFTAHIARVR DVELLTGLDF 860 870
YQDKVQPVSE ILQLKTYLPT FETTI exENPP3 sequence (SEQ ID NO: 33)
LLVIMSLGLG LGLGLRK ENPP7 protein export signal sequence (SEQ ID NO: 34)
MRGPAVLLTV ALATLLAPGA GA ENPP121GLK protein export signal sequence (SEQ ID NO: 35)
*MERDGCAGGGSRGGEGGRAPREGPAGNGRDRGRSHAAEAPGDPQAAASLLAPMDVGEEPLEKAARART AKDPNTYKIIS*LFTFAVGVNICLGFTAGLK Bold Italics: ENPP1 cytoplasmic and transmembrane; Singly Underlined: Swapped residues with ENPP2 residues 1-27 to give cleavage at transition position (); Doubly Underlined: ENPP1 transmembrane ENPP121 protein export signal sequence (SEQ ID NO: 36)
*MERDGCAGGGSRGGEGGRAPREGPAGNGRDRGRSHAAEAPGDPQAAASLLAPMDVGEEPLEKAARART AKDPNTYKIIS*LFTFAVGVNICLGFTA Bold Italics: ENPP1 cytoplasmic and transmembrane; Singly Underlined: Swapped residues with ENPP2 residues 1-27 to give cleavage at transition position (); Doubly Underlined: ENPP1 transmembrane ENPP5 protein export signal sequence (SEQ ID NO: 37)
MISKELLVSFILAALSLSTIFS-$Xaa_{23}$, wherein $Xaa_{23}$ is absent, L or LQ ENPP7 signal sequence (SEQ ID NO: 38)
MRGPAVLLTV ALATLLAPGA ENPP7 signal sequence (SEQ ID NO: 39)
MRGPAVLLTV ALATLLAPGA GA

LVIMSLGLGLGLGLRK (SEQ ID NO: 40)

VIMSLGLGLGLGLRK (SEQ ID NO: 41)

IMSLGLGLGLGLRK (SEQ ID NO: 42)

MSLGLGLGLGLRK (SEQ ID NO: 43)

SLGLGLGLGLRK (SEQ ID NO: 44)

LGLGLGLGLRK (SEQ ID NO: 45)

GLGLGLGLRK (SEQ ID NO: 46)

LGLGLGLRK (SEQ ID NO: 47)

GLGLGLRK (SEQ ID NO: 48)

LGLGLRK (SEQ ID NO: 49)

GLGLRK (SEQ ID NO: 50)

LGLRK (SEQ ID NO: 51)

GLRK (SEQ ID NO: 52)

LRK (SEQ ID NO: 53)

RK (SEQ ID NO: 54)

K (SEQ ID NO: 55)

ENPP121-NPP3-Fc sequence (SEQ ID NO: 56)
MERDGCAGGG SRGGEGGRAP REGPAGNGRD RGRSHAAEAP GDPQAAASLL APMDVGEEPL EKAARARTAK DPNTYKIISL FTFAVGVNIC LGFTAKQGSC RKKCFDASFR GLENCRCDVA -continued

SEQUENCES

CKDRGDCCWD FEDTCVESTR IWMCNKFRCG ERLEASLCSC SDDCLQRKDC CADYKSVCQG
ETSWLEENCD TAQQSQCPEG FDLPPVILFS MDGFRAEYLY TWDTLMPNIN KLKTCGIHSK
YMRAMYPTKT FPNHYTIVTG LYPESHGIID NNMYDVNLNK NFSLSSKEQN NPAWWHGQPM
WLTAMYQGLK AATYFWPGSE VAINGSFPSI YMPYNGSVPF EERISTLLKW LDLPKAERPR
FYTMYFEEPD SSGHAGGPVS ARVIKALQVV DHAFGMLMEG LKQRNLHNCV NIILLADHGM
DQTYCNKMEY MTDYFPRINF FYMYEGPAPR IRAHNIPHDF FSFNSEEIVR NLSCRKPDQH
FKPYLTPDLP KRLHYAKNVR IDKVHLFVDQ QWLAVRSKSN TNCGGGNHGY NNEFRSMEAI
FLAHGPSFKE KTEVEPFENI EVYNLMCDLL RIQPAPNNGT HGSLNHLLKV PFYEPSHAEE
VSKFSVCGFA NPLPTESLDC FCPHLQNSTQ LEQVNQMLNL TQEEITATVK VNLPFGRPRV
LQKNVDHCLL YHREYVSGFG KAMRMPMWSS YTVPQLGDTS PLPPTVPDCL RADVRVPPSE
SQKCSFYLAD KNITHGFLYP PASNRTSDSQ YDALITSNLV PMYEEFRKMW DYFHSVLLIK
HATERNGVNV VSGPIFDYNY DGHFDAPDEI TKHLANTDVP IPTHYFVVLT SCKNKSHTPE
NCPGWLDVLP FIIPHRPTNV ESCPEGKPEA LWVEERFTAH IARVRDVELL TGLDFYQDKV
QPVSEILQLK TYLPTFETTI DKTHTCPPCP APELLGGPSV FLFPPKPKDT LMISRTPEVT
CVVVDVSHED PEVKFNWYVD GVEVHNAKTK PREEQYNSTY RVVSVLTVLH QDWLNGKEYK
CKVSNKALPA PIEKTISKAK GQPREPQVYT LPPSREEMTK NQVSLTCLVK GFYPSDIAVE
WESNGQPENN YKTTPPVLDS DGSFFLYSKL TVDKSRWQQG NVFSCSVMHE ALHNHYTQKS
LSLSPGK

Bold residues: sequence from ENPP1. Single underlined residues: signal peptide sequence fro mENPP2. Double underlined residues: sequence of IgG Fc domain, which can be from any of the sub classes IgG1, IgG2, IgG3 and IgG4. Alternatively instead of Fc domain, albumin domain can be used. In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

ENPP7-ENPP3-Fc sequence (SEQ ID NO: 57)
MRGPAVLLTV ALATLLAPGA KQGSC RKKCFDASFR GLENCRCDVA
CKDRGDCCWD FEDTCVESTR IWMCNKFRCG ERLEASLCSC SDDCLQRKDC CADYKSVCQG
ETSWLEENCD TAQQSQCPEG FDLPPVILFS MDGFRAEYLY TWDTLMPNIN KLKTCGIHSK
YMRAMYPTKT FPNHYTIVTG LYPESHGIID NNMYDVNLNK NFSLSSKEQN NPAWWHGQPM
WLTAMYQGLK AATYFWPGSE VAINGSFPSI YMPYNGSVPF EERISTLLKW LDLPKAERPR
FYTMYFEEPD SSGHAGGPVS ARVIKALQVV DHAFGMLMEG LKQRNLHNCV NIILLADHGM
DQTYCNKMEY MTDYFPRINF FYMYEGPAPR IRAHNIPHDF FSFNSEEIVR NLSCRKPDQH
FKPYLTPDLP KRLHYAKNVR IDKVHLFVDQ QWLAVRSKSN TNCGGGNHGY NNEFRSMEAI
FLAHGPSFKE KTEVEPFENI EVYNLMCDLL RIQPAPNNGT HGSLNHLLKV PFYEPSHAEE
VSKFSVCGFA NPLPTESLDC FCPHLQNSTQ LEQVNQMLNL TQEEITATVK VNLPFGRPRV
LQKNVDHCLL YHREYVSGFG KAMRMPMWSS YTVPQLGDTS PLPPTVPDCL RADVRVPPSE
SQKCSFYLAD KNITHGFLYP PASNRTSDSQ YDALITSNLV PMYEEFRKMW DYFHSVLLIK
HATERNGVNV VSGPIFDYNY DGHFDAPDEI TKHLANTDVP IPTHYFVVLT SCKNKSHTPE
NCPGWLDVLP FIIPHRPTNV ESCPEGKPEA LWVEERFTAH IARVRDVELL TGLDFYQDKV
QPVSEILQLK TYLPTFETTI DKTHTCPPCP APELLGGPSV FLFPPKPKDT LMISRTPEVT
CVVVDVSHED PEVKFNWYVD GVEVHNAKTK PREEQYNSTY RVVSVLTVLH QDWLNGKEYK
CKVSNKALPA PIEKTISKAK GQPREPQVYT LPPSREEMTK NQVSLTCLVK GFYPSDIAVE
WESNGQPENN YKTTPPVLDS DGSFFLYSKL TVDKSRWQQG NVFSCSVMHE ALHNHYTQKS
LSLSPGK Single underlined: signal peptide sequence from ENPP7. Double underlined: sequence of IgG Fc domain, which can be from any of the sub classes IgG1, IgG2, IgG3 and IgG4. Alternatively instead of Fc domain, albumin domain can be used. In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

ENPP5-ENPP3-Fc sequence (SEQ ID NO: 58)
MTSKFLLVSF ILAALSLSTT FSKQGSC RKKCFDASFR GLENCRCDVA
CKDRGDCCWD FEDTCVESTR IWMCNKFRCG ERLEASLCSC SDDCLQRKDC CADYKSVCQG
ETSWLEENCD TAQQSQCPEG FDLPPVILFS MDGFRAEYLY TWDTLMPNIN KLKTCGIHSK
YMRAMYPTKT FPNHYTIVTG LYPESHGIID NNMYDVNLNK NFSLSSKEQN NPAWWHGQPM
WLTAMYQGLK AATYFWPGSE VAINGSFPSI YMPYNGSVPF EERISTLLKW LDLPKAERPR
FYTMYFEEPD SSGHAGGPVS ARVIKALQVV DHAFGMLMEG LKQRNLHNCV NIILLADHGM
DQTYCNKMEY MTDYFPRINF FYMYEGPAPR IRAHNIPHDF FSFNSEEIVR NLSCRKPDQH
FKPYLTPDLP KRLHYAKNVR IDKVHLFVDQ QWLAVRSKSN TNCGGGNHGY NNEFRSMEAI
FLAHGPSFKE KTEVEPFENI EVYNLMCDLL RIQPAPNNGT HGSLNHLLKV PFYEPSHAEE
VSKFSVCGFA NPLPTESLDC FCPHLQNSTQ LEQVNQMLNL TQEEITATVK VNLPFGRPRV
LQKNVDHCLL YHREYVSGFG KAMRMPMWSS YTVPQLGDTS PLPPTVPDCL RADVRVPPSE
SQKCSFYLAD KNITHGFLYP PASNRTSDSQ YDALITSNLV PMYEEFRKMW DYFHSVLLIK
HATERNGVNV VSGPIFDYNY DGHFDAPDEI TKHLANTDVP IPTHYFVVLT SCKNKSHTPE
NCPGWLDVLP FIIPHRPTNV ESCPEGKPEA LWVEERFTAH IARVRDVELL TGLDFYQDKV
QPVSEILQLK TYLPTFETTI DKTHTCPPCP APELLGGPSV FLFPPKPKDT LMISRTPEVT
CVVVDVSHED PEVKFNWYVD GVEVHNAKTK PREEQYNSTY RVVSVLTVLH QDWLNGKEYK
CKVSNKALPA PIEKTISKAK GQPREPQVYT LPPSREEMTK NQVSLTCLVK GFYPSDIAVE
WESNGQPENN YKTTPPVLDS DGSFFLYSKL TVDKSRWQQG NVFSCSVMHE ALHNHYTQKS
LSLSPGK -continued

SEQUENCES

Single underlined: signal peptide sequence from ENPP5. Double underlined: sequence of IgG Fc domain, which can be from any of the sub classes IgG1, IgG2, IgG3 and IgG4. Alternatively instead of Fc domain, albumin domain can be used. In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

Albumin sequence (SEQ ID NO: 59)
GGGGSGGGGSGGGGSMKWVTFLLLLFVSGSAFSRGVFRREAHKSEIAHRYNDLGEQHFKGLVLIAFSQ
YLQKCSYDEHAKLVQEVTDFAKTCVADESAANCDKSLHTLFGDKLCAIPNLRENYGELADCCTKQEPE
RNECFLQHKDDNPSLPPFERPEAEAMCTSFKENPTTFMGHYLHEVARRHPYFYAPELLYYAEQYNEIL
TQCCAEADKESCLTPKLDGVKEKALVSSVRQRMKCSSMQKFGERAFKAWAVARLSQTFPNADFAEITK
LATDLTKVNKECCHGDLLECADDRAELAKYMCENQATISSKLQTCCDKPLLKKAHCLSEVEHDTMPAD
LPAIAADFVEDQEVCKNYAEAKDVFLGTFLYEYSRRHPDYSVSLLLRLAKKYEATLEKCCAEANPPAC
YGTVLAEFQPLVEEPKNLVKTNCDLYEKLGEYGFQNAILVRYTQKAPQVSTPTLVEAARNLGRVGTKC
CTLPEDQRLPCVEDYLSAILNRVCLLHEKTPVSEHVTKCCSGSLVERRPCFSALTVDETYVPKEFKAE
TFTFHSDICTLPEKEKQIKKQTALAELVKHKPKATAEQLKTVMDDFAQFLDTCCKAADKDTCFSTEGP
NLVTRCKDALA ENPP121-ENPP3-Albumin sequence (SEQ ID NO: 60)
MERDGCAGGG SRGGEGGRAP REGPAGNGRD RGRSHAAEAP GDPQAAASLL APMDVGEEPL
EKAARARTAK DPNTYKIISL FTFAVGVNIC LGFTAKQGSC RKKCFDASFR GLENCRCDVA
CKDRGDCCWD FEDTCVESTR IWMCNKFRCG ERLEASLCSC SDDCLQRKDC CADYKSVCQG
ETSWLEENCD TAQQSQCPEG FDLPPVILFS MDGFRAEYLY TWDTLMPNIN KLKTCGIHSK
YMRAMYPTKT FPNHYTIVTG LYPESHGIID NNMYDVNLNK NFSLSSKEQN NPAWWHGQPM
WLTAMYQGLK AATYFWPGSE VAINGSFPSI YMPYNGSVPF EERISTLLKW LDLPKAERPR
FYTMYFEEPD SSGHAGGPVS ARVIKALQVV DHAFGMLMEG LKQRNLHNCV NIILLADHGM
DQTYCNKMEY MTDYFPRINF FYMYEGPAPR IRAHNIPHDF FSFNSEEIVR NLSCRKPDQH
FKPLYTPDLP KRLHYAKNVR IDKVHLFVDQ QWLAVRSKSN TNCGGGNHGY NNEFRSMEAI
FLAHGPSFKE KTEVEPFENI EVYNLMCDLL RIQPAPNNGT HGSLNHLLKV PFYEPSHAEE
VSKFSVCGFA NPLPTESLDC FCPHLQNSTQ LEQVNQMLNL TQEEITATVK VNLPFGRPRV
LQKNVDHCLL YHREYVSGFG KAMRMPMWSS YTVPQLGDTS PLPPTVPDCL RADVRVPPSE
SQKCSFYLAD KNITHGFLYP PASNRTSDSQ YDALITSNLV PMYEEFRKMW DYFHSVLLIK
HATERNGVNV VSGPIFDYNY DGHFDAPDEI TKHLANTDVP IPTHYFVVLT SCKNKSHTPE
NCPGWLDVLP FIIPHRPTNV ESCPEGKPEA LWVEERFTAH IARVRDVELL TGLDFYQDKV
QPVSEILQLK TYLPTFETTI DKTHTCPPCP APELLGGPSV FLFPPKPKDT LMISRTPEVT
GGGSGGGGSG GGGSMKWVTF LLLLFVSGSA FSRGVFRREA HKSEIAHRYN DLGEQHFKGL
VLIAFSQYLQ KCSYDEHAKL VQEVTDFAKT CVADESAANC DKSLHTLFGD KLCAIPNLRE
NYGELADCCT KQEPERNECF LQHKDDNPSL PPFERPEAEA MCTSFKENPT TFMGHYLHEV
ARRHPYFYAP ELLYYAEQYN EILTQCCAEA DKESCLTPKL DGVKEKALVS SVRQRMKCSS
MQKFGERAFK AWAVARLSQT FPNADFAEIT KLATDLTKVN KECCHGDLLE CADDRAELAK
YMCENQATIS SKLQTCCDKP LLKKAHCLSE VEHDTMPADL PAIAADFVED QEVCKNYAEA
KDVFLGTFLY EYSRRHPDYS VSLLLRLAKK YEATLEKCCA EANPPACYGT VLAEFQPLVE
EPKNLVKTNC DLYEKLGEYG FQNAILVRYT QKAPQVSTPT LVEAARNLGR VGTKCCTLPE
DQRLPCVEDY LSAILNRVCL LHEKTPVSEH VTKCCSGSLV ERRPCFSALT VDETYVPKEF
KAETFTFHSD ICTLPEKEKQ IKKQTALAEL VKHKPKATAE QLKTVMDDF QFLDTCCKAA
DKDTCFSTEG PNLVTRCKDA LA Bold residues: sequence from ENPP1. Single underlined: signal peptide sequences from ENPP2. Double underlined: sequence of albumin domain In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

ENPP7-ENPP3-Albumin sequence (SEQ ID NO: 61)
MRGPAVLLTV ALATLLAPGA KQGSC RKKCFDASFR GLENCRCDVA
CKDRGDCCWD FEDTCVESTR IWMCNKFRCG ERLEASLCSC SDDCLQRKDC CADYKSVCQG
ETSWLEENCD TAQQSQCPEG FDLPPVILFS MDGFRAEYLY TWDTLMPNIN KLKTCGIHSK
YMRAMYPTKT FPNHYTIVTG LYPESHGIID NNMYDVNLNK NFSLSSKEQN NPAWWHGQPM
WLTAMYQGLK AATYFWPGSE VAINGSFPSI YMPYNGSVPF EERISTLLKW LDLPKAERPR
FYTMYFEEPD SSGHAGGPVS ARVIKALQVV DHAFGMLMEG LKQRNLHNCV NIILLADHGM
DQTYCNKMEY MTDYFPRINF FYMYEGPAPR IRAHNIPHDF FSFNSEEIVR NLSCRKPDQH
FKPYLTPDLP KRLHYAKNVR IDKVHLFVDQ QWLAVRSKSN TNCGGGNHGY NNEFRSMEAI
FLAHGPSFKE KTEVEPFENI EVYNLMCDLL RIQPAPNNGT HGSLNHLLKV PFYEPSHAEE
VSKFSVCGFA NPLPTESLDC FCPHLQNSTQ LEQVNQMLNL TQEEITATVK VNLPFGRPRV
LQKNVDHCLL YHREYVSGFG KAMRMPMWSS YTVPQLGDTS PLPPTVPDCL RADVRVPPSE
SQKCSFYLAD KNITHGFLYP RASNRTSDSQ YDALITSNLV PMYEEFRKMW DYFHSVLLIK
HATERNGVNV VSGPIFDYNY DGHFDAPDEI TKHLANTDVP IPTHYFVVLT SCKNKSHTPE
NCPGWLDVLP FIIPHRPTNV ESCPEGKPEA LWVEERFTAH IARVRDVELL TGLDFYQDKV
QPVSEILQLK TYLPTFETTI DKTHTCPPCP APELLGGPSV FLFPPKPKDT LMISRTPEVT
GGGSGGGGSG GGGSMKWVTF LLLLFVSGSA FSRGVFRREA HKSEIAHRYN DLGEQHFKGL
VLIAFSQYLQ KCSYDEHAKL VQEVTDFAKT CVADESAANC DKSLHTLFGD KLCAIPNLRE
NYGELADCCT KQEPERNECF LQHKDDNPSL PPFERPEAEA MCTSFKENPT TFMGHYLHEV
ARRHPYFYAP ELLYYAEQYN EILTQCCAEA DKESCLTPKL DGVKEKALVS SVRQRMKCSS
MQKFGERAFK AWAVARLSQT FPNADFAEIT KLATDLTKVN KECCHGDLLE CADDRAELAK
YMCENQATIS SKLQTCCDKP LLKKAHCLSE VEHDTMPADL PAIAADFVED QEVCKNYAEA

SEQUENCES

KDVFLGTFLY EYSRRHPDYS VSLLLRLAKK YEATLEKCCA EANPPACYGT VLAEFQPLVE
EPKNLVKTNC DLYEKLGEYG FQNAILVRYT QKAPQVSTPT LVEAARNLGR VGTKCCTLPE
DQRLPCVEDY LSAILNRVCL LHEKTPVSEH VTKCCSGSLV ERRPCFSALT VDETYVPKEF
KAETFTFHSD ICTLPEKEKQ IKKQTALAEL VKHKPKATAE QLKTVMDDFA QFLDTCCKAA
DKDTCFSTEG PNLVTRCKDA LA

Single underlined: signal peptide sequence from ENPP7. Double underlined: sequence of albumin domain In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

ENPP5-ENPP3-albumin sequence (SEQ ID NO: 62)
MTSKFLLVSF ILAALSLSTT FSKQGSC RKKCFDASFR GLENCRCDVA
CKDRGDCCWD FEDTCVESTR IWMCNKFRCG ERLEASLCSC SDDCLQRKDC CADYKSVCQG
ETSWLEENCD TAQQSQCPEG FDLPPVILFS MDGFRAEYLY TWDTLMPNIN KLKTCGIHSK
YMRAMYPTKT FPNHYTIVTG LYPESHGIID NNMYDVNLNK NFSLSSKEQN NPAWWHGQPM
WLTAMYQGLK AATYFWPGSE VAINGSFPSI YMPYNGSVPF EERISTLLKW LDLPKAERPR
FYTMYFEEPD SSGHAGGPVS ARVIKALQVV DHAFGMLMEG LKQRNLHNCV NIILLADHGM
DQTYCNKMEY MTDYFPRINF FYMYEGPAPR IRAHNIPHDF FSFNSEEIVR NLSCRKPDQH
FKPYLTPDLP KRLHYAKNVR IDKVHLFVDQ QWLAVRSKSN TNCGGGNHGY NNEFRSMEAI
FLAHGPSFKE KTEVEPFENI EVYNLMCDLL RIQPAPNNGT HGSLNHLLKV PFYEPSHAEE
VSKFSVCGFA NPLPTESLDC FCPHLQNSTQ LEQVNQMLNL TQEEITATVK VNLPFGRPRV
LQKNVDHCLL YHREYVSGFG KAMRMPMWSS YTVPQLGDTS PLPPTVPDCL RADVRVPPSE
SQKCSFYLAD KNITHGFLYP PASNRTSDSQ YDALITSNLV PMYEEFRKMW DYFHSVLLIK
HATERNGVNV VSGPIFDYNY DGHFDAPDEI TKHLANTDVP IPTHYFVVLT SCKNKSHTPE
NCPGWLDVLP FIIPHRPTNV ESCPEGKPEA LWVEERFTAH IARVRDVELL TGLDFYQDKV
QPVSEILQLK TYLPTFETTI DKTHTCPPCP APELLGGPSV FLFPPKPKDT LMISRTPEVT
GGGSGGGGSG GGGSMKWVTF LLLLFVSGSA FSRGVFRREA HKSEIAHRYN DLGEQHFKGL
VLIAFSQYLQ KCSYDEHAKL VQEVTDFAKT CVADESAANC DKSLHTLFGD KLCAIPNLRE
NYGELADCCT KQEPERNECF LQHKDDNPSL PPFERPEAEA MCTSFKENPT TFMGHYLHEV
ARRHPYFYAP ELLYYAEQYN EILTQCCAEA DKESCLTPKL DGVKEKALVS SVRQRMKCSS
MQKFGERAFK AWAVARLSQT FPNADFAEIT KLATDLTKVN KECCHGDLLE CADDRAELAK
YMCENQATIS SKLQTCCDKP LLKKAHCLSE VEHDTMPADL PAIAADFVED QEVCKNYAEA
KDVFLGTFLY EYSRRHPDYS VSLLLRLAKK YEATLEKCCA EANPPACYGT VLAEFQPLVE
EPKNLVKTNC DLYEKLGEYG FQNAILVRYT QKAPQVSTPT LVEAARNLGR VGTKCCTLPE
DQRLPCVEDY LSAILNRVCL LHEKTPVSEH VTKCCSGSLV ERRPCFSALT VDETYVPKEF
KAETFTFHSD ICTLPEKEKQ IKKQTALAEL VKHKPKATAE QLKTVMDDFA QFLDTCCKAA
DKDTCFSTEG PNLVTRCKDA LA Single underlined: signal peptide sequence from ENPP5. Double underlined: sequence of albumin domain In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

Nucleotide sequence of ENPP121-ENPP3-Fc (SEQ ID NO: 63)
ATGGAAAGGGACGGATGCGCCGGTGGTGGATCTCG
CGGAGGCGAAGGTGGAAGGGCCCCTAGGGAAGGACCTGCCGGAAACGGAAGGGACAGGGG
ACGCTCTCACGCCGCTGAAGCTCCAGGCGACCCTCAGGCCGCTGCCTCTCTGCTGGCTCC
TATGGACGTCGGAGAAGAACCCCTGGAAAAGGCCGCCAGGGCCAGGACTGCCAAGGACCC
CAACACCTACAAGATCATCTCCCTCTTCACTTTCGCCGTCGGAGTCAACATCTGCCTGGG
ATTCACCGCCGAAAAGCAAGGCAGCTGCAGGAAGAAGTGCTTTGATGCATCATTTAGAGG
ACTGGAGAACTGCCGGTGTGATGTGGCATGTAAAGACCGAGGTGATTGCTGCTGGGATTT
TGAAGACACCTGTGTGGAATCAACTCGAATATGGATGTGCAATAAATTTCGTTGTGGAGA
GACCAGATTAGAGGCCAGCCTTTGCTCTTGTTCAGATGACTGTTTGCAGAGGAAAGATTG
CTGTGCTGACTATAAGAGTGTTTGCCAAGGAGAAACCTCATGGCTGGAAGAAAACTGTGA
CACAGCCCAGCAGTCTCAGTGCCCAGAAGGGTTTGACCTGCCACCAGTTATCTTGTTTTC
TATGGATGGATTTAGAGCTGAATATTTATACACATGGGATACTTTAATGCCAAATATCAA
TAAACTGAAAACATGTGGAATTCATTCAAAATACATGAGAGCTATGTATCCTACCAAAAC
CTTCCCAAATCATTACACCATTGTCACGGGCTTGTATCCAGAGTCACATGGCATCATTGA
CAATAATATGTATGATGTAAATCTCAACAAGAATTTTTCACTTTCTTCAAAGGAACAAAA
TAATCCAGCCTGGTGGCATGGGCAACCAATGTGGCTGACAGCAATGTATCAAGGTTTAAA
AGCCGCTACCTACTTTTGGCCCGGATCAGAAGTGGCTATAAATGGCTCCTTTCCTTCCAT
ATACATGCCTTACAACGGAAGTGTCCCATTTGAAGAGAGGATTTCTACACTGTTAAAATG
GCTGGACCTGCCCAAAGCTGAAAGACCCAGGTTTTATACCATGTATTTTGAAGAACCTGA
TTCCTCTGGACATGCAGGTGGACCAGTCAGTGCCAGAGTAATTAAAGCCTTACAGGTAGT
AGATCATGCTTTTGGGATGTTGATGGAAGGCCTGAAGCAGCGGAATTTGCACAACTGTGT
CAATATCATCCTTCTGGCTGACCATGGAATGGACCAGACTTATTGTAACAAGATGGAATA
CATGACTGATTATTTTCCCAGAATAAACTTCTTCTACATGTACGAAGGGCCTGCCCCCCG
CATCCGAGCTCATAATATACCTCATGACTTTTTTAGTTTTAATTCTGAGGAAATTGTTAG
AAACCTCAGTTGCCGAAAACCTGATCAGCATTTCAAGCCCTATTTGACTCCTGATTTGCC
AAAGCGACTGCACTATGCCAAGAACGTCAGAATCGACAAAGTTCATCTCTTTGTGGATCA
ACAGTGGCTGGCTGTTAGGAGTAAATCAAATACAAATTGTGGAGGAGGCAACCATGGTTA
TAACAATGAGTTTAGGAGCATGGAGGCTATCTTTCTGGCACATGGACCCAGTTTTAAAGA
GAAGACTGAAGTTGAACCATTTGAAAATATTGAAGTCTATAACCTAATGTGTGATCTTCT
ACGCATTCAACCAGCACCAAACAATGGAACCCATGGTAGTTTAAACCATCTTCTGAAGGT -continued

SEQUENCES

GCCTTTTTATGAGCCATCCCATGCAGAGGAGGTGTCAAAGTTTTCTGTTTGTGGCTTTGC
TAATCCATTGCCCACAGAGTCTCTTGACTGTTTCTGCCCTCACCTACAAAATAGTACTCA
GCTGGAACAAGTGAATCAGATGCTAAATCTCACCCAAGAAGAAATAACAGCAACAGTGAA
AGTAAATTTGCCATTTGGGAGGCCTAGGGTACTGCAGAAGAACGTGGACCACTGTCTCCT
TTACCACAGGGAATATGTCAGTGGATTTGGAAAAGCTATGAGGATGCCCATGTGGAGTTC
ATACACAGTCCCCCAGTTGGGAGACACATCGCCTCTGCCTCCCACTGTCCCAGACTGTCT
GCGGGCTGATGTCAGGGTTCCTCCTTCTGAGAGCCAAAAATGTTCCTTCTATTTAGCAGA
CAAGAATATCACCCACGGCTTCCTCTATCCTCCTGCCAGCAATAGAACATCAGATAGCCA
ATATGATGCTTTAATTACTAGCAATTTGGTACCTATGTATGAAGAATTCAGAAAAATGTG
GGACTACTTCCACAGTGTTCTTCTTATAAAACATGCCACAGAAAGAAATGGAGTAAATGT
GGTTAGTGGACCAATATTTGATTATAATTATGATGGCCATTTTGATGCTCCAGATGAAAT
TACCAAACATTTAGCCAACACTGATGTTCCCATCCCAACACACTACTTTGTGGTGCTGAC
CAGTTGTAAAAACAAGAGCCACACACCGGAAAACTGCCCTGGGTGGCTGGATGTCCTACC
CTTTATCATCCCTCACCGACCTACCAACGTGGAGAGCTGTCCTGAAGGTAAACCAGAAGC
TCTTTGGGTTGAAGAAAGATTTACAGCTCACATTGCCCGGGTCCGTGATGTAGAACTTCT
CACTGGGCTTGACTTCTATCAGGATAAAGTGCAGCCTGTCTCTGAAATTTTGCAACTAAA
GACATATTTACCAACATTTGAAACCACTATTGACAAAACTCACACATGCCCACCGTGCCC
AGCACCTGAACTCCTGGGGGGACCGTCAGTCTTCCTCTTCCCCCCAAAACCCAAGGACAC
CCTCATGATCTCCCGGACCCCTGAGGTCACATGCGTGGTGGTGGACGTGAGCCACGAAGA
CCCTGAGGTCAAGTTCAACTGGTACGTGGACGGCGTGGAGGTGCATAATGCCAAGACAAA
GCCGCGGGAGGAGCAGTACAACAGCACGTACCGTGTGGTCAGCGTCCTCACCGTCCTGCA
CCAGGACTGGCTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCACAGGTGTACAC
CCTGCCCCCATCCCGGGAGGAGATGACCAAGAACCAGGTCAGCCTGACCTGCCTGGTCAA
AGGCTTCTATCCCAGCGACATCGCCGTGGAGTGGGAGAGCAATGGGCAGCCGGAGAACAA
CTACAAGACCACGCCTCCCGTGCTGGACTCCGACGGCTCCTTCTTCCTCTATAGCAAGCT
CACCGTGGACAAGAGCAGGTGGCAGCAGGGGAACGTCTTCTCATGCTCCGTGATGCATGA
GGCTCTGCACAACCACTACACGCAGAAGAGCCTCTCCCTGTCCCCGGGTAAA

Nucleotide sequence of ENPP121-ENPP3-Albumin (SEQ ID NO: 64)
ATGGAAAGGGACGGATGCGCCGGTGGTGGATCTCGCGGAGGCGAAGGTGGAAGGGCCCCT
AGGGAAGGACCTGCCGGAAACGGAAGGGACAGGGGACGCTCTCACGCCGCTGAAGCTCCA
GGCGACCCTCAGGCCGCTGCCTCTCTGCTGGCTCCTATGGACGTCGGAGAAGAACCCCTG
GAAAAGGCCGCCAGGGCCAGGACTGCCAAGGACCCCAACACCTACAAGATCATCTCCCTC
TTCACTTTCGCCGTCGGAGTCAACATCTGCCTGGGATTCACCGCCGAAAAGCAAGGCAGC
TGCAGGAAGAAGTGCTTTGATGCATCATTTAGAGGACTGGAGAACTGCCGGTGTGATGTG
GCATGTAAAGACCGAGGTGATTGCTGCTGGGATTTTGAAGACACCTGTGTGGAATCAACT
CGAATATGGATGTGCAATAAATTTCGTTGTGGAGAGACCAGATTAGAGGCCAGCCTTTGC
TCTTGTTCAGATGACTGTTTGCAGAGGAAAGATTGCTGTGCTGACTATAAGAGTGTTTGC
CAAGGAGAAACCTCATGGCTGGAAGAAAACTGTGACACAGCCCAGCAGTCTCAGTGCCCA
GAAGGGTTTGACCTGCCACCAGTTATCTTGTTTTCTATGGATGGATTTAGAGCTGAATAT
TTATACACATGGGATACTTTAATGCCAAATATCAATAAACTGAAAACATGTGGAATTCAT
TCAAAATACATGAGAGCTATGTATCCTACCAAAACCTTCCCAAATCATTACACCATTGTC
ACGGGCTTGTATCCAGAGTCACATGGCATCATTGACAATAATATGTATGATGTAAATCTC
AACAAGAATTTTTCACTTTCTTCAAAGGAACAAAATAATCCAGCCTGGTGGCATGGGCAA
CCAATGTGGCTGACAGCAATGTATCAAGGTTTAAAAGCCGCTACCTACTTTTGGCCCGGA
TCAGAAGTGGCTATAAATGGCTCCTTTCCTTCCATATACATGCCTTACAACGGAAGTGTC
CCATTTGAAGAGAGGATTTCTACACTGTTAAAATGGCTGGACCTGCCCAAAGCTGAAAGA
CCCAGGTTTTATACCATGTATTTTGAAGAACCTGATTCCTCTGGACATGCAGGTGGACCA
GTCAGTGCCAGAGTAATTAAAGCCTTACAGGTAGTAGATCATGCTTTTGGGATGTTGATG
GAAGGCCTGAAGCAGCGGAATTTGCACAACTGTGTCAATATCATCCTTCTGGCTGACCAT
GGAATGGACCAGACTTATTGTAACAAGATGGAATACATGACTGATTATTTTCCCAGAATA
AACTTCTTCTACATGTACGAAGGGCCTGCCCCCCGCATCCGAGCTCATAATATACCTCAT
GACTTTTTTAGTTTTAATTCTGTGGAAATTGTTAGAAACCTCAGTTGCCGAAAACCTGAT
CAGCATTTCAAGCCCTATTTGACTCCTGATTTGCCAAAGCGACTGCACTATGCCAAGAAC
GTCAGAATCGACAAAGTTCATCTCTTTGTGGATCAACAGTGGCTGGCTGTTAGGAGTAAA
TCAAATACAAATTGTGGAGGAGGCAACCATGGTTATAACAATGAGTTTAGGAGCATGGAG
GCTATCTTTCTGGCACATGGACCCAGTTTTAAAGAGAAGACTGAAGTTGAACCATTTGAA
AATATTGAAGTCTATAACCTAATGTGTGATCTTCTACGCATTCAACCAGCACCAAACAAT
GGAACCCATGGTAGTTTAAACCATCTTCTGAAGGTGCCTTTTTATGAGCCATCCCATGCA
GAGGAGGTGTCAAAGTTTTCTGTTTGTGGCTTTGCTAATCCATTGCCCACAGAGTCTCTT
GACTGTTTCTGCCCTCACCTACAAAATAGTACTCAGCTGGAACAAGTGAATCAGATGCTA
AATCTCACCCAAGAAGAAATAACAGCAACAGTGAAAGTAAATTTGCCATTTGGGAGGCCT
AGGGTACTGCAGAAGAACGTGGACCACTGTCTCCTTTACCACAGGGAATATGTCAGTGGA
TTTGGAAAAGCTATGAGGATGCCCATGTGGAGTTCATACACAGTCCCCCAGTTGGGAGAC
ACATCGCCTCTGCCTCCCACTGTCCCAGACTGTCTGCGGGCTGATGTCAGGGTTCCTCCT
TCTGAGAGCCAAAAATGTTCCTTCTATTTAGCAGACAAGAATATCACCCACGGCTTCCTC
TATCCTCCTGCCAGCAATAGAACATCAGATAGCCAATATGATGCTTTAATTACTAGCAAT
TTGGTACCTATGTATGAAGAATTCAGAAAAATGTGGGACTACTTCCACAGTGTTCTTCTT
ATAAAACATGCCACAGAAAGAAATGGAGTAAATGTGGTTAGTGGACCAATATTTGATTAT
AATTATGATGGCCATTTTGATGCTCCAGATGAAATTACCAAACATTTAGCCAACACTGAT
GTTCCCATCCCAACACACTACTTTGTGGTGCTGACCAGTTGTAAAAACAAGAGCCACACA
CCGGAAAACTGCCCTGGGTGGCTGGATGTCCTACCCTTTATCATCCCTCACCGACCTACC
AACGTGGAGAGCTGTCCTGAAGGTAAACCAGAAGCTCTTTGGGTTGAAGAAAGATTTACA
GCTCACATTGCCCGGGTCCGTGATGTAGAACTTCTCACTGGGCTTGACTTCTATCAGGAT
AAAGTGCAGCCTGTCTCTGAAATTTTGCAACTAAAGACATATTTACCAACATTTGAAACC
ACTATTGGTGGAGGAGGCTCTGGTGGAGGCGGTAGCGGAGGCGGAGGGTCGATGAAGTGG -continued

SEQUENCES

GTAACCTTTATTTCCCTTCTTTTTCTCTTTAGCTCGGCTTATTCCAGGGGTGTGTTTCGT
CGAGATGCACACAAGAGTGAGGTTGCTCATCGGTTTAAAGATTTGGGAGAAGAAAATTTC
AAAGCCTTGGTGTTGATTGCCTTTGCTCAGTATCTTCAGCAGTGTCCATTTGAAGATCAT
GTAAAATTAGTGAATGAAGTAACTGAATTTGCAAAAACATGTGTTGCTGATGAGTCAGCT
GAAAATTGTGACAAATCACTTCATACCCTTTTTGGAGACAAATTATGCACAGTTGCAACT
CTTCGTGAAACCTATGGTGAAATGGCTGACTGCTGTGCAAAACAAGAACCTGAGAGAAAT
GAATGCTTCTTGCAACACAAAGATGACAACCCAAACCTCCCCCGATTGGTGAGACCAGAG
GTTGATGTGATGTGCACTGCTTTTCATGACAATGAAGAGACATTTTTGAAAAAATACTTA
TATGAAATTGCCAGAAGACATCCTTACTTTTATGCCCCGGAACTCCTTTTCTTTGCTAAA
AGGTATAAAGCTGCTTTTACAGAATGTTGCCAAGCTGCTGATAAAGCTGCCTGCCTGTTG
CCAAAGCTCGATGAACTTCGGGATGAAGGGAAGGCTTCGTCTGCCAAACAGAGACTCAAG
TGTGCCAGTCTCCAAAAATTTGGAGAAAGAGCTTTCAAAGCATGGGCAGTAGCTCGCCTG
AGCCAGAGATTTCCCAAAGCTGAGTTTGCAGAAGTTTCCAAGTTAGTGACAGATCTTACC
AAAGTCCACACGGAATGCTGCCATGGAGATCTGCTTGAATGTGCTGATGACAGGGCGGAC
CTTGCCAAGTATATCTGTGAAAATCAAGATTCGATCTCCAGTAAACTGAAGGAATGCTGT
GAAAAACCTCTGTTGGAAAAATCCCACTGCATTGCCGAAGTGGAAAATGATGAGATGCCT
GCTGACTTGCCTTCATTAGCTGCTGATTTTGTTGAAAGTAAGGATGTTTGCAAAAACTAT
GCTGAGGCAAAGGATGTCTTCCTGGGCATGTTTTTGTATGAATATGCAAGAAGGCATCCT
GATTACTCTGTCGTGOTGCTGCTGAGACTTGCCAAGACATATGAAACCACTCTAGAGAAG
TGCTGTGCCGCTGCAGATCCTCATGAATGCTATGCCAAAGTGTTCGATGAATTTAAACCT
CTTGTGGAAGAGCCTCAGAATTTAATCAAACAAAATTGTGAGCTTTTTGAGCAGCTTGGA
GAGTACAAATTCCAGAATGCGCTATTAGTTCGTTACACCAAGAAAGTACCCCAAGTGTCA
ACTCGAACTCTTGTAGAGGTCTCAAGAAACCTAGGAAAAGTGGGCAGCAAATGTTGTAAA
CATCCTGAAGCAAAAAGAATGCCCTGTGCAGAAGACTATCTATCCGTGGTCCTGAACCAG
TTATGTGTGTTGCATGAGAAAACGCCAGTAAGTGACAGAGTCACCAAATGCTGCACAGAA
TCCTTGGTGAACAGGCGACCATGCTTTTCAGCTCTGGAAGTCGATGAAACATACGTTCCC
AAAGAGTTTAATGCTGAAACATTCACCTTCCATGCAGATATATGCACACTTTCTGAGAAG
GAGAGACAAATCAAGAAACAAACTGCACTTGTTGAGCTCGTGAAACACAAGCCCAAGGCA
ACAAAAGAGCAACTGAAAGCTGTTATGGATGATTTCGCAGCTTTTGTAGAGAAGTGCTGC
AAGGCTGACGATAAGGAGACCTGCTTTGCCGAGGAGGGTAAAAAACTTGTTGCTGCAAGT
CAAGCTGCCTTAGGCTTA

Nucleotide sequence of hNPP3-hFc-pcDNA3 (SEQ ID NO: 65)
GACGGATCGGGAGATCTCCCGATCCCCTATGGTCGACTCTCAGTACAATCTGCTCTGATG
CCGCATAGTTAAGCCAGTATCTGCTCCCTGCTTGTGTGTTGGAGGTCGCTGAGTAGTGCG
CGAGCAAAATTTAAGCTACAACAAGGCAAGGCTTGACCGACAATTGCATGAAGAATCTGC
TTAGGGTTAGGCGTTTTGCGCTGCTTCGCGATGTACGGGCCAGATATACGCGTTGACATT
GATTATTGACTAGTTATTAATAGTAATCAATTACGGGGTCATTAGTTCATAGCCCATATA
TGGAGTTCCGCGTTACATAACTTACGGTAAATGGCCCGCCTGGCTGACCGCCCAACGACC
CCCGCCCATTGACGTCAATAATGACGTATGTTCCCATAGTAACGCCAATAGGGACTTTCC
ATTGACGTCAATGGGTGGACTATTTACGGTAAACTGCCCACTTGGCAGTACATCAAGTGT
ATCATATGCCAAGTACGCCCCCTATTGACGTCAATGACGGTAAATGGCCCGCCTGGCATT
ATGCCCAGTACATGACCTTATGGGACTTTCCTACTTGGCAGTACATCTACGTATTAGTCA
TCGCTATTACCATGGTGATGCGGTTTTGGCAGTACATCAATGGGCGTGGATAGCGGTTTG
ACTCACGGGGATTTCCAAGTCTCCACCCCATTGACGTCAATGGGAGTTTGTTTTGGCACC
AAAATCAACGGGACTTTCCAAAATGTCGTAACAACTCCGCCCCATTGACGCAAATGGGCG
GTAGGCGTGTACGGTGGGAGGTCTATATAAGCAGAGCTCTCTGGCTAACTAGAGAACCCA
CTGCTTACTGGCTTATCGAAATTAATACGACTCACTATAGGGAGACCCAAGCTTATGGAA
AGGGACGGATGCGCCGGTGGTGGATCTCGCGGAGGCGAAGGTGGAAGGGCCCCTAGGGAA
GGACCTGCCGGAAACGGAAGGGACAGGGGACGCTCTCACGCCGCTGAAGCTCCAGGCGAC
CCTCAGGCCGCTGCCTCTCTGCTGGCTCCTATGGACGTCGGAGAAGAACCCCTGGAAAAG
GCCGCCAGGGCCAGGACTGCCAAGGACCCCAACACCTACAAGATCATCTCCCTCTTCACT
TTCGCCGTCGGAGTCAACATCTGCCTGGGATTCACCGCCGAAAAGCAAGGCAGCTGCAGG
AAGAAGTGCTTTGATGCATCATTTAGAGGACTGGAGAACTGCCGGTGTGATGTGGCATGT
AAAGACCGAGGTGATTGCTGCTGGGATTTTGAAGACACCTGTGTGGAATCAACTCGAATA
TGGATGTGCAATAAATTTCGTTGTGGAGAGACCAGATTAGAGGCCAGCCTTTGCTCTTGT
TCAGATGACTGTTTGCAGAGGAAAGATTGCTGTGCTGACTATAAGAGTGTTTGCCAAGGA
GAAACCTCATGGCTGGAAGAAAACTGTGACACAGCCCAGCAGTCTCAGTGCCCAGAAGGG
TTTGACCTGCCACCAGTTATCTTGTTTTCTATGGATGGATTTAGAGCTGAATATTTATAC
ACATGGGATACTTTAATGCCAAATATCAATAAACTGAAAACATGTGGAATTCATTCAAAA
TACATGAGAGCTATGTATCCTACCAAAACCTTCCCAAATCATTAGACCATTGTCACGGGC
TTGTATCCAGAGTCACATGGCATCATTGACAATAATATGTATGATGTAAATCTCAACAAG
AATTTTTCACTTTCTTCAAAGGAACAAAATAATCCAGCCTGGTGGCATGGGCAACCAATG
TGGCTGACAGCAATGTATCAAGGTTTAAAAGCCGCTACCTACTTTTGGCCCGGATCAGAA
GTGGCTATAAATGGCTCCTTTCCTTCCATATACATGCCTTACAACGGAAGTGTCCCATTT
GAAGAGAGGATTTCTACACTGTTAAAATGGCTGGACCTGCCCAAAGCTGAAAGACCCAGG
TTTTATACCATGTATTTTGAAGAACCTGATTCCTCTGGACATGCAGGTGGACCAGTCAGT
GCCAGAGTAATTAAAGCCTTACAGGTAGTAGATCATGCTTTTGGGATGTTGATGGAAGGC
CTGAAGCAGCGGAATTTGCACAACTGTGTCAATATCATCCTTCTGGCTGACCATGGAATG
GACCAGACTTATTGTAACAAGATGGAATACATGACTGATTATTTTCCCAGAATAAACTTC
TTCTACATGTACGAAGGGCCTGCCCCCCGCATCCGAGCTCATAATATACCTCATGACTTT
TTTAGTTTTAATTCTGAGGAAATTGTTAGAAACCTCAGTTGCCGAAAACCTGATCAGCAT
TTCAAGCCCTATTTGACTCCTGATTTGCCAAAGCGACTGCACTATGCCAAGAACGTCAGA
ATCGACAAAGTTCATCTCTTTGTGGATCAACAGTGGCTGGCTGTTAGGAGTAAATCAAAT
ACAAATTGTGGAGGAGGCAACCATGGTTATAACAATGAGTTTAGGAGCATGGAGGCTATC
TTTCTGGCACATGGACCCAGTTTTAAAGAGAAGACTGAAGTTGAACCATTTGAAAATATT
GAAGTCTATAACCTAATGTGTGATCTTCTACGCATTCAACCAGCACCAAACAATGGAACC -continued

| SEQUENCES |
|---|
| CATGGTAGTTTAAACCATCTTCTGAAGGTGCCTTTTTATGAGCCATCCCATGCAGAGGAG |
| GTGTCAAAGTTTTCTGTTTGTGGCTTTGCTAATCCATTGCCCACAGAGTCTCTTGACTGT |
| TTCTGCCCTCACCTACAAAATAGTACTCAGCTGGAACAAGTGAATCAGATGCTAAATCTC |
| ACCCAAGAAGAAATAACAGCAACAGTGAAAGTAAATTTGCCATTTGGGAGGCCTAGGGTA |
| CTGCAGAAGAACGTGGACCACTGTCTCCTTTACCACAGGGAATATGTCAGTGGATTTGGA |
| AAAGCTATGAGGATGCCCATGTGGAGTTCATACACAGTCCCCCAGTTGGGAGACACATCG |
| CCTCTGCCTCCCACTGTCCCAGACTGTCTGCGGGCTGATGTCAGGGTTCCTCCTTCTGAG |
| AGCCAAAAATGTTCCTTCTATTTAGCAGACAAGAATATCACCCACGGCTTCCTCTATCCT |
| CCTGCCAGCAATAGAACATCAGATAGCCAATATGATGCTTTAATTACTAGCAATTTGGTA |
| CCTATGTATGAAGAATTCAGAAAAATGTGGGACTACTTCCACAGTGTTCTTCTTATAAAA |
| CATGCCACAGAAAGAAATGGAGTAAATGTGGTTASTGGACCAATATTTGATTATAATTAT |
| GATGGCCATTTTGATGCTCCAGATGAAATTACCAAACATTTAGCCAACACTGATGTTCCC |
| ATCCCAACACACTACTTTGTGGTGCTGACCAGTTGTAAAAAGAAGAGCCACACACCGGAA |
| AACTGCCCTGGGTGGCTGGATGTCCTACCCTTTATCATCCCTCACCGACCTACCAACGTG |
| GAGAGCTGTCCTGAAGGTAAACCAGAAGCTCTTTGGGTTGAAGAAAGATTTACAGCTCAC |
| ATTGCCCGGGTCCGTGATGTAGAACTTCTCACTGGGCTTGACTTCTATCAGGATAAAGTG |
| CAGCCTGTCTCTGAAATTTTGCAACTAAAGACATATTTACCAACATTTGAAACCACTATT |
| GACAAAACTCACACATGCCCACCGTGCCCAGCACCTGAACTCCTGGGGGGACCGTCAGTC |
| TTCCTCTTCCCCCCAAAACCCAAGGACACCGTCATGATCTCCCGGACCCCTGAGGTCAGA |
| TGCGTGGTGGTGGACGTGAGCCACGAAGACCCTGAGGTCAAGTTCAACTGGTACGTGGAC |
| GGCGTGGAGGTGCATAATGCCAAGACAAAGCCGCGGGAGGAGCAGTACAACAGCACGTAC |
| CGTGTGGTCAGCGTCCTCACCGTCCTGCACCAGGACTGGCTGAATGGCAAGGAGTACAAG |
| TGCAAGGTCTCCAACAAAGCCCTCCCAGCCCCCATCGAGAAAACCATCTCCAAAGCCAAA |
| GGGCAGCCCCGAGAACCACAGGTGTACACCCTGCCCCCATCCCGGGAGGAGATGACCAAG |
| AACCAGGTGAGCCTGACCTGCCTGGTCAAAGGCTTCTATCCCAGCGACATCGCCGTGGAG |
| TGGGAGAGCAATGGGCAGCCGGAGAACAACTACAAGACCACGCCTCCCGTGCTGGACTCC |
| GACGGCTCCTTCTTCCTCTATAGCAAGCTCACCGTGGACAAGAGCAGGTGGCAGCAGGGG |
| AACGTCTTCTCATGCTCCGTGATGCATGAGGCTCTGCACAACCACTACACGCAGAAGAGC |
| CTCTCCCTGTCCCCGGGTAAATGAAATTCTGCAGATATCCATCACACTGGCGGCCGCTCG |
| AGCATGCATCTAGAGGGCCCTATTCTATAGTGTCACCTAAATGCTAGAGCTCGCTGATCA |
| GCCTCGACTGTGCCTTCTAGTTGCCAGCCATCTGTTGTTTGCCCCTCCCCCGTGCCTTCC |
| TTGACCCTGGAAGGTGCCACTCCCACTGTCCTTTCCTAATAAAATGAGGAAATTGCATCG |
| CATTGTCTGAGTAGGTGTCATTCTATTCTGGGGGGTGGGGTGGGGCAGGACAGCAAGGGG |
| GAGGATTGGGAAGACAATAGCAGGCATGCTGGGGATGCGGTGGGCTCTATGGCTTCTGAG |
| GCGGAAAGAACCAGCTGGGGCTCTAGGGGGTATCCCCACGCGCCCTGTAGCGGCGCATTA |
| AGCGCGGCGGGTGTGGTGGTTACGCGCAGCGTGACCGCTACACTTGCCAGCGCCCTAGCG |
| CCCGCTCCTTTCGCTTTCTTCCCTTCCTTTCTCGCCACGTTCGCCGGCTTTCCCCGTCAA |
| GCTCTAAATCGGGGCATCCCTTTAGGGTTCCGATTTAGTGCTTTACGGCACCTCGACCCC |
| AATAAACTTGATTAGGGTGATGGTTCACGTAGTGGGCCATCGCCCTGATAGACGGTTTTT |
| CGCCCTTTGACGTTGGAGTCCACGTTCTTTAATAGTGGACTCTTGTTCCAAACTGGAACA |
| ACACTCAACCCTATCTCGGTCTATTCTTTTGATTTATAAGGGATTTTGGGGATTTCGGCC |
| TATTGGTTAAAAAATGAGCTGATTTAACAAAAATTTAACGCGAATTAATTCTGTGGAATG |
| TGTGTCAGTTAGGGTGTGGAAAGTCCCCAGGCTCCCCAGGCAGGCAGAAGTATGCAAAGC |
| ATGCATCTCAATTAGTCAGCAACCAGGTGTGGAAAGTCCCCAGGCTCCCCAGCAGGCAGA |
| AGTATGCAAAGCATGCATCTCAATTAGTCAGCAACCATAGTCCCGCCCCTAACTCCGCCC |
| ATCCCGCCCCTAACTCCGCCCAGTTCCGCCCATTCTCCGCCCCATGGCTGACTAATTTTT |
| TTTATTTATGCAGAGGCCGAGGCCGCCTCTGCCTCTGAGCTATTCCAGAAGTAGTGAGGA |
| GGCTTTTTTGGAGGCCTAGGCTTTTGCAAAAAGCTCCCGGGAGCTTGTATATCCATTTTC |
| GGATCTGATCAAGAGACAGGATGAGGATCGTTTCGCATGATTGAACAAGATGGATTGCAC |
| GCAGGTTCTCCGGCCGCTTGGGTGGAGAGGCTATTCGGCTATGACTGGGCACAACAGACA |
| ATCGGCTGCTCTGATGCCGCCGTGTTCCGGCTGTCAGCGCAGGGGCGCCCGGTTCTTTTT |
| GTCAAGACCGACCTGTCCGGTGCCCTGAATGAACTGCAGGACGAGGCAGCGCGGCTATCG |
| TGGCTGGCCACGACGGGCGTTCCTTGCGCAGCTGTGCTCGACGTTGTCACTGAAGCGGGA |
| AGGGACTGGCTGCTATTGGGCGAAGTGCCGGGGCAGGATCTCCTGTCATCTCACCTTGCT |
| CCTGCCGAGAAAGTATCCATCATGGCTGATGCAATGCGGCGGCTGCATACGCTTGATCCG |
| GCTACCTGCCCATTCGACCACCAAGCGAAACATCGCATCGAGCGAGCACGTACTCGGATG |
| GAAGCCGGTCTTGTCGATCAGGATGATCTGGACGAAGAGCATCAGGGGCTCGCGCCAGCC |
| GAACTGTTCGCCAGGCTCAAGGCGCGCATGCCCGACGGCGAGGATCTCGTCGTGACCCAT |
| GGCGATGCCTGCTTGCCGAATATCATGGTGGAAAATGGCCGGTTTTCTGGATTCATCGAC |
| TGTGGCCGGCTGGGTGTGGCGGACCGCTATCAGGACATAGCGTTGGCTACCCGTGATATT |
| GCTGAAGAGCTTGGCGGCGAATGGGCTGACCGCTTCCTCGTGCTTTACGGTATCGCCGCT |
| CCCGATTCGCAGCGCATCGCCTTCTATCGCCTTCTTGACGAGTTCTTCTGAGCGGGACTC |
| TGGGGTTCGAAATGACCGACCAAGCGACGCCCAACCTGCCATCACGAGATTTCGATTCCA |
| CCGCCGCCTTCTATGAAAGGTTGGGCTTCGGAATCGTTTTCCGGGACGCCGGCTGGATGA |
| TCCTCCAGCGCGGGGATCTCATGCTGGAGTTCTTCGCCCACCCCAACTTGTTTATTGCAG |
| CTTATAATGGTTACAAATAAAGCAATAGCATCACAAATTTCACAAATAAAGCATTTTTTT |
| CACTGCATTCTAGTTGTGGTTTGTCCAAACTCATCAATGTATCTTATCATGTCTGTATAC |
| CGTCGACCTCTAGCTAGAGCTTGGCGTAATCATGGTCATAGCTGTTTCCTGTGTGAAATT |
| GTTATCCGCTCACAATTCCACACAACATACGAGCCGGAAGCATAAAGTGTAAAGCCTGGG |
| GTGCCTAATGAGTGAGCTAACTCACATTAATTGCGTTGCGCTCACTGCCCGCTTTCCAGT |
| CGGGAAACCTGTCGTGCCAGCTGCATTAATGATTCGGCCAACGCGCGGGGAGAGGCGGTT |
| TGCGTATTGGGCGCTCTTCCGCTTCCTCGCTCACTGACTCGCTGCGCTCGGTCGTTCGGC |
| TGCGGCGAGCGGTATCAGCTCACTCAAAGGCGGTAATACGGTTATCCACAGAATCAGGGG |
| ATAACGCAGGAAAGAACATGTGAGCAAAAGGCCAGCAAAAGGCCAGGAACCGTAAAAAGG |
| CCGCGTTGCTGGCGTTTTTCCATAGGCTCCGCCCCCCTGACGAGCATCACAAAAATCGAC |
| GCTCAAGTCAGAGGTGGCGAAACCCGACAGGACTATAAAGATACCAGGCGTTTCCCCCTG |
| GAAGCTCCCTCGTGCGCTCTCCTGTTCCGACCCTGCCGCTTACCGGATACCTGTCCGCCT |

SEQUENCES

TTCTCCCTTCGGGAAGCGTGGCGCTTTCTCAATGCTCACGCTGTAGGTATCTCAGTTCGG
TGTAGGTCGTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACAGAGT
TCTTGAAGTGGTGGCCTAACTACGGCTACACTAGAAGGACAGTATTTGGTATCTGCGCTC
TGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGAT
CTCAAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAAATT
AAAAATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAGTG
CTGCAATGATACCGCGAGACCCACGCTCACCGGCTCCAGATTTATCAGCAATAAACCAGC
CAGCCGGAAGGGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCTTCATTCAGCT
CCGGTTCCCAACGATCAAGGCGAGTTACATGATCCCCCATGTTGTGGAAAAAAGCGGTTA
GCTCCTTCGGTCCTCCGATCGTTGTCAGAAGTAAGTTGGCCGCAGTGTTATCACTCATGG
TTATGGCAGCACTGCATAATTCTCTTACTGTCATGCCATCCGTAAGATGCTTTTCTGTGA
CTGGTGAGTACTCAACCAAGTCATTCTGAGAATAGTGTATGCGGCGACCGAGTTGCTCTT
GCCCGGCGTCAATACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTT
CGATGTAACCCACTCGTGCACCCAACTGATCTTCAGCATCTTTTACTTTCACCAGCGTTT
CTGGGTGAGCAAAAACAGGAAGGCAAAATGCCGCAAAAAAGGGAATAAGGGCGACACGGA
AATGTTGAATACTCATACTCTTCCTTTTTCAATATTATTGAAGCATTTATCAGGGTTATT
GTCTCATGAGCGGATACATATTTGAATGTATTTAGAAAAATAAACAAATAGGGGTTCCGC
GCACATTTCCCCGAAAAGTGCCACCTGACGTC

ENPP121-Fc Amino acid sequence (SEQ ID NO: 66)
MERDGCAGGGSRGGEGGRAPREGPAGNGRDRGRSHAAEAPGDPQAAASLLAPMDVGEEPLEKAARARTAKD
PNTYKIISLFTFAVGVNICLG**FTAGLKPSCAKEVKSCKGRCFERTFGNCRCDAACVELGNCCLDYQETC
IEPEHIWTCNKFRCGEKRLTRSLCACSDDCKDKGDCCINYSSVCQGEKSWVEEPCESINEPQCPAGFETPP
TLLFSLDGFRAEYLHTWGGLLPVISKLKKCGTYTKNMRPVYPTKTFPNHYSIVTGLYPESHGIIDNKMYDP
KMNASFSLKSKEKFNPEWYKGEPIWVTAKYQGLKSGTFFWPGSDVEINGIFPDIYKMYNGSVPFEERILAV
LQWLQLPKDERPHFYTLYLEEPDSSGHSYGPVSSEVIKALQRVDGMVGMLMDGLKELNLHRCLNLILISDH
GMEQGSCKKYIYLNKYLGDVKNIKVIYGPAARLRPSDVPDKYYSFNYEGIARNLSCREPNQHFKPYLKHFL
PKRLHFAKSDRIEPLTFYLDPQWQLALNPSERKYCGSGFHGSDNVFSNMQALFVGYGPGEKHGTEADTFEN
IEVYNLMCDLLNLTPAPNNGTHGSLNHLLKNPVYTPKHPKEVHPLVQCPFTRNPRDNLGCSCNPSILPIED
FQTQFNLTVAEEKIIKHETLPYGRPRVLQKENTICLLSQHQFMSGYSQDILMPLWTSYTVDRNDSFSTEDF
SNCLYQDFRIPLSPVHKCSFYKNNTKVSYGFLSPPQLNKNSSGIYSEALLTTNIVPMYQSFQVIWRYFHDT
LLRKYAEERNGVNVVSGPVFDFDYDGRCDSLENLRQKRRVIRNQEILIPTHFFIVLTSCKDTSQTPLHCEN
LDTLAFILPHRTDNSESCVHGKHDSSWVEELLMLHRARITDVEHITGLSFYQQRKEPVSDILKLKTHLPTF
SQEDDKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNVFSCSVMH
EALHNHYTQKSLSLSPGK

Singly underlined: residues swapped with ENPP2 residues to afford cleavage at transition position (**), Doubly underlined: connote the beginning and the end of ENPP1 residues. Bold residues indicate residues of IgG Fc domain.

ENPP71-Fc Amino acid sequence (SEQ ID NO: 67)
MRGPAVLLTVALATLLAPGAGLKPSCAKEVKSCKGRCFERTFGNCRCDAACVELGNCCLDYQETC
IEPEHIWTCNKFRCGEKRLTRSLCACSDDCKDKGDCCINYSSVCQGEKSWVEEPCESINEPQCPAGFETPP
TLLFSLDGFRAEYLHTWGGLLPVISKLKKCGTYTKNMRPVYPTKTFPNHYSIVTGLYPESHGIIDNKMYDP
KMNASFSLKSKEKFNPEWYKGEPIWVTAKYQGLKSGTFFWPGSDVEINGIFPDIYKMYNGSVPFEERILAV
LQWLQLPKDERPHFYTLYLEEPDSSGHSYGPVSSEVIKALQRVDGMVGMLMDGLKELNLHRCLNLILISDH
GMEQGSCKKYIYLNKYLGDVKNIKVIYGPAARLRPSDVPDKYYSFNYEGIARNLSCREPNQHFKPYLKHFL
PKRLHFAKSDRIEPLTFYLDPQWQLALNPSERKYCGSGFHGSDNVFSNMQALFVGYGPGEKHGTEADTFEN
IEVYNLMCDLLNLTPAPNNGTHGSLNHLLKNPVYTPKHPKEVHPLVQCPFTRNPRDNLGCSCNPSILPIED
FQTQFNLTVAEEKIIKHETLPYGRPRVLQKENTICLLSQHQFMSGYSQDILMPLWTSYTVDRNDSFSTEDF
SNCLYQDFRIPLSPVHKCSFYKNNTKVSYGFLSPPQLNKNSSGIYSEALLTTNIVPMYQSFQVIWRYFHDT
LLRKYAEERNGVNVVSGPVFDFDYDGRCDSLENLRQKRRVIRNQEILIPTHFFIVLTSCKDTSQTPLHCEN
LDTLAFILPHRTDNSESCVHGKHDSSWVEELLMLHRARITDVEHITGLSFYQQRKEPVSDILKLKTHLPTF
SQEDDKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNVFSCSVMHE
ALHNHYTQKSLSLSPGK

Singly underlined: ENPP7 residues. Doubly underlined: beginning and end of ENPP1 residues. Bold: residues of IgG Fc domain ENPP51-Fc Amino acid sequence (SEQ ID NO: 68)
MTSKFLLVSFILAALSLSTTFSGLKPSCAKEVKSCKGRCFERTFGNCRCDAACVELGNCCLDYQETC
IEPEHIWTCNKFRCGEKRLTRSLCACSDDCKDKGDCCINYSSVCQGEKSWVEEPCESINEPQCPAGFETPP
TLLFSLDGFRAEYLHTWGGLLPVISKLKKCGTYTKNMRPVYPTKTFPNHYSIVTGLYPESHGIIDNKMYDP
KMNASFSLKSKEKFNPEWYKGEPIWVTAKYQGLKSGTFFWPGSDVEINGIFPDIYKMYNGSVPFEERILAV -continued

| SEQUENCES |
| --- |

LQWLQLPKDERPHFYTLYLEEPDSSGHSYGPVSSEVIKALQRVDGMVGMLMDGLKELNLHRCLNLILISDH
GMEQGSCKKYIYLNKYLGDVKNIKVIYGPAARLRPSDVPDKYYSFNYEGIARNLSCREPNQHFKPYLKHFL
PKRLHFAKSDRIEPLTFYLDPQWQLALNPSERKYCGSGFHGSDNVFSNMQALFVGYGPGEKHGTEADTFEN
IEVYNLMCDLLNLTPAPNNGTHGSLNHLLKNPVYTPKHPKEVHPLVQCPFTRNPRDNLGCSCNPSILPIED
FQTQFNLTVAEEKIIKHETLPYGRPRVLQKENTICLLSQHQFMSGYSQDILMPLWTSYTVDRNDSFSTEDF
SNCLYQDFRIPLSPVHKCSFYKNNTKVSYGFLSPPQLNKNSSGIYSEALLTTNIVPMYQSFQVIWRYFHDT
LLRKYAEERNGVNVVSGPVFDFDYDGRCDSLENLRQKRRVIRNQEILIPTHFFIVLTSCKDTSQTPLHCEN
LDTLAFILPHRTDNSESCVHGKHDSSWVEELLMLHRARITDVEHITGLSFYQQRKEPVSDILKLKTHLPTF
SQEDDKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNVFSCSVMHE
ALHNHYTQKSLSLSPGK

Singly underlined: ENPP5 residues. Doubly underlined: beginning and end of ENPP1 residues. Bold: residues of IgG Fc domain ENPP121-ALB Amino acid sequence (SEQ ID NO: 69)
MERDGCAGGGSRGGEGGRAPREGPAGNGRDRGRSHAAEAPGDPQAAASLLAPMDVGEEPLEKAARARTAKD
PNTYKIISLFTFAVGVNICLG**FTAGLKPSCAKEVKSCKGRCFERTFGNCRCDAACVELGNCCLDYQETC
IEPEHIWTCNKFRCGEKRLTRSLCACSDDCKDKGDCCINYSSVCQGEKSWVEEPCESINEPQCPAGFETPP
TLLFSLDGFRAEYLHTWGGLLPVISKLKKCGTYTKNMRPVYPTKTFPNHYSIVTGLYPESHGIIDNKMYDP
KMNASFSLKSKEKFNPEWYKGEPIWVTAKYQGLKSGTFFWPGSDVEINGIFPDIYKMYNGSVPFEERILAV
LQWLQLPKDERPHFYTLYLEEPDSSGHSYGPVSSEVIKALQRVDGMVGMLMDGLKELNLHRCLNLILISDH
GMEQGSCKKYIYLNKYLGDVKNIKVIYGPAARLRPSDVPDKYYSFNYEGIARNLSCREPNQHFKPYLKHFL
PKRLHFAKSDRIEPLTFYLDPQWQLALNPSERKYCGSGFHGSDNVFSNMQALFVGYGPGEKHGTEADTFEN
IEVYNLMCDLLNLTPAPNNGTHGSLNHLLKNPVYTPKHPKEVHPLVQCPFTRNPRDNLGCSCNPSILPIED
FQTQFNLTVAEEKIIKHETLPYGRPRVLQKENTICLLSQHQFMSGYSQDILMPLWTSYTVDRNDSFSTEDF
SNCLYQDFRIPLSPVHKCSFYKNNTKVSYGFLSPPQLNKNSSGIYSEALLTTNIVPMYQSFQVIWRYFHDT
LLRKYAEERNGVNVVSGPVFDFDYDGRCDSLENLRQKRRVIRNQEILIPTHFFIVLTSCKDTSQTPLHCEN
LDTLAFILPHRTDNSESCVHGKHDSSWVEELLMLHRARITDVEHITGLSFYQQRKEPVSDILKLKTHLPTF
SQEDRSGSGGSMKWVTFLLLLFVSGSAFSRGVFRREAHKSEIAHRYNDLGEQHFKGLVLIAFSQYLQKCSY
DEHAKLVQEVTDFAKTCVADESAANCDKSLHTLFGDKLCAIPNLRENYGELADCCTKQEPERNECFLQHKD
DNPSLPPFERPEAEAMCTSFKENPTTFMGHYLHEVARRHPYFYAPELLYYAEQYNEILTQCCAEADKESCL
TPKLDGVKEKALVSSVRQRMKCSSMQKFGERAFKAWAVARLSQTFPNADFAEITKLATDLTKVNKECCHGD
LLECADDRAELAKYMCENQATISSKLQTCCDKPLLKKAHCLSEVEHDTMPADLPAIAADFVEDQEVCKNYA
EAKDVFLGTFLYEYSRRHPDYSVSLLLRLAKKYEATLEKCCAEANPPACYGTVLAEFQPLVEEPKNLVKTN
CDLYEKLGEYGFQNAILVRYTQKAPQVSTPTLVEAARNLGRVGTKCCTLPEDQRLPCVEDYLSATLNRVCL
LHEKTPVSEHVTKCCSGSLVERRPCFSALTVDETYVPKEFKAETFTFHSDICTL

Singly underlined: residues swapped with ENPP2 residues to afford cleavage at transition position (**), Doubly underlined: connote the beginning and the end of ENPP1 residues. Bold: residues of Albumin Bold underlined: linker region.

NPP71-ALB Amino acid sequence (SEQ ID NO: 70)
MRGPAVLLTVALATLLAPGAGLKPSCAKEVKSCKGRCFERTFGNCRCDAACVELGNCCLDYQETC
IEPEHIWTCNKFRCGEKRLTRSLCACSDDCKDKGDCCINYSSVCQGEKSWVEEPCESINEPQCPAGFETPP
TLLFSLDGFRAEYLHTWGGLLPVISKLKKCGTYTKNMRPVYPTKTFPNHYSIVTGLYPESHGIIDNKMYDP
KMNASFSLKSKEKFNPEWYKGEPIWVTAKYQGLKSGTFFWPGSDVEINGIFPDIYKMYNGSVPFEERILAV
LQWLQLPKDERPHFYTLYLEEPDSSGHSYGPVSSEVIKALQRVDGMVGMLMDGLKELNLHRCLNLILISDH
GMEQGSCKKYIYLNKYLGDVKNIKVIYGPAARLRPSDVPDKYYSFNYEGIARNLSCREPNQHFKPYLKHFL
PKRLHFAKSDRIEPLTFYLDPQWQLALNPSERKYCGSGFHGSDNVFSNMQALFVGYGPGEKHGTEADTFEN
IEVYNLMCDLLNLTPAPNNGTHGSLNHLLKNPVYTPKHPKEVHPLVQCPFTRNPRDNLGCSCNPSILPIED
FQTQFNLTVAEEKIIKHETLPYGRPRVLQKENTICLLSQHQFMSGYSQDILMPLWTSYTVDRNDSFSTEDF
SNCLYQDFRIPLSPVHKCSFYKNNTKVSYGFLSPPQLNKNSSGIYSEALLTTNIVPMYQSFQVIWRYFHDT
LLRKYAEERNGVNVVSGPVFDFDYDGRCDSLENLRQKRRVIRNQEILIPTHFFIVLTSCKDTSQTPLHCEN
LDTLAFILPHRTDNSESCVHGKHDSSWVEELLMLHRARITDVEHITGLSFYQQRKEPVSDILKLKTHLPTF
SQEDGGSGGSMKWVTFLLLLFVSGSAFSRGVFRREAHKSEIAHRYNDLGEQHFKGLVLIAFSQYLQKCSYD
EHAKLVQEVTDFAKTCVADESAANCDKSLHTLFGDKLCAIPNLRENYGELADCCTKQEPERNECFLQHKDD
NPSLPPFERPEAEAMCTSFKENPTTFMGHYLHEVARRHPYFYAPELLYYAEQYNEILTQCCAEADKESCLT
PKLDGVKEKALVSSVRQRMKCSSMQKFGERAFKAWAVARLSQTFPNADFAEITKLATDLTKVNKECCHGDL
LECADDRAELAKYMCENQATISSKLQTCCDKPLLKKAHCLSEVEHDTMPADLPAIAADFVEDQEVCKNYAE
AKDVFLGTFLYEYSRRHPDYSVSLLLRLAKKYEATLEKCCAEANPPACYGTVLAEFQPLVEEPKNLVKTNC
DLYEKLGEYGFQNAILVRYTQKAPQVSTPTLVEAARNLGRVGTKCCTLPEDQRLPCVEDYLSAILNRVCLL
HEKTPVSEHVTKCCSGSLVERRPCFSALTVDETYVPKEFKAETFTFHSDICTL

Singly underlined: ENPP7 residues. Doubly underlined: beginning and end of ENPP1 residues. Bold: residues of Albumin Bold underline linker region.

Nucleotide sequence of ENPP121-Fc (SEQ ID NO: 71)
ATGGAAAGGGACGGATGCGCCGGTGGTGGATCTCGCGGAGGCGAAGGTGGAAGGGCCCCTAGGGAAGG
ACCTGCCGGAAACGGAAGGGACAGGGGACGCTCTCACGCCGCTGAAGCTCCAGGCGACCCTCAGGCCG
CTGCCTCTCTGCTGGCTCCTATGGACGTCGGAGAAGAACCCCTGGAAAAGGCCGCCAGGGCCAGGACT
GCCAAGGACCCCAACACCTACAAGATCATCTCCCTCTTCACTTTCGCCGTCGGAGTCAACATCTGCCT
GGGATTCACCGCCGGACTGAAGcccagCTGCGCCAAAGAAGTGAAGTCCTGCAAGGGCCGGTGCTTCG
AGCGGACCTTCGGCAACTGCAGATGCGACGCCGCCTGTGTGGAACTGGGCAACTGCTGCCTGGACTAC
CAGGAAACCTGCATCGAGCCCGAGCACATCTGGACCTGCAACAAGTTCAGATGCGGCGAGAAGCGGCT
GACCAGATCCCTGTGTGCCTGCAGCGACGACTGCAAGGACAAGGGCGACTGCTGCATCAACTACAGCA

| SEQUENCES |
|---|
| GCGTGTGCCAGGGCGAGAAGTCCTGGGTGGAAGAACCCTGCGAGAGCATCAACGAGCCCCAGTGCCCT<br>GCCGGCTTCGAGACACCTCCTACCCTGCTGTTCAGCCTGGACGGCTTTCGGGCCGAGTACCTGCACAC<br>ATGGGGAGGCCTGCTGCCCGTGATCAGCAAGCTGAAGAAGTGCGGCACCTACACCAAGAACATGCGGC<br>CCGTGTACCCCACCAAGACCTTCCCCAACCACTACTCCATCGTGACCGGCCTGTACCCCGAGAGCCAC<br>GGCATCATCGACAACAAGATGTACGACCCCAAGATGAACGCCAGCTTCAGCCTGAAGTCCAAAGAGAA<br>GTTCAACCCCGAGTGGTATAAGGGCGAGCCCATCTGGGTCACCGCCAAGTACCAGGGCCTGAAAAGCG<br>GCACATTCTTTTGGCCCGGCAGCGACGTGGAAATCAACGGCATCTTCCCCGACATCTATAAGATGTAC<br>AACGGCAGCGTGCCCTTCGAGGAACGGATCCTGGCTGTGCTGCAGTGGCTGCAGCTGCCCAAGGATGA<br>GCGGCCCCACTTCTACACCCTGTACCTGGAAGAACCTGACAGCAGCGGCCACAGCTACGGCCCTGTGT<br>CCAGCGAAGTGATCAAGGCCCTGCAGCGGGTGGACGGCATGGTGGGAATGCTGATGGACGGCCTGAAA<br>GAGCTGAACCTGCACAGATGCCTGAACCTGATCCTGATCAGCGACCACGGCATGGAACAGGGATCCTG<br>CAAGAAGTACATCTACCTGAACAAGTACCTGGGCGACGTGAAGAACATCAAAGTGATCTACGGCCCAG<br>CCGCCAGACTGAGGCCTAGCGACGTGCCCGACAAGTACTACAGCTTCAACTACGAGGGAATCGCCCGG<br>AACCTGAGCTGCAGAGAGCCCAACCAGCACTTCAAGCCCTACCTGAAGCACTTCCTGCCCAAGCGGCT<br>GCACTTCGCCAAGAGCGACAGAATCGAGCCCCTGACCTTCTACCTGGACCCCCAGTGGCAGCTGGCCC<br>TGAATCCCAGCGAGAGAAAGTACTGCGGCAGCGGCTTCCACGGCTCCGACAACGTGTTCAGCAACATG<br>CAGGCCCTGTTCGTGGGCTACGGACCCGGCTTTAAGCACGGCATCGAGGCCGACACCTTCGAGAACAT<br>CGAGGTGTACAATCTGATGTGCGACCTGCTGAATCTGACCCCTGCCCCCAACAATGGCACCCACGGCA<br>GCCTGAACCATCTGCTGAAGAACCCCGTGTACACCCCTAAGCACCCCAAAGAGGTGCACCCCCTGGTG<br>CAGTGCCCCTTCACCAGAAACCCCAGAGACAACCTGGGCTGTAGCTGCAACCCCAGCATCCTGCCCAT<br>CGAGGACTTCCAGACCCAGTTCAACCTGACCGTGGCCGAGGAAAAGATCATCAAGCACGAGACACTGC<br>CCTACGGCAGACCCCGGGTGCTGCAGAAAGAGAACACCATCTGCCTGCTGAGCCAGCACCAGTTCATG<br>AGCGGCTACTCCCAGGACATCCTGATGCCCCTGTGGACCAGCTACACCGTGGACCGGAACGACAGCTT<br>CTCCACCGAGGATTTCAGCAACTGCCTGTACCAGGATTTCCGGATCCCCCTGAGCCCCGTGCACAAGT<br>GCAGCTTCTACAAGAACAACACCAAGGTGTCCTACGGCTTCCTGAGCCCTCCCCAGCTGAACAAGAAC<br>AGCTCCGGCATCTACAGCGAGGCCCTGCTGACTACCAACATCGTGCCCATGTACCAGAGCTTCCAAGT<br>GATCTGGCGGTACTTCCACGACACCCTGCTGCGGAAGTACGCCGAAGAACGGAACGGCGTGAACGTGG<br>TGTCCGGCCCAGTGTTCGACTTCGACTACGACGGCAGATGTGACAGCCTGGAAAATCTGCGGCAGAAA<br>AGAAGAGTGATCCGGAACCAGGAAATTCTGATCCCTACCCACTTCTTTATCGTGCTGACAAGCTGCAA<br>GGATACCAGCCAGACCCCCCTGCACTGCGAGAACCTGGATACCCTGGCCTTCATCCTGCCTCACCGGA<br>CCGACAACAGCGAGAGCTGTGTGCACGGCAAGCACGACAGCTCTTGGGTGGAAGAACTGCTGATGCTG<br>CACCGGGCCAGAATCACCGATGTGGAACACATCACCGGCCTGAGCTTTTACCAGCAGCGGAAAGAACC<br>CGTGTCCGATATCCTGAAGCTGAAAACCCATCTGCCCACCTTCAGCCAGGAAGATGACAAGACCCACA<br>CTTGCCCCCCCTGCCCAGCTCCTGAACTGCTGGGAGGACCCTCTGTGTTCCTGTTCCCCCCAAAGCCC<br>AAGGACACCCTGATGATCTCTAGGACCCCCGAAGTCACTTGCGTCGTCGTCGACGTGTCCCACGAGGA<br>CCCTGAAGTCAAGTTCAACTGGTACGTCGACGGTGTCGAAGTCCACAACGCCAAGACCAAGCCCAGGG<br>AAGAACAGTACAACTCTACCTACCGCGTCGTCAGCGTCCTGACCGTCCTGCACCAGGACTGGCTGAAC<br>GGAAAGGAATACAAGTGCAAGGTGTCCAACAAGGCCCTGCCTGCCCCCATCGAAAAGACCATCTCTAA<br>GGCCAAGGGACAGCCCCGCGAACCCCAGGTCTACACCCTGCCACCCTCTAGGGAAGAAATGACCAAGA<br>ACCAGGTGTCCCTGACCTGCCTGGTCAAGGGATTCTACCCCTCTGACATCGCCGTCGAATGGGAATCT<br>AACGGACAGCCCGAAAACAACTACAAGACCACCCCCCCTGTCCTGGACTCTGACGGATCATTCTTCCT<br>GTACTCTAAGCTGACTGTCGACAAGTCTAGGTGGCAGCAGGGAAACGTGTTCTCTTGCTCTGTCATGC<br>ACGAAGCCCTGCACAACCACTACACCCAGAAGTCTCTGTCTCTGTCCCCCGGAAAG<br><br>Nucleotide sequence of ENPP121-Albumin (SEQ ID NO: 72)<br>ATGGAAAGGGACGGATGCGCCGGTGGTGGATCTCGCGGAGGCGAAGGTGGAAGGGCCCCTAGGGAAGG<br>ACCTGCCGGAAACGGAAGGGACAGGGGACGCTCTCACGCCGCTGAAGCTCCAGGCGACCCTCAGGCCG<br>CTGCCTCTCTGCTGGCTCCTATGGACGTCGGAGAAGAACCCCTGGAAAAGGCCGCCAGGGCCAGGACT<br>GCCAAGGACCCCAACACCTACAAGATCATCTCCCTCTTCACTTTCGCCGTCGGAGTCAACATCTGCCT<br>GGGATTCACCGCCGGACTGAAGcccagCTGCGCCAAAGAAGTGAAGTCCTGCAAGGGCCGGTGCTTCG<br>AGCGGACCTTCGGCAACTGCAGATGCGACGCCGCCTGTGTGGAACTGGGCAACTGCTGCCTGGACTAC<br>CAGGAAACCTGCATCGAGCCCGAGCACATCTGGACCTGCAACAAGTTCAGATGCGGCGAGAAGCGGCT<br>GACCAGATCCCTGTGTGCCTGCAGCGACGACTGCAAGGACAAGGGCGACTGCTGCATCAACTACAGCA<br>GCGTGTGCCAGGGCGAGAAGTCCTGGGTGGAAGAACCCTGCGAGAGCATCAACGAGCCCCAGTGCCCT<br>GCCGGCTTCGAGACACCTCCTACCCTGCTGTTCAGCCTGGACGGCTTTCGGGCCGAGTACCTGCACAC<br>ATGGGGAGGCCTGCTGCCCGTGATCAGCAAGCTGAAGAAGTGCGGCACCTACACCAAGAACATGCGGC<br>CCGTGTACCCCACCAAGACCTTCCCCAACCACTACTCCATCGTGACCGGCCTGTACCCCGAGAGCCAC<br>GGCATCATCGACAACAAGATGTACGACCCCAAGATGAACGCCAGCTTCAGCCTGAAGTCCAAAGAGAA<br>GTTCAACCCCGAGTGGTATAAGGGCGAGCCCATCTGGGTCACCGCCAAGTACCAGGGCCTGAAAAGCG<br>GCACATTCTTTTGGCCCGGCAGCGACGTGGAAATCAACGGCATCTTCCCCGACATCTATAAGATGTAC<br>AACGGCAGCGTGCCCTTCGAGGAACGGATCCTGGCTGTGCTGCAGTGGCTGCAGCTGCCCAAGGATGA<br>GCGGCCCCACTTCTACACCCTGTACCTGGAAGAACCTGACAGCAGCGGCCACAGCTACGGCCCTGTGT<br>CCAGCGAAGTGATCAAGGCCCTGCAGCGGGTGGACGGCATGGTGGGAATGCTGATGGACGGCCTGAAA<br>GAGCTGAACCTGCACAGATGCCTGAACCTGATCCTGATCAGCGACCACGGCATGGAACAGGGATCCTG<br>CAAGAAGTACATCTACCTGAACAAGTACCTGGGCGACGTGAAGAACATCAAAGTGATCTACGGCCCAG<br>CCGCCAGACTGAGGCCTAGCGACGTGCCCGACAAGTACTACAGCTTCAACTACGAGGGAATCGCCCGG<br>AACCTGAGCTGCAGAGAGCCCAACCAGCACTTCAAGCCCTACCTGAAGCACTTCCTGCCCAAGCGGCT<br>GCACTTCGCCAAGAGCGACAGAATCGAGCCCCTGACCTTCTACCTGGACCCCCAGTGGCAGCTGGCCC<br>TGAATCCCAGCGAGAGAAAGTACTGCGGCAGCGGCTTCCACGGCTCCGACAACGTGTTCAGCAACATG<br>CAGGCCCTGTTCGTGGGCTACGGACCCGGCTTTAAGCACGGCATCGAGGCCGACACCTTCGAGAACAT<br>CGAGGTGTACAATCTGATGTGCGACCTGCTGAATCTGACCCCTGCCCCCAACAATGGCACCCACGGCA<br>GCCTGAACCATCTGCTGAAGAACCCCGTGTACACCCCTAAGCACCCCAAAGAGGTGCACCCCCTGGTG<br>CAGTGCCCCTTCACCAGAAACCCCAGAGACAACCTGGGCTGTAGCTGCAACCCCAGCATCCTGCCCAT<br>CGAGGACTTCCAGACCCAGTTCAACCTGACCGTGGCCGAGGAAAAGATCATCAAGCACGAGACACTGC<br>CCTACGGCAGACCCCGGGTGCTGCAGAAAGAGAACACCATCTGCCTGCTGAGCCAGCACCAGTTCATG<br>AGCGGCTACTCCCAGGACATCCTGATGCCCCTGTGGACCAGCTACACCGTGGACCGGAACGACAGCTT<br>CTCCACCGAGGATTTCAGCAACTGCCTGTACCAGGATTTCCGGATCCCCCTGAGCCCCGTGCACAAGT |

-continued

SEQUENCES

GCAGCTTCTACAAGAACAACACCAAGGTGTCCTACGGCTTCCTGAGCCCTCCCCAGCTGAACAAGAAC
AGCTCCGGCATCTACAGCGAGGCCCTGCTGACTACCAACATCGTGCCCATGTACCAGAGCTTCCAAGT
GATCTGGCGGTACTTCCACGACACCCTGCTGCGGAAGTACGCCGAAGAACGGAACGGCGTGAACGTGG
TGTCCGGCCCAGTGTTCGACTTCGACTACGACGGCAGATGTGACAGCCTGGAAAATCTGCGGCAGAAA
AGAAGAGTGATCCGGAACCAGGAAATTCTGATCCCTACCCACTTCTTTATCGTGCTGACAAGCTGCAA
GGATACCAGCCAGACCCCCCTGCACTGCGAGAACCTGGATACCCTGGCCTTCATCCTGCCTCACCGGA
CCGACAACAGCGAGAGCTGTGTGCACGGCAAGCACGACAGCTCTTGGGTGGAAGAACTGCTGATGCTG
CACCGGGCCAGAATCACCGATGTGGAACACATCACCGGCCTGAGCTTTTACCAGCAGCGGAAAGAACC
CGTGTCCGATATCCTGAAGCTGAAAACCCATCTGCCCACCTTCAGCCAGGAAGATGGTGGAGGAGGCT
CTGGTGGAGGCGGTAGCGGAGGCGGAGGGTCGGGAGGTTCTGGATCAATGAAGTGGGTAACCTTTATT
TCCCTTCTTTTTCTCTTTAGCTCGGCTTATTCCAGGGGTGTGTTTCGTCGAGATGCACACAAGAGTGA
GGTTGCTCATCGGTTTAAAGATTTGGGAGAAGAAAATTTCAAAGCCTTGGTGTTGATTGCCTTTGCTC
AGTATCTTCAGCAGTGTCCATTTGAAGATCATGTAAAATTAGTGAATGAAGTAACTGAATTTGCAAAA
ACATGTGTTGCTGATGAGTCAGCTGAAAATTGTGACAAATCACTTCATACCCTTTTTGGAGACAAATT
ATGCACAGTTGCAACTCTTCGTGAAACCTATGGTGAAATGGCTGACTGCTGTGCAAAACAAGAACCTG
AGAGAAATGAATGCTTCTTGCAACACAAAGATGACAACCCAAACCTCCCCCGATTGGTGAGACCAGAG
GTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTT
TTACAGAATGTTGCCAAGCTGCTGATAAAGCTGCCTGCCTGTTGCCAAAGCTCGATGAACTTCGGGAT
GAAGGGAAGGCTTCGTCTGCCAAACAGAGACTCAAGTGTGCCAGTCTCCAAAAATTTGGAGAAAGAGC
TTTCAAAGCATGGGCAGTAGCTCGCCTGAGCCAGAGATTTCCCAAAGCTGAGTTTGCAGAAGTTTCCA
AGTTAGTGACAGATCTTACCAAAGTCCACACGGAATGCTGCCATGGAGATCTGCTTGAATGTGCTGAT
GACAGGGCGGACCTTGCCAAGTATATCTGTGAAAATCAAGATTCGATCTCCAGTAAACTGAAGGAATG
CTGTGAAAAACCTCTGTTGGAAAAATCCCACTGCATTGCCGAAGTGGAAAATGATGAGATGCCTGCTG
ACTTGCCTTCATTAGCTGCTGATTTTGTTGAAAGTAAGGATGTTTGCAAAAACTATGCTGAGGCAAAG
GATGTCTTCCTGGGCATGTTTTTGTATGAATATGCAAGAAGGCATCCTGATTACTCTGTCGTGCTGCT
GCTGAGACTTGCCAAGACATATGAAACCACTCTAGAGAAGTGCTGTGCCGCTGCAGATCCTCATGAAT
GCTATGCCAAAGTGTTCGATGAATTTAAACCTCTTGTGGAAGAGCCTCAGAATTTAATCAAACAAAAT
TGTGAGCTTTTTGAGCAGCTTGGAGAGTACAAATTCCAGAATGCGCTATTAGTTCGTTACACCAAGAA
AGTACCCCAAGTGTCAACTCCAACTCTTGTAGAGGTCTCAAGAAACCTAGGAAAAGTGGGCAGCAAAT
GTTGTAAACATCCTGAAGCAAAAAGAATGCCCTGTGCAGAAGACTATCTATCCGTGGTCCTGAACCAG
TTATGTGTGTTGCATGAGAAAACGCCAGTAAGTGACAGAGTCACCAAATGCTGCACAGAATCCTTGGT
GAACAGGCGACCATGCTTTTCAGCTCTGGAAGTCGATGAAACATACGTTCCCAAAGAGTTTAATGCTG
AAACATTCACCTTCCATGCAGATATATGCACACTTTCTGAGAAGGAGAGACAAATCAAGAAACAAACT
GCACTTGTTGAGCTCGTGAAACACAAGCCCAAGGCAACAAAAGAGCAACTGAAAGCTGTTATGGATGA
TTTCGCAGCTTTTGTAGAGAAGTGCTGCAAGGCTGACGATAAGGAGACCTGCTTTGCCGAGGAGGGTA
AAAAACTTGTTGCTGCAAGTCAAGCTGCCTTAGGCTTA

Nucleotide sequence of ENPP7-1-Fc (SEQ ID NO: 73)
ATGAGAGGACCTGCCGTCCTGCTGACCGTCGCCCTGGCTACCTTGCTGGCCCCTGGTGCTGGTGCAcc
cagCTGCGCCAAAGAAGTGAAGTCCTGCAAGGGCCGGTGCTTCGAGCGGACCTTCGGCAACTGCAGAT
GCGACGCCGCCTGTGTGGAACTGGGCAACTGCTGCCTGGACTACCAGGAAACCTGCATCGAGCCCGAG
CACATCTGGACCTGCAACAAGTTCAGATGCGGCGAGAAGCGGCTGACCAGATCCCTGTGTGCCTGCAG
CGACGACTGCAAGGACAAGGGCGACTGCTGCATCAACTACAGCAGCGTGTGCCAGGGCGAGAAGTCCT
GGGTGGAAGAACCCTGCGAGAGCATCAACGAGCCCCAGTGCCCTGCCGGCTTCGAGACACCTCCTACC
CTGCTGTTCAGCCTGGACGGCTTTCGGGCCGAGTACCTGCACACATGGGGAGGCCTGCTGCCCGTGAT
CAGCAAGCTGAAGAAGTGCGGCACCTACACCAAGAACATGCGGCCCGTGTACCCCACCAAGACCTTCC
CCAACCACTACTCCATCGTGACCGGCCTGTACCCCGAGAGCCACGGCATCATCGACAACAAGATGTAC
GACCCCAAGATGAACGCCAGCTTCAGCCTGAAGTCCAAAGAGAAGTTCAACCCCGAGTGGTATAAGGG
CGAGCCCATCTGGGTCACCGCCAAGTACCAGGGCCTGAAAAGCGGCACATTCTTTTGGCCCGGCAGCG
ACGTGGAAATCAACGGCATCTTCCCCGACATCTATAAGATGTACAACGGCAGCGTGCCCTTCGAGGAA
CGGATCCTGGCTGTGCTGCAGTGGCTGCAGCTGCCCAAGGATGAGCGGCCCCACTTCTACACCCTGTA
CCTGGAAGAACCTGACAGCAGCGGCCACAGCTACGGCCCTGTGTCCAGCGAAGTGATCAAGGCCCTGC
AGCGGGTGGACGGCATGGTGGGAATGCTGATGGACGGCCTGAAAGAGCTGAACCTGCACAGATGCCTG
AACCTGATCCTGATCAGCGACCACGGCATGGAACAGGGATCCTGCAAGAAGTACATCTACCTGAACAA
GTACCTGGGCGACGTGAAGAACATCAAAGTGATCTACGGCCCAGCCGCCAGACTGAGGCCTAGCGACG
TGCCCGACAAGTACTACAGCTTCAACTACGAGGGAATCGCCCGGAACCTGAGCTGCAGAGAGCCCAAC
CAGCACTTCAAGCCCTACCTGAAGCACTTCCTGCCCAAGCGGCTGCACTTCGCCAAGAGCGACAGAAT
CGAGCCCCTGACCTTCTACCTGGACCCCCAGTGGCAGCTGGCCCTGAATCCCAGCGAGAGAAAGTACT
GCGGCAGCGGCTTCCACGGCTCCGACAACGTGTTCAGCAACATGCAGGCCCTGTTCGTGGGCTACGGA
CCCGGCTTTAAGCACGGCATCGAGGCCGACACCTTCGAGAACATCGAGGTGTACAATCTGATGTGCGA
CCTGCTGAATCTGACCCCTGCCCCCAACAATGGCACCCACGGCAGCCTGAACCATCTGCTGAAGAACC
CCGTGTACACCCCTAAGCACCCCAAAGAGGTGCACCCCCTGGTGCAGTGCCCCTTCACCAGAAACCCC
AGAGACAACCTGGGCTGTAGCTGCAACCCCAGCATCCTGCCCATCGAGGACTTCCAGACCCAGTTCAA
CCTGACCGTGGCCGAGGAAAAGATCATCAAGCACGAGACACTGCCCTACGGCAGACCCCGGGTGCTGC
AGAAAGAGAACACCATCTGCCTGCTGAGCCAGCACCAGTTCATGAGCGGCTACTCCCAGGACATCCTG
ATGCCCCTGTGGACCAGCTACACCGTGGACCGGAACGACAGCTTCTCCACCGAGGATTTCAGCAACTG
CCTGTACCAGGATTTCCGGATCCCCCTGAGCCCCGTGCACAAGTGCAGCTTCTACAAGAACAACACCA
AGGTGTCCTACGGCTTCCTGAGCCCTCCCCAGCTGAACAAGAACAGCTCCGGCATCTACAGCGAGGCC
CTGCTGACTACCAACATCGTGCCCATGTACCAGAGCTTCCAAGTGATCTGGCGGTACTTCCACGACAC
CCTGCTGCGGAAGTACGCCGAAGAACGGAACGGCGTGAACGTGGTGTCCGGCCCAGTGTTCGACTTCG
ACTACGACGGCAGATGTGACAGCCTGGAAAATCTGCGGCAGAAAAGAAGAGTGATCCGGAACCAGGAA
ATTCTGATCCCTACCCACTTCTTTATCGTGCTGACAAGCTGCAAGGATACCAGCCAGACCCCCCTGCA
CTGCGAGAACCTGGATACCCTGGCCTTCATCCTGCCTCACCGGACCGACAACAGCGAGAGCTGTGTGC
ACGGCAAGCACGACAGCTCTTGGGTGGAAGAACTGCTGATGCTGCACCGGGCCAGAATCACCGATGTG
GAACACATCACCGGCCTGAGCTTTTACCAGCAGCGGAAAGAACCCGTGTCCGATATCCTGAAGCTGAA
AACCCATCTGCCCACCTTCAGCCAGGAAGATGACAAGACCCACACTTGCCCCCCCTGCCCAGCTCCTG -continued

SEQUENCES

AACTGCTGGGAGGACCCTCTGTGTTCCTGTTCCCCCCAAAGCCCAAGGACACCCTGATGATCTCTAGG
ACCCCCGAAGTCACTTGCGTCGTCGTCGACGTGTCCCACGAGGACCCTGAAGTCAAGTTCAACTGGTA
CGTCGACGGTGTCGAAGTCCACAACGCCAAGACCAAGCCCAGGGAAGAACAGTACAACTCTACCTACC
GCGTCGTCAGCGTCCTGACCGTCCTGCACCAGGACTGGCTGAACGGAAAGGAATACAAGTGCAAGGTG
TCCAACAAGGCCCTGCCTGCCCCCATCGAAAAGACCATCTCTAAGGCCAAGGGACAGCCCCGCGAACC
CCAGGTCTACACCCTGCCACCCTCTAGGGAAGAAATGACCAAGAACCAGGTGTCCCTGACCTGCCTGG
TCAAGGGATTCTACCCCTCTGACATCGCCGTCGAATGGGAATCTAACGGACAGCCCGAAAACAACTAC
AAGACCACCCCCCCTGTCCTGGACTCTGACGGATCATTCTTCCTGTACTCTAAGCTGACTGTCGACAA
GTCTAGGTGGCAGCAGGGAAACGTGTTCTCTTGCTCTGTCATGCACGAAGCCCTGCACAACCACTACA
CCCAGAAGTCTCTGTCTCTGTCCCCCGGAAAG

Nucleotide sequence of ENPP7-NPP1-Albumin (SEQ ID NO: 74)
ATGAGAGGACCTGCCGTCCTGCTGACCGTCGCCCTGGCTACCTTGCTGGCCCCTGGTGCTGGTGCAcc
cagCTGCGCCAAAGAAGTGAAGTCCTGCAAGGGCCGGTGCTTCGAGCGGACCTTCGGCAACTGCAGAT
GCGACGCCGCCTGTGTGGAACTGGGCAACTGCTGCCTGGACTACCAGGAAACCTGCATCGAGCCCGAG
CACATCTGGACCTGCAACAAGTTCAGATGCGGCGAGAAGCGGCTGACCAGATCCCTGTGTGCCTGCAG
CGACGACTGCAAGGACAAGGGCGACTGCTGCATCAACTACAGCAGCGTGTGCCAGGGCGAGAAGTCCT
GGGTGGAAGAACCCTGCGAGAGCATCAACGAGCCCCAGTGCCCTGCCGGCTTCGAGACACCTCCTACC
CTGCTGTTCAGCCTGGACGGCTTTCGGGCCGAGTACCTGCACACATGGGGAGGCCTGCTGCCCGTGAT
CAGCAAGCTGAAGAAGTGCGGCACCTACACCAAGAACATGCGGCCCGTGTACCCCACCAAGACCTTCC
CCAACCACTACTCCATCGTGACCGGCCTGTACCCCGAGAGCCACGGCATCATCGACAACAAGATGTAC
GACCCCAAGATGAACGCCAGCTTCAGCCTGAAGTCCAAAGAGAAGTTCAACCCCGAGTGGTATAAGGG
CGAGCCCATCTGGGTCACCGCCAAGTACCAGGGCCTGAAAAGCGGCACATTCTTTTGGCCCGGCAGCG
ACGTGGAAATCAACGGCATCTTCCCCGACATCTATAAGATGTACAACGGCAGCGTGCCCTTCGAGGAA
CGGATCCTGGCTGTGCTGCAGTGGCTGCAGCTGCCCAAGGATGAGCGGCCCCACTTCTACACCCTGTA
CCTGGAAGAACCTGACAGCAGCGGCCACAGCTACGGCCCTGTGTCCAGCGAAGTGATCAAGGCCCTGC
AGCGGGTGGACGGCATGGTGGGAATGCTGATGGACGGCCTGAAAGAGCTGAACCTGCACAGATGCCTG
AACCTGATCCTGATCAGCGACCACGGCATGGAACAGGGATCCTGCAAGAAGTACATCTACCTGAACAA
GTACCTGGGCGACGTGAAGAACATCAAAGTGATCTACGGCCCAGCCGCCAGACTGAGGCCTAGCGACG
TGCCCGACAAGTACTACAGCTTCAACTACGAGGGAATCGCCCGGAACCTGAGCTGCAGAGAGCCCAAC
CAGCACTTCAAGCCCTACCTGAAGCACTTCCTGCCCAAGCGGCTGCACTTCGCCAAGAGCGACAGAAT
CGAGCCCCTGACCTTCTACCTGGACCCCCAGTGGCAGCTGGCCCTGAATCCCAGCGAGAGAAAGTACT
GCGGCAGCGGCTTCCACGGCTCCGACAACGTGTTCAGCAACATGCAGGCCCTGTTCGTGGGCTACGGA
CCCGGCTTTAAGCACGGCATCGAGGCCGACACCTTCGAGAACATCGAGGTGTACAATCTGATGTGCGA
CCTGCTGAATCTGACCCCTGCCCCCAACAATGGCACCCACGGCAGCCTGAACCATCTGCTGAAGAACC
CCGTGTACACCCCTAAGCACCCCAAAGAGGTGCACCCCCTGGTGCAGTGCCCCTTCACCAGAAACCCC
AGAGACAACCTGGGCTGTAGCTGCAACCCCAGCATCCTGCCCATCGAGGACTTCCAGACCCAGTTCAA
CCTGACCGTGGCCGAGGAAAAGATCATCAAGCACGAGACACTGCCCTACGGCAGACCCCGGGTGCTGC
AGAAAGAGAACACCATCTGCCTGCTGAGCCAGCACCAGTTCATGAGCGGCTACTCCCAGGACATCCTG
ATGCCCCTGTGGACCAGCTACACCGTGGACCGGAACGACAGCTTCTCCACCGAGGATTTCAGCAACTG
CCTGTACCAGGATTTCCGGATCCCCCTGAGCCCCGTGCACAAGTGCAGCTTCTACAAGAACAACACCA
AGGTGTCCTACGGCTTCCTGAGCCCTCCCCAGCTGAACAAGAACAGCTCCGGCATCTACAGCGAGGCC
CTGCTGACTACCAACATCGTGCCCATGTACCAGAGCTTCCAAGTGATCTGGCGGTACTTCCACGACAC
CCTGCTGCGGAAGTACGCCGAAGAACGGAACGGCGTGAACGTGGTGTCCGGCCCAGTGTTCGACTTCG
ACTACGACGGCAGATGTGACAGCCTGGAAAATCTGCGGCAGAAAAGAAGAGTGATCCGGAACCAGGAA
ATTCTGATCCCTACCCACTTCTTTATCGTGCTGACAAGCTGCAAGGATACCAGCCAGACCCCCCTGCA
CTGCGAGAACCTGGATACCCTGGCCTTCATCCTGCCTCACCGGACCGACAACAGCGAGAGCTGTGTGC
ACGGCAAGCACGACAGCTCTTGGGTGGAAGAACTGCTGATGCTGCACCGGGCCAGAATCACCGATGTG
GAACACATCACCGGCCTGAGCTTTTACCAGCAGCGGAAAGAACCCGTGTCCGATATCCTGAAGCTGAA
AACCCATCTGCCCACCTTCAGCCAGGAAGATGGTGGAGGAGGCTCTGGTGGAGGCGGTAGCGGAGGCG
GAGGGTCGGGAGGTTCTGGATCAATGAAGTGGGTAACCTTTATTTCCCTTCTTTTTCTCTTTAGCTCG
GCTTATTCCAGGGGTGTGTTTCGTCGAGATGCACACAAGAGTGAGGTTGCTCATCGGTTTAAAGATTT
GGGAGAAGAAAATTTCAAAGCCTTGGTGTTGATTGCCTTTGCTCAGTATCTTCAGCAGTGTCCATTTG
AAGATCATGTAAAATTAGTGAATGAAGTAACTGAATTTGCAAAAACATGTGTTGCTGATGAGTCAGCT
GAAAATTGTGACAAATCACTTCATACCCTTTTTGGAGACAAATTATGCACAGTTGCAACTCTTCGTGA
AACCTATGGTGAAATGGCTGACTGCTGTGCAAAACAAGAACCTGAGAGAAATGAATGCTTCTTGCAAC
ACAAAGATGACAACCCAAACCTCCCCCGATTGGTGAGACCAGAGGTTGATGTGATGTGCACTGCTTTT
CATGACAATGAAGAGACATTTTTGAAAAAATACTTATATGAAATTGCCAGAAGACATCCTTACTTTTA
TGCCCCGGAACTCCTTTTCTTTGCTAAAAGGTATAAAGCTGCTTTTACAGAATGTTGCCAAGCTGCTG
ATAAAGCTGCCTGCCTGTTGCCAAAGCTCGATGAACTTCGGGATGAAGGGAAGGCTTCGTCTGCCAAA
CAGAGACTCAAGTGTGCCAGTCTCCAAAAATTTGGAGAAAGAGCTTTCAAAGCATGGGCAGTAGCTCG
CCTGAGCCAGAGATTTCCCAAAGCTGAGTTTGCAGAAGTTTCCAAGTTAGTGACAGATCTTACCAAAG
TCCACACGGAATGCTGCCATGGAGATCTGCTTGAATGTGCTGATGACAGGGCGGACCTTGCCAAGTAT
ATCTGTGAAAATCAAGATTCGATCTCCAGTAAACTGAAGGAATGCTGTGAAAAACCTCTGTTGGAAAA
ATCCCACTGCATTGCCGAAGTGGAAAATGATGAGATGCCTGCTGACTTGCCTTCATTAGCTGCTGATT
TTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGA
AACCACTCTAGAGAAGTGCTGTGCCGCTGCAGATCCTCATGAATGCTATGCCAAAGTGTTCGATGAAT
TTAAACCTCTTGTGGAAGAGCCTCAGAATTTAATCAAACAAAATTGTGAGCTTTTTGAGCAGCTTGGA
GAGTACAAATTCCAGAATGCGCTATTAGTTCGTTACACCAAGAAAGTACCCCAAGTGTCAACTCCAAC
TCTTGTAGAGGTCTCAAGAAACCTAGGAAAAGTGGGCAGCAAATGTTGTAAACATCCTGAAGCAAAAA
GAATGCCCTGTGCAGAAGACTATCTATCCGTGGTCCTGAACCAGTTATGTGTGTTGCATGAGAAAACG
CCAGTAAGTGACAGAGTCACCAAATGCTGCACAGAATCCTTGGTGAACAGGCGACCATGCTTTTCAGC
TCTGGAAGTCGATGAAACATACGTTCCCAAAGAGTTTAATGCTGAAACATTCACCTTCCATGCAGATA

SEQUENCES

TATGCACACTTTCTGAGAAGGAGAGACAAATCAAGAAACAAACTGCACTTGTTGAGCTCGTGAAACAC
AAGCCCAAGGCAACAAAAGAGCAACTGAAAGCTGTTATGGATGATTTCGCAGCTTTTGTAGAGAAGTG
CTGCAAGGCTGACGATAAGGAGACCTGCTTTGCCGAGGAGGGTAAAAAACTTGTTGCTGCAAGTCAAG
CTGCCTTAGGCTTA

Nucleotide sequence of ENPP3 (SEQ ID NO: 75)
ATGGAATCTACGTTGACTTTAGCAACGGAACAACCTGTTAAGAAGAACACTCTTAAGAAATATAAAAT
AGCTTGCATTGTTCTTCTTGCTTTGCTGGTGATCATGTCACTTGGATTAGGCCTGGGGCTTGGACTCA
GGAAACTGGAAAAGCAAGGCAGCTGCAGGAAGAAGTGCTTTGATGCATCATTTAGAGGACTGGAGAAC
TGCCGGTGTGATGTGGCATGTAAAGACCGAGGTGATTGCTGCTGGGATTTTGAAGACACCTGTGTGGA
ATCAACTCGAATATGGATGTGCAATAAATTTCGTTGTGGAGAGACCAGATTAGAGGCCAGCCTTTGCT
CTTGTTCAGATGACTGTTTGCAGAGGAAAGATTGCTGTGCTGACTATAAGAGTGTTTGCCAAGGAGAA
ACCTCATGGCTGGAAGAAAACTGTGACACAGCCCAGCAGTCTCAGTGCCCAGAAGGGTTTGACCTGCC
ACCAGTTATCTTGTTTTCTATGGATGGATTTAGAGCTGAATATTTATACACATGGGATACTTTAATGC
CAAATATCAATAAACTGAAAACATGTGGAATTCATTCAAAATACATGAGAGCTATGTATCCTACCAAA
ACCTTCCCAAATCATTACACCATTGTCACGGGCTTGTATCCAGAGTCACATGGCATCATTGACAATAA
TATGTATGATGTAAATCTCAACAAGAATTTTTCACTTTCTTCAAAGGAACAAAATAATCCAGCCTGGT
GGCATGGGCAACCAATGTGGCTGACAGCAATGTATCAAGGTTTAAAAGCCGCTACCTACTTTTGGCCC
GGATCAGAAGTGGCTATAAATGGCTCCTTTCCTTCCATATACATGCCTTACAACGGAAGTGTCCCATT
TGAAGAGAGGATTTCTACACTGTTAAAATGGCTGGACCTGCCCAAAGCTGAAAGACCCAGGTTTTATA
CCATGTATTTTGAAGAACCTGATTCCTCTGGACATGCAGGTGGACCAGTCAGTGCCAGAGTAATTAAA
GCCTTACAGGTAGTAGATCATGCTTTTGGGATGTTGATGGAAGGCCTGAAGCAGCGGAATTTGCACAA
CTGTGTCAATATCATCCTTCTGGCTGACCATGGAATGGACCAGACTTATTGTAACAAGATGGAATACA
TGACTGATTATTTTCCCAGAATAAACTTCTTCTACATGTACGAAGGGCCTGCCCCCCGCATCCGAGCT
CATAATATACCTCATGACTTTTTTAGTTTTAATTCTGAGGAAATTGTTAGAAACCTCAGTTGCCGAAA
ACCTGATCAGCATTTCAAGCCCTATTTGACTCCTGATTTGCCAAAGCGACTGCACTATGCCAAGAACG
TCAGAATCGACAAAGTTCATCTCTTTGTGGATCAACAGTGGCTGGCTGTTAGGAGTAAATCAAATACA
AATTGTGGAGGAGGCAACCATGGTTATAACAATGAGTTTAGGAGCATGGAGGCTATCTTTCTGGCACA
TGGACCCAGTTTTAAAGAGAAGACTGAAGTTGAACCATTTGAAAATATTGAAGTCTATAACCTAATGT
GTGATCTTCTACGCATTCAACCAGCACCAAACAATGGAACCCATGGTAGTTTAAACCATCTTCTGAAG
GTGCCTTTTTATGAGCCATCCCATGCAGAGGAGGTGTCAAAGTTTTCTGTTTGTGGCTTTGCTAATCC
ATTGCCCACAGAGTCTCTTGACTGTTTCTGCCCTCACCTACAAAATAGTACTCAGCTGGAACAAGTGA
ATCAGATGCTAAATCTCACCCAAGAAGAAATAACAGCAACAGTGAAAGTAAATTTGCCATTTGGGAGG
CCTAGGGTACTGCAGAAGAACGTGGACCACTGTCTCCTTTACCACAGGGAATATGTCAGTGGATTTGG
AAAAGCTATGAGGATGCCCATGTGGAGTTCATACACAGTCCCCCAGTTGGGAGACACATCGCCTCTGC
CTCCCACTGTCCCAGACTGTCTGCGGGCTGATGTCAGGGTTCCTCCTTCTGAGAGCCAAAAATGTTCC
TTCTATTTAGCAGACAAGAATATCACCCACGGCTTCCTCTATCCTCCTGCCAGCAATAGAACATCAGA
TAGCCAATATGATGCTTTAATTACTAGCAATTTGGTACCTATGTATGAAGAATTCAGAAAAATGTGGG
ACTACTTCCACAGTGTTCTTCTTATAAAACATGCCACAGAAAGAAATGGAGTAAATGTGGTTAGTGGA
CCAATATTTGATTATAATTATGATGGCCATTTTGATGCTCCAGATGAAATTACCAAACATTTAGCCAA
CACTGATGTTCCCATCCCAACACACTACTTTGTGGTGCTGACCAGTTGTAAAAACAAGAGCCACACAC
CGGAAAACTGCCCTGGGTGGCTGGATGTCCTACCCTTTATCATCCCTCACCGACCTACCAACGTGGAG
AGCTGTCCTGAAGGTAAACCAGAAGCTCTTTGGGTTGAAGAAAGATTTACAGCTCACATTGCCCGGGT
CCGTGATGTAGAACTTCTCACTGGGCTTGACTTCTATCAGGATAAAGTGCAGCCTGTCTCTGAAATTT
TGCAACTAAAGACATATTTACCAACATTTGAAACCACTATT Nucleotide sequence of ENPP1 (SEQ ID NO: 76)
ATGGAACGGGACGGCTGTGCCGGCGGAGGATCAAGAGGCGGAGAAGGCGGCAGAGCCCCTAGAGAAGG
ACCTGCCGGCAACGGCAGAGACAGAGGCAGATCTCATGCCGCCGAAGCCCCTGGCGATCCTCAGGCTG
CTGCTTCTCTGCTGGCCCCCATGGATGTGGGCGAGGAACCTCTGGAAAAGGCCGCCAGAGCCAGAACC
GCCAAGGACCCCAACACCTACAAGGTGCTGAGCCTGGTGCTGTCCGTGTGCGTGCTGACCACCATCCT
GGGCTGCATCTTCGGCCTGAAGCCCAGCTGCGCCAAAGAAGTGAAGTCCTGCAAGGGCCGGTGCTTCG
AGCGGACCTTCGGCAACTGCAGATGCGACGCCGCCTGTGTGGAACTGGGCAACTGCTGCCTGGACTAC
CAGGAAACCTGCATCGAGCCCGAGCACATCTGGACCTGCAACAAGTTCAGATGCGGCGAGAAGCGGCT
GACCAGATCCCTGTGTGCCTGCAGCGACGACTGCAAGGACAAGGGCGACTGCTGCATCAACTACAGCA
GCGTGTGCCAGGGCGAGAAGTCCTGGGTGGAAGAACCCTGCGAGAGCATCAACGAGCCCCAGTGCCCT
GCCGGCTTCGAGACACCTCCTACCCTGCTGTTCAGCCTGGACGGCTTTCGGGCCGAGTACCTGCACAC
ATGGGGAGGCCTGCTGCCCGTGATCAGCAAGCTGAAGAAGTGCGGCACCTACACCAAGAACATGCGGC
CCGTGTACCCCACCAAGACCTTCCCCAACCACTACTCCATCGTGACCGGCCTGTACCCCGAGAGCCAC
GGCATCATCGACAACAAGATGTACGACCCCAAGATGAACGCCAGCTTCAGCCTGAAGTCCAAAGAGAA
GTTCAACCCCGAGTGGTATAAGGGCGAGCCCATCTGGGTCACCGCCAAGTACCAGGGCCTGAAAAGCG
GCACATTCTTTTGGCCCGGCAGCGACGTGGAAATCAACGGCATCTTCCCCGACATCTATAAGATGTAC
AACGGCAGCGTGCCCTTCGAGGAACGGATCCTGGCTGTGCTGCAGTGGCTGCAGCTGCCCAAGGATGA
GCGGCCCCACTTCTACACCCTGTACCTGGAAGAACCTGACAGCAGCGGCCACAGCTACGGCCCTGTGT
CCAGCGAAGTGATCAAGGCCCTGCAGCGGGTGGACGGCATGGTGGGAATGCTGATGGACGGCCTGAAA
GAGCTGAACCTGCACAGATGCCTGAACCTGATCCTGATCAGCGACCACGGCATGGAACAGGGATCCTG
CAAGAAGTACATCTACCTGAACAAGTACCTGGGCGACGTGAAGAACATCAAAGTGATCTACGGCCCAG
CCGCCAGACTGAGGCCTAGCGACGTGCCCGACAAGTACTACAGCTTCAACTACGAGGGAATCGCCCGG
AACCTGAGCTGCAGAGAGCCCAACCAGCACTTCAAGCCCTACCTGAAGCACTTCCTGCCCAAGCGGCT
GCACTTCGCCAAGAGCGACAGAATCGAGCCCCTGACCTTCTACCTGGACCCCCAGTGGCAGCTGGCCC
TGAATCCCAGCGAGAGAAAGTACTGCGGCAGCGGCTTCCACGGCTCCGACAACGTGTTCAGCAACATG
CAGGCCCTGTTCGTGGGCTACGGACCCGGCTTTAAGCACGGCATCGAGGCCGACACCTTCGAGAACAT
CGAGGTGTACAATCTGATGTGCGACCTGCTGAATCTGACCCCTGCCCCCAACAATGGCACCCACGGCA
GCCTGAACCATCTGCTGAAGAACCCCGTGTACACCCCTAAGCACCCCAAAGAGGTGCACCCCCTGGTG
CAGTGCCCCTTCACCAGAAACCCCAGAGACAACCTGGGCTGTAGCTGCAACCCCAGCATCCTGCCCAT
CGAGGACTTCCAGACCCAGTTCAACCTGACCGTGGCCGAGGAAAAGATCATCAAGCACGAGACACTGC
CCTACGGCAGACCCCGGGTGCTGCAGAAAGAGAACACCATCTGCCTGCTGAGCCAGCACCAGTTCATG -continued

| SEQUENCES |
|---|
| AGCGGCTACTCCCAGGACATCCTGATGCCCCTGTGGACCAGCTACACCGTGGACCGGAACGACAGCTT<br>CTCCACCGAGGATTTCAGCAACTGCCTGTACCAGGATTTCCGGATCCCCCTGAGCCCCGTGCACAAGT<br>GCAGCTTCTACAAGAACAACACCAAGGTGTCCTACGGCTTCCTGAGCCCTCCCCAGCTGAACAAGAAC<br>AGCTCCGGCATCTACAGCGAGGCCCTGCTGACTACCAACATCGTGCCCATGTACCAGAGCTTCCAAGT<br>GATCTGGCGGTACTTCCACGACACCCTGCTGCGGAAGTACGCCGAAGAACGGAACGGCGTGAACGTGG<br>TGTCCGGCCCAGTGTTCGACTTCGACTACGACGGCAGATGTGACAGCCTGGAAAATCTGCGGCAGAAA<br>AGAAGAGTGATCCGGAACCAGGAAATTCTGATCCCTACCCACTTCTTTATCGTGCTGACAAGCTGCAA<br>GGATACCAGCCAGACCCCCCTGCACTGCGAGAACCTGGATACCCTGGCCTTCATCCTGCCTCACCGGA<br>CCGACAACAGCGAGAGCTGTGTGCACGGCAAGCACGACAGCTCTTGGGTGGAAGAACTGCTGATGCTG<br>CACCGGGCCAGAATCACCGATGTGGAACACATCACCGGCCTGAGCTTTTACCAGCAGCGGAAAGAACC<br>CGTGTCCGATATCCTGAAGCTGAAAACCCATCTGCCCACCTTCAGCCAGGAAGAT |

Methods

The invention provides methods of treating or preventing stroke in a sickle cell anemia (SCA) patient. In certain embodiments, the subject is administered a therapeutically effective amount of at least one compound of the invention. In other embodiments, the subject is administered a therapeutically effective amount of formula (I), or a salt or solvate thereof:

PROTEIN-Z-DOMAIN-X-Y (I), wherein in (I):

PROTEIN is at least one selected from the group consisting of ENPP1 (SEQ ID NO:1), ENPP121 (SEQ ID NO:15), ENPP71 (SEQ ID NO:17), ENPP71 lacking ENPP1 N-terminus GLK (SEQ ID NO:19), ENPP51 (SEQ ID NO:24), and A-B-SEQ ID NO:32;

A is a protein export sequence;

B is absent or a sequence corresponding to residues $Xaa_p$-$Xaa_{17}$ in SEQ ID NO:33, wherein p is an integer ranging from 1 to 17;

DOMAIN is absent or at least one selected from the group consisting of a human IgG Fc domain (Fc) (such as but not limited to IgG1, IgG2, IgG3 and/or IgG4), human serum albumin protein (ALB) and a fragment thereof;

X and Z are independently absent or a polypeptide comprising 1-20 amino acids; and, Y is absent or a sequence selected from the "bone targeting" sequence group consisting of: $D_m$ (SEQ ID NO:3), $(DSS)_n$ (SEQ ID NO:4), $(ESS)_n$ (SEQ ID NO:5), $(RQQ)_n$ (SEQ ID NO:6), $(KR)_n$ (SEQ ID NO:7), $R_m$ (SEQ ID NO:8), DSSSEEKFLRRIGRFG (SEQ ID NO:9), EEEEEEEPRGDT (SEQ ID NO:10), APWHLSSQYSRT (SEQ ID NO:11), STLPIPHEFSRE (SEQ ID NO:12), VTKHLNQISQSY (SEQ ID NO:13), and $E_m$ (SEQ ID NO:14), wherein m is an integer ranging from 1 to 15, and wherein n is an integer ranging from 1 to 10.

The invention provides a kit comprising at least one anti-stroke treatment and a compound of the invention, or a salt or solvate thereof, and instructions for using the anti-stroke treatment and the compound for treating or preventing stroke in a sickle cell anemia patient.

The invention further provides a method of detecting whether a SCA patient is at risk for stroke. In certain embodiments, the method comprises measuring the amount of pyrophosphate (PPi) in a sample from the SCA patient, and comparing the amount of PPi in the sample from the SCA patient with the amount of PPi in a reference sample. In other embodiments, if the amount of PPi is lower in the sample from the SCA patient than in the reference sample, the patient is at risk for stroke. In yet other embodiments, the method further comprises administering to the patient at risk for stroke a therapeutically effective amount of a compound of the invention, or a salt or solvate thereof.

The invention further provides a method of treating or preventing stroke in a SCA patient who is at high risk for stroke. In certain embodiments, the method comprises administering to the patient a therapeutically effective amount of a compound of the invention, or a salt or solvate thereof.

In certain embodiments of formula (I), or a salt or solvate thereof, Y is absent and the compound lacks a negatively-charged bone-targeting sequence. In other embodiments, the PROTEIN comprises an ecto-nucleotide pyrophosphate/phosphodiesterase-2 (ENPP2) transmembrane domain. In yet other embodiments, the PROTEIN lacks the ENPP1 transmembrane domain. In yet other embodiments, the ENPP2 transmembrane domain comprises residues 12-30 of NCBI accession no. NP_001124335 (SEQ ID NO:2), which corresponds to IISLFTFAVGVNICLGFTA (SEQ ID NO:23). In yet other embodiments, DOMAIN comprises ALB and the compound of formula (I) lacks a polyaspartic acid domain. In yet other embodiments, DOMAIN comprises an IgG Fc domain.

In certain embodiments, the compound is administered by at least one route selected from the group consisting of subcutaneous, oral, aerosol, inhalational, rectal, vaginal, transdermal, subcutaneous, intranasal, buccal, sublingual, parenteral, intrathecal, intragastrical, ophthalmic, pulmonary and topical. In other embodiments, the compound is intravenously administered to the patient. In yet other embodiments, the compound is administered acutely or chronically to the patient. In yet other embodiments, the compound is administered locally, regionally or systemically to the patient. In yet other embodiments, the compound is administered to the patient as a pharmaceutical composition further comprising at least one pharmaceutically acceptable carrier.

In certain embodiments, the patient is further administered at least one anti-stroke treatment. Examples of anti-stroke treatments include, but are not limited to, anticoagulant medication (i.e., warfarin/coumadin), antiplatelet medication (i.e., aspirin, clopidogrel), antihypertensive medication, tissue plasminogen activator (tPA), surgical intervention (i.e., carotid endarterectomy, angioplasty/stents), endovascular procedures (mechanical thrombectomy) and treatments specific to SCA such as hydroxyurea.

In certain embodiments, the compound of the invention and the at least one anti-stroke treatment are co-administered to the patient. In other embodiments, the compound of the invention and the at least one anti-stroke treatment are co-formulated. In yet other embodiments, the compound of the invention is the only anti-stroke treatment administered to the patient. In yet other embodiments, the compound of the invention is the only anti-stroke treatment administered to the patient in an amount sufficient to treat or prevent stroke in the patient.

In certain embodiments, the subject is a mammal. In yet other embodiments, the mammal is human.

In certain embodiments, the risk of developing stroke or the severity of the stroke is minimized in the patient. In other embodiments, a person at risk of developing stroke is advised to get treatment. In yet other embodiments, anti-stroke treatment is administered to the SCA patient. In yet other embodiments, treating the patient according to the methods of the invention increases the patient's extracellular pyrophosphate concentrations.

It will be appreciated by one of skill in the art, when armed with the present disclosure including the methods detailed herein, that the invention is not limited to treatment of a disease or disorder once it is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that a compound of the invention, or a mutant thereof, as discussed elsewhere herein, can be administered to a subject prior to the onset of the disease or disorder, thereby preventing the disease or disorder from developing.

One of skill in the art, when armed with the disclosure herein, would appreciate that the prevention of a disease or disorder in a subject encompasses administering to a subject a compound of the invention, or a mutant thereof as a preventative measure against a disease or disorder.

The invention encompasses administration of a compound of the invention, or a mutant thereof to practice the methods of the invention; the skilled artisan would understand, based on the disclosure provided herein, how to formulate and administer the compound of the invention, or a mutant thereof to a subject. However, the present invention is not limited to any particular method of administration or treatment regimen. This is especially true where it would be appreciated by one skilled in the art, equipped with the disclosure provided herein, including the reduction to practice using an art-recognized model of stroke, that methods of administering a compound of the invention can be determined by one of skill in the pharmacological arts.

Pharmaceutical Compositions and Formulations

The invention provides pharmaceutical compositions comprising a compound of the invention within the methods of the invention.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between about 0.1% and about 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

In certain embodiments, the compositions are formulated using one or more pharmaceutically acceptable excipients or carriers. In certain embodiments, the pharmaceutical compositions comprise a therapeutically effective amount of the active agent and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences, 1991, Mack Publication Co., New Jersey.

The composition of the invention may comprise a preservative from about 0.005% to 2.0% by total weight of the composition. The composition may include an antioxidant and a chelating agent, which inhibit the degradation of the compound. Illustrative antioxidants for some compounds are BHT, BHA, alpha-tocopherol and ascorbic acid in the illustrative range of about 0.01% to 0.3%, for example BHT in the range of 0.03% to 0.1% by weight by total weight of the composition.

Administration/Dosing

The regimen of administration may affect what constitutes an effective amount. For example, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation. In certain embodiments, administration of the compound of the invention to a subject elevates the subject's plasma PPi to a level of about 2.5 μM.

Administration of the compositions of the present invention to a patient, such as a mammal, such as a human, may be carried out using known procedures, at dosages and for periods of time effective to treat a disease or disorder in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an patient as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the patient.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 μg to about 7,500 mg, about 20 μg to about 7,000 mg, about 40 μg to about 6,500 mg, about 80 μg to about 6,000 mg, about 100 μg to about 5,500 mg, about 200 μg to about 5,000 mg, about 400 μg to about 4,000 mg, about 800 μg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween.

In some embodiments, the dose of a compound of the invention is from about 0.5 μg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Single unit dosage forms suitable for oral administration, such as tablets, capsules, gelcaps, and caplets, which are adapted for controlled-release are encompassed by the present invention.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form. For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation. In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours. The term pulsatile release is used herein in its conventional sense to refer to a drug formulation that provides release of the drug in such a way as to produce pulsed plasma profiles of the drug after drug administration. The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1

Polymorphisms in the ENPP1 enzyme are associated with stroke risk or protection in pediatric sickle cell anemia (SCA) patients: specifically, the presence of a glutamine or a lysine at position 121 of the mature ENPP1 enzyme. Patients with the homoallelic QQ genotype are more likely to have a stroke as compared to patients with a heteroallelic KQ genotype, or patients with the homoallelic KK genotype.

Plasma inorganic pyrophosphate (PPi) levels were measured in sickle cell anemia patients with homoallelic QQ genotype, heteroallelic KQ genotype, or homoallelic KK genotype. Plasma PPi levels were extremely low in SCA patients with homoallelic QQ genotype, with average levels of 0.89±0.30 μM (FIG. 1). This is compared to ~3.3±0.20 μM plasma levels reported in homallelic KK genotype individuals who are not at risk for stroke. In fact, the plasma PPi levels for SCA patients with homoallelic QQ genotype (at risk for stroke) were in the same range as for those patients with Pseudoxanthoma Elasticum (PxE), a monogenic disease that induces vascular, tissue, and retinal calcifications. PxE patients exhibit plasma PPi levels around 0.5 μM. PxE patients are also at risk for vascular calcifications. Without wishing to be bound by any specific theory, reduced enzyme activity of ENPP1 reduces plasma PPi levels and can be causal in the pathogenesis of stroke in pediatric sickle cell anemia patients through a physiologic mechanism of increased vascular calcification. Supplementing sickle cell anemia patients with the homoallelic QQ genotype (who are at risk for stroke) with the compounds of the present invention, including exogenous ENPP1 or ENPP3, as described herein can help prevent the thrombotic strokes inherent in these children.

Figure 2:
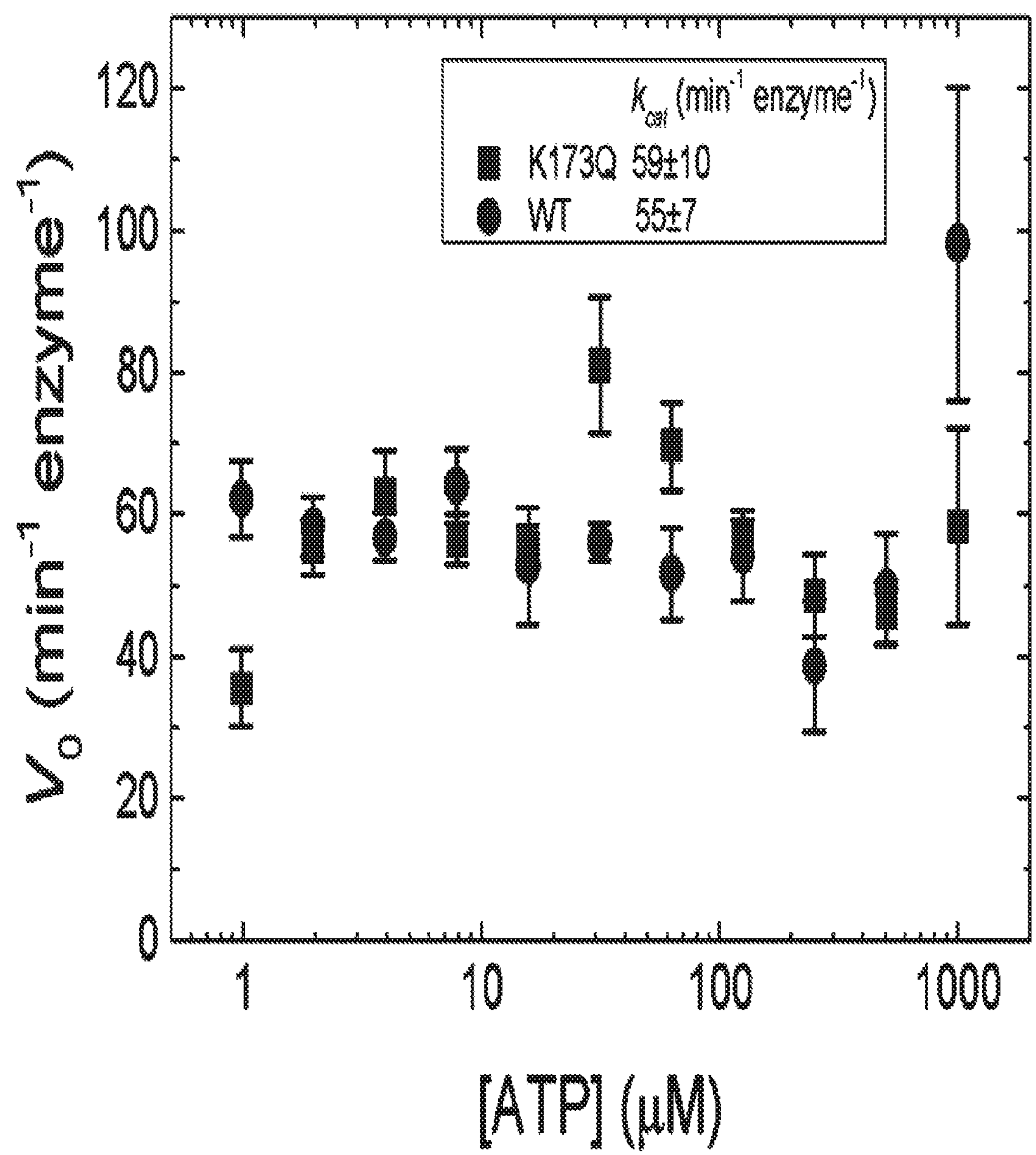
FIG. 2 is a graph illustrating ATP dependence of initial steady state rate of ENPP1 K121 (circles) and ENPP1 Q121 (squares) isoforms. $K_M$ for both proteins with the substrate ATP is less than 1 μM, as initial rates at 1 μM ATP for both proteins reach $V_{max}$ value. ENPP1 K121 $k_{cat}$=0.92±0.11 $sec^{-1}$ $enzyme^{-1}$ and ENPP1 Q121 $k_{cat}$=0.98±0.11 $sec^{-1}$ $enzyme^{-1}$, demonstrating no statistical difference between the catalytic activities of these two isoforms of ENPP1 (Student's t-test p=0.779).

A series of experiments was designed to determine whether the KQ polymorphisms in ENPP1 resulted in increased catalytic activity of the ENPP1 enzyme. The ATP hydrolytic rates of the K121 and Q121 ENPP1 isoforms were directly compared, revealing that the two enzymes had identical catalytic activities (FIG. 2), and therefore the polymorphism did not induce alterations in the catalytic rate of the enzyme.

Polymorphisms in enzymes may affect catalytic activity independent of catalytic rate, such as by reducing protein stability, reducing protein expression, or unknown mechanisms. To assess whether polymorphisms at position 121 of the mature enzyme effected overall catalytic activity, plasma PPi in patients homoallelic for Q at position 121 were compared with those heteroallelic for Q or K at the same position. The Q polymorphism was observed to have statistically significant reductions in plasma PPi, thereby establishing a physiologic mechanism for increase stroke risk.

The findings of the present invention establish a direct link between stroke in pediatric sickle cell patients, ENPP1 activity, and plasma PPi, and provide a surprising basis for treatment using enzyme supplementation designed to elevate plasma PPi using the compounds and methods described herein.

The findings of the present invention also enable a method of prophylactic treatment for stroke based on genotypic risk assessment (ENPP1 121 Q polymorphism) and biomarker risk assessment (plasma PPi concentration) for stroke in the pediatric sickle cell population. This method directly addresses a novel and heretofore unknown pathogenic mechanism of stroke risk in sickle cell anemia patients—reduced ENPP1 activity.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating or ameliorating stroke in a sickle cell anemia (SCA) patient in need thereof, the method comprising administering to the patient a therapeutically effective amount of a compound of formula (I), or a salt or solvate thereof:

PROTEIN-Z-DOMAIN-X-Y (I), wherein in (I):

PROTEIN comprises amino acid residues 23 to 849 (PSCAKE . . . to . . . QED) of SEQ ID NO:19;

DOMAIN is absent or at least one selected from the group consisting of a human IgG Fc domain (Fc), human serum albumin protein (ALB), and a fragment thereof;

X and Z are independently absent or a polypeptide comprising 1-20 amino acids; and Y is absent.

2. The method of claim 1, wherein the risk of developing stroke, or the severity of the stroke, is reduced in the SCA patient being administered the compound as compared to a SCA patient who has not been administered the compound.

3. The method of claim 1, wherein the compound lacks a negatively-charged bone-targeting sequence.

4. The method of claim 1, wherein the patient is administered the compound by at least one route selected from the group consisting of subcutaneous, oral, aerosol, inhalational, rectal, vaginal, transdermal, intranasal, buccal, sublingual, parenteral, intrathecal, intragastrical, ophthalmic, pulmonary, and topical.

5. The method of claim 1, wherein the compound is intravenously or subcutaneously administered to the patient.

6. The method of claim 1, wherein administering the compound to the patient increases, or prevents further decrease of, the patient's extracellular pyrophosphate concentrations.

7. The method of claim 1, wherein the PROTEIN comprises an ecto-nucleotide pyrophosphate/phosphodiesterase-2 (ENPP2) transmembrane domain.

8. The method of claim 7, wherein the ENPP2 transmembrane domain comprises amino acid residues 12-30 of SEQ ID NO:2, which corresponds to SEQ ID NO:23.

9. The method of claim 1, wherein DOMAIN comprises ALB and the compound lacks a polyaspartic acid domain.

10. The method of claim 1, wherein the PROTEIN lacks the ENPP1 transmembrane domain.

11. The method of claim 1, wherein DOMAIN comprises an IgG Fc domain.

12. The method of claim 1, wherein the compound is administered to the patient as a pharmaceutical composition further comprising at least one pharmaceutically acceptable carrier.

13. The method of claim 1, wherein the patient is further administered at least one additional anti-stroke treatment.

14. The method of claim 13, wherein the at least one additional anti-stroke treatment is selected from the group consisting of an anticoagulant medication, hydroxyurea, an antiplatelet medication, an antihypertensive medication, a tissue plasminogen activator (tPA), a surgical intervention, and an endovascular procedure.

15. The method of claim 13, wherein the compound and the at least one additional anti-stroke treatment are co-administered to the patient.

16. The method of claim 13, wherein the compound and the at least one additional anti-stroke treatment are co-formulated.

17. The method of claim 1, wherein the compound is the only anti-stroke treatment administered to the patient.

18. The method of claim 1, wherein the compound is the only anti-stroke treatment administered to the patient in an amount sufficient to treat or ameliorate stroke in the patient.

19. The method of claim 1, wherein the patient is a mammal.

20. The method of claim 19, wherein the mammal is a human.

21. A method of treating or ameliorating stroke in a SCA patient in need thereof, the method comprising:

measuring the amount of pyrophosphate (PPi) in a sample from the SCA patient, comparing the amount of PPi in the sample from the SCA patient with the amount of PPi in a reference sample, wherein, if the amount of PPi is lower in the sample from the SCA patient than in the reference sample, the patient is determined to be at risk for stroke, and further administering to the patient at risk for stroke a therapeutically effective amount of a compound of formula (I), or a salt or solvate thereof:

PROTEIN-Z-DOMAIN-X-Y (I), wherein in (I):

PROTEIN comprises amino acid residues 23 to 849 (PSCAKE . . . to . . . QED) of SEQ ID NO:19;

DOMAIN is absent or at least one selected from the group consisting of a human IgG Fc domain (Fc), human serum albumin protein (ALB) and a fragment thereof;

X and Z are independently absent or a polypeptide comprising 1-20 amino acids; and Y is absent.

22. The method of claim 21, wherein the patient is a mammal.

23. The method of claim 22, wherein the mammal is a human.

24. The method of claim 21, further comprising administering at least one additional anti-stroke treatment to the SCA patient.

* * * * *